US009700672B2

(12) United States Patent
Capone et al.

(10) Patent No.: US 9,700,672 B2
(45) Date of Patent: Jul. 11, 2017

(54) CONTINUOUS MULTI-FLUID PUMP DEVICE, DRIVE AND ACTUATING SYSTEM AND METHOD

(71) Applicant: Bayer Medical Care Inc., Indianola, PA (US)

(72) Inventors: Christopher D. Capone, Pittsburgh, PA (US); Richard A. Seman, Delmont, PA (US); John A. Haury, Sewickley, PA (US); Edward K. Prem, Allison Park, PA (US); Ronald Heller, Monroeville, PA (US); Jason L. Bazala, Irwin, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 423 days.

(21) Appl. No.: 14/346,064

(22) PCT Filed: Sep. 20, 2012

(86) PCT No.: PCT/US2012/056355
§ 371 (c)(1),
(2) Date: Mar. 20, 2014

(87) PCT Pub. No.: WO2013/043881
PCT Pub. Date: Mar. 28, 2013

(65) Prior Publication Data
US 2014/0228762 A1    Aug. 14, 2014

Related U.S. Application Data

(60) Provisional application No. 61/537,371, filed on Sep. 21, 2011.

(51) Int. Cl.
*A61M 5/168*    (2006.01)
*F04B 49/06*    (2006.01)
(Continued)

(52) U.S. Cl.
CPC ........ *A61M 5/16881* (2013.01); *A61M 5/007* (2013.01); *A61M 5/1408* (2013.01);
(Continued)

(58) Field of Classification Search
CPC ............ A61M 5/16881; A61M 39/223; A61M 2039/229; B23P 15/001; F16K 11/07;
(Continued)

(56) References Cited

U.S. PATENT DOCUMENTS

| 205,069 A | 6/1878 | Farnsworth |
|---|---|---|
| 339,417 A | 4/1886 | Horen |

(Continued)

FOREIGN PATENT DOCUMENTS

| CA | 2045070 A1 | 2/1992 |
|---|---|---|
| CN | 2829775 | 10/2006 |

(Continued)

OTHER PUBLICATIONS

The International Preliminary Report on Patentability from corresponding PCT Application No. PCT/US2012/056355 mailed Apr. 3, 2014.

(Continued)

*Primary Examiner* — Laura Bouchelle
*Assistant Examiner* — Anh Bui
(74) *Attorney, Agent, or Firm* — Joseph L. Kent; David Schramm; James R. Stevenson

(57) ABSTRACT

A selector valve for a medical fluid delivery device is disclosed. The valve includes a valve bore in fluid communication with an outlet channel, first and second outlet ports, and a selector valve body which includes a valve stem located within the valve bore and having a flow passage. The selector valve body is adapted to place the flow passage in fluid communication with one of the first outlet port, the second outlet port, and a shut-off position. Further, the
(Continued)

selector valve body includes a sealing arrangement having an elastomeric core disposed within a thin-walled valve stem which comprises a thin cylindrical sidewall in direct contact with the valve bore. When the elastomeric core and the valve stem are subjected to internal fluid pressure, the thin cylindrical sidewall of the valve stem expands outward to increase a sealing force between an outer diameter of the valve stem and the valve bore.

6 Claims, 67 Drawing Sheets

(51) Int. Cl.
| | |
|---|---|
| F04B 49/22 | (2006.01) |
| F04B 53/16 | (2006.01) |
| A61M 5/00 | (2006.01) |
| A61M 5/14 | (2006.01) |
| B05B 11/00 | (2006.01) |
| A61M 5/142 | (2006.01) |
| F16K 11/07 | (2006.01) |
| B23P 15/00 | (2006.01) |
| G05D 7/06 | (2006.01) |
| A61M 39/22 | (2006.01) |
| A61M 5/145 | (2006.01) |

(52) U.S. Cl.
CPC ........ *A61M 5/1422* (2013.01); *A61M 39/223* (2013.01); *B05B 11/3015* (2013.01); *B23P 15/001* (2013.01); *F04B 49/06* (2013.01); *F04B 49/065* (2013.01); *F04B 49/22* (2013.01); *F04B 53/16* (2013.01); *F16K 11/07* (2013.01); *G05D 7/0635* (2013.01); *A61M 5/1452* (2013.01); *A61M 2039/229* (2013.01); *A61M 2205/50* (2013.01); *A61M 2205/6063* (2013.01); *A61M 2207/00* (2013.01); *Y10T 29/49229* (2015.01); *Y10T 29/49236* (2015.01); *Y10T 29/49412* (2015.01); *Y10T 29/5191* (2015.01); *Y10T 137/86879* (2015.04)

(58) Field of Classification Search
CPC ......... F16K 11/0712; Y10T 137/86863; Y10T 137/86871; Y10T 137/86879; Y10T 137/86887; Y10T 137/97161; Y10T 137/86566

See application file for complete search history.

(56) References Cited

U.S. PATENT DOCUMENTS

| | | |
|---|---|---|
| 372,093 A | 10/1887 | Struck |
| 373,292 A | 11/1887 | Jacobson et al. |
| 375,160 A | 12/1887 | Housel |
| 388,876 A | 9/1888 | Humans |
| 503,778 A | 8/1893 | Trimble |
| 517,192 A | 3/1894 | Prior |
| 567,115 A | 9/1896 | Atkinson et al. |
| 783,317 A | 2/1905 | Salsman |
| 921,691 A | 5/1909 | Friday |
| 1,103,212 A | 7/1914 | Kraemer |
| 1,324,654 A | 12/1919 | Ferguson |
| 1,346,127 A | 7/1920 | Lewis |
| 1,531,698 A | 3/1925 | Janes |
| 1,708,112 A | 4/1929 | Henry |
| 1,748,810 A | 2/1930 | Wandel |
| 1,845,882 A | 2/1932 | Litshge |
| 1,873,304 A | 8/1932 | De Mooy |
| 1,973,351 A | 9/1934 | Meeker |
| 2,019,402 A | 10/1935 | Duffy |
| 2,206,816 A | 7/1940 | Levitt |
| 2,335,085 A | 11/1943 | Roberts |
| 2,409,650 A | 10/1946 | Wiggins |
| 2,412,597 A | 12/1946 | Brewer |
| 2,417,250 A | 3/1947 | Harvey |
| 2,485,842 A | 10/1949 | Pennington |
| 2,642,258 A | 6/1953 | Stone et al. |
| 2,702,008 A | 2/1955 | Stockard |
| 2,728,550 A | 12/1955 | Sinkler |
| 2,776,104 A | 1/1957 | Sinkler |
| 2,876,985 A | 3/1959 | Birchall, Jr. et al. |
| 2,946,606 A | 7/1960 | Smith |
| 2,985,192 A | 5/1961 | Taylor et al. |
| 3,038,694 A | 6/1962 | Dunbeck et al. |
| 3,048,191 A | 8/1962 | Crang |
| 3,057,350 A | 10/1962 | Cowley |
| 3,093,359 A | 6/1963 | De Woody |
| 3,142,474 A | 7/1964 | Nelson |
| 3,146,775 A | 9/1964 | Moore et al. |
| 3,157,201 A | 11/1964 | Littmann |
| 3,181,895 A | 5/1965 | Cator |
| 3,185,179 A | 5/1965 | Harautuneian |
| 3,206,163 A | 9/1965 | Freed |
| 3,245,698 A | 4/1966 | Fromknecht |
| 3,268,203 A | 8/1966 | Gilmont et al. |
| 3,276,472 A | 10/1966 | Jinkens et al. |
| 3,277,922 A | 10/1966 | Eisel |
| 3,349,713 A | 10/1967 | Fassbender |
| 3,394,954 A | 7/1968 | Sarns |
| 3,395,925 A | 8/1968 | Dreiding |
| 3,411,534 A | 11/1968 | Rose |
| 3,434,691 A | 3/1969 | Hamilton |
| 3,447,468 A | 6/1969 | Kinne |
| 3,450,152 A | 6/1969 | Ouellette |
| 3,464,359 A | 9/1969 | King et al. |
| 3,484,077 A | 12/1969 | Porter |
| 3,485,265 A | 12/1969 | Buono |
| 3,489,158 A | 1/1970 | MacKay |
| 3,523,523 A | 8/1970 | Reich et al. |
| 3,548,827 A | 12/1970 | Abel |
| 3,552,393 A | 1/1971 | Willgerodt |
| 3,554,488 A | 1/1971 | Alexander |
| 3,569,903 A | 3/1971 | Brishka |
| 3,582,040 A | 6/1971 | Gutierrez |
| 3,586,049 A | 6/1971 | Adamson |
| 3,614,060 A | 10/1971 | Freed et al. |
| 3,623,474 A | 11/1971 | Heilman et al. |
| 3,638,973 A | 2/1972 | Poletti |
| 3,678,960 A | 7/1972 | Leibinsohn |
| 3,687,416 A | 8/1972 | Mueller |
| 3,701,345 A | 10/1972 | Heilman et al. |
| 3,731,679 A | 5/1973 | Wilhelmson et al. |
| 3,739,943 A | 6/1973 | Wilhelmson et al. |
| 3,755,655 A | 8/1973 | Senecal |
| 3,768,476 A | 10/1973 | Raitto |
| 3,793,600 A | 2/1974 | Grosbard |
| 3,812,843 A | 5/1974 | Wootten et al. |
| 3,828,775 A | 8/1974 | Armel |
| 3,834,372 A | 9/1974 | Turney |
| 3,855,129 A | 12/1974 | Abrahams et al. |
| 3,865,134 A | 2/1975 | Holcomb |
| 3,866,957 A | 2/1975 | Norton |
| 3,888,239 A | 6/1975 | Rubinstein |
| 3,895,220 A | 7/1975 | Nelson et al. |
| 3,898,983 A | 8/1975 | Elam |
| 3,916,943 A | 11/1975 | Hester et al. |
| 3,927,955 A | 12/1975 | Spinosa et al. |
| 3,935,971 A | 2/1976 | Papoff et al. |
| 3,940,325 A | 2/1976 | Hirao |
| 3,941,126 A | 3/1976 | Dietrich et al. |
| 3,957,082 A | 5/1976 | Fuson et al. |
| 3,958,103 A | 5/1976 | Oka et al. |
| 3,968,195 A | 7/1976 | Bishop |
| 3,976,311 A | 8/1976 | Spendlove |
| 3,986,508 A | 10/1976 | Barrington |
| 3,990,727 A | 11/1976 | Gallagher |
| 3,991,975 A | 11/1976 | Sibrava |
| 3,995,381 A | 12/1976 | Manfred et al. |
| 3,997,195 A | 12/1976 | Bartholomew |
| 4,001,549 A | 1/1977 | Corwin |

(56) References Cited

U.S. PATENT DOCUMENTS

| | | |
|---|---|---|
| 4,014,467 A | 3/1977 | Ferguson |
| 4,014,514 A | 3/1977 | Priese et al. |
| 4,026,581 A | 5/1977 | Pasbrig |
| 4,030,494 A | 6/1977 | Tenczar |
| 4,032,263 A | 6/1977 | Pareja |
| 4,038,981 A | 8/1977 | LeFevre et al. |
| 4,044,757 A | 8/1977 | McWhorter et al. |
| 4,044,758 A | 8/1977 | Patel |
| 4,049,295 A | 9/1977 | Piers |
| 4,061,142 A | 12/1977 | Tuttle |
| 4,065,230 A | 12/1977 | Gezari |
| 4,071,039 A | 1/1978 | Goof |
| 4,072,056 A | 2/1978 | Lee |
| 4,090,502 A | 5/1978 | Tajika |
| 4,121,622 A | 10/1978 | Forgberg |
| 4,123,091 A | 10/1978 | Cosentino et al. |
| 4,137,011 A | 1/1979 | Rock |
| 4,147,184 A | 4/1979 | Jess |
| 4,151,845 A | 5/1979 | Clemens |
| 4,161,949 A | 7/1979 | Thanawalla |
| 4,177,835 A | 12/1979 | Paley |
| 4,181,223 A | 1/1980 | Millet |
| 4,187,057 A | 2/1980 | Xanthopoulos |
| 4,191,183 A | 3/1980 | Mendelson |
| 4,198,080 A | 4/1980 | Carpenter |
| 4,199,000 A | 4/1980 | Edstrom |
| 4,207,871 A | 6/1980 | Jenkins |
| 4,207,923 A | 6/1980 | Giurtino |
| 4,215,847 A | 8/1980 | Hoos |
| 4,223,675 A | 9/1980 | Williams |
| 4,225,290 A | 9/1980 | Allington |
| 4,230,151 A | 10/1980 | Jonsson |
| 4,233,156 A | 11/1980 | Tsukada et al. |
| 4,252,126 A | 2/1981 | Mandl |
| 4,253,501 A | 3/1981 | Ogle |
| 4,259,985 A | 4/1981 | Bergmann |
| 4,260,180 A | 4/1981 | Halushka et al. |
| 4,262,824 A | 4/1981 | Hrynewycz |
| 4,262,880 A | 4/1981 | Danko et al. |
| 4,275,868 A | 6/1981 | Crone |
| 4,280,494 A | 7/1981 | Cosgrove et al. |
| 4,284,073 A | 8/1981 | Krause et al. |
| 4,306,705 A | 12/1981 | Svensson |
| 4,310,420 A | 1/1982 | Konishi et al. |
| 4,311,586 A | 1/1982 | Baldwin et al. |
| 4,319,568 A | 3/1982 | Tregoning |
| 4,326,697 A | 4/1982 | Autage et al. |
| 4,328,833 A | 5/1982 | Aurther |
| 4,328,834 A | 5/1982 | Oates, Sr. et al. |
| 4,340,153 A | 7/1982 | Spivey |
| 4,341,153 A | 7/1982 | Bowser |
| 4,352,636 A | 10/1982 | Patterson et al. |
| 4,365,635 A | 12/1982 | Bowman |
| 4,372,336 A | 2/1983 | Cornell et al. |
| 4,392,847 A | 7/1983 | Whitney et al. |
| 4,392,849 A | 7/1983 | Petre et al. |
| 4,396,385 A | 8/1983 | Kelly et al. |
| 4,398,757 A | 8/1983 | Floyd et al. |
| 4,402,310 A | 9/1983 | Kimura |
| 4,409,966 A | 10/1983 | Lambrecht et al. |
| 4,410,003 A | 10/1983 | Sandling |
| 4,412,834 A | 11/1983 | Kulin et al. |
| 4,431,009 A | 2/1984 | Marino, Jr. et al. |
| 4,433,973 A | 2/1984 | Kurtz et al. |
| 4,434,822 A | 3/1984 | Bellamy et al. |
| 4,444,198 A | 4/1984 | Petre |
| 4,447,230 A | 5/1984 | Gula et al. |
| 4,453,927 A | 6/1984 | Sinko |
| 4,468,914 A | 9/1984 | Pestes |
| 4,469,121 A | 9/1984 | Moen |
| 4,469,935 A | 9/1984 | Candela |
| 4,478,388 A | 10/1984 | George |
| 4,479,760 A | 10/1984 | Bilstad et al. |
| 4,479,761 A | 10/1984 | Bilstad et al. |
| 4,479,762 A | 10/1984 | Bilstad et al. |
| 4,479,792 A | 10/1984 | Lazarus et al. |
| 4,484,599 A | 11/1984 | Hanover et al. |
| 4,491,156 A | 1/1985 | Lee, II |
| 4,494,730 A | 1/1985 | George |
| 4,503,333 A | 3/1985 | Kulin et al. |
| RE31,873 E | 4/1985 | Howes |
| 4,508,103 A | 4/1985 | Calisi |
| 4,508,367 A | 4/1985 | Oreopoulos et al. |
| 4,511,359 A | 4/1985 | Vaillancourt |
| 4,512,364 A | 4/1985 | Phillips |
| 4,512,764 A | 4/1985 | Wunsch |
| 4,535,820 A | 8/1985 | Raines |
| 4,544,949 A | 10/1985 | Kurihara |
| 4,551,133 A | 11/1985 | Zegers de Beyl et al. |
| 4,552,513 A | 11/1985 | Miller et al. |
| 4,559,036 A | 12/1985 | Wunsch |
| 4,563,175 A | 1/1986 | LaFond |
| 4,572,231 A | 2/1986 | Katayama |
| 4,585,009 A | 4/1986 | Barker et al. |
| 4,585,941 A | 4/1986 | Bergner |
| 4,595,495 A | 6/1986 | Yotam et al. |
| 4,604,093 A | 8/1986 | Brown et al. |
| 4,610,670 A | 9/1986 | Spencer |
| 4,610,790 A | 9/1986 | Reti et al. |
| 4,613,325 A * | 9/1986 | Abrams ............ A61M 5/16886 128/DIG. 13 |
| 4,633,307 A | 12/1986 | Honda |
| 4,634,426 A | 1/1987 | Kamen |
| 4,636,144 A | 1/1987 | Abe et al. |
| 4,637,817 A | 1/1987 | Archibald et al. |
| 4,655,197 A | 4/1987 | Atkinson |
| 4,655,762 A | 4/1987 | Rogers |
| 4,662,906 A | 5/1987 | Matkovich et al. |
| 4,681,513 A | 7/1987 | Saito et al. |
| 4,682,170 A | 7/1987 | Kubota et al. |
| 4,684,102 A | 8/1987 | Dykstra |
| 4,695,276 A | 9/1987 | Shinno et al. |
| 4,710,166 A | 12/1987 | Thompson et al. |
| 4,737,148 A | 4/1988 | Blake |
| 4,750,643 A | 6/1988 | Wortrich |
| 4,752,292 A | 6/1988 | Lopez et al. |
| 4,754,786 A | 7/1988 | Roberts |
| 4,756,706 A | 7/1988 | Kerns et al. |
| 4,758,235 A | 7/1988 | Tu |
| 4,775,173 A | 10/1988 | Sauer |
| 4,778,152 A * | 10/1988 | Logman ................ F16K 5/0414 251/310 |
| 4,778,447 A | 10/1988 | Velde et al. |
| 4,781,687 A | 11/1988 | Wall |
| 4,783,273 A | 11/1988 | Knutsson et al. |
| 4,797,207 A | 1/1989 | Honganen et al. |
| 4,798,590 A | 1/1989 | O'Leary et al. |
| 4,807,666 A | 2/1989 | Morse |
| 4,808,077 A | 2/1989 | Kan et al. |
| 4,810,168 A | 3/1989 | Nogami et al. |
| 4,810,241 A | 3/1989 | Rogers |
| 4,813,210 A | 3/1989 | Masuda et al. |
| 4,819,637 A | 4/1989 | Dormandy, Jr. et al. |
| 4,820,288 A | 4/1989 | Isono |
| 4,821,996 A | 4/1989 | Bellotti et al. |
| 4,823,833 A | 4/1989 | Hogan et al. |
| 4,834,108 A | 5/1989 | Vaillancourt |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,844,413 A | 7/1989 | Weber et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,874,378 A | 10/1989 | Hillstead |
| 4,875,718 A | 10/1989 | Marken |
| 4,879,880 A | 11/1989 | Harrison |
| 4,880,014 A | 11/1989 | Zarowitz et al. |
| 4,883,409 A | 11/1989 | Strohmeier et al. |
| 4,887,208 A | 12/1989 | Schneider et al. |

(56) References Cited

U.S. PATENT DOCUMENTS

| | | |
|---|---|---|
| 4,887,554 A | 12/1989 | Whitford |
| 4,890,817 A | 1/1990 | Uri |
| 4,904,245 A * | 2/1990 | Chen ............... A61M 3/0233 137/625.47 |
| 4,913,624 A | 4/1990 | Seki et al. |
| 4,915,591 A | 4/1990 | Funke |
| 4,915,688 A | 4/1990 | Bischof et al. |
| 4,925,444 A | 5/1990 | Orkin et al. |
| 4,929,818 A | 5/1990 | Bradbury et al. |
| 4,935,005 A | 6/1990 | Haines |
| 4,936,753 A | 6/1990 | Kozumplik, Jr. et al. |
| 4,936,832 A | 6/1990 | Vaillancourt |
| 4,941,308 A | 7/1990 | Grabenkort et al. |
| 4,943,279 A | 7/1990 | Samiotes et al. |
| 4,946,047 A | 8/1990 | Kurokawa et al. |
| 4,946,256 A | 8/1990 | Woodruff |
| 4,946,434 A | 8/1990 | Plaisted et al. |
| 4,946,439 A | 8/1990 | Eggers |
| 4,947,856 A | 8/1990 | Beard |
| 4,950,245 A | 8/1990 | Brown et al. |
| 4,954,129 A | 9/1990 | Giuliani et al. |
| 4,954,239 A | 9/1990 | Mueller |
| 4,966,199 A | 10/1990 | Ruschke |
| 4,966,579 A | 10/1990 | Polaschegg |
| 4,967,797 A | 11/1990 | Manska |
| 4,969,879 A | 11/1990 | Lichte |
| 4,976,687 A | 12/1990 | Martin |
| 4,978,335 A | 12/1990 | Arthur et al. |
| 4,981,467 A | 1/1991 | Bobo et al. |
| 4,982,760 A | 1/1991 | Mustaklem |
| 4,987,335 A | 1/1991 | Yamamoto et al. |
| 4,993,546 A | 2/1991 | Southard |
| 4,994,035 A | 2/1991 | Mokros |
| 5,002,055 A | 3/1991 | Merki et al. |
| 5,004,472 A | 4/1991 | Wallace |
| 5,009,654 A | 4/1991 | Minshall et al. |
| 5,014,494 A | 5/1991 | George |
| 5,029,973 A | 7/1991 | Rink |
| 5,032,112 A | 7/1991 | Fairchild et al. |
| 5,033,777 A | 7/1991 | Blenkush |
| 5,037,067 A | 8/1991 | Ray |
| 5,047,021 A | 9/1991 | Utterberg |
| 5,053,002 A | 10/1991 | Barlow |
| 5,057,076 A | 10/1991 | Polaschegg |
| 5,059,173 A | 10/1991 | Sacco |
| 5,061,243 A | 10/1991 | Winchell et al. |
| 5,074,334 A | 12/1991 | Onodera |
| 5,078,580 A | 1/1992 | Miller et al. |
| 5,078,683 A | 1/1992 | Sancoff et al. |
| 5,084,031 A | 1/1992 | Todd et al. |
| 5,087,086 A | 2/1992 | Snedeker |
| 5,088,981 A | 2/1992 | Howson et al. |
| 5,097,840 A | 3/1992 | Wallace et al. |
| 5,098,407 A | 3/1992 | Okamura |
| 5,100,103 A | 3/1992 | Conley et al. |
| 5,100,380 A | 3/1992 | Epstein et al. |
| 5,104,158 A | 4/1992 | Meyer et al. |
| 5,104,374 A | 4/1992 | Bishko et al. |
| 5,104,387 A | 4/1992 | Pokorney et al. |
| 5,108,365 A | 4/1992 | Woods et al. |
| 5,113,904 A | 5/1992 | Aslanian |
| 5,113,906 A | 5/1992 | Hogner |
| 5,116,086 A | 5/1992 | Psajd |
| 5,117,870 A | 6/1992 | Goodale et al. |
| 5,128,121 A | 7/1992 | Berg et al. |
| 5,133,336 A | 7/1992 | Savitt et al. |
| 5,135,000 A | 8/1992 | Akselrod et al. |
| 5,135,026 A | 8/1992 | Manska |
| 5,143,257 A | 9/1992 | Austin et al. |
| 5,153,827 A | 10/1992 | Coutre et al. |
| 5,163,909 A | 11/1992 | Stewart |
| 5,165,728 A | 11/1992 | Mayer |
| 5,176,415 A | 1/1993 | Choksi |
| 5,180,896 A | 1/1993 | Gibby et al. |
| 5,190,071 A | 3/1993 | Sule |
| 5,190,534 A | 3/1993 | Kendell |
| 5,191,878 A | 3/1993 | Iida et al. |
| 5,196,007 A | 3/1993 | Ellman et al. |
| 5,196,197 A | 3/1993 | Talwar et al. |
| 5,197,438 A | 3/1993 | Kumano et al. |
| 5,199,604 A | 4/1993 | Palmer et al. |
| 5,205,322 A | 4/1993 | Merick et al. |
| 5,207,641 A | 5/1993 | Allton |
| 5,207,642 A | 5/1993 | Orkin et al. |
| 5,213,376 A | 5/1993 | Szabo |
| 5,226,886 A | 7/1993 | Skakoon et al. |
| 5,230,614 A | 7/1993 | Zanger et al. |
| 5,234,193 A | 8/1993 | Neal et al. |
| 5,242,390 A | 9/1993 | Goldrath |
| 5,249,579 A | 10/1993 | Hobbs et al. |
| 5,254,101 A | 10/1993 | Trombley, III |
| 5,260,020 A | 11/1993 | Wilk et al. |
| 5,267,174 A | 11/1993 | Kaufman et al. |
| 5,267,964 A | 12/1993 | Karg |
| 5,269,756 A | 12/1993 | Dryden |
| 5,273,537 A | 12/1993 | Haskvitz et al. |
| 5,274,218 A | 12/1993 | Urata et al. |
| 5,288,290 A | 2/1994 | Brody |
| 5,310,007 A | 5/1994 | Parikh |
| 5,310,997 A | 5/1994 | Roach et al. |
| 5,313,992 A | 5/1994 | Grabenkort |
| 5,317,506 A | 5/1994 | Coutre et al. |
| 5,318,328 A | 6/1994 | Dawson |
| 5,328,463 A | 7/1994 | Barton et al. |
| 5,329,459 A | 7/1994 | Kaufman et al. |
| 5,334,163 A | 8/1994 | Sinnett |
| 5,339,799 A | 8/1994 | Kami et al. |
| 5,346,470 A | 9/1994 | Hobbs et al. |
| 5,349,625 A | 9/1994 | Born et al. |
| 5,354,273 A | 10/1994 | Hagen |
| 5,361,761 A | 11/1994 | Van Lysel et al. |
| 5,362,291 A | 11/1994 | Williamson, IV |
| 5,362,948 A | 11/1994 | Morimoto |
| 5,368,562 A | 11/1994 | Blomquist et al. |
| 5,376,070 A | 12/1994 | Purvis et al. |
| 5,377,718 A | 1/1995 | Sand |
| 5,378,231 A | 1/1995 | Johnson et al. |
| 5,382,232 A | 1/1995 | Hague et al. |
| 5,385,540 A | 1/1995 | Abbott et al. |
| 5,411,490 A | 5/1995 | Tennican et al. |
| 5,417,213 A | 5/1995 | Prince |
| 5,417,667 A | 5/1995 | Tennican et al. |
| 5,419,354 A | 5/1995 | Krynicki |
| 5,423,323 A | 6/1995 | Orth |
| 5,431,627 A | 7/1995 | Pastrone et al. |
| 5,443,453 A | 8/1995 | Walker et al. |
| 5,445,621 A | 8/1995 | Poli et al. |
| 5,449,206 A | 9/1995 | Lockwood |
| 5,450,847 A | 9/1995 | Kampfe et al. |
| 5,452,748 A | 9/1995 | Simmons et al. |
| 5,454,792 A | 10/1995 | Tennican et al. |
| 5,454,972 A | 10/1995 | Williams et al. |
| 5,458,128 A | 10/1995 | Polanyi et al. |
| 5,460,609 A | 10/1995 | O Donnell |
| 5,462,251 A | 10/1995 | Kawabe |
| 5,464,391 A | 11/1995 | DeVale |
| 5,466,228 A | 11/1995 | Evans |
| 5,468,240 A | 11/1995 | Gentelia et al. |
| 5,472,403 A | 12/1995 | Cornacchia et al. |
| 5,474,099 A | 12/1995 | Boehmer et al. |
| 5,474,683 A | 12/1995 | Bryant et al. |
| 5,478,338 A | 12/1995 | Reynard |
| 5,480,386 A | 1/1996 | Brohy et al. |
| 5,485,831 A | 1/1996 | Holdsworth et al. |
| 5,489,265 A | 2/1996 | Montalvo et al. |
| 5,494,036 A | 2/1996 | Uber et al. |
| 5,494,822 A | 2/1996 | Sadri |
| 5,496,273 A | 3/1996 | Pastrone et al. |
| 5,507,412 A | 4/1996 | Ebert et al. |
| 5,507,733 A | 4/1996 | Larkin et al. |
| 5,515,851 A | 5/1996 | Goldstein |
| 5,522,798 A | 6/1996 | Johnson et al. |
| 5,529,463 A | 6/1996 | Layer et al. |
| 5,531,679 A | 7/1996 | Schulman et al. |

(56) References Cited

U.S. PATENT DOCUMENTS

| | | |
|---|---|---|
| 5,531,697 A | 7/1996 | Olsen et al. |
| 5,531,698 A | 7/1996 | Olsen |
| 5,531,712 A | 7/1996 | Malcolm et al. |
| 5,533,978 A | 7/1996 | Teirstein |
| 5,547,470 A | 8/1996 | Johnson et al. |
| 5,552,130 A | 9/1996 | Kraus et al. |
| 5,553,619 A | 9/1996 | Prince |
| 5,558,669 A | 9/1996 | Reynard |
| 5,560,317 A | 10/1996 | Bunyan et al. |
| 5,569,181 A | 10/1996 | Heilman et al. |
| 5,569,208 A | 10/1996 | Woelpper et al. |
| 5,573,505 A | 11/1996 | Johnson et al. |
| 5,573,515 A | 11/1996 | Wilson et al. |
| 5,578,016 A | 11/1996 | Zinger |
| 5,579,767 A | 12/1996 | Prince |
| 5,580,530 A | 12/1996 | Kowatsch et al. |
| 5,583,902 A | 12/1996 | Bae |
| 5,590,654 A | 1/1997 | Prince |
| 5,592,940 A | 1/1997 | Kampfe et al. |
| 5,603,900 A | 2/1997 | Clark et al. |
| 5,616,124 A | 4/1997 | Hague et al. |
| 5,632,606 A | 5/1997 | Jacobsen et al. |
| 5,645,538 A | 7/1997 | Richmond |
| 5,647,854 A | 7/1997 | Olsen et al. |
| 5,655,897 A | 8/1997 | Neftel et al. |
| 5,687,208 A | 11/1997 | Bae et al. |
| 5,697,899 A | 12/1997 | Hillman et al. |
| 5,704,914 A | 1/1998 | Stocking et al. |
| 5,714,060 A | 2/1998 | Kenley et al. |
| 5,718,568 A | 2/1998 | Neftel et al. |
| 5,739,508 A | 4/1998 | Uber, III |
| 5,741,125 A | 4/1998 | Neftel et al. |
| 5,755,683 A | 5/1998 | Houle et al. |
| 5,764,159 A | 6/1998 | Neftel |
| 5,768,405 A | 6/1998 | Makram-Ebeid |
| 5,772,585 A | 6/1998 | Lavin et al. |
| 5,782,611 A | 7/1998 | Neftel et al. |
| 5,788,669 A | 8/1998 | Peterson |
| 5,795,333 A | 8/1998 | Reilly et al. |
| 5,799,649 A | 9/1998 | Prince |
| 5,799,987 A | 9/1998 | Sampson |
| 5,800,397 A | 9/1998 | Wilson et al. |
| 5,806,519 A | 9/1998 | Evans et al. |
| 5,808,203 A | 9/1998 | Nolan, Jr. et al. |
| 5,817,067 A | 10/1998 | Tsukada |
| 5,817,068 A | 10/1998 | Urrutia |
| 5,819,229 A | 10/1998 | Boppe |
| 5,822,544 A | 10/1998 | Chaco et al. |
| 5,827,262 A | 10/1998 | Neftel et al. |
| 5,830,195 A | 11/1998 | Peters et al. |
| 5,832,959 A | 11/1998 | Szymczakowski et al. |
| 5,840,026 A | 11/1998 | Uber et al. |
| 5,843,037 A | 12/1998 | Uber et al. |
| 5,852,231 A | 12/1998 | Kaji |
| 5,865,797 A | 2/1999 | Zeeman |
| 5,873,861 A | 2/1999 | Hitchins et al. |
| 5,882,343 A | 3/1999 | Wilson et al. |
| 5,885,216 A | 3/1999 | Evans et al. |
| 5,901,745 A | 5/1999 | Buchtel |
| 5,901,944 A | 5/1999 | Ramakrishnan et al. |
| 5,911,687 A | 6/1999 | Sato et al. |
| 5,916,165 A | 6/1999 | Duchon et al. |
| 5,916,197 A | 6/1999 | Reilly et al. |
| 5,916,201 A | 6/1999 | Wilson, Jr. et al. |
| 5,920,054 A | 7/1999 | Uber, III |
| 5,924,074 A | 7/1999 | Evans |
| 5,927,885 A | 7/1999 | Duez et al. |
| 5,935,099 A | 8/1999 | Peterson et al. |
| 5,937,885 A | 8/1999 | Sampson |
| 5,947,935 A | 9/1999 | Rhinehart et al. |
| 5,947,958 A | 9/1999 | Woodard et al. |
| 5,953,453 A | 9/1999 | Fan et al. |
| 5,954,700 A | 9/1999 | Kovelman |
| 5,964,485 A | 10/1999 | Hame et al. |
| 5,968,014 A | 10/1999 | Neftel et al. |
| 5,980,501 A | 11/1999 | Gray |
| 5,984,378 A | 11/1999 | Ostrander et al. |
| 5,988,587 A | 11/1999 | Duchon et al. |
| 5,993,654 A | 11/1999 | Black |
| 6,022,053 A | 2/2000 | Hukuda |
| 6,036,458 A | 3/2000 | Cole et al. |
| RE36,648 E | 4/2000 | Uber, III et al. |
| 6,047,259 A | 4/2000 | Campbell et al. |
| 6,068,617 A | 5/2000 | Richmond |
| 6,077,055 A | 6/2000 | Vilks |
| 6,079,691 A | 6/2000 | Dragone |
| 6,083,205 A | 7/2000 | Bourne et al. |
| 6,085,574 A | 7/2000 | Neftel et al. |
| 6,092,722 A | 7/2000 | Heinrichs et al. |
| 6,096,011 A | 8/2000 | Trombley, III et al. |
| 6,099,502 A | 8/2000 | Duchon et al. |
| 6,099,511 A | 8/2000 | Devos et al. |
| 6,106,498 A | 8/2000 | Friedli et al. |
| 6,110,152 A | 8/2000 | Kovelman |
| 6,120,490 A | 9/2000 | Neftel |
| 6,123,686 A | 9/2000 | Olsen et al. |
| 6,149,627 A | 11/2000 | Uber et al. |
| 6,155,307 A | 12/2000 | Vanneste |
| 6,155,607 A | 12/2000 | Hewitt et al. |
| 6,157,914 A | 12/2000 | Seto et al. |
| 6,158,467 A | 12/2000 | Loo |
| 6,164,044 A | 12/2000 | Porfano et al. |
| 6,189,704 B1 | 2/2001 | Dennehey et al. |
| 6,197,000 B1 | 3/2001 | Reilly et al. |
| 6,200,111 B1 | 3/2001 | Foss |
| 6,220,487 B1 | 4/2001 | Srivastava et al. |
| 6,221,045 B1 | 4/2001 | Duchon et al. |
| 6,250,052 B1 | 6/2001 | Porfano et al. |
| 6,260,021 B1 | 7/2001 | Wong et al. |
| 6,263,641 B1 | 7/2001 | Odell et al. |
| 6,269,704 B1 | 8/2001 | Ziv et al. |
| 6,270,478 B1 | 8/2001 | Mernøe |
| 6,272,469 B1 | 8/2001 | Koritzinsky et al. |
| 6,280,430 B1 | 8/2001 | Neftel et al. |
| 6,283,761 B1 | 9/2001 | Joao |
| 6,285,285 B1 | 9/2001 | Mongrenier |
| 6,293,756 B1 | 9/2001 | Andersson |
| 6,305,724 B1 | 10/2001 | Sampson |
| 6,306,117 B1 | 10/2001 | Uber et al. |
| 6,317,623 B1 | 11/2001 | Griffiths et al. |
| 6,319,236 B1 | 11/2001 | Böck |
| 6,339,718 B1 | 1/2002 | Zatezalo et al. |
| 6,344,030 B1 | 2/2002 | Duchon et al. |
| RE37,602 E | 3/2002 | Uber, III et al. |
| 6,361,051 B1 | 3/2002 | Babin |
| 6,364,279 B1 | 4/2002 | Neftel et al. |
| 6,366,206 B1 | 4/2002 | Ishikawa et al. |
| 6,371,444 B1 | 4/2002 | Hahn et al. |
| 6,385,483 B1 | 5/2002 | Uber et al. |
| 6,397,098 B1 | 5/2002 | Uber, III et al. |
| 6,398,513 B1 | 6/2002 | Amsler et al. |
| 6,402,717 B1 | 6/2002 | Reilly et al. |
| 6,418,966 B2 | 7/2002 | Loo |
| 6,436,072 B1 | 8/2002 | Kullas et al. |
| 6,440,107 B1 | 8/2002 | Trombley, III et al. |
| 6,442,418 B1 | 8/2002 | Evans et al. |
| 6,443,496 B2 | 9/2002 | Campau |
| 6,454,162 B1 | 9/2002 | Teller |
| 6,457,488 B2 | 10/2002 | Loo |
| 6,468,261 B1 | 10/2002 | Small et al. |
| 6,468,424 B1 | 10/2002 | Dönig et al. |
| 6,471,671 B1 | 10/2002 | Urick et al. |
| 6,471,674 B1 | 10/2002 | Emig et al. |
| 6,475,192 B1 | 11/2002 | Reilly et al. |
| 6,488,660 B1 | 12/2002 | Futterknecht |
| 6,491,189 B2 | 12/2002 | Friedman |
| 6,502,937 B2 | 1/2003 | Yang |
| 6,503,225 B1 | 1/2003 | Kirsch et al. |
| 6,511,459 B1 | 1/2003 | Fago |
| 6,519,569 B1 | 2/2003 | White et al. |
| 6,520,930 B2 | 2/2003 | Critchlow et al. |
| 6,530,907 B1 | 3/2003 | Sugahara et al. |
| 6,536,742 B2 | 3/2003 | Lotz et al. |
| RE38,074 E | 4/2003 | Recinella |

(56) References Cited

U.S. PATENT DOCUMENTS

| | | |
|---|---|---|
| 6,540,486 B2 | 4/2003 | Amsler et al. |
| 6,558,125 B1 | 5/2003 | Futterknecht |
| 6,558,343 B1 | 5/2003 | Neftel |
| 6,575,930 B1 | 6/2003 | Trombley, III et al. |
| 6,607,179 B2 | 8/2003 | Moretti et al. |
| 6,623,455 B2 | 9/2003 | Small et al. |
| 6,626,355 B2 | 9/2003 | Sasse et al. |
| 6,626,862 B1 | 9/2003 | Duchon et al. |
| 6,635,033 B1 | 10/2003 | Hill et al. |
| 6,638,258 B2 | 10/2003 | Schwartz et al. |
| 6,638,263 B1 | 10/2003 | Theeuwes et al. |
| 6,643,537 B1 | 11/2003 | Zatezalo et al. |
| 6,648,017 B2 | 11/2003 | Lamas et al. |
| 6,649,829 B2 | 11/2003 | Garber et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,676,104 B2 | 1/2004 | Tillander |
| 6,682,044 B2 | 1/2004 | Miller |
| 6,685,831 B2 | 2/2004 | Dönig et al. |
| 6,699,219 B2 | 3/2004 | Emig et al. |
| 6,708,944 B2 | 3/2004 | Pfeil et al. |
| 6,708,948 B2 | 3/2004 | Nosel |
| 6,716,193 B1 | 4/2004 | Neftel |
| 6,722,705 B2 | 4/2004 | Korkor |
| 6,731,971 B2 | 5/2004 | Evans, III et al. |
| 6,733,477 B2 | 5/2004 | Cowan et al. |
| 6,733,478 B2 | 5/2004 | Reilly et al. |
| 6,742,680 B2 | 6/2004 | Friedman |
| 6,743,202 B2 | 6/2004 | Hirschman et al. |
| 6,749,090 B2 | 6/2004 | Bailey |
| 6,767,034 B2 | 7/2004 | Le Clinche |
| 6,796,965 B2 | 9/2004 | Dumaresq Lucas et al. |
| 6,857,617 B2 | 2/2005 | Forberg |
| 6,861,954 B2 | 3/2005 | Levin |
| 6,871,660 B2 | 3/2005 | Hampsch |
| 6,874,759 B2 | 4/2005 | Aoshima et al. |
| 6,880,808 B2 | 4/2005 | McPeak et al. |
| 6,884,255 B1 | 4/2005 | Newton |
| 6,889,074 B2 | 5/2005 | Uber, III et al. |
| 6,892,996 B2 | 5/2005 | Starchevich |
| 6,897,374 B2 | 5/2005 | Garber et al. |
| 6,901,283 B2 | 5/2005 | Evans, III et al. |
| 6,908,118 B2 | 6/2005 | Fumioka |
| 6,918,893 B2 | 7/2005 | Houde et al. |
| 6,929,235 B1 | 8/2005 | Height et al. |
| 6,929,236 B1 | 8/2005 | Height et al. |
| 6,937,150 B2 | 8/2005 | Medema et al. |
| 6,939,302 B2 | 9/2005 | Griffiths et al. |
| 6,953,450 B2 | 10/2005 | Baldwin et al. |
| 6,953,453 B2 | 10/2005 | Recinella et al. |
| 6,967,974 B1 | 11/2005 | Partyka |
| 6,972,001 B2 | 12/2005 | Emig et al. |
| 6,976,628 B2 | 12/2005 | Krupa |
| 6,985,870 B2 | 1/2006 | Martucci et al. |
| 7,005,078 B2 | 2/2006 | Van Lintel et al. |
| 7,014,624 B2 | 3/2006 | Meythaler et al. |
| 7,017,800 B2 | 3/2006 | Ulrich et al. |
| 7,017,948 B2 | 3/2006 | Sunohara et al. |
| 7,041,941 B2 | 5/2006 | Faries, Jr. et al. |
| 7,047,058 B1 | 5/2006 | Dvorsky et al. |
| 7,047,984 B2 | 5/2006 | Blattner et al. |
| 7,047,994 B2 | 5/2006 | McPeak et al. |
| 7,048,193 B2 | 5/2006 | Tsukada et al. |
| 7,060,049 B2 | 6/2006 | Trombley, III et al. |
| 7,079,886 B2 | 7/2006 | Zatezalo et al. |
| 7,091,864 B2 | 8/2006 | Veitch et al. |
| 7,094,216 B2 | 8/2006 | Trombley, III et al. |
| 7,097,690 B2 | 8/2006 | Usher et al. |
| 7,108,184 B2 | 9/2006 | Mase et al. |
| 7,115,113 B2 | 10/2006 | Evans et al. |
| 7,128,347 B2 | 10/2006 | Kerin |
| 7,137,974 B2 | 11/2006 | Almasian et al. |
| 7,160,020 B2 | 1/2007 | Sand |
| 7,169,135 B2 | 1/2007 | Duchon et al. |
| 7,172,572 B2 | 2/2007 | Diamond et al. |
| 7,174,923 B2 | 2/2007 | Schorn et al. |
| 7,178,515 B2 | 2/2007 | Carpenter et al. |
| 7,189,320 B2 | 3/2007 | Takao et al. |
| 7,193,519 B2 | 3/2007 | Root et al. |
| 7,195,624 B2 | 3/2007 | Lockwood et al. |
| 7,204,421 B2 | 4/2007 | Austin |
| 7,213,760 B2 | 5/2007 | Mase et al. |
| 7,213,767 B2 | 5/2007 | Tethrake et al. |
| 7,214,039 B2 | 5/2007 | Angove |
| 7,217,105 B2 | 5/2007 | Angove |
| 7,236,936 B2 | 6/2007 | White et al. |
| 7,278,778 B2 | 10/2007 | Sand |
| 7,309,014 B2 | 12/2007 | Truong |
| 7,311,503 B2 | 12/2007 | Van Lintel et al. |
| 7,326,188 B1 | 2/2008 | Russell et al. |
| 7,364,657 B2 | 4/2008 | Mandrusov et al. |
| 7,367,358 B2 | 5/2008 | Malcolm |
| 7,374,718 B2 | 5/2008 | Dhara et al. |
| 7,431,989 B2 | 10/2008 | Sakhrani et al. |
| 7,451,959 B2 | 11/2008 | Matzner |
| 7,497,840 B2 | 3/2009 | Neftel et al. |
| 7,553,304 B2 | 6/2009 | Neftel |
| 7,695,445 B2 | 4/2010 | Yuki |
| 7,771,383 B2 | 8/2010 | Truitt et al. |
| 7,782,467 B2 | 8/2010 | Chappel |
| 7,887,308 B2 | 2/2011 | Navarro |
| 7,887,509 B2 | 2/2011 | Thiebaud et al. |
| 7,901,386 B2 | 3/2011 | Hishikawa et al. |
| 7,901,727 B2 | 3/2011 | Hofmann et al. |
| 7,905,861 B2 | 3/2011 | Rhinehart et al. |
| 7,935,077 B2 | 5/2011 | Thor et al. |
| 7,951,112 B2 | 5/2011 | Patzer |
| 7,963,951 B2 | 6/2011 | Kitani et al. |
| 7,984,730 B2 | 7/2011 | Ziv et al. |
| 8,011,897 B2 | 9/2011 | Raleigh et al. |
| 8,061,687 B2 | 11/2011 | Anderson |
| 8,062,009 B2 | 11/2011 | Cueni |
| 8,172,199 B2 | 5/2012 | Ushigusa et al. |
| 8,353,688 B2 | 1/2013 | Navarro |
| 8,382,712 B2 | 2/2013 | Kim |
| 2002/0026148 A1 | 2/2002 | Uber |
| 2002/0061375 A1 | 5/2002 | Cartledge et al. |
| 2002/0084437 A1 | 7/2002 | Nitsche et al. |
| 2002/0099334 A1 | 7/2002 | Hanson et al. |
| 2002/0139088 A1 | 10/2002 | Woodworth et al. |
| 2002/0143294 A1 | 10/2002 | Duchon et al. |
| 2002/0147429 A1 | 10/2002 | Cowan et al. |
| 2002/0172615 A1 | 11/2002 | Woodworth et al. |
| 2002/0188259 A1 | 12/2002 | Hickle et al. |
| 2002/0191487 A1 | 12/2002 | Sand et al. |
| 2003/0050556 A1 | 3/2003 | Uber et al. |
| 2003/0071233 A1 | 4/2003 | Stewart et al. |
| 2003/0140929 A1 | 7/2003 | Wilkes et al. |
| 2003/0155385 A1 | 8/2003 | Sohoel et al. |
| 2003/0181850 A1 | 9/2003 | Diamond et al. |
| 2003/0216643 A1 | 11/2003 | Zatezalo et al. |
| 2004/0008123 A1 | 1/2004 | Carrender et al. |
| 2004/0015078 A1 | 1/2004 | Evans et al. |
| 2004/0021120 A1* | 2/2004 | Turnau, III ............ F16K 5/0414 251/309 |
| 2004/0064041 A1 | 4/2004 | Lazzaro et al. |
| 2004/0074281 A1 | 4/2004 | Lobdell et al. |
| 2004/0092908 A1 | 5/2004 | Harper et al. |
| 2004/0104271 A1 | 6/2004 | Martucci et al. |
| 2004/0116862 A1 | 6/2004 | Ray |
| 2004/0130438 A1 | 7/2004 | Garber |
| 2004/0171982 A1 | 9/2004 | Danchin |
| 2004/0193328 A1 | 9/2004 | Zaitsu et al. |
| 2004/0193453 A1 | 9/2004 | Butterfield et al. |
| 2004/0199075 A1 | 10/2004 | Evans et al. |
| 2004/0221904 A1 | 11/2004 | Usher et al. |
| 2004/0222180 A1 | 11/2004 | Wicks et al. |
| 2004/0241023 A1 | 12/2004 | Pinkerton et al. |
| 2005/0010175 A1 | 1/2005 | Beedon et al. |
| 2005/0019187 A1 | 1/2005 | Whitworth et al. |
| 2005/0057042 A1 | 3/2005 | Wicks |
| 2005/0070978 A1 | 3/2005 | Bek et al. |
| 2005/0075611 A1 | 4/2005 | Hetzler et al. |

(56) References Cited

U.S. PATENT DOCUMENTS

| | | |
|---|---|---|
| 2005/0082828 A1 | 4/2005 | Wicks et al. |
| 2005/0084410 A1 | 4/2005 | Meyer et al. |
| 2005/0089994 A1 | 4/2005 | Neftel |
| 2005/0113763 A1 | 5/2005 | Reynolds et al. |
| 2005/0118048 A1 | 6/2005 | Traxinger |
| 2005/0129569 A1 | 6/2005 | Zhao et al. |
| 2005/0194722 A1 | 9/2005 | Muratoglu et al. |
| 2005/0194723 A1 | 9/2005 | Muratoglu et al. |
| 2005/0211905 A1 | 9/2005 | Stark |
| 2005/0211934 A1 | 9/2005 | Garber et al. |
| 2005/0245883 A1 | 11/2005 | Baldwin et al. |
| 2005/0277873 A1 | 12/2005 | Stewart et al. |
| 2005/0277890 A1 | 12/2005 | Stewart et al. |
| 2006/0013849 A1 | 1/2006 | Strickler et al. |
| 2006/0016897 A1 | 1/2006 | Yasuda et al. |
| 2006/0049629 A1 | 3/2006 | Naumann et al. |
| 2006/0065739 A1 | 3/2006 | Falls et al. |
| 2006/0069356 A1 | 3/2006 | Witowski |
| 2006/0076419 A1 | 4/2006 | Johnson |
| 2006/0086363 A1 | 4/2006 | Qin et al. |
| 2006/0089603 A1* | 4/2006 | Truitt .................. A61M 39/02 604/246 |
| 2006/0091209 A1 | 5/2006 | He |
| 2006/0108008 A1 | 5/2006 | Guala |
| 2006/0116639 A1 | 6/2006 | Russell |
| 2006/0153716 A1 | 7/2006 | Shoji et al. |
| 2006/0155248 A1 | 7/2006 | Hashimoto et al. |
| 2006/0167415 A1 | 7/2006 | Nemoto |
| 2006/0184008 A1 | 8/2006 | Zatezalo et al. |
| 2006/0224128 A1 | 10/2006 | Lurvey et al. |
| 2006/0235297 A1 | 10/2006 | Kawamoto |
| 2006/0243804 A1 | 11/2006 | Christoffersen et al. |
| 2007/0053788 A1 | 3/2007 | Zhao |
| 2007/0056871 A1 | 3/2007 | Griffiths et al. |
| 2007/0060874 A1 | 3/2007 | Nesbitt et al. |
| 2007/0073246 A1 | 3/2007 | Simon |
| 2007/0078203 A1 | 4/2007 | Gohill |
| 2007/0084524 A1 | 4/2007 | Py |
| 2007/0085049 A1 | 4/2007 | Houle et al. |
| 2007/0096906 A1 | 5/2007 | Lyons et al. |
| 2007/0100315 A1 | 5/2007 | Traxinger |
| 2007/0100316 A1 | 5/2007 | Traxinger |
| 2007/0106264 A1 | 5/2007 | Proulx et al. |
| 2007/0112265 A1 | 5/2007 | Zatezalo et al. |
| 2007/0115125 A1 | 5/2007 | Lyon et al. |
| 2007/0119929 A1 | 5/2007 | Swan et al. |
| 2007/0123620 A1 | 5/2007 | Nayak et al. |
| 2007/0125870 A1 | 6/2007 | Mase et al. |
| 2007/0129680 A1 | 6/2007 | Hagg et al. |
| 2007/0159337 A1 | 7/2007 | Tethrake et al. |
| 2007/0167919 A1 | 7/2007 | Nemoto et al. |
| 2007/0187475 A1 | 8/2007 | MacLeod |
| 2007/0191760 A1 | 8/2007 | Iguchi et al. |
| 2007/0197974 A1 | 8/2007 | Gibson |
| 2007/0204612 A1 | 9/2007 | Klimowicz |
| 2007/0213662 A1 | 9/2007 | Kalafut et al. |
| 2007/0225601 A1 | 9/2007 | Uber et al. |
| 2007/0244437 A1 | 10/2007 | Castillo et al. |
| 2007/0287954 A1 | 12/2007 | Zhao et al. |
| 2008/0014105 A1 | 1/2008 | Neftel et al. |
| 2008/0024310 A1 | 1/2008 | Baker et al. |
| 2008/0034959 A1 | 2/2008 | Vu |
| 2008/0045919 A1 | 2/2008 | Jakob et al. |
| 2008/0058711 A1 | 3/2008 | Neftel et al. |
| 2008/0069970 A1 | 3/2008 | Wu |
| 2008/0071228 A1 | 3/2008 | Wu et al. |
| 2008/0131300 A1 | 6/2008 | Junod et al. |
| 2008/0172002 A1 | 7/2008 | Bell et al. |
| 2008/0287887 A1 | 11/2008 | Mack et al. |
| 2008/0294029 A1 | 11/2008 | Piveteau et al. |
| 2008/0294040 A1 | 11/2008 | Mohiuddin et al. |
| 2008/0319401 A1 | 12/2008 | Funamura et al. |
| 2009/0012466 A1 | 1/2009 | Zhao et al. |
| 2009/0043253 A1 | 2/2009 | Podaima |
| 2009/0112164 A1 | 4/2009 | Reilly et al. |
| 2009/0118695 A1 | 5/2009 | Neftel |
| 2009/0152098 A1 | 6/2009 | Hooper et al. |
| 2009/0173903 A1 | 7/2009 | Kaneko et al. |
| 2009/0187139 A1 | 7/2009 | Mastalli et al. |
| 2009/0199917 A1 | 8/2009 | Vallet et al. |
| 2009/0240233 A1 | 9/2009 | Neftel |
| 2009/0277276 A1 | 11/2009 | Evering et al. |
| 2009/0324676 A1 | 12/2009 | Hofmann et al. |
| 2010/0012207 A1 | 1/2010 | Satoh et al. |
| 2010/0022968 A1 | 1/2010 | Kitani |
| 2010/0028170 A1 | 2/2010 | Schneeberger et al. |
| 2010/0030070 A1 | 2/2010 | Duffour et al. |
| 2010/0106012 A1 | 4/2010 | De Marco |
| 2010/0191106 A1 | 7/2010 | Koyama |
| 2010/0256569 A1 | 10/2010 | Cachemaille et al. |
| 2010/0280458 A1 | 11/2010 | Cachemaille et al. |
| 2010/0298699 A1 | 11/2010 | Reilly et al. |
| 2010/0324504 A1 | 12/2010 | Chappel et al. |
| 2011/0002802 A1 | 1/2011 | Capone et al. |
| 2011/0024657 A1 | 2/2011 | Tower |
| 2011/0054397 A1 | 3/2011 | Menot et al. |
| 2011/0132480 A1 | 6/2011 | Chappel |
| 2011/0142688 A1 | 6/2011 | Chappel et al. |
| 2011/0144585 A1 | 6/2011 | Bianchi et al. |
| 2011/0152681 A1 | 6/2011 | Reilly |
| 2011/0178493 A1 | 7/2011 | Okiyama |
| 2011/0200456 A1 | 8/2011 | Patzer |
| 2011/0308651 A1 | 12/2011 | Ziv et al. |
| 2012/0046610 A1 | 2/2012 | Rankin |
| 2012/0244018 A1 | 9/2012 | Reilly |
| 2013/0072880 A1 | 3/2013 | Finke |
| 2013/0116620 A1 | 5/2013 | Rotem et al. |

FOREIGN PATENT DOCUMENTS

| | | |
|---|---|---|
| DE | 3726452 A1 | 2/1989 |
| DE | 4121568 A1 | 10/1992 |
| DE | 4426387 A1 | 8/1995 |
| EP | 0068555 A1 | 1/1983 |
| EP | 0189491 A1 | 8/1986 |
| EP | 0337924 A2 | 10/1989 |
| EP | 0343501 A2 | 11/1989 |
| EP | 0600448 A2 | 6/1994 |
| EP | 0619122 A1 | 10/1994 |
| EP | 0650738 A1 | 5/1995 |
| EP | 0702966 A2 | 3/1996 |
| FR | 2493708 A1 | 5/1982 |
| FR | 2561949 A1 | 10/1985 |
| FR | 2715310 A1 | 7/1995 |
| GB | 0511715 A | 8/1939 |
| GB | 2044888 | 10/1980 |
| GB | 2207749 A | 2/1989 |
| GB | 2252656 A | 8/1992 |
| JP | H06142200 A | 5/1944 |
| JP | H05272685 A | 10/1993 |
| JP | H06142199 A | 5/1994 |
| JP | 2007113433 A | 5/2007 |
| NL | 9500612 | 11/1996 |
| WO | 8001754 A1 | 9/1980 |
| WO | 8500292 A1 | 1/1985 |
| WO | 8803815 A1 | 6/1988 |
| WO | 9323740 A1 | 11/1993 |
| WO | 9415664 A1 | 7/1994 |
| WO | 9531643 A1 | 11/1995 |
| WO | 9611025 A1 | 4/1996 |
| WO | 9621151 A1 | 7/1996 |
| WO | 9632975 A1 | 10/1996 |
| WO | 9700093 A1 | 1/1997 |
| WO | 9702853 A1 | 1/1997 |
| WO | 9716217 A1 | 5/1997 |
| WO | 9924095 A2 | 5/1999 |
| WO | 99/34846 | 7/1999 |
| WO | 99/38558 | 8/1999 |
| WO | 02/48589 | 6/2002 |
| WO | 0248589 | 6/2002 |
| WO | 03039646 A1 | 5/2003 |
| WO | 03/063929 A1 | 8/2003 |

(56) References Cited

FOREIGN PATENT DOCUMENTS

| WO | 2005106251 A1 | 11/2005 |
| WO | 2006056828 | 6/2006 |
| WO | 2011033440 A1 | 3/2011 |

OTHER PUBLICATIONS

The International Preliminary Report on Patentability from corresponding PCT Application No. PCT/US2012/056328 mailed Apr. 3, 2014.
The International Preliminary Report on Patentability from corresponding PCT Application No. PCT/US2012/056364 mailed Apr. 3, 2014.
The Extended/Supplementary European Search Report dated Jun. 3, 2015 from corresponding EP Application No. 12834408.2.
The Extended/Supplementary European Search Report dated Jun. 3, 2015 from corresponding EP Application No. 12832808.5.
The Written Opinion, International Search Report and International Preliminary Report on Patentability from corresponding PCT Application No. PCT/US12/56328 filed Sep. 20, 2012.
The Written Opinion, International Search Report and International Preliminary Report on Patentability from corresponding PCT Application No. PCT/US12/56355 filed Sep. 20, 2012.
The Written Opinion, International Search Report and International Preliminary Report on Patentability from corresponding PCT Application No. PCT/US12/56364 filed Sep. 20, 2012.
Debiotech Switzerland, Sales Brochure, Lausanne 9, Switzerland, distributed week of Dec. 1, 1996 at the Radiological Society of North American in Chicago, Illinois.
International Search Report from PCT Application No. PCT/US1998/02027.

* cited by examiner

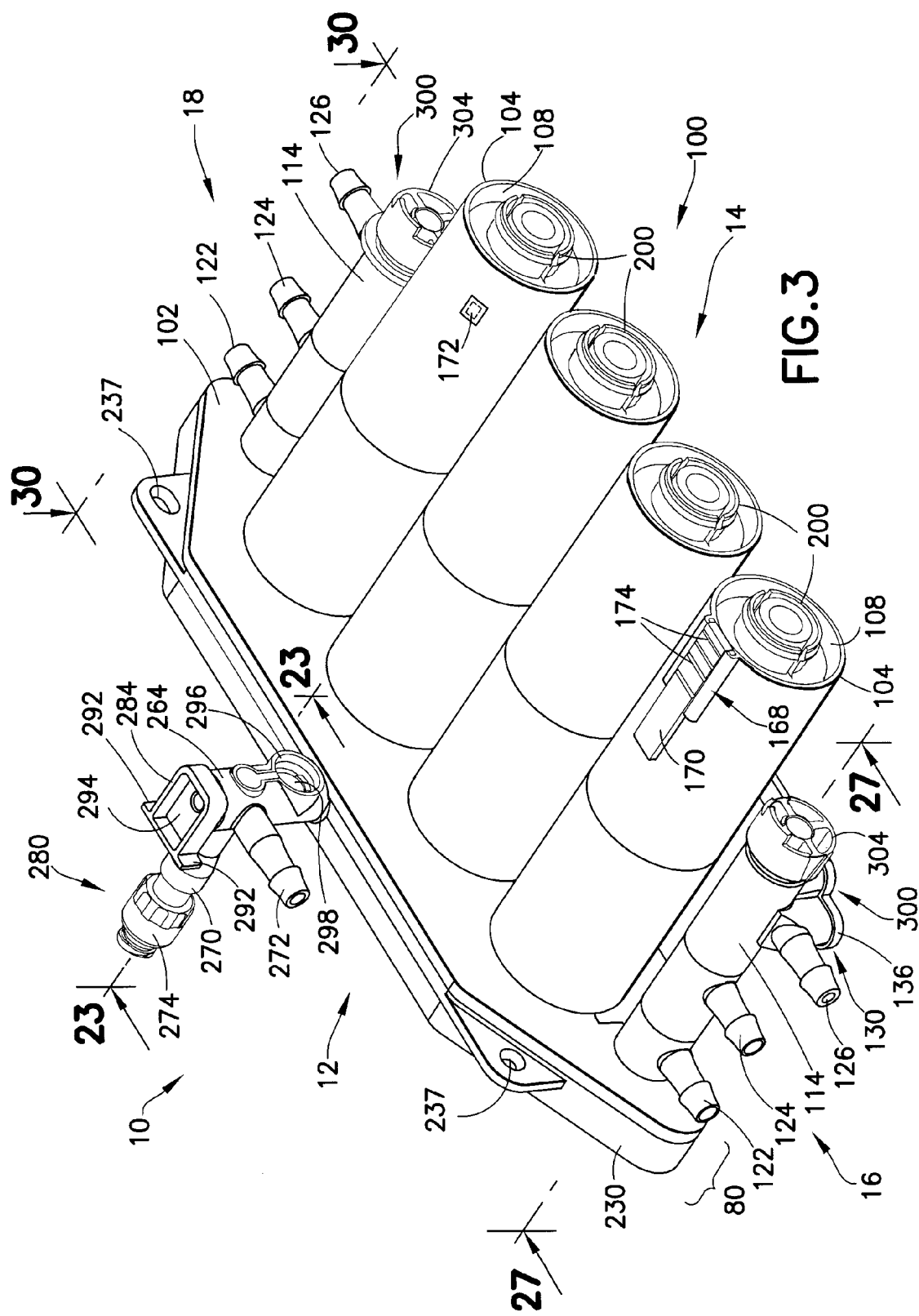

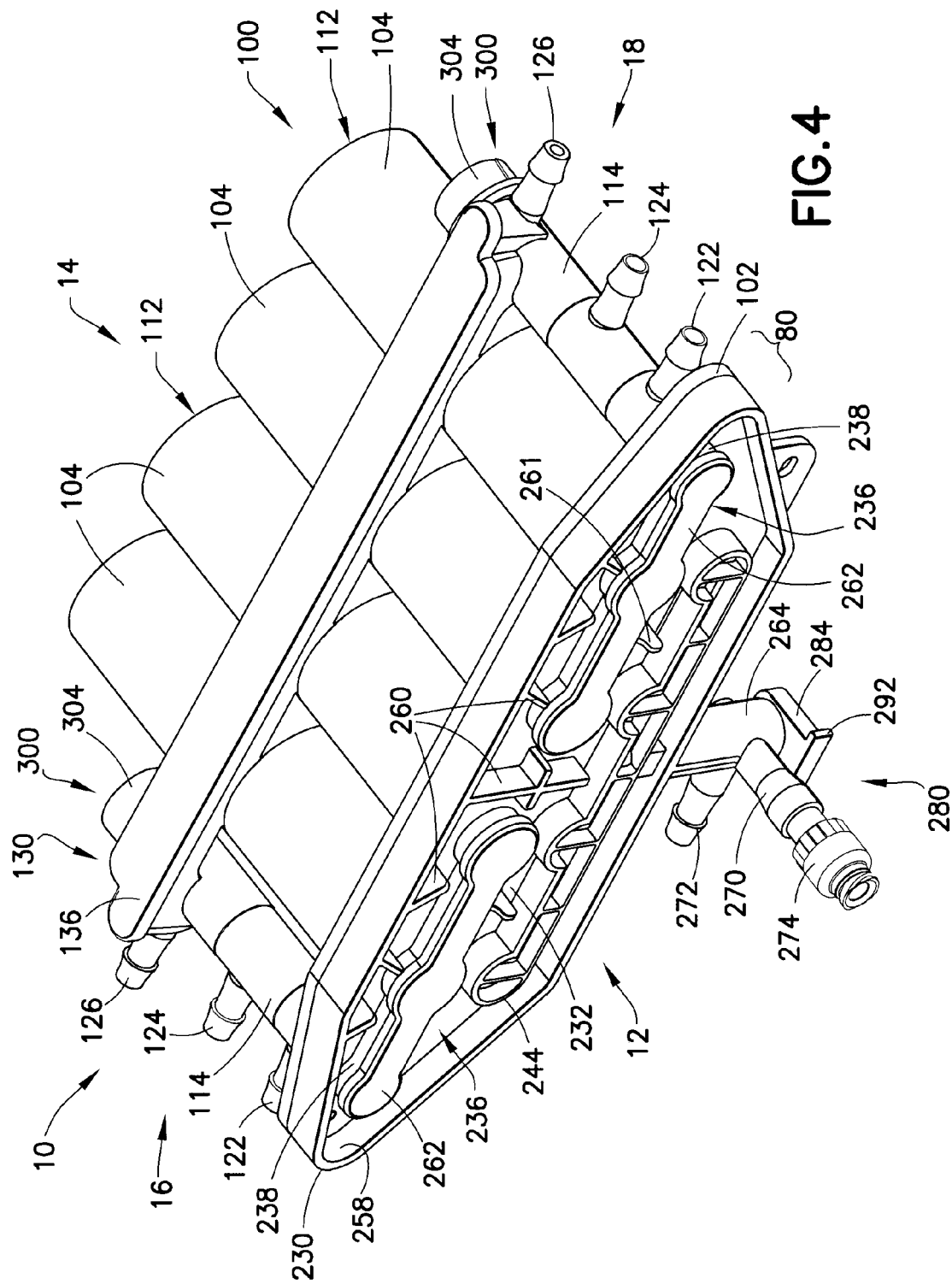

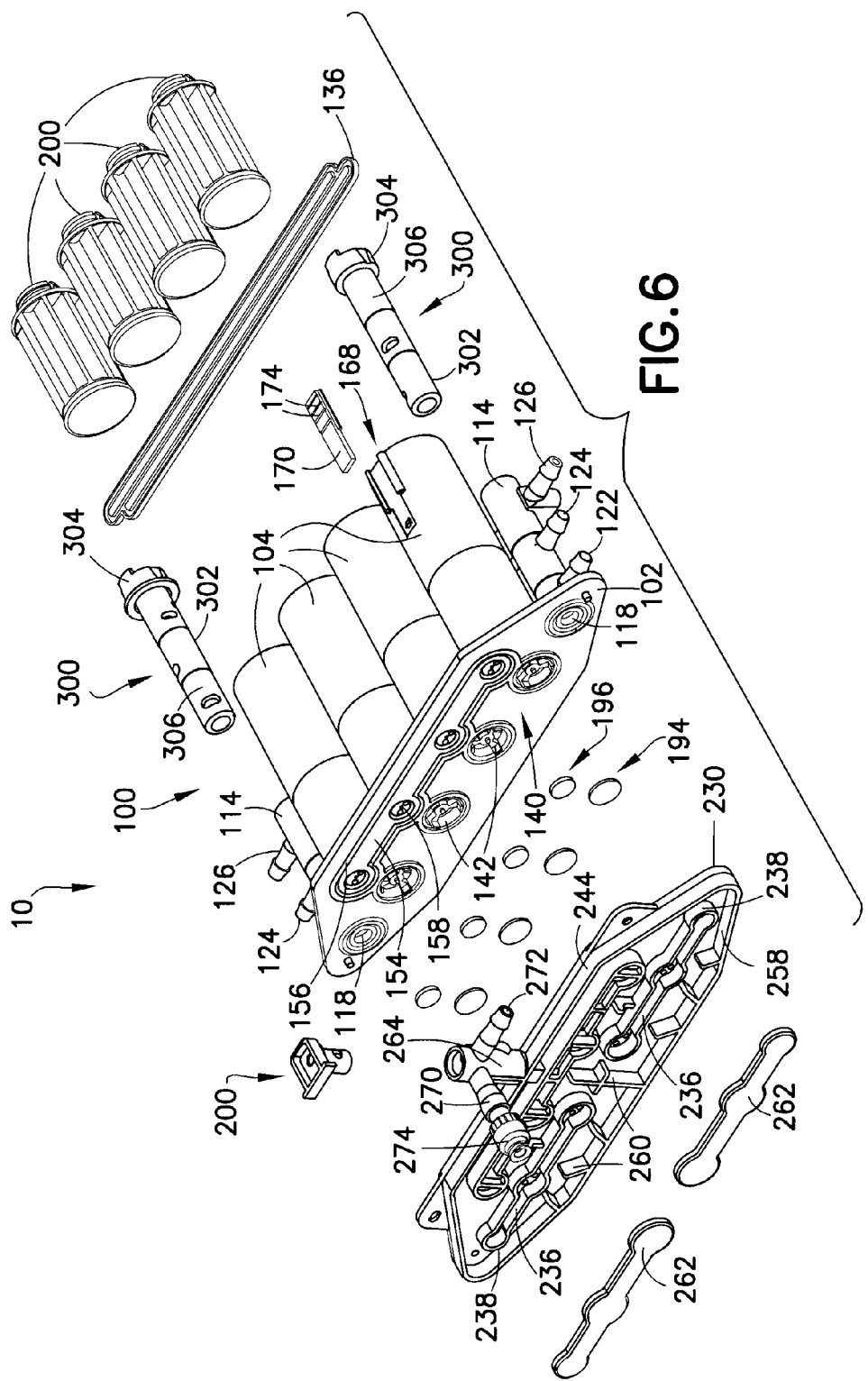

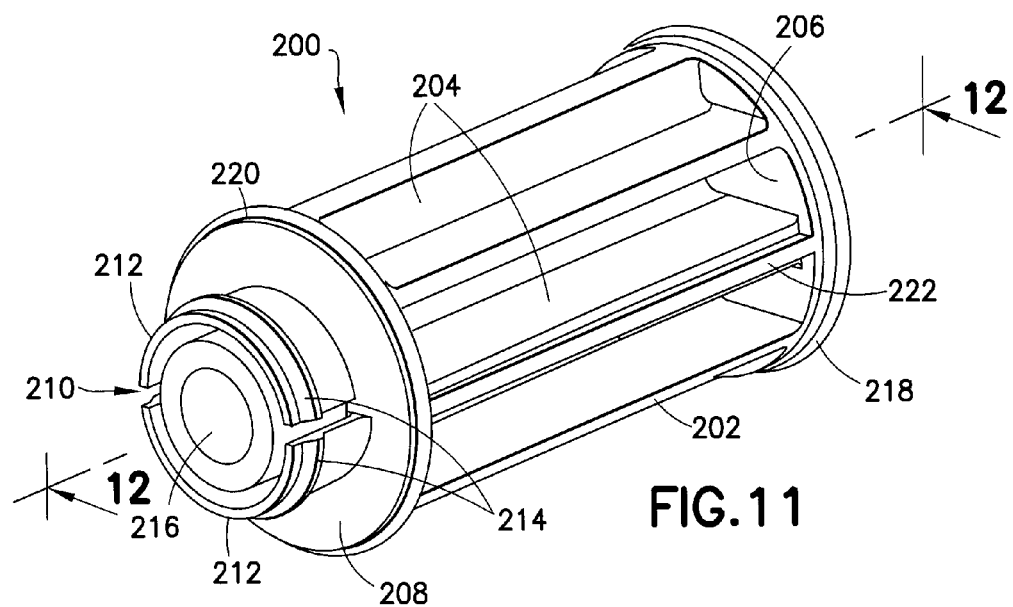
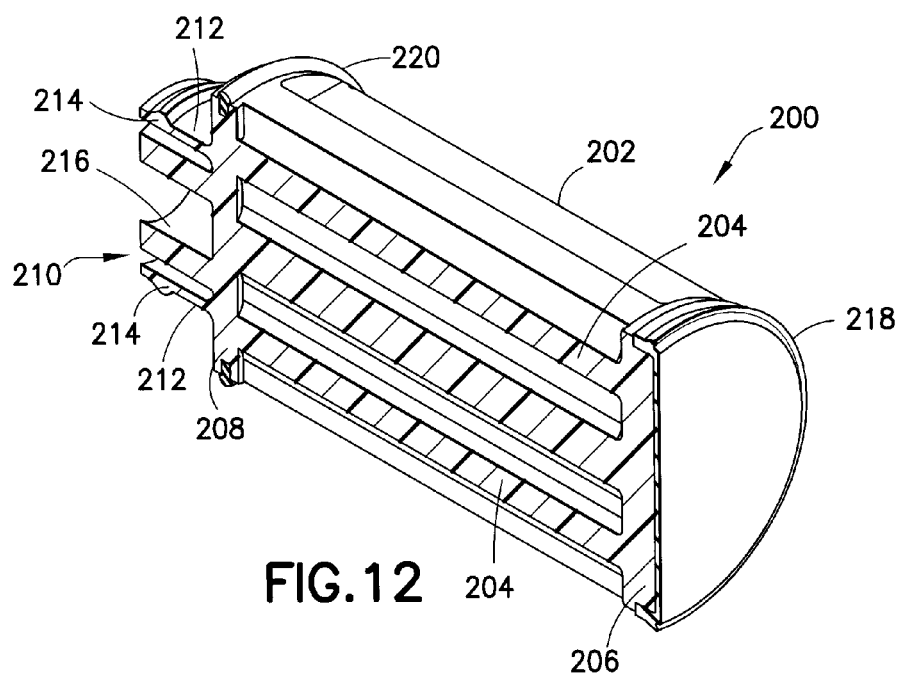

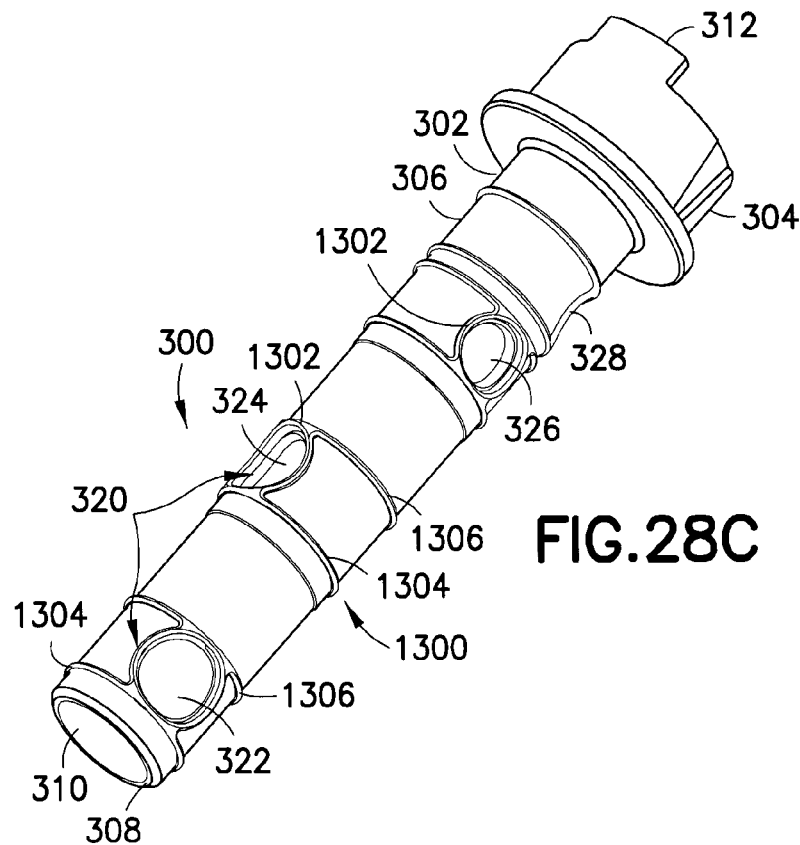
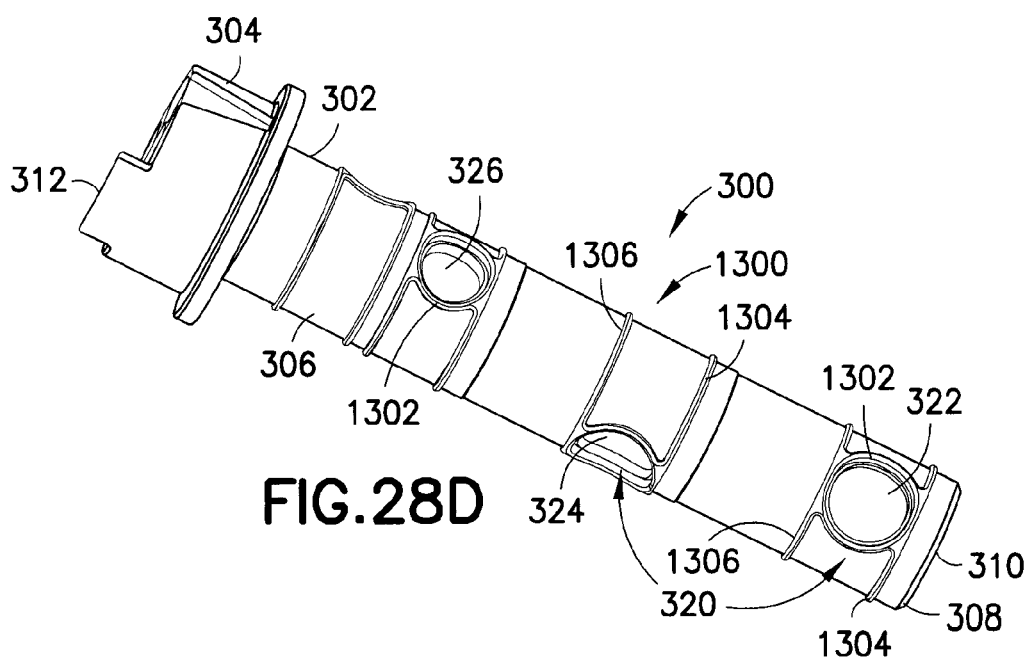

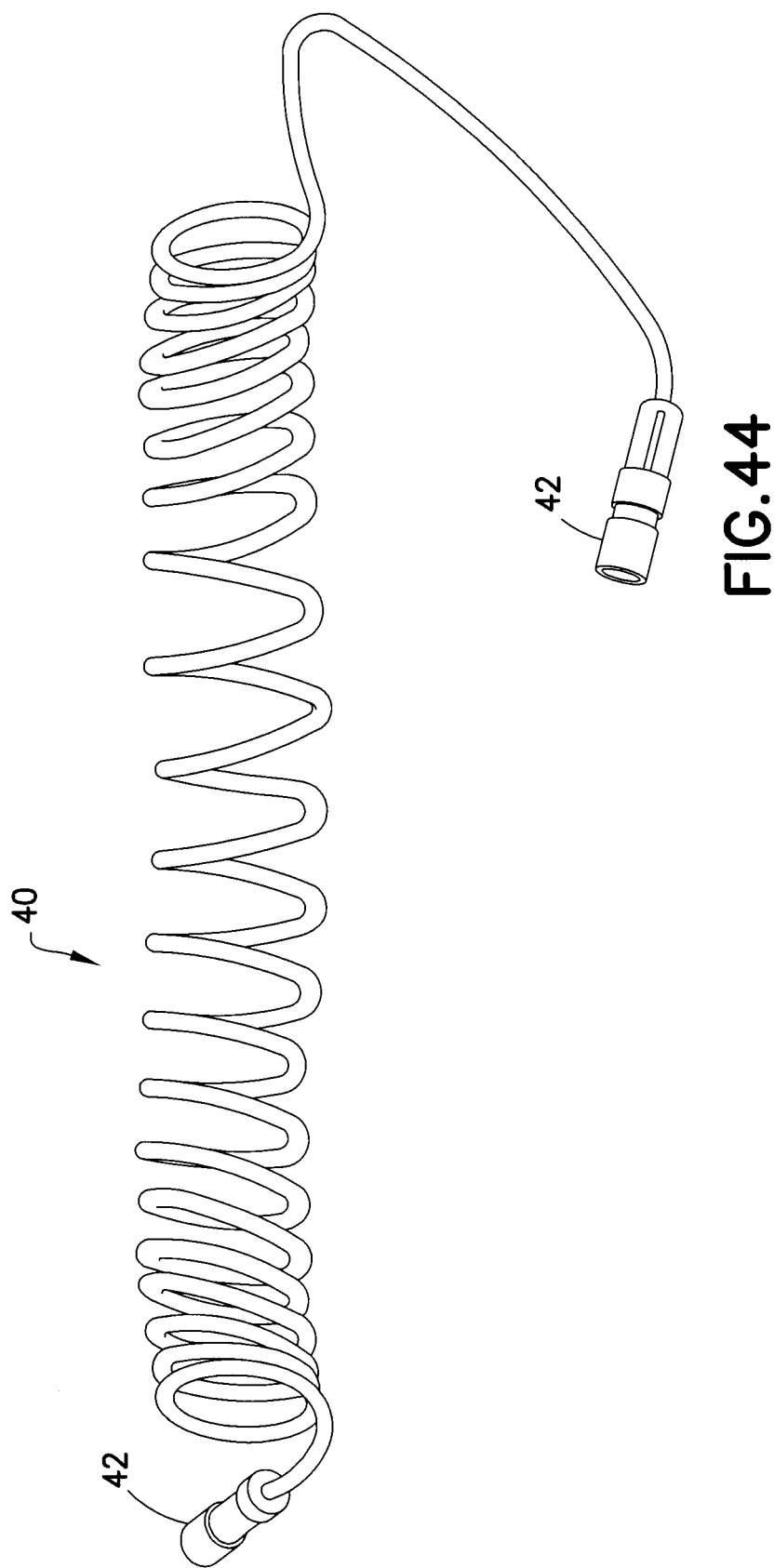

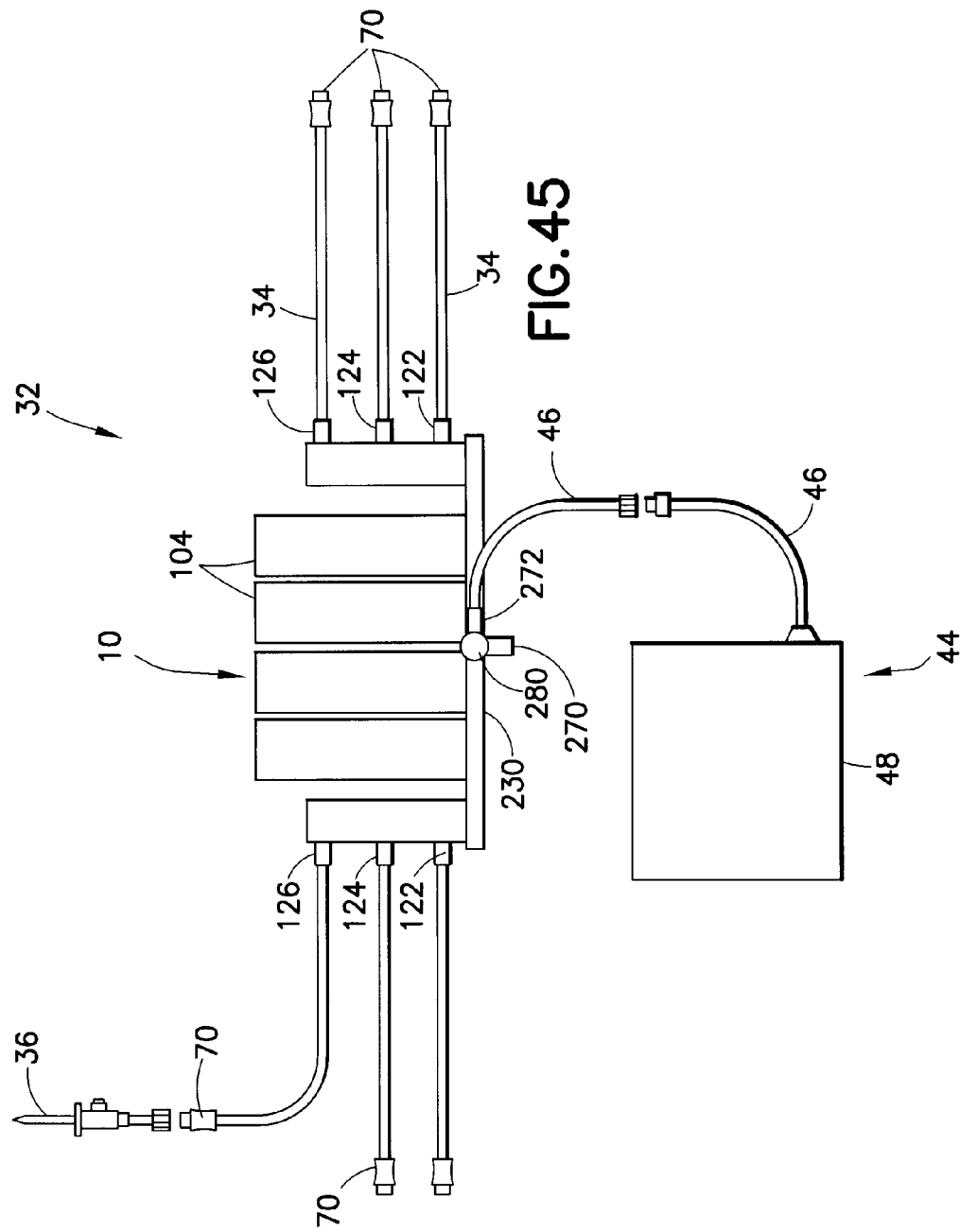

CONTINUOUS MULTI-FLUID PUMP DEVICE, DRIVE AND ACTUATING SYSTEM AND METHOD

CROSS-REFERENCE TO RELATED APPLICATIONS

This application claims the benefit of U.S. Provisional Application No. 61/537,371, filed Sep. 21, 2011 and entitled "Continuous Multi-Fluid Delivery System and Method", and International Application No. PCT/2012/056355, filed Sep. 20, 2012 and entitled "Continuous Multi-Fluid Pump Device, Drive and Actuating System and Method", the disclosures of which are incorporated herein in their entirety.

BACKGROUND OF THE INVENTION

Field of the Invention

The invention described herein is directed to a fluid delivery system comprising a fluid pump device and an associated drive and actuating system for continuous multi-fluid delivery applications in medical diagnostic and therapeutic procedures wherein one or more fluids are infused/injected into a patient.

Description of Related Art

In the medical field, fluid delivery devices used to provide fluids to patients are generally well-known and exist in many different forms. A system commonly used for this purpose is a gravity-feed system wherein a fluid containing bag is supported above the level of the patient's body and wherein the flow rate to the patient is controlled by the gross pressure of a clamp upon the flexible tube extending between the bag and the patient. It will be readily understood that the flow rate of fluid through the tube is a function of the amount of constriction of the tube. Manually operated devices are known in the medical field for delivery of fluid under pressure to a patient. Examples of such manually-operated pumping devices are known from U.S. Pat. No. 3,464,359 to King et al.; U.S. Pat. No. 2,062,285 to Bergman; and U.S. Pat. No. 1,748,810 to Wandel, as examples.

Syringe-based infusion pumps and peristaltic pumps have also been used in the medical field for delivering fluids to patients under pressure and provide more precise control over the flow rate and volumetric delivery of fluids to patients. An example of a syringe pump adapted to deliver fluid to a patient is described in U.S. Pat. No. 5,529,463 to Layer et al., which discloses a multi-syringe pump for this purpose. A peristaltic pump system suitable for delivering a constant flow of fluid under pressure to a patient is described in U.S. Pat. Nos. 6,558,125 and 6,488,660, both to Futterknecht.

There are a number of medical procedures which require the delivery of fluids to a patient in a precisely controlled manner. One such application involves the delivery of contrast media fluid to a patient during a diagnostic computed tomography (CT) scan to provide enhanced x-ray images. Traditionally, such contrast media fluid has been delivered to the patient using a syringe-based injection system. Such injection systems require the contrast media fluid to be transferred from its original container to a disposable syringe. The injection system then pressurizes the fluid within the syringe to deliver the fluid to the patient at a controlled flow rate, precisely when needed. Some syringe-based injection systems are capable of accommodating two separate syringes to facilitate sequential or simultaneous delivery of two different types of fluid.

One limitation of a syringe-based fluid injection system is the need to refill and replace the disposable syringes prior to each patient procedure. U.S. Pat. No. 5,806,519 to Evans, III et al. describes a fluid delivery system which could be used to deliver fluid to multiple patients in succession without the need to refill and replace syringes for each patient. Another fluid delivery system that purports to overcome this limitation is disclosed in U.S. Pat. Nos. 6,558,125 and 6,488,660 (Futterknecht). These latter patents disclose a fluid delivery system that utilizes a peristaltic pump to deliver fluid directly from contrast media bottles to the patient. While this system eliminates the need to replace disposable syringes after each patient, the use of a roller-type peristaltic pump inherently limits the pressure capability of the system to approximately 200 psi. Unfortunately, many CT procedures and virtually all angiographic procedures require fluid to be delivered at higher pressures.

In order to provide more precise control of flow rates and volumetric delivery of fluids to patients, positive displacement pump platforms have been developed in the medical field. These devices eliminate the use of syringes and provide increased pressure ranges over peristaltic pumps. One such positive displacement pump device is disclosed in U.S. Pat. Nos. 5,196,197 and 6,197,000 to Reilly et al., which describe a system for the continuous delivery of contrast media fluid to a patient that uses a cam-driven multi-piston pump. Such a pump is capable of delivering fluids at relatively high pressures in a controlled manner. Another example of a positive displacement pump platform intended for use in delivering fluid to a patient undergoing a medical procedure is disclosed in International Publication No. WO 2006/056828, which discloses a volumetric pump with reciprocating and rotating pistons that are adapted to deliver a controlled and continuous flow rate of fluid during a medical procedure. Japanese Publication Nos. JP 61-42199 and JP 61-42200, both assigned to Nemoto Kiyourindou KK, disclose another multi-piston cylinder pump which enables the controlled and continuous delivery of fluids during a medical procedure.

There are several disadvantages present in positive displacement pump platforms known in the medical field for fluid delivery to a patient. One disadvantage is that these pump platforms are, typically, limited to pumping a single fluid type. Many medical procedures, such as CT procedures, often involve the use of a combination of contrast media fluid and saline delivered precisely to the region of interest within a patient's body. For example, after an initial injection of contrast media fluid is performed, a bolus of saline fluid may be administered to move the contrast fluid into the region of interest. In order to have the capability of delivering two or more different types of fluids, an external selection valve (such as a stopcock) must be added upstream of the pump inlet to allow the fluid delivery system to select from one of the two available fluid sources or possibly both if a mixing device is also provided. If two interconnected pumps are present in the fluid delivery system, the system may be capable of delivering a controlled mixture of two fluids. However, each of the two pumps must be independently controlled to provide the required flow rate of its respective fluid type. Downstream mixing devices may also be used in such a two-pump system.

SUMMARY OF THE INVENTION

This disclosure presents exemplary embodiments of a fluid pump device for association with a drive and actuating system, exemplary embodiments of the drive and actuating system, and exemplary embodiments of a fluid delivery system comprising the drive and actuating system and fluid pump device, as well as methods of assembling the fluid pump device and methods of operating one or more embodiments of the fluid pump device, drive and actuating system, and fluid delivery system. In one embodiment, a fluid pump device comprises a plurality of pump cylinders, a plunger reciprocally operable within each of the pump cylinders, and an inlet selector valve to establish selective fluid communication between at least one fluid source and the pump cylinders. The inlet selector valve may be located laterally outboard of the pump cylinders.

The inlet selector valve may be oriented generally parallel to the pump cylinders. The fluid pump device may further comprise a pump manifold controlling fluid communication to the pump cylinders, and the inlet selector valve controls fluid communication with the at least one fluid source to control fluid flow into the pump manifold. The pump manifold comprises an inlet manifold channel and an outlet manifold channel, and further comprises an outlet selector valve in fluid communication with the outlet manifold channel to control fluid flow from the pump manifold. The outlet selector valve comprises an outlet selector valve cylinder having a valve stem disposed therein, and wherein the outlet selector valve comprises a patient outlet port and a waste outlet port. The outlet selector valve stem defines a flow passage to establish selective fluid communication with the patient outlet port or the waste outlet port. The outlet selector valve stem may define a tapered end. The pump manifold may comprise an inlet manifold channel and an outlet manifold channel, and the pump cylinders may each comprise at least one inlet opening for fluid communication with the inlet manifold channel and at least one outlet opening for fluid communication with the outlet manifold channel. The pump cylinders may be in selective fluid communication with the inlet manifold channel and the outlet manifold channel via respective inlet check valves and outlet check valves. The at least one outlet opening may be positioned at a high point in each of the pump cylinders for air bubble egress.

The inlet selector valve may comprise an inlet selector valve cylinder having a valve stem disposed therein, the valve stem defining an axial passage and a plurality of radial inlet ports connected to the axial passage. The radial inlet ports may be disposed at different angular orientations around the valve stem. The radial inlet ports may alternatively be disposed at different angular orientations around the valve stem and at different axial locations along the valve stem. A saline manifold may be in selective fluid communication with the pump cylinders via the inlet selector valve to establish selective fluid communication between a saline fluid source and the pump cylinders. The saline manifold may extend across the plurality of pump cylinders.

In another embodiment, the fluid pump device may comprise a plurality of pump cylinders, a plunger reciprocally operable within each of the pump cylinders, and an inlet selector valve to establish selective fluid communication between at least one fluid source and the pump cylinders. The inlet selector valve may be located laterally outboard of the pump cylinders, and identifying indicia may be provided on the fluid pump device and encoded with identifying information for the fluid pump device.

The inlet selector valve may comprise an inlet selector valve cylinder having a valve stem disposed therein, the valve stem defining an axial passage and plurality of radial inlet ports connected to the axial passage, and the identifying information comprising at least an initial angular orientation of the valve stem in the inlet selector valve cylinder or a representation thereof. The radial inlet ports may be disposed at different angular orientations around the valve stem. Alternatively, the radial inlet ports may be disposed at different angular orientations around the valve stem and at different axial locations along the valve stem. The inlet selector valve cylinder may be oriented generally parallel to the pump cylinders.

The identifying indicia may be an optically encoded transparent member. The identifying indicia may be disposed on one of the pump cylinders. The inlet selector valve may comprise an inlet selector valve cylinder having a valve stem disposed therein, and the identifying information may comprise at least an initial angular orientation of the valve stem in the inlet selector valve cylinder or a representation thereof. The valve stem may comprise a plurality of radial inlet ports disposed at different angular orientations around the valve stem. Alternatively, the valve stem may comprise a plurality of radial inlet ports disposed at different angular orientations around the valve stem and at different axial locations along the valve stem. The inlet selector valve cylinder may be oriented generally parallel to the pump cylinders. The inlet selector valve cylinder may comprise multiple inlet ports for connection to multiple fluid sources.

The identifying information may comprise at least one of a pump configuration/type number, a manufacturing batch number, a pump type identifier, a pump sequential identification number, or any combination thereof.

In yet another embodiment, the fluid pump device comprises a plurality of pump cylinders, a plunger reciprocally operable within each of the pump cylinders, each plunger comprising a piston interface member extending proximally therefrom that is split into at least two parts that are compressible towards one another, and an inlet selector valve to establish selective fluid communication between at least one fluid source and the pump cylinders. The inlet selector valve located may be laterally outboard of the pump cylinders.

The plungers may each comprise a distal end disc and a proximal end disc. The plungers may be reciprocally operable in the respective pump cylinders such that the distal end disc of each plunger is operable within a pumping zone of the pump cylinders and the proximal end disc is operable within an isolation zone of the pump cylinders. A seal may be provided at least circumferentially about each of the distal end disc and the proximal end disc.

A radial lip may be provided on each of the at least two parts of the piston interface member to interface with a drive piston. A support member may be coaxially disposed in the piston interface member. The radial lip on each of the at least two parts of the piston interface member may interface with a receiving groove defined in a socket in a drive piston. The piston interface member may be generally cylindrical shaped and the at least two parts may define at least two arcuate segments.

In another embodiment, a fluid delivery system is provided including a fluid pump device comprising a plurality of pump cylinders, a plunger reciprocally operable within each of the pump cylinders, and an inlet selector valve to establish selective fluid communication between at least one fluid source container and the pump cylinders, the inlet selector valve located laterally outboard of the pump cylinders. A drive and actuating system independently and reciprocally operates the plungers in the pump cylinders.

The inlet selector valve may be oriented generally parallel to the pump cylinders.

A pump manifold may control fluid communication to the pump cylinders, and the inlet selector valve may control fluid communication with the at least one fluid source to control fluid flow into the pump manifold. The pump manifold may comprise an inlet manifold channel and an outlet manifold channel, and the pump cylinders may each comprise at least one inlet opening for fluid communication with the inlet manifold channel and at least one outlet opening for fluid communication with the outlet manifold channel. The pump cylinders may be in selective fluid communication with the inlet manifold channel and the outlet manifold channel via respective inlet check valves and outlet check valves. The at least one outlet opening may be positioned at a high point in each of the pump cylinders for air bubble egress.

The inlet selector valve may comprise an inlet selector valve cylinder having a valve stem disposed therein, and the valve stem may define an axial passage and a plurality of radial inlet ports connected to the axial passage. The radial inlet ports may be disposed at different angular orientations around the valve stem. The valve stem may alternatively comprise a plurality of radial inlet ports disposed at different angular orientations around the valve stem and at different axial locations along the valve stem.

A saline manifold may be in selective fluid communication with the pump cylinders via the inlet selector valve to establish selective fluid communication between a saline fluid source and the pump cylinders. The saline manifold may extend across the plurality of pump cylinders. The inlet selector valve may be operable by the drive and actuating system independently of the plungers.

Identifying indicia may be provided on the fluid pump device and encoded with identifying information for the fluid pump device. The inlet selector valve may comprise an inlet selector valve cylinder having a valve stem disposed therein, and the identifying information may comprise at least an initial angular orientation of the valve stem in the inlet selector valve cylinder or a representation thereof. The valve stem may comprise a plurality of radial inlet ports. The radial inlet ports may be disposed at different angular orientations around the valve stem. Alternatively, the radial inlet ports may be disposed at different angular orientations around the valve stem and at different axial locations along the valve stem. The inlet selector valve cylinder may be oriented generally parallel to the pump cylinders.

The identifying indicia may be an optically encoded transparent member. The identifying indicia may be disposed on one of the pump cylinders.

Each of the plungers may comprise a piston interface member extending proximally therefrom, and the piston interface member may be split into at least two parts that are compressible towards one another. The plungers may each comprise a distal end disc and a proximal end disc. The plungers may be reciprocally operable in the respective pump cylinders such that the distal end disc of each of the plungers is operable within a pumping zone of the pump cylinders and the proximal end disc is operable within an isolation zone of the pump cylinders. A seal may be provided at least circumferentially about each of the distal end disc and the proximal end disc. A radial lip may be provided on each of the at least two parts of the piston interface member to interface with a drive piston of the drive and actuating system. A support member may be coaxially disposed in the piston interface member.

A drive and actuating system may be provided for operating the fluid pump device. The drive and actuating system includes an extendable and retractable pump drawer to accept the fluid pump device, with the fluid pump device comprising a plurality of pump cylinders and a plunger reciprocally operable within each of the pump cylinders. Drive pistons are provided and adapted for mechanical connection to the plungers, respectively, to independently and reciprocally operate the plungers in the pump cylinders. Piston linear actuators are respectively coupled to the drive pistons, and drive motors are operatively coupled to the piston linear actuators, respectively, to provide motive forces to the piston linear actuators to independently and reciprocally operate the plungers.

The fluid pump device may further comprise an inlet selector valve to establish selective fluid communication between at least one fluid source container and the pump cylinders, and the inlet selector valve may be located laterally outboard of the pump cylinders.

An inlet selector valve actuator may be provided adapted for mechanical connection to the inlet selector valve to control operation of the inlet selector valve to establish the selective fluid communication between the at least one fluid source container and the pump cylinders.

A pump manifold may control fluid communication to the pump cylinders, and a pump clamping mechanism may be operable to secure the fluid pump device in the pump drawer and apply a compressive force to the pump manifold when the fluid pump device is loaded in the pump drawer. The pump clamping mechanism may comprise a clamping block to engage the pump manifold when the fluid pump device is loaded in the pump drawer. The clamping block may be operated by a clamp actuating mechanism to engage and disengage the clamping block with the pump manifold. The pump manifold may comprise a pressure sensing port with a pressure sensing diaphragm, and the drive and actuating system may further comprise a pressure measuring mechanism adapted to interface with the pressure sensing port. The operation of the clamp actuating mechanism to engage the clamping block with the pump manifold may concurrently cause the pressure measuring mechanism to operatively interface with the pressure sensing diaphragm. The drive and actuating system may further comprise a pressure measuring mechanism adapted to interface with the pressure sensing port.

The pump manifold may comprise an inlet manifold channel and an outlet manifold channel, and an outlet selector valve may be in fluid communication with the outlet manifold channel to control fluid flow from the pump manifold. The drive and actuating system may further comprise an outlet selector valve actuator to control operation of the outlet selector valve.

The plungers of the fluid pump device may each comprise a piston interface member split into at least two parts that are compressible towards one another to enable the mechanical connection with the respective drive pistons. A radial lip may be provided on each of the at least two parts to interface with the respective drive pistons. A support member may be coaxially disposed in the piston interface member. Further, a radial lip may be provided on each of the at least two parts of the respective piston interface members to interface with a receiving groove in socket in the corresponding drive pistons of the drive and actuating system.

Another embodiment is directed to a method of interfacing a fluid pump device with a drive and actuating system of a fluid delivery system. The fluid pump device generally comprises a plurality of pump cylinders, and a plunger reciprocally operable within each of the pump cylinders, each of the plungers comprising a piston interface member extending proximally therefrom. The piston interface member is split into at least two parts that are compressible towards one another. The plungers are interfaced with respective drive pistons of the drive and actuating system, such that the at least two parts of each of the piston interface members compress towards one another to enable mechanical engagement with the respective drive pistons. The drive pistons independently and reciprocally operate the plungers in the respective pump cylinders.

The fluid pump device may further comprise an inlet selector valve to establish selective fluid communication between at least one fluid source container and the pump cylinders, with the inlet selector valve located laterally outboard of the pump cylinders.

The plungers may each comprise a distal end disc and a proximal end disc. The plungers may be reciprocally operable in the respective pump cylinders such that the distal end disc of each of the plungers is operable within a pumping zone of the pump cylinders and the proximal end disc is operable within an isolation zone of the pump cylinders. A seal may be provided at least circumferentially about each of the distal end disc and the proximal end disc. A radial lip may be provided on each of the at least two parts of the respective piston interface members to interface with a receiving groove in a socket in the respective drive pistons of the drive and actuating system. A support member may be coaxially disposed in the piston interface member. In an alternative configuration, a radial lip may be provided on each of the at least two parts of the piston interface members, and the respective drive pistons may each comprise a distal end socket defining a receiving groove, such that the step of interfacing the plungers with the respective drive pistons comprises receiving the piston interface members into the distal end socket in the respective drive pistons and engaging the radial lip on the at least two parts with the receiving groove in the distal end socket in each of the respective drive pistons.

Another embodiment is directed to a method of assembling a fluid pump device, comprising providing a pump body having a plurality of pump cylinders and at least one inlet selector valve cylinder located laterally outboard of the pump cylinders, inserting an inlet selector valve body comprising a valve stem into the inlet selector valve cylinder such that the valve stem is in a predetermined angular orientation in the inlet selector valve cylinder, and inserting respective plungers into the pump cylinders.

The pump body may further comprise a saline manifold extending across the pump cylinders and defining at least one saline channel, and the method may further comprise installing a saline manifold cap onto the pump body to enclose the at least one saline channel.

The pump body may comprise a front plate and the pump cylinders may extend proximally from the front plate, and the method may further comprise installing a pump manifold plate onto the front plate to form a pump manifold. At least one check valve may be captured between the manifold plate and the front plate during the step of installing the manifold plate onto the front plate to form the pump manifold. The front plate may comprise at least one inlet manifold channel defined by at least one channel member, and the method may further comprise installing an inlet manifold cap on the at least one channel member to enclose the at least one inlet manifold channel. The manifold plate may comprise an outlet selector valve cylinder, and the method may further comprise inserting an outlet selector valve body comprising a valve stem into the outlet selector valve cylinder. The outlet selector valve cylinder may comprise a patient outlet port and a waste outlet port and the valve stem of the outlet selector valve body defines a flow passage, and the step of inserting the outlet selector valve body into the outlet selector valve cylinder may comprise aligning the flow passage to be in fluid communication with the waste outlet port. The step of inserting the outlet selector valve body into the outlet selector valve cylinder may be preceded by spraying lubricant onto the interior wall surface of the outlet selector valve cylinder.

The method may further comprise spraying lubricant onto the interior wall surface of the pump cylinders and onto the interior surface of the at least one inlet selector valve cylinders prior to the steps of inserting the inlet selector valve body into the inlet selector valve cylinder and inserting the respective plungers into the pump cylinders.

The steps of inserting the inlet selector valve body into the inlet selector valve cylinder and inserting the respective plungers into the pump cylinders can occur concurrently.

The predetermined angular orientation of the valve stem of the inlet selector valve body may be encoded in identifying indicia provided on the pump body, and the identifying indicia may be a bar code.

The method may further comprise generating an inlet selector valve position number and encoding the inlet selector valve position number as identifying indicia provided on the pump body. The inlet selector valve position number may correspond to the predetermined angular orientation of the valve stem of the inlet selector valve body in the inlet selector valve cylinder. The method may further comprise etching the identifying indicia on one of the pump cylinders.

Further details and advantages of the various embodiments described in detail herein will become clear upon reviewing the following detailed description of the various embodiments in conjunction with the accompanying drawing figures.

BRIEF DESCRIPTION OF THE DRAWINGS

FIG. 3 is a rear perspective view of the fluid pump device shown in FIG. 2.

FIG. 4 is a bottom perspective view of the fluid pump device shown in FIG. 2.

FIG. 6 is an exploded perspective view of the fluid pump device shown in FIG. 2.

FIG. 11 is a rear perspective view of a plunger for the fluid pump device shown in FIG. 2.

FIG. 12 is a cross-sectional view taken along line 12-12 in FIG. 11.

FIGS. 28C-28D are isometric perspective view of the inlet selector valve stem shown in FIGS. 28A-28B and further comprising a first exemplary sealing arrangement.

FIG. 44 is a perspective view of an exemplary patient supply set for use with the fluid pump device shown in FIG. 2.

FIG. 45 is a schematic view showing the fluid pump device with the second or high-use embodiment of the fluid supply set as shown in FIG. 41, and further showing a waste collection system associated with the fluid pump device.

DESCRIPTION OF THE PREFERRED EMBODIMENTS

Figure 1:
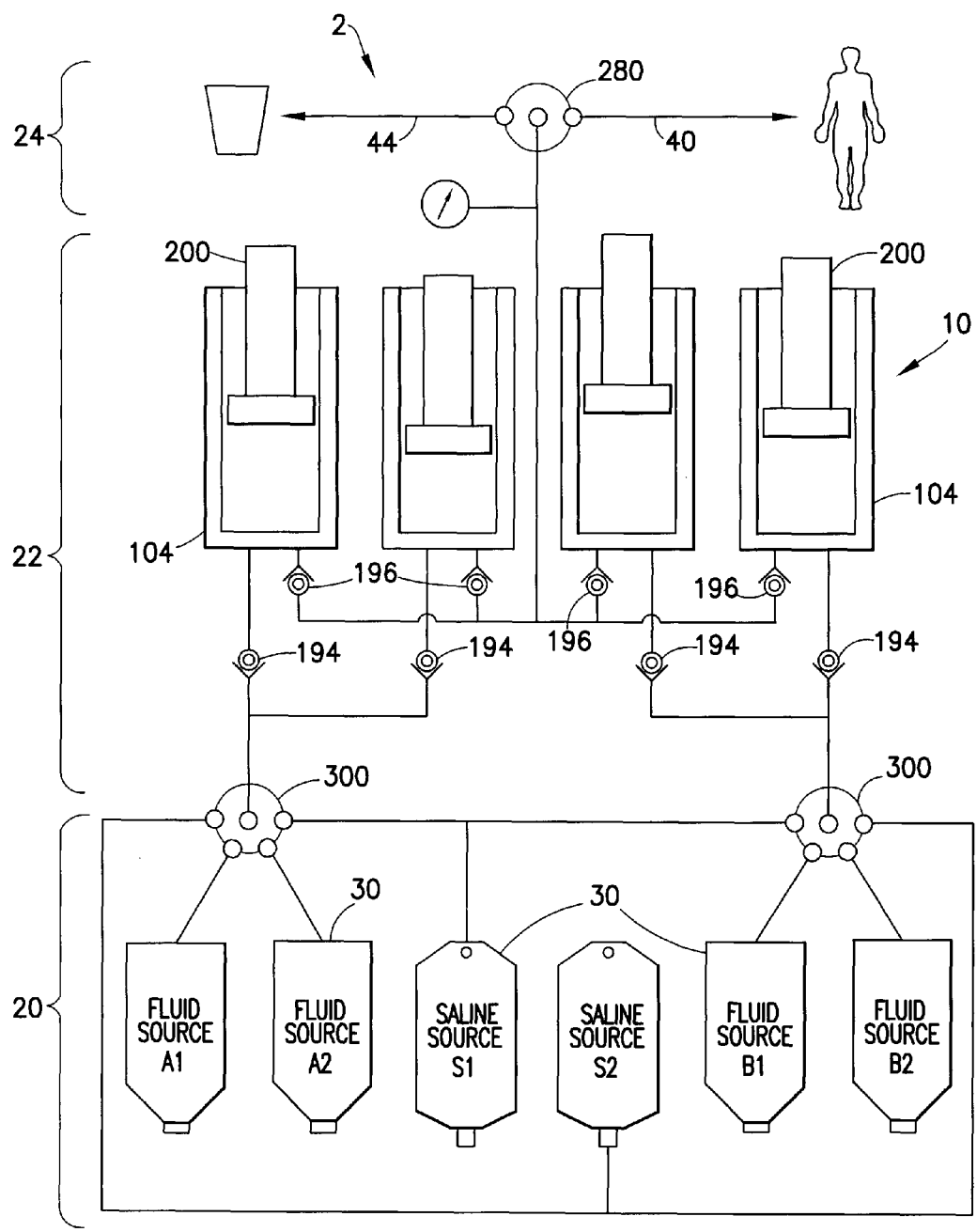
FIG. 1 is a schematic view of a fluid delivery system for continuous multi-fluid delivery applications.

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, features, and operational sequences illustrated in the accompanying drawing figures and described herein are simply exemplary and should not be considered as limiting.

Referring initially to FIGS. 1-6, a fluid pump device 10, generally provided in the form of a disposable pump cassette, is shown. While fluid pump device or pump cassette 10 (hereinafter referred to as "pump 10") is intended as a disposable component, the pump 10 is intended for multiple uses prior to disposal. Such multiple uses may be for multiple patients or for a multiple and discrete number of uses in medical diagnostic and therapeutic procedures which may involve a single or multiple patients. The pump 10 is adapted to interface with a drive and actuating system 400 that accepts, drives, and actuates various components on the pump 10. The drive and actuating system 400 is described herein in connection with FIGS. 46-60. A control system 800 is also provided to control operation of the various components of the drive and actuating system 800, as described herein in connection with FIGS. 46-60.

The pump 10 may be considered to have a front or distal side 12, a rear or proximal side 14, a right side 16 as viewed looking from the front or distal side 12 toward the rear or proximal side 14, and a left side 18 as viewed looking from the front or distal side 12 toward the rear or proximal side 14. Generally, as shown schematically in FIG. 1, the pump 10 may be part of a fluid delivery system 2 which includes the drive and actuating system 400, discussed herein. The pump 10 generally comprises a fluid supply section 20, a pump metering and pressurizing section 22, and a pump outlet section 24. The fluid supply section 20 includes one or more fluid source containers 30 containing various fluids to be supplied to the pump 10, and a fluid supply set 32 (see FIGS. 40-43 discussed herein) that conducts the one or more fluids to the pump 10. Various versions and embodiments of the fluid supply set 32 may be associated with the pump 10 to meet different patient and/or procedural needs. Each of the various versions and embodiments of the fluid supply set 32 comprises one or more fluid supply tubes 34 each having one end connected to the pump 10 and the opposing end connected to a spike 36 used to access a fluid source container 30.

The pump outlet section 24 includes a disposable single-use or single-patient supply set 40 (hereinafter "patient supply set 40"; see FIG. 44 discussed herein) comprising medical tubing having opposed free ends each having a fluid connector 42 used to make a fluid connection, such as to a catheter inserted into a patient to convey a desired fluid or mixture of fluids to a desired location within a patient's body. At least one of the fluid connectors 42 may include a check valve (not shown) to prevent reverse flow from the patient. Additionally, the pump outlet section 24 comprises a waste collection system 44 that is associated with the pump 10 to collect and store waste fluids. The waste collection system 44 generally comprises a waste collection tube set 46 connected to a waste collection container 48, as shown in FIG. 45 discussed further herein. The waste collection tube set 46 is adapted to make a fluid connection with the pump 10.

The pump 10 forms a part of the pump metering and pressurizing section 22. The pump 10 generally comprises a pump manifold 80, a pump body 100, a plurality of independently operable plungers 200 operatively associated with the pump body 100, a pump manifold plate 230 which is joined to the pump body 100 to form the pump manifold 80, an outlet selector valve 280 associated with the pump body 100 for controlling fluid delivery or output from the pump 10, and a plurality of inlet selector valves 300 associated with the pump body 100 for controlling fluid flow to the pump body 100. In operation, the pump 10 is typically interfaced with multiple and different fluids contained in the fluid source containers 30, and is actuated or operated by the drive and actuating system 400 to select a fluid type from the several fluid source containers 30 and continuously deliver fluids, either individually or as a fluid mixture, to the patient. The pump 10, under the directed operation of the drive and actuating system 400, draws in fluid directly from the fluid source containers 30 and accurately meters the appropriate volumes and specified fluid flow rates and infusion time to the patient via the patient supply set 40 (shown in FIG. 44). As noted in the foregoing, various fluid supply sets 32 may be associated with the pump 10 to meet different patient and/or procedural needs, and these various versions or embodiments are detailed further herein in connection with FIGS. 40-43.

The drive and actuating system 400 which operates the pump 10 pressurizes the fluid dispensed from the pump 10 to the patient supply set 40 sufficiently to overcome any resistance through the patient supply set 40 and the catheter connected thereto so that accurate fluid volume and pressure are delivered to the desired treatment or diagnostic location within the patient's body. Fluid flow from the pump 10 is delivered substantially continuously to the patient via an indwelling catheter and may be a single fluid, or multiple fluids delivered substantially simultaneously that are combined into a mixture of any desired proportions and delivered as a single stream via the outlet selector valve 280.

Referring additionally to FIGS. 7-10, the pump body 100 is typically formed as an integral or singular body formed from polycarbonate and like polymeric materials via an injection molding process. The pump body 100 comprises a front or distal plate 102 and a plurality of pump cylinders 104 extending proximally from the front plate 102. In the illustrated embodiment, a total of four (4) pump cylinders 104 are provided in the pump 10, with the two (2) right side pump cylinders 104 providing one fluid circuit and the two (2) left side pump cylinders 104 providing a second fluid circuit, as described in further detail herein. While of four (4) pump cylinders 104 are provided in the pump 10, the pump 10 may be "scalable" to include additional pairs of pump cylinders 104 or may be provided with just two (2) tandem pump cylinders 104. While the pump cylinders 104 are preferred to have a cylindrical shape, they may also have other symmetrical or non-symmetrical cross-sectional shapes (such as D-shaped) in vertical or transverse cross-section. Each pump cylinder 104 defines a pump chamber 106 and accepts a plunger 200 which is reciprocally operable within the pump cylinder 104. The plungers 200 are independently operable by the drive and actuating system 400. The respective pump cylinders 104 each have an interior wall or surface 108 that defines the pump chamber 106. The pump cylinders 104 each have a generally enclosed front or distal end wall 110 formed by the front plate 102 and an open rear or proximal end 112.

Additionally, the pump body 100 comprises a plurality of inlet selector valve cylinders 114 that extend proximally from the front plate 102 laterally outboard of the two (2) outer pump cylinders 104. Each inlet selector valve cylinder 114 defines a cylindrical chamber 116 that accepts an inlet selector valve 300 which is rotationally operable within the inlet selector valve cylinder 114. The drive and actuating system 400 also independently operates the respective inlet selector valves 300 disposed within the inlet selector valve cylinders 114. In the illustrated embodiment, two (2) inlet selector valve cylinders 114 are provided in pump 10 to respectively control inflow to the two (2) "right side" pump cylinders 104 providing one fluid circuit and the two (2) "left side" pump cylinders 104 providing the second fluid circuit in pump 10. The respective inlet selector valve cylinders 114 have a front or distal end opening 118 formed in the front plate 102 and a rear or proximal end opening 120 to accept the inlet selector valve 300.

Each inlet selector valve cylinder 114 comprises, in the illustrated embodiment, a pair of inlet ports 122, 124 for use in connecting the pump 10 to two (2) fluid sources of diagnostic or therapeutic (e.g., pharmaceutical) fluids, such as imaging contrast media, to be received in the pump chambers 106 of the pump cylinders 104. Further, each inlet selector valve cylinder 114 comprises, in the illustrated embodiment, an additional rear or proximal inlet port 126 for use in connecting the pump 10 to, typically, a source of flushing or diluting fluid such as saline. As such, the rearmost inlet port 126 is referred to hereinafter as a "saline port 126", while inlet ports 122, 124 are referred to hereinafter as "first and second inlet ports 122, 124", respectively. The inlet ports 122, 124, 126 are axially spaced along the inlet selector valve cylinder 114, with the first inlet port 122 located near the front plate 102 and the saline port 126 located near the rear or proximal end opening 120 of the inlet selector valve cylinder 114. The saline port 126 is located at a lower level than the first and second inlet ports 122, 124, and connects to a saline manifold located on the underside of the pump body 100, as described herein. Accordingly, the saline port 126 is located at a lower level and opens into the inlet selector valve cylinder 114 and the saline manifold 130 to access one of two (2) saline channels in the saline manifold 130, as described herein, rather than intersecting or directly opposing the valve body of the inlet selector valve 300 as in the case of the first and second inlet ports 122, 124. The first and second inlet ports 122, 124 and the saline ports 126 on the inlet selector valve cylinders 114 may be formed with luer-type connector tips or barbed connection tips, and like fluid connections arrangements, for making either removable or permanent fluid connections to the fluid supply tubes 34 used to connect the pump 10 to the one or more fluid source containers 30 that provide therapeutic or diagnostic (e.g., pharmaceutical) fluids or saline to the pump 10.

The illustrated embodiment of the pump 10 is shown for exemplary purposes with six (6) supply ports, three (3) on each of the right and left sides 16, 18 of the pump 10. These supply ports include the two (2) right side inlet ports 122, 124 and the right side saline port 126 on the pump body 100 and the two (2) left side inlet ports 122, 124 and the left side saline port 126 on the pump body 100. However, this specific configuration is illustrated for expediency in explaining the various components, features, and desirable operational characteristics of the pump 10 and should be considered as non-limiting. Accordingly, the pump 10 may comprise a fewer or a greater number of ports 122, 124, 126 on each side 16, 18, as desired.

The saline port 126 on the respective inlet selector valve cylinders 114 is in fluid communication with a saline manifold 130 that extends across the underside of the pump body 100 and across the pump cylinders 104. The saline manifold 130 is oriented generally parallel to the front plate 102. The saline manifold 130 is typically adapted to be placed in fluid communication via the two (2) saline ports 126 to two (2) sources of saline S1, S2 contained in two (2) respective fluid source containers 30. The saline manifold 130 is bifurcated into two (2) saline channels 132, 134. The respective inlet selector valves 300 are configured so that saline may be drawn from either of the sources of S1, S2 in the saline fluid source containers 30 via the saline channels 132, 134, even though the saline fluid source container 30 may be physically on the opposite side of the pump 10 from the inlet selector valve 300, as described further herein. In the illustrated embodiment of the pump 10, the forward or distal or "first" saline channel 132 of the saline manifold 130 is supplied by the saline source S2 in the fluid source container 30 connected to the saline port 126 located on the right side inlet selector valve cylinder 114, and the rear or proximal or "second" saline channel 134 of the saline manifold 130 is supplied by the saline source S1 in the fluid source container 30 connected to the saline port 126 located on the left side inlet selector valve cylinder 114. The shape of the saline channels 132, 134 may be formed with smooth interior surfaces and curvatures to minimize the potential for trapped air and pressure drop (e.g., flow restriction) through each saline channel 132, 134. A saline manifold cap 136 encloses the saline channels 132, 134 and may be secured in place on the saline manifold 130 formed on the underside of the pump body 100 via medical grade adhesive, solvent bonding, laser and ultrasonic welding, and like joining techniques.

As the forward saline channel 132 is connected to the right saline source S2 and the rear saline channel 134 is connected to the left saline source S1, it is desirable to purge air using saline from the left saline source S1 as this is the rearmost saline channel. By using the rearmost saline channel 134 connected to the left saline source S1 for fluid priming operations, the fluid passages in the pump 10 may be primed from rear to front with saline, and air is purged forward from the rear of each of the inlet selector valves 300. This result occurs because there are no other ports "behind" the rearmost saline channel 134. For example, it would not be possible to purge all of the air from the inlet selector valves 300 if one of the inlet ports 122, 124 was used to supply a priming fluid. This is because there would be a "dead space" in the inlet selector valve 300 behind the two (2) front inlet ports 122, 124 through which no fluid would flow. Any air in this portion of the inlet selector valve 300 would remain after priming.

Figure 9:
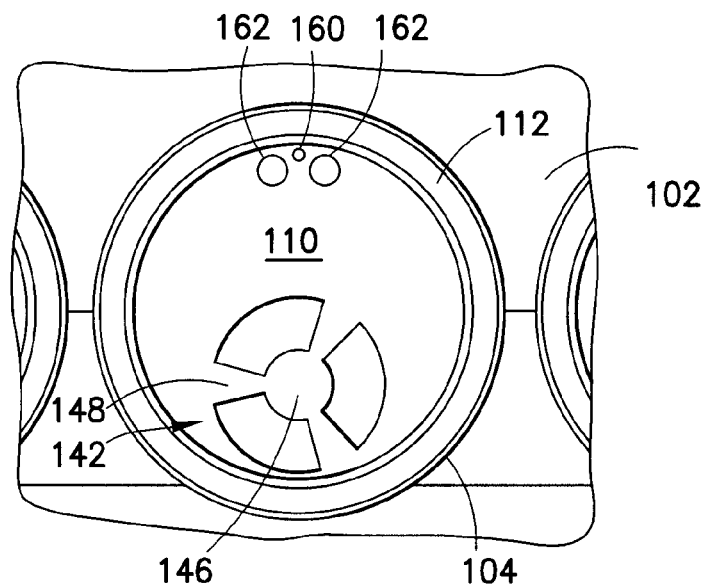
FIG. 9 is a rear view of a pump cylinder of the pump body shown in FIG. 7.

A front or distal side 140 of the front plate 102 defines a plurality of inlet openings 142, one for each of the pump cylinders 104. The inlet openings 142 are provided in the distal end wall 110 of each of the pump cylinders 104. The inlet openings 142 permit fluid to enter the pump chamber 106 of the respective pump cylinders 104. The inlet openings 142 are spaced apart on the front plate 102 to respectively coincide with the pump chambers 106 of the respective pump cylinders 104. Accordingly, four (4) spaced inlet openings 142 are provided in the illustrated embodiment, one for each pump cylinder 104, and are positioned to be near the bottom center of each of the pump cylinders 104, as shown in FIG. 9. An inlet check valve support structure 144 is provided in each of the inlet openings 142 and is desirably recessed within each of the inlet openings 142 for supporting an inlet check valve 194. The inlet check valves 194 are flexible polymeric, typically polyurethane, disks that regulate the fluid flow into each pump cylinder 104. The inlet check valve support structure 144 comprises a central hub 146 and one or more prongs 148 extending radially outward from the central hub 146. A total of three (3) prongs 148 is present in the inlet check valve support structure 144 in the illustrated embodiment. The central hub 146 desirably includes a centrally-located preload pin 150 that allows a preload force to be applied to the inlet check valve 194 to ensure that the inlet check valve 194 closes when there is no pressure gradient present across the inlet check valve 194. The preload force is not set too high so as to overly increase the "cracking" or opening pressure of the inlet check valve 194 as this would undesirably cause a higher pressure drop across the check valve 194. The preload pins 150 also help to counteract the effects of long-term storage, which could cause the inlet check valves 194 to develop a compression set over time. The front or distal end openings 118 in the front plate 102 leading to the inlet selector valve cylinders 114 are circumferentially bordered by one or more concentric ribs or rims 152 formed on the front side 140 of the front plate 102 and which extend around the front or distal end openings 118.

The front side 140 of the front plate 102 further defines an elongated recess 154 extending across the front side 140 above the elevational location of the inlet openings 142, but still coinciding with the pump chambers 106 of the respective pump cylinders 104. The elongated recess 154 is bordered by a perimetrical recess 156 so that a sealing element, such as an elongated O-ring or gasket or like sealing element, may be placed in the perimetrical recess 156 and form a fluid sealing border about the elongated recess 154. A plurality of recessed areas 158 is defined in the elongated recess 154 and is spaced apart in the elongated recess 154 to coincide, respectively, with the pump chamber 106 defined by the pump cylinders 104. Accordingly, a total of four (4) recessed areas 158 are provided in the illustrated embodiment. Each recessed area 158 typically defines at least one top or air egress opening 160 in the distal end wall 110 of each of the pump cylinders 104, and is desirably positioned to be near the top center of each of the pump cylinders 104, as shown in FIG. 9, for providing an egress opening for air bubbles in the pump chambers 106 of the respective pump cylinders 104. Each of the recessed areas 158 further defines one or more outlet openings 162 in the front plate 102, typically on either side of the top air egress opening 160, and in the distal end wall 110 of each of the pump cylinders 104 to permit fluid to exit the respective pump cylinders 104. It is also noted that the upper surface or leg of the elongated recess 154 is substantially flat and horizontal and its centerline is raised slightly above the recessed areas 158 which allows any air that is present in the elongated recess 154 to be ejected upward through the outlet selector valve 280.

Figure 10:
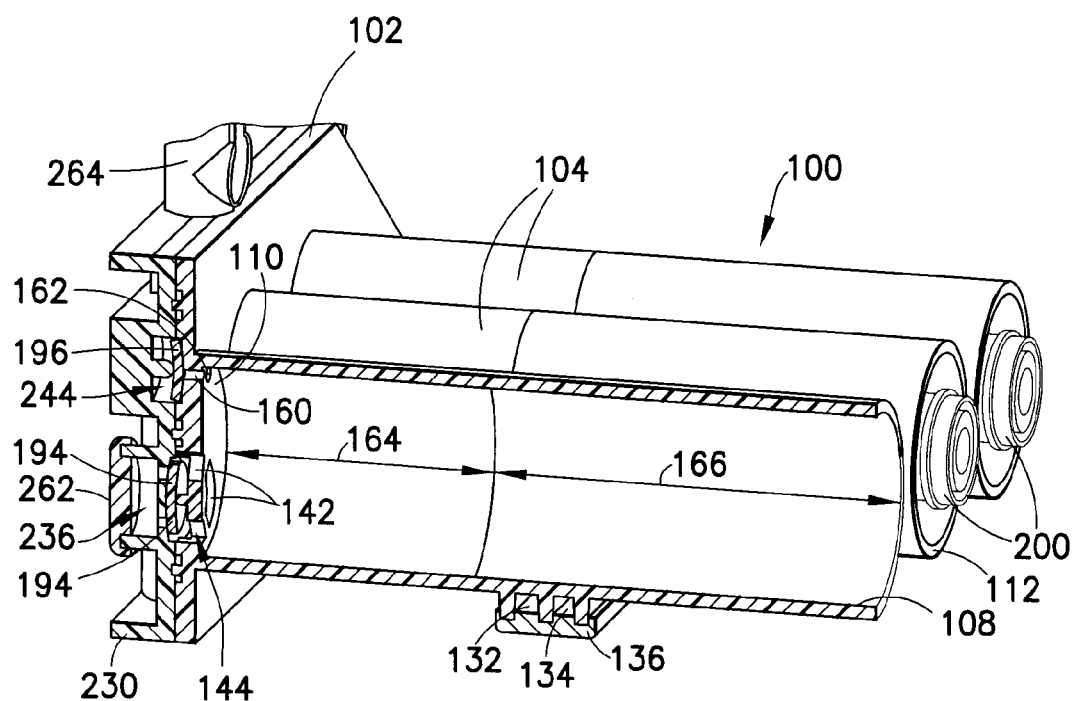
FIG. 10 is a cross-sectional view of the fluid pump device taken along line 10-10 in FIG. 2 and with a plunger of the fluid pump device removed for clarity.
Figure 13:
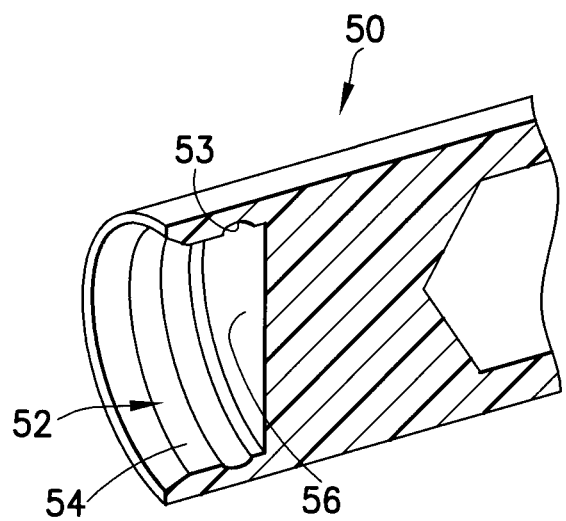
FIG. 13 is a cross-sectional perspective view of a distal portion of a drive piston adapted to capture and actuate the plunger shown in FIG. 11.
Figure 14:
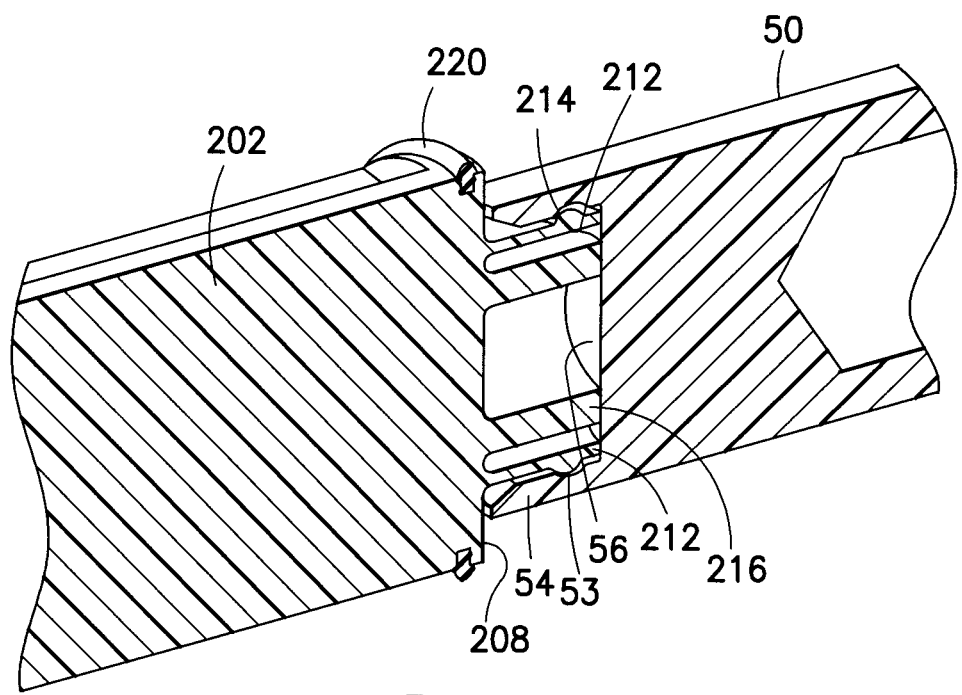
FIG. 14 is a cross-sectional perspective view showing engagement of the drive piston shown in FIG. 13 with the plunger shown in FIG. 11.
Figure 15:
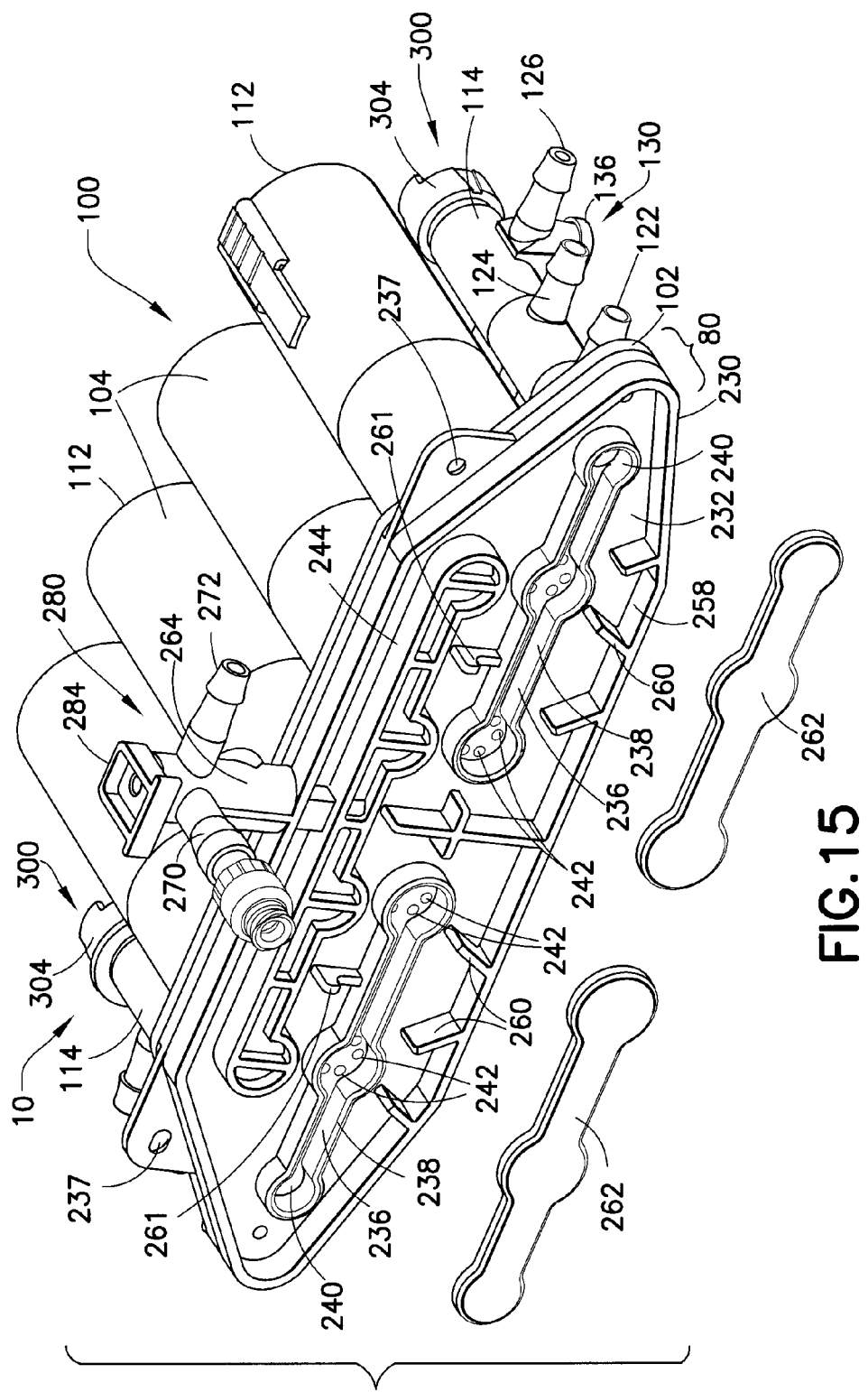
FIG. 15 is a perspective view of the fluid pump device showing inlet manifold caps exploded from the fluid pump device.
Figure 16:
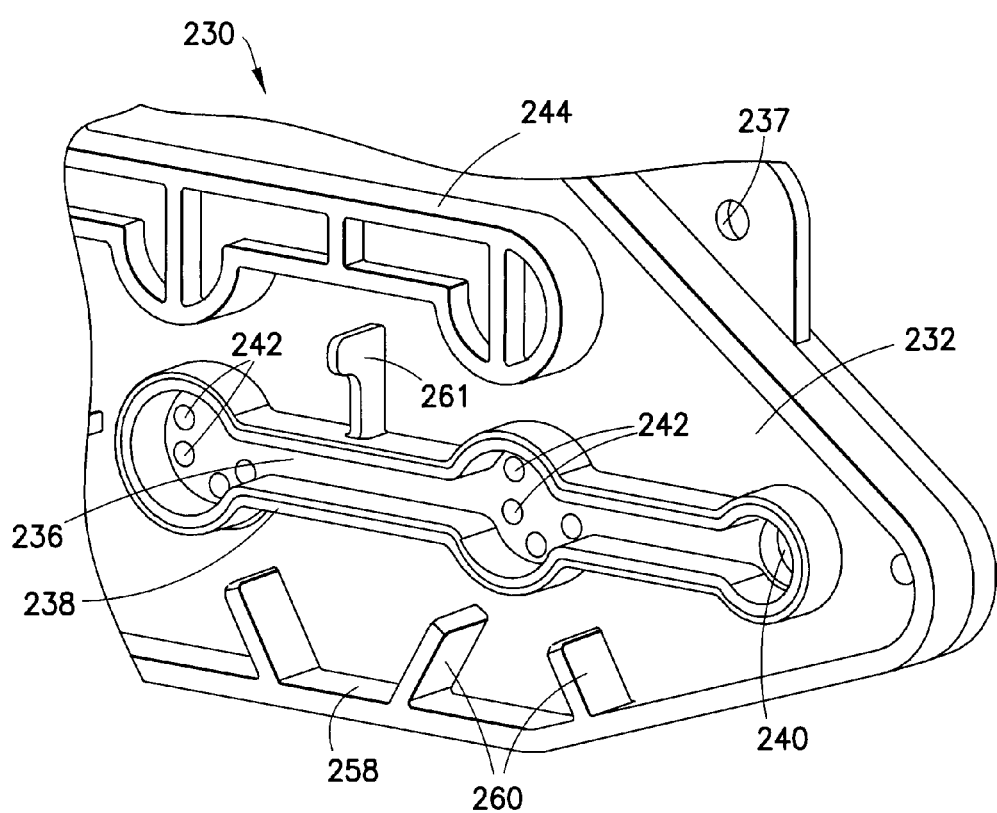
FIG. 16 is a perspective view of a right front portion of a pump manifold plate adapted for association with the pump body shown in FIG. 7.
Figure 17:
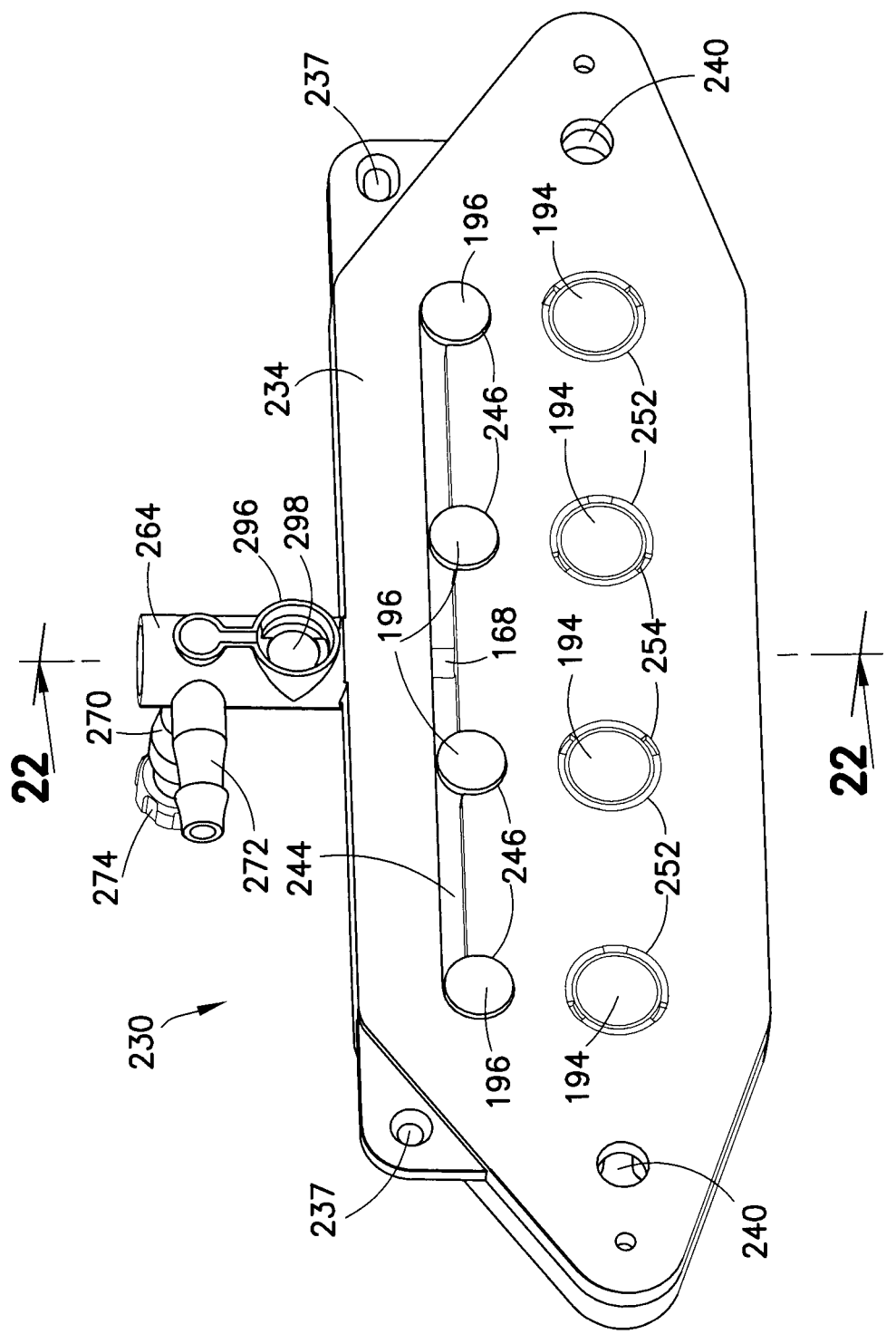
FIG. 17 is a rear perspective view of the pump manifold plate supporting inlet and outlet check valves of the fluid pump device.
Figure 18:
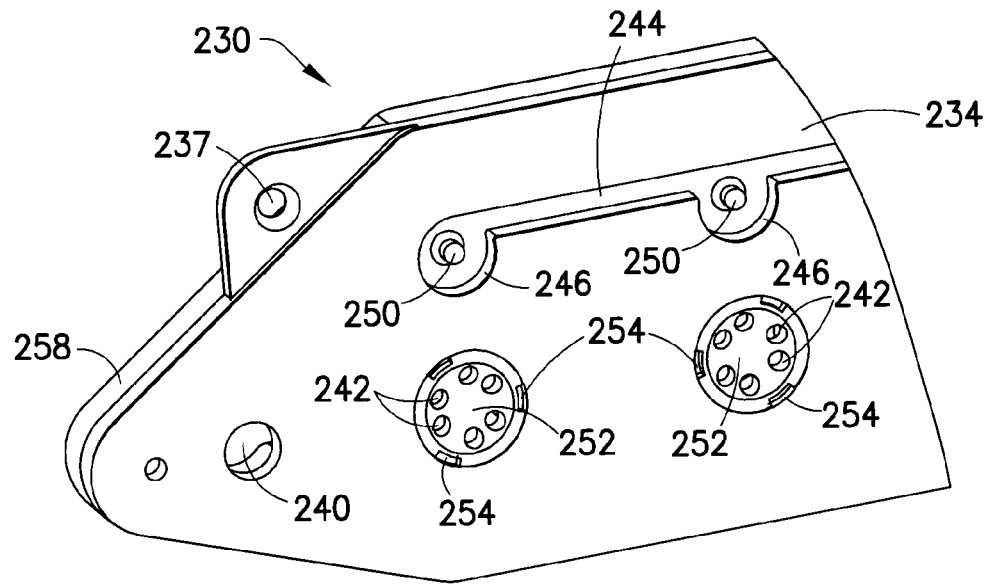
FIG. 18 is a rear perspective view of a right portion of a pump manifold plate adapted for association with the pump body shown in FIG. 7.
Figure 19:
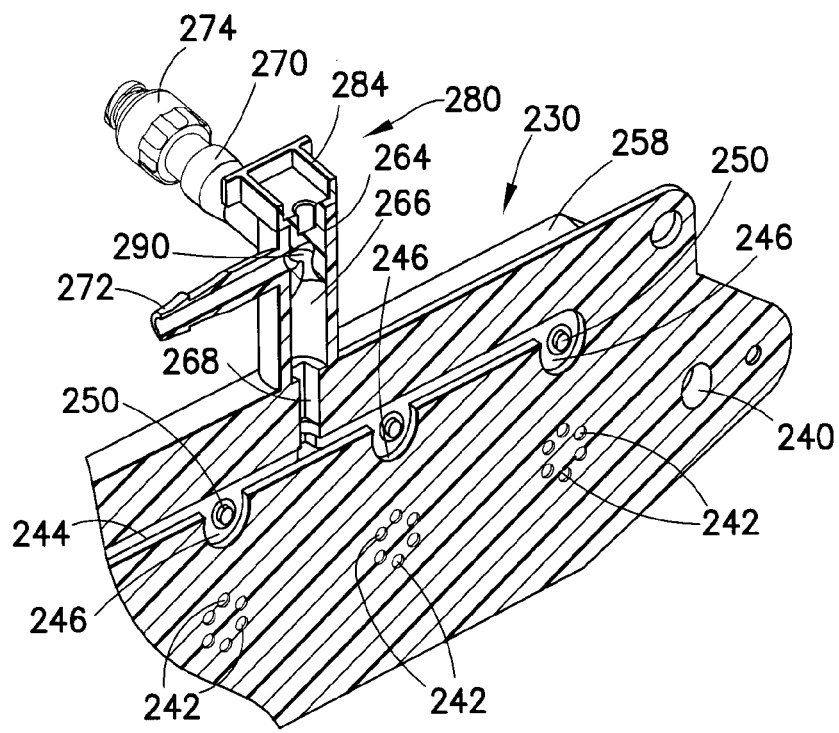
FIG. 19 is a longitudinal cross-sectional and perspective view of a portion of the pump manifold plate adapted for association with the pump body shown in FIG. 7.

In summary, each pump cylinder 104 has an inlet opening 142 in fluid communication with its pump chamber 106 and one or more outlet openings 162 in fluid communication with its pump chamber 106, with the one or more outlet openings 162 defined in one of the recessed areas 158 in the elongated recess 154 defined in the front side 140 of the front plate 102. Referring next to FIG. 10, the pump cylinder 104 generally has a working or pumping region or zone identified by arrow 164 in the pump chamber 106 and an isolation region or zone identified by arrow 166 in the pump chamber 106. The plunger 200 is removed in the view of FIG. 10 for clarity.

A plate support structure or groove 168 may be provided on at least one of the pump cylinders 104, such as provided on a top or upper facing side of one of the outboard pump cylinders 104. The plate support structure 168 supports a pump indicator plate 170 which is encoded with identifying information regarding the pump 10 to enable the control system 800 which controls operation of the drive and actuating system 400 to determine, for example, the configuration of the pump 10. The configuration of the pump 10 is dependent, typically, on the type or configuration of the fluid supply set 32 as manufactured or associated with the pump 10 and used to meet different patient and/or procedural needs.

Figure 2:
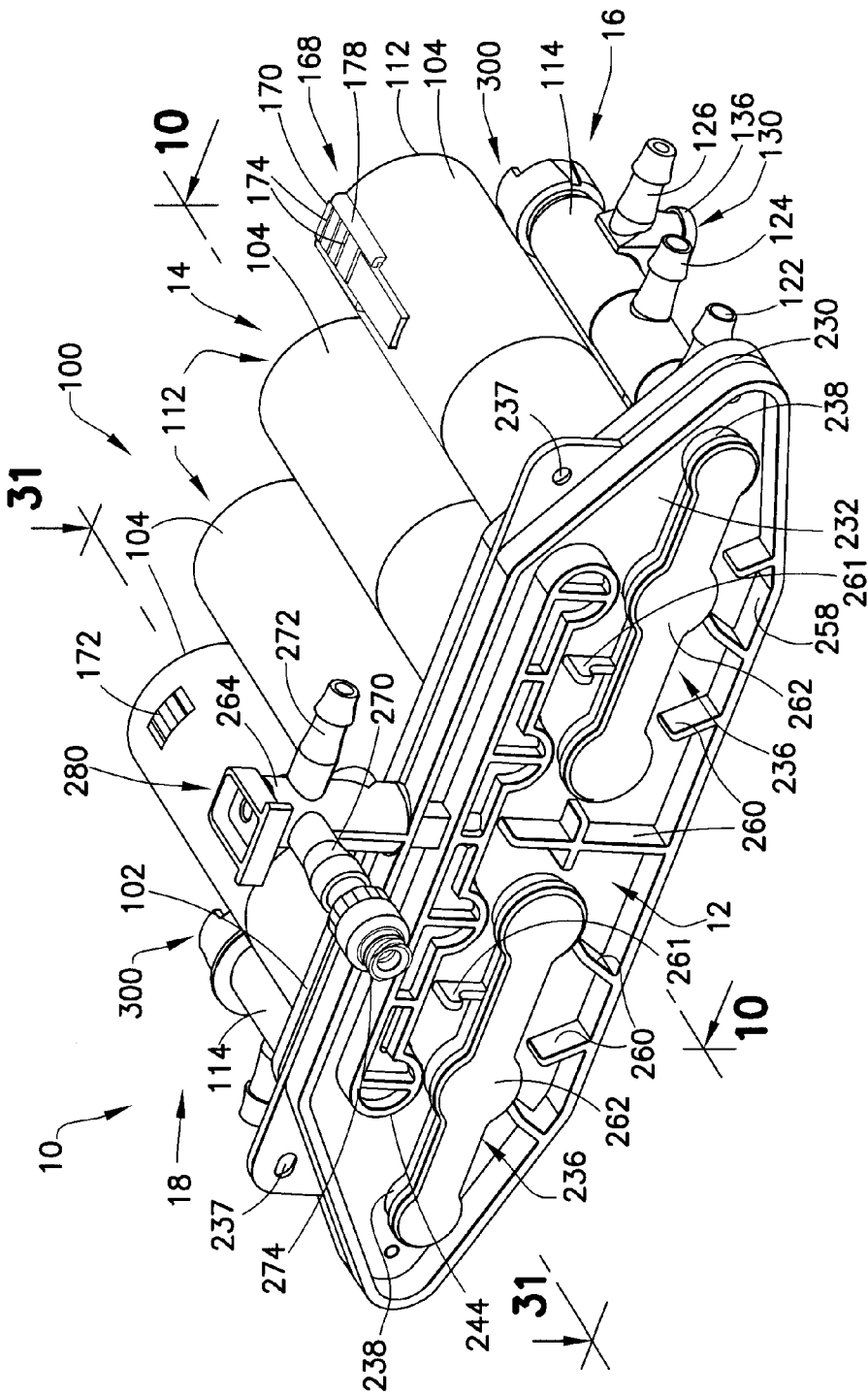
FIG. 2 is a front perspective view of a fluid pump device for use in the fluid delivery system shown in FIG. 1.

The configuration of the pump 10 may also, or alternatively, be encoded into identifying indicia 172, such as bar code indicia as shown in FIG. 2, that is affixed on or etched into a top or upper facing side of one of the pump cylinders 104, such as affixed on or etched into the opposite outboard pump cylinder 104 from the pump cylinder 104 carrying the pump indicator plate 170. It will be understood that the pump indicator plate 170 and identifying indicia 172 may be located on any suitable surface or location on the pump body 100 or on the pump manifold plate 230. The identifying indicia 172 may also be a suitable RFID (radio frequency identification device) tag, as shown in FIG. 3, as a suitable arrangement for storing pertinent information about the pump 10. The identifying indicia 172 is scanned prior to installation of the pump 10 in association with the drive and actuating system 400 to determine the configuration of the pump 10, and other identifying information. The pump indicator plate 170 and/or the identifying indicia 172 may contain additional pertinent information, such as pump serial number, manufacturing identification number, use-by date, manufacturing lot code/batch number, initial angular orientation of the inlet selector valves 300 in their respective inlet selector valve cylinders 114 on the pump body 100, cryptographic hash code to confirm validity of information, and like information. More limited information may be carried by the pump indicator plate 170 than the identifying indicia 172, with the identifying indicia 172 typically including all of the foregoing information. Thus, the pump indicator plate 170 may alternatively be encoded with only limited information, such as pump type information to identify the specific configuration of the pump 10 as shown, for example, in FIGS. 40-43 discussed herein. Moreover, if the identifying indicia 172 is an RFID (radio frequency identification device) tag, the RFID tag or device can store the same information listed above, such as: pump type/configuration, pump serial number, manufacturing identification number, use-by date, manufacturing lot code/batch number, and initial angular orientation of the inlet selector valves 300 in their respective inlet selector valve cylinders 114 on the pump body 100. Because RFID tags can have read/write capability, the RFID tag could also store information on how many times the "tagged" pump 10 has been used, the volume of pumped fluid, peak pressure, and like operational information. The RFID tag may be located on any suitable surface of the pump 10 and can be read and written to by an antenna in close proximity to the pump 10, such as associated with the drive and actuating system 400.

The pump indicator plate 170 is typically provided as an optically encoded transparent polymeric member that fits within and is secured by the plate support structure 168. The indicator plate 170 provides a length of material disposed along at least a portion of the wall. The length of material propagates electromagnetic energy therethrough. The length of material may include at least two indicators or grooves 174, each of the grooves being located at a different predetermined longitudinal position along the length of material and each of the grooves being positioned to longitudinally align with a sensor when a barrel, such as one of the pump cylinders 104, is engaged with the drive and actuating system 400 and thereby attached to the fluid injector portion of the fluid delivery system 2. The pump indicator plate 170 comprises a series of grooves 174 that permits at least the configuration of the pump 10 to be optically read or verified after installation in association with the drive and actuating system 400. Thus, the drive and actuating system 400 may include an optical detector and like technology and the pump indicator plate 170 may be provided and encoded with information in accordance with the disclosures of U.S. Pat. Nos. 7,018,363 and 7,462,166, both to Cowan et al., which disclose optical technology for determining configuration, including size of a fluid pumping component mounted to a power fluid injector and are incorporated herein by reference in their entirety for these and any other pertinent applications. The foregoing Cowan patents are generally directed to syringes and like pump devices such that the optical technology therein may be applied to the pump cylinders 104 of the pump 10. The pump cylinders 104 are analogous and operable generally in the same manner as cylindrical syringe bodies and like pump devices as disclosed in the foregoing Cowan patents. Thus, the optical technology described in the foregoing Cowan patents may be applied to the pump cylinders 104 whereby the pump indicator plate 170 is provided with the optical technology detailed in these patents or the pump cylinders 104 are marked or otherwise identified in the various manners and embodiments disclosed in these patents. The pump indicator plate 170 is provided as an exemplary element for applying the identifying indicia 172 to the pump 10 and should not be deemed limiting as this application expressly includes application of the optical technology found in the foregoing Cowan patents to the pump 10 generally and the pump body 100 in particular. The pump body 100 may be opaque to absorb laser light during a laser welding process during assembly of the pump 10, but the opaque pump body 100 also helps with optical sensor performance in the optical reading of the information contained in the grooves 174 in the pump indicator plate 170. Additionally, the plate support structure 168 may be adapted for a snap-lock fit with the pump indicator plate 170. The plate support structure 168 may comprise a recessed groove 176 in the pump cylinder 104 for accepting the pump indicator plate 170, and a pair of flanges 178 for restraining the pump indicator plate 170 in the groove 176. Further, the snap-lock fit may be provided by a snap-lock tab 180 formed within the groove 176 in the pump cylinder 104 and a corresponding mating recess (not shown) defined in the underside of the pump indicator plate 170.

Referring further to FIGS. 11-14, as noted previously, a plunger 200 is reciprocally operable within each of the pump cylinders 104 and is independently controlled by the drive and actuating system 400. Each plunger 200 comprises a rigid plunger body 202 that is injection molded from polycarbonate and like polymeric materials. The plunger body 202 may be a unitary, solid body formed to include a series of wall segments 204 that extend between a front or distal end disc 206 and a rear or proximal end disc 208. The rear or proximal end disc 208 is formed with a piston interface member or device 210 which is adapted to interface with an independent drive piston 50 associated with the drive and actuating system 400 for the pump 10. The piston interface member 210 is split into at least two (2) parts or halves to form opposing halves or legs 212 that may compress towards one another, or radially inward toward a central longitudinal axis of the plunger 200, to be received in a distal end recess or socket 52 in the drive piston 50. Additionally, the piston interface member 210 comprises a circumferential radial lip or rim 214, which is provided on each of the interface halves or legs 212, to engage a corresponding groove or recess 53 defined proximally inward from radial lip or rim 54 provided in the distal end socket 52 in the drive piston 50. The engaging lips or rims 54, 214 secure the engagement between the plunger 200 and drive piston 50. Thus, the rear or proximal end disc 208 of each plunger body 202 includes several features that allow the plunger 200 to "snap" into the distal end socket 52 in the actuating drive piston 50. A desirable result of the foregoing "snap-fit" connection is that it is non-orientation specific and the drive piston 50 may engage the plunger 200 in any radial orientation of the plunger 200. Moreover, it will be understood that the piston interface member 210 may be split into a plurality of portions or parts 212 that may compress inwardly toward a central longitudinal axis of the plunger 200. Additionally, the piston interface member 210 may be generally cylindrical shaped and, as such, the plurality of portions or parts may be formed as arcuate sections or segments.

Once the plunger 200 is "snapped" into place in association with the drive piston 50, the drive piston 50 can move the plunger 200 in a reciprocal manner in the associated pump cylinder 104. When the plunger 200 is pressurizing fluid in the pump chamber 106 of the pump cylinder 104 by moving forward or distally in the pump cylinder 104, a central ring or cylinder support member 216 extending proximally from the rear or proximal end disc 208 seats against a flat interior end or bottom 56 of the distal end socket 52 in the actuating drive piston 50, thereby transferring the compressive axial load to the drive piston 50. The support member 216 coaxially disposed in the piston interface member 212. When the pump 10 is to be removed from the drive and actuating system 400, the drive piston 50 is retracted rearward or proximally until the rear or proximal end disc 208 of the plunger body 202 contacts a stationary projection. Further retraction of the drive piston 50 disengages the snap-fit interface between the piston interface member 210 and the drive piston 50.

Each plunger 200 comprises two (2) over-molded seals, a front or distal end lip seal 218 provided circumferentially about and on the front side of the front or distal end disc 206, and a rear or proximal bead seal 220 provided circumferentially about the rear or proximal end disc 208. The front end disc 206 with over-molded lip seal 218 is used to seal liquid within the pumping zone 164 of the pump cylinder 104, and the rear end disc 208 with over-molded bead seal 220 is used to prevent wetted portions of the interior wall 108 of the pump cylinder 104 from being exposed to the ambient environment. The seals 218, 220 may be made of polyurethane and like polymeric materials. The front lip seal 218 is desirably adapted to withstand fluid pressure of at least 400 psi and, desirably, at least 500 psi and is desirably hydraulically energized by fluid pressure. Accordingly, higher pressures result in greater sealing force. The rear bead seal 220 typically seals against dust and particulates that may be pulled into the open rear or proximal end 112 of the pump cylinder 104, and is actuated by compression within the isolation zone 166 of the pump cylinder 104. Seal runners 222 may extend from the front lip seal 218 to the rear bead seal 220 along two (2) or more or all of the wall segments 204. In the illustrated embodiment, seal runners 222 extend along two (2) of the wall segments 204 located on opposite lateral sides of the plunger body 202. The seal runners 222 are typically formed during the over-molding process used to form the front lip seal 218 and the rear bead seal 220 on the front and rear end discs 206, 208, respectively. The "flat" front of the front end disc 206 is desirable for minimizing residual fluid volume in the pump chamber 106 of the pump cylinder 104, helps to eject air bubbles from the pump chamber 106 during fluid priming of the pump 10 and, further, helps clean the pump chamber 106 during flushing procedures.

It is noted that the retaining force of the snap-fit connection between the drive piston 50 and the plunger 200 is significantly greater than the expected retraction force to be applied to the plunger 200. The expected retraction force is the sum of the vacuum/suction force on the plunger 200 during filling of the pump cylinder 104 and the friction between the foregoing plunger seals 218, 220 and the interior wall 108 of the pump cylinder 104. If snap-fit retention force is too low, the plunger 200 could disconnect prematurely from the drive piston 50 during use.

Referring additionally to FIGS. 15-19, the pump 10, as noted previously, comprises a pump manifold 80 that is formed by the connection or joining of the pump manifold plate 230 with the pump body 100. The pump manifold 80 is generally formed by assembling the pump manifold plate 230 to front plate 102 of the pump body 100. The pump manifold plate 230 (hereinafter "manifold plate 230") comprises a front or distal side 232 and a rear or proximal side 234. The manifold plate 230 is generally shaped to correspond to the shape of the front plate 102 of the pump body 100 and is joined with the front plate 102 so that the rear side 234 of the manifold plate 230 is in engagement with the front side 140 of the front plate 102. The front side 232 of the manifold plate 230 includes right and left inlet manifold channels 236 provided on lateral right and left halves of the manifold plate 230. The inlet manifold channels 236 generally extend longitudinally along the front side 232 of the manifold plate 230. The two inlet manifold channels 236 correspond, respectively, to the two (2) right side pump cylinders 104 and the two (2) left side pump cylinders 104 of the pump body 100. As noted previously, in the illustrated embodiment, a total of four (4) pump cylinders 104 is provided in pump 10, with the two (2) "right" side pump cylinders 104 providing one fluid circuit and the two (2) "left" side pump cylinders 104 providing a second fluid circuit. The "right" inlet manifold channel 236 corresponds to the two (2) "right" side pump cylinders 104, and the "left" inlet manifold channel 236 corresponds to the two (2) "left" side pump cylinders 104. Alignment slots or holes 237 may be provided in the manifold plate 230 to facilitate loading of the pump 10 in association with the drive and actuating system 400, which is described herein.

Each of the right and left inlet manifold channels 236 is defined by a raised channel member or flange wall 238 provided on the front side 232 of the manifold plate 230. The manifold plate 230 defines a lateral opening 240 in each of the inlet manifold channels 236 that coincides with the distal or front end opening 118 in the front plate 102 of the pump body 100 which leads to the inlet selector valve cylinder 114. Accordingly, each lateral opening 240 registers with a corresponding front end opening 118 to place the "right" and "left" inlet selector valves 300 in fluid communication with the corresponding "right" and "left" inlet manifold channels 236, respectively. Additionally, the manifold plate 230 defines two (2) sets of inlet openings 242 in each of the right and left inlet manifold channels 236 that correspond to the inlet openings 142 in the front plate 102 of the pump body 100. As noted previously, the inlet openings 142 are spaced apart on the front plate 102 to respectively coincide with the pump chambers 106 of the respective pump cylinders 104, and the inlet openings 142 are positioned to be near the bottom center of each of the pump cylinders 104, as shown in FIG. 9. The respective sets of inlet openings 242 are, desirably, a plurality of openings 242 arranged in a predetermined pattern, such as a circular pattern, and enable fluid communication with the inlet openings 142 in the front plate 102 of the pump body 100. However, the two (2) sets of inlet openings 242 in each inlet manifold channel 236 may alternatively be provided as two (2) singular large openings in the respective inlet manifold channels 236. The illustrated circular arrangement of the inlet openings 242 desirably includes at least one inlet opening 242 located at a "high" point, such as near to the top part of the channel member 238 defining the inlet manifold channel 236. This "high point" inlet opening 242 minimizes the potential for air bubbles to become trapped within the inlet manifold channels 236 because any air present in the inlet manifold channels 236 is pulled into the pump cylinders 104 during the initial fluid priming process for the pump 10. The number and size of inlet openings 242 may be selected to minimize pressure drop across the underlying inlet check valves 194 during filling of the pump cylinders 104, while minimizing the potential for high pressures in the pump cylinders 104 which could cause the polymeric material of the inlet check valves 194 to "extrude" into the inlet openings 242 under high pressure.

The rear or proximal side 234 of the manifold plate 230 also defines an elongated outlet manifold channel or recess 244 extending across the rear side 234 above the elevational location of the sets of inlet openings 242 in the manifold plate 230, but still coinciding with or corresponding to the pump chambers 106 of the respective pump cylinders 104. The outlet manifold channel 244 generally corresponds to the elongated recess 154 defined in the front side 140 of the front plate 102 of the pump body 100. The elongated recess 154 is sized larger than the outlet manifold channel 244 and is bordered by the perimetrical recess 156, as described previously, so that an elongated O-ring or gasket and the like, may be placed in the perimetrical recess 156 and form a fluid sealing border around the outlet manifold channel 244 when the manifold plate 230 is joined to the front plate 102 of the pump body 100 to form the pump manifold 80. In a variation of the foregoing sealing arrangement, a weld joint, typically a laser weld, occupies the location of the perimetrical recess 156 and the sealing O-ring or gasket is not required, and this embodiment or variation is illustrated in the accompanying figures. The elongated recess 154 also forms the back wall of the outlet manifold channel 244 when the manifold plate 230 is joined to the front plate 102 of the pump body 100.

The outlet manifold channel 244 is used to place the respective pump cylinders 104 in fluid communication with the outlet selector valve 280 on the manifold plate 230. A plurality of outlet check valve receiving recesses 246 is defined as part of the outlet manifold channel 244. The outlet check valve receiving recesses 246 are spaced apart in the outlet manifold channel 244. Each of the receiving recesses 246 accommodates an outlet check valve 196. Thus, an outlet check valve receiving recess 246 is provided for each of the pump cylinders 104 of the pump body 100 so that an outlet check valve 196 opposes each of the respective sets of air egress openings 160 and outlet openings 162 in the front plate 102 of the pump body 100. The outlet check valve receiving recesses 246 are located directly above the sets of inlet openings 242 defined in the manifold plate 230, respectively. Each of the outlet check valve receiving recesses 246 further includes a centrally located preload pin 250 that allows a preload force to be applied to the outlet check valve 196 to ensure that the outlet check valve 196 closes when there is no pressure gradient present across the outlet check valve 196. The outlet check valves 196 are flexible polymeric discs, typically polyurethane discs, which regulate the fluid flow from each pump cylinder 104. Thus, the outlet check valves 196 are located within the respective outlet check valve receiving recesses 246 in the outlet manifold channel 244, with each of the outlet check valves 196 associated, respectively, with a corresponding set of outlet openings 162 and top openings 160 in the front plate 102 leading to the pump chambers 106 of the pump cylinders 104.

The rear or proximal side 234 of the manifold plate 230 further comprises dish-shaped areas or recesses 252 opposite the inlet openings 142 in the front plate 102 leading to the pump chambers 106 of the pump cylinders 104. The dish-shaped areas or recesses 252 form valve seats for the respective inlet check valves 194. As shown, for example, in FIG. 7, the perimetrical recess 156, which extends around the elongated recess 154 defined in the front side 140 of the front plate 102 of the pump body 100, also extends around or borders each of the inlet openings 142. Thus, the inlet openings 142 may be sealed by the same sealing element, such as an O-ring, gasket, or weld, disposed about the elongated recess 154, to form a fluid sealing border around the respective dish-shaped recessed areas 252. The sealing element (e.g., O-ring, gasket, or weld) forms a fluid sealing border around the outlet manifold channel 244 and the respective dish-shaped recessed areas 252 when the manifold plate 230 is joined to the front plate 102 of the pump body 100 to form the pump manifold 80. As noted previously, a welded joint, a laser or ultrasonic weld, is preferred in the location of the perimetrical recess 156 in the accompanying figures.

As described previously, the inlet check valves 194 are held in place in the opposing inlet openings 142 by the respective inlet check valve support structure 144 provided on the front plate 102 of the pump body 100. One or more receiving slots 254 may further be provided in the rear side 234 of the manifold plate 230 and located at spaced circumferential locations around the dish-shaped recesses 252. The one or more receiving slots 254 are adapted to receive corresponding tabs 256 extending from the radial prongs 148 of the inlet check valve support structures 144 provided on the opposing front plate 102 of the pump body 100, thereby securing the inlet check valves 194 opposite the dish-shaped recesses 252 formed in the rear or proximal side 234 of the manifold plate 230. A further purpose of the tabs 256 is to maintain the inlet check valves 194 centered relative to the inlet openings 142. Generally, it is desirable to provide some clearance between the disc edge of the inlet check valves 194 and the wall of the inlet openings 142 to permit fluid to flow past the inlet check valves 194 when opened. The three small tabs 256 keep the inlet check valves 194 centered during operation while leaving most of their circumference free from contact with the wall of the inlet openings 142.

The front side 232 of the manifold plate 230 comprises an outer circumferential flange or channel 258 which forms a border around the front side 232 of the manifold plate 230, and a series of stiffening ribs 260. The outer flange 258 and stiffening ribs 260 stiffen or provide rigidity to the pump manifold 80 without increasing the thickness of the molded polymeric material forming the pump body 100 and the manifold plate 230. Additionally, the outer flange 258 and the stiffening ribs 260 transfer the clamping force that is applied by the drive and actuating system 400 to the welded joints that are subjected to high stress, as described herein. Moreover, the outer flange 258 and stiffening ribs 260 may also be used for orienting and positioning the pump 10 in association with the drive and actuating system 400 used to operate the pump 10 so that the drive and actuating system 400 may operate the respective drive pistons 50 to capture and independently operate the respective plungers 200 disposed within the pump cylinders 104. The stiffening ribs 260 may be located on the face of the front side 232 of the manifold plate 230, or be formed as part of the outer flange 258 on the front side 232 of the manifold plate 230. A pair of positioning or stiffening tabs 261 may be provided on each of the respective channel members 238 defining the inlet manifold channels 236, and disposed generally between the two (2) circular sets of inlet openings 242 in inlet manifold channels 236. The stiffening tabs 261 help to prevent deflection of the ends of the pump cylinders 104 when they are subjected to internal fluid pressure, for example, on the order of at least 400 psi and, often, at least 500 psi and greater. Manifold caps 262 are provided for each of the right and left inlet manifold channels 236 and are secured to the respective channel members 238 defining the inlet manifold channels 236 via an ultrasonic or laser welding process and like joining techniques.

The manifold plate 230 is joined to the front side 140 of the front plate 102 of the pump body 100 via a laser welding process and like joining process. This laser welding process secures the manifold plate 230 to the front plate 102 of the pump body 100 and forms a hermetic seal around the fluid paths defined between the manifold plate 230 and the front plate 102. As a result of this laser welding process, the respective sets of inlet openings 242 in the manifold plate 230 are placed in correspondence with the respective inlet openings 142 in the front plate 102 of the pump body 100 to provide fluid communication (across the separating inlet check valves 194) between the right and left inlet manifold channels 236 and the two (2) right and the two (2) left pump cylinders 104, respectively. Further, the laser welding process secures the inlet check valves 194 in association with the respective dish-shaped recesses 252 which form the valve seats for the inlet check valves 194. The inlet check valves 194 are held in place in the inlet openings 142 by the respective inlet check valve support structures 144, as mentioned previously. Additionally, the laser welding process secures the engaging tabs 256 associated with the radial prongs 148 of the inlet check valve support structures 144 in their corresponding receiving slots 254 in the rear proximal side 234 of the manifold plate 230, thereby further securing and aligning the inlet check valves 194 in the dish-shaped recesses 252 forming the valve seats for the inlet check valves 194. Moreover, the laser welding process places the outlet manifold channel 244 in fluid communication (across the separating outlet check valves 196) with the respective sets of outlet openings 162 and top openings 160 in the front plate 102 to permit fluid to exit the pump chambers 106 of the respective pump cylinders 104 and enter the outlet manifold channel 244. The outlet check valves 196 are similarly secured and aligned in the outlet check valve receiving recesses 246 in the outlet manifold channel 244 and opposite the plurality of recessed areas 158 defined in the elongated recess 154 on the front side 140 of the front plate 100 during the laser welding process. The plurality of recessed areas 158 forms the valve seats for the respective outlet check valves 196 in a similar manner to the way the dish-shaped recesses 252 form valve seats for the inlet check valves 194. Furthermore, the laser welding process provides a weld joint in the perimetrical recess 156, described previously, which forms a fluid sealing border around the outlet manifold channel 244 and the respective dish-shaped recessed areas 252 when the manifold plate 230 is joined to the front plate 102 of the pump body 100.

Figure 20:
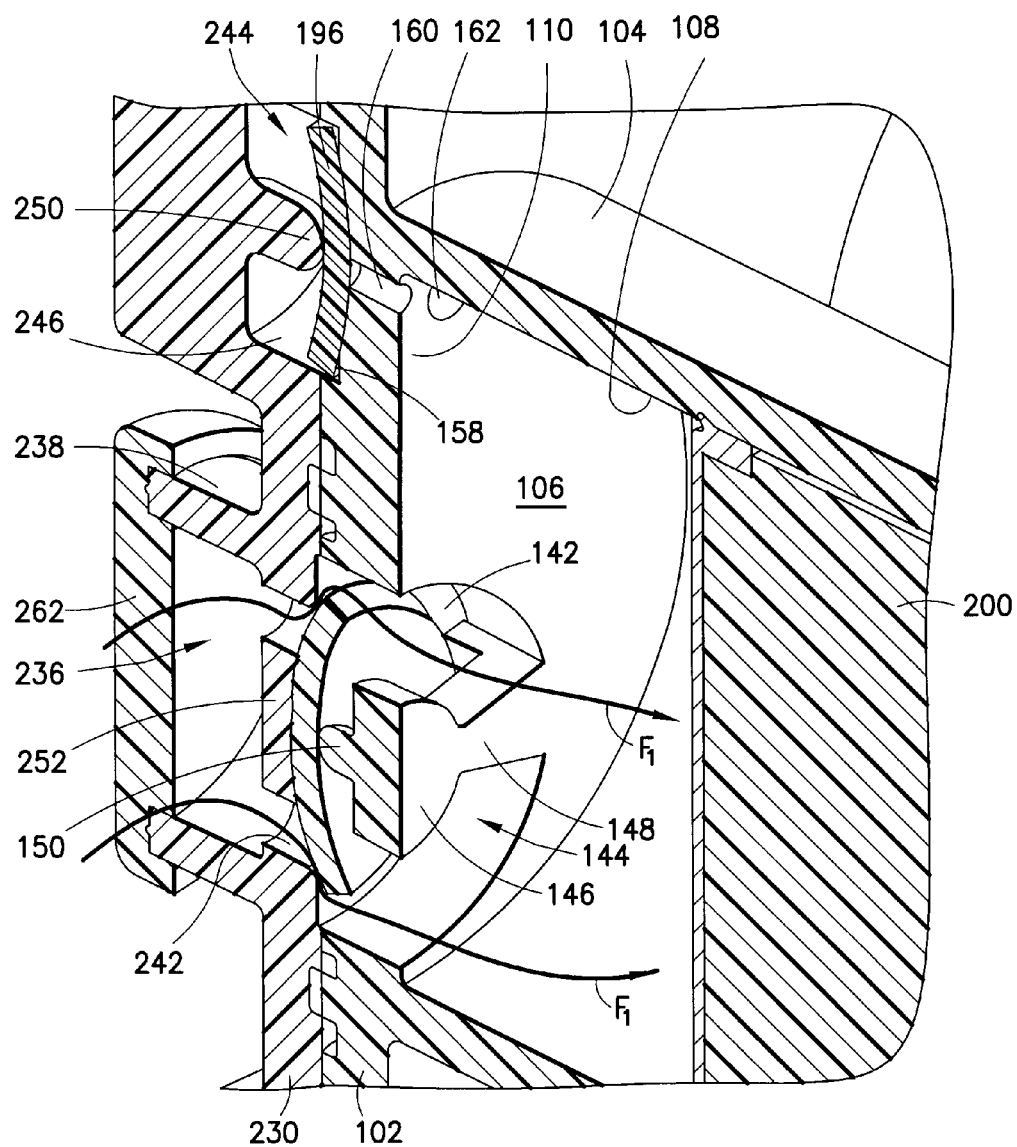
FIG. 20 is a cross-sectional perspective view of a portion of the fluid pump device shown in FIG. 2 showing operation of an inlet check valve of the fluid pump device.
Figure 21:
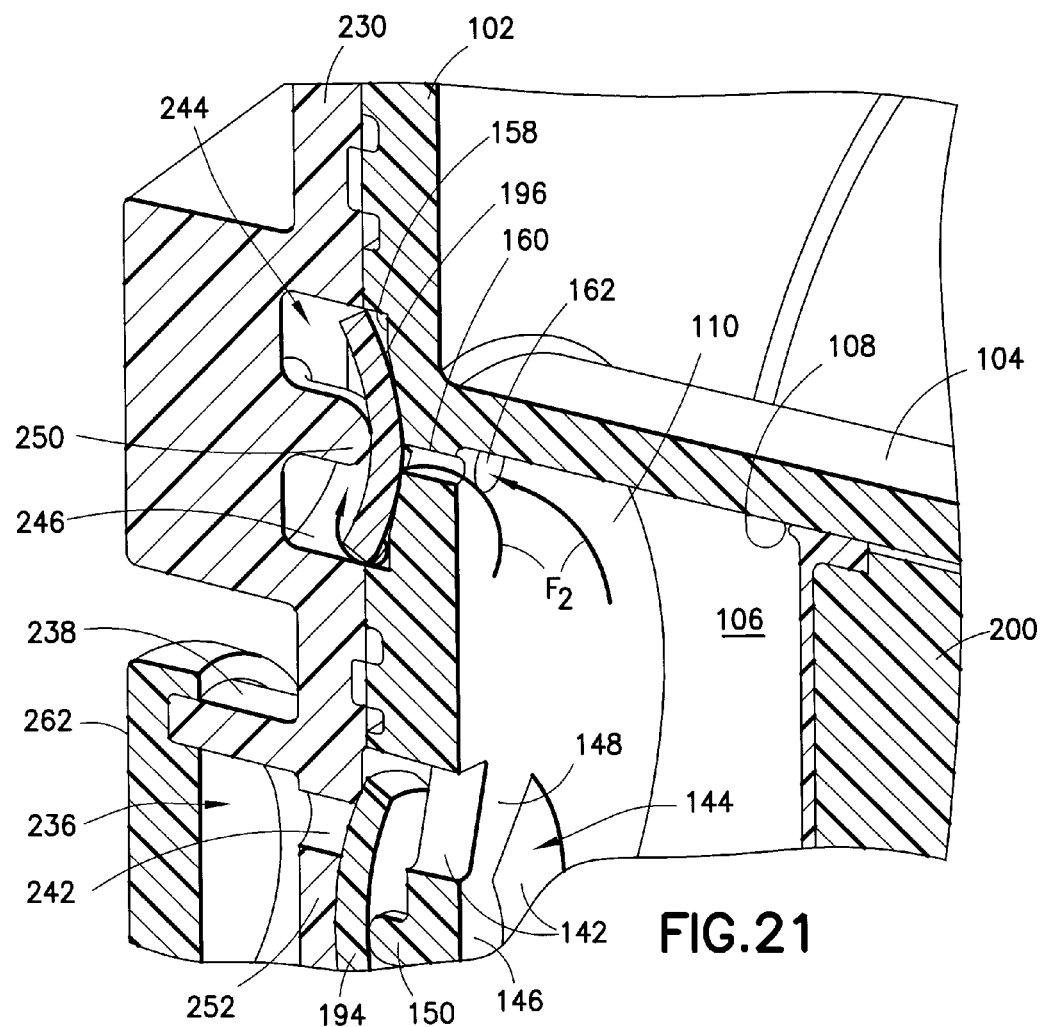
FIG. 21 is a cross-sectional perspective view of a portion of the fluid pump device shown in FIG. 2 showing operation of an outlet check valve of the fluid pump device.
Figure 22:
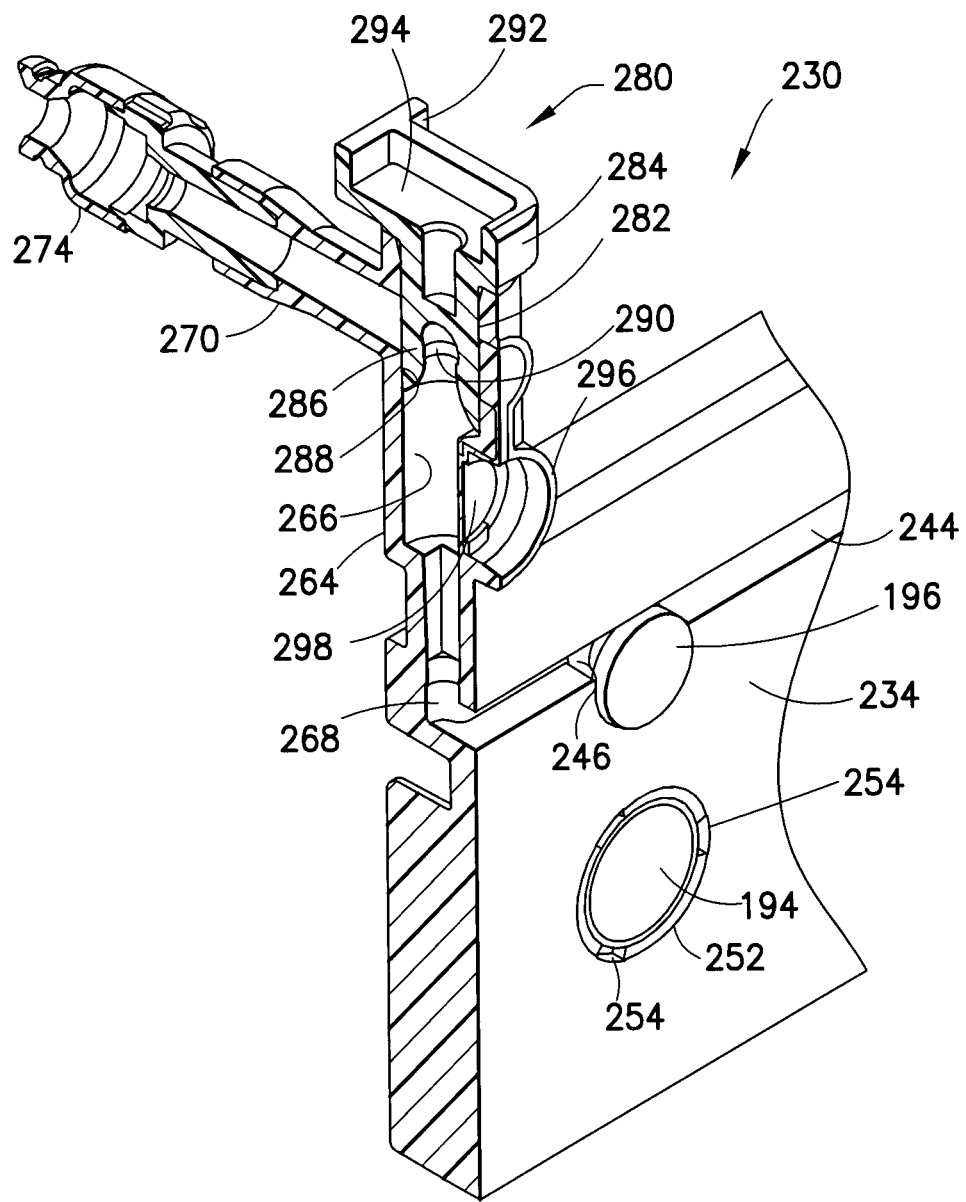
FIG. 22 is a cross-sectional perspective view taken along line 22-22 in FIG. 17.
Figure 23:
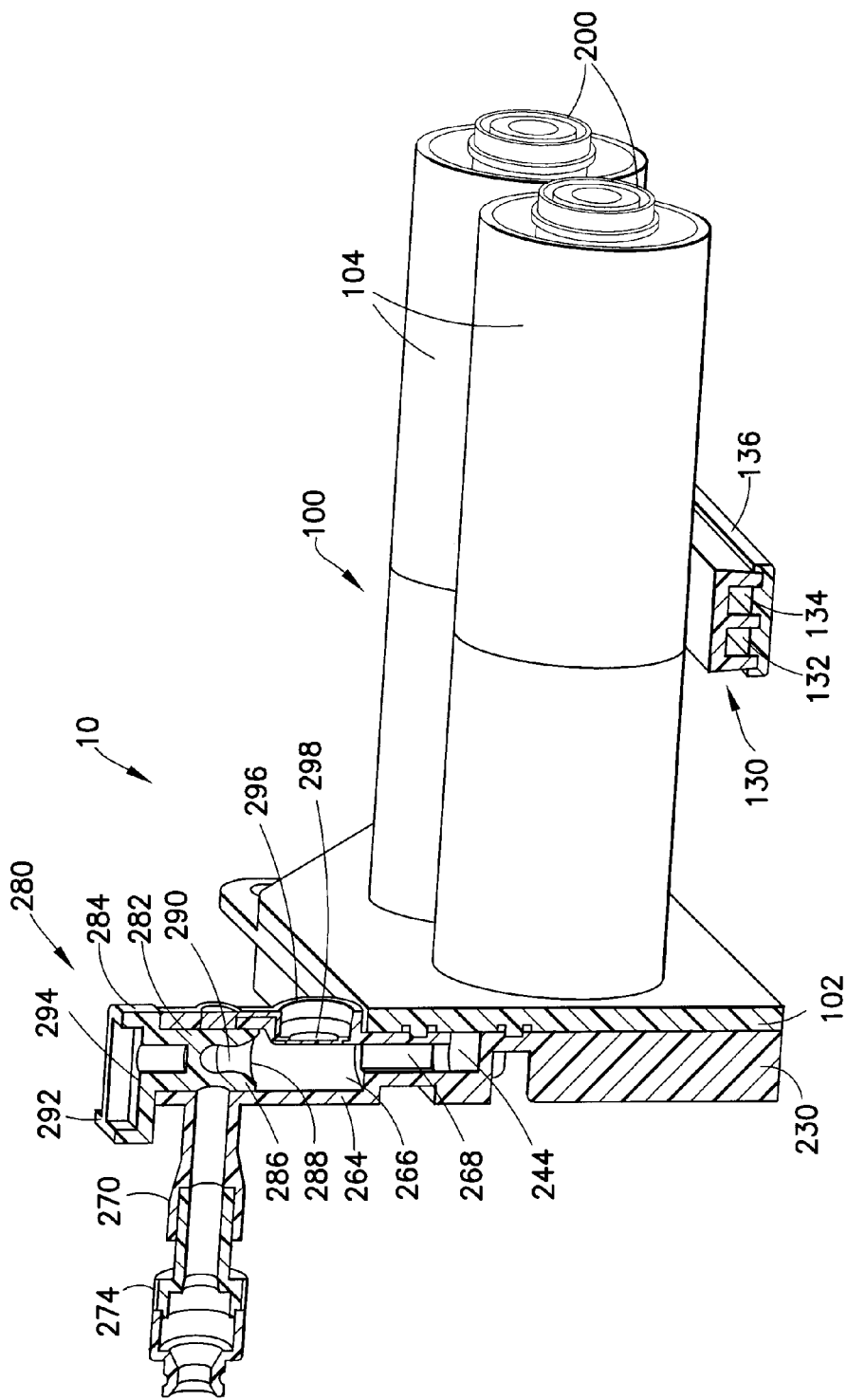
FIG. 23 is a cross-sectional perspective view taken along line 23-23 in FIG. 3.
Figure 24B:
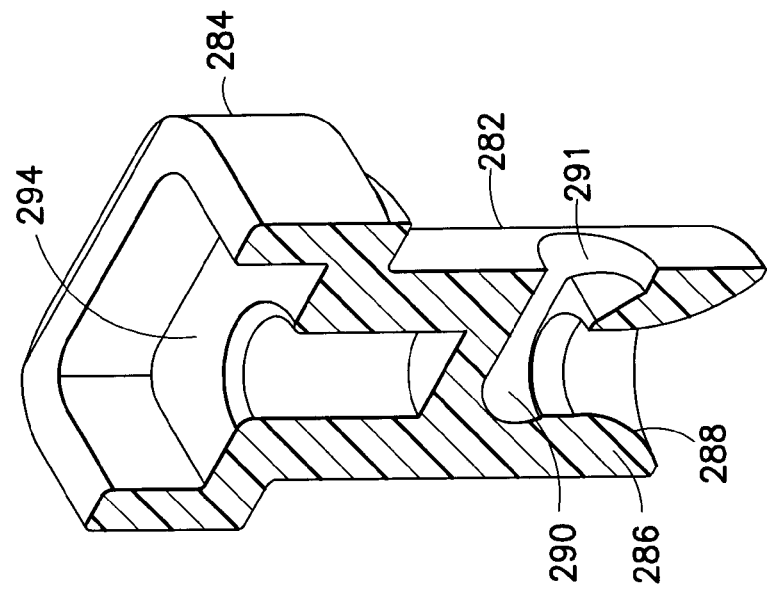
FIG. 24B is a cross-sectional perspective view taken along line 24B-24B in FIG. 24A.
Figure 24A:
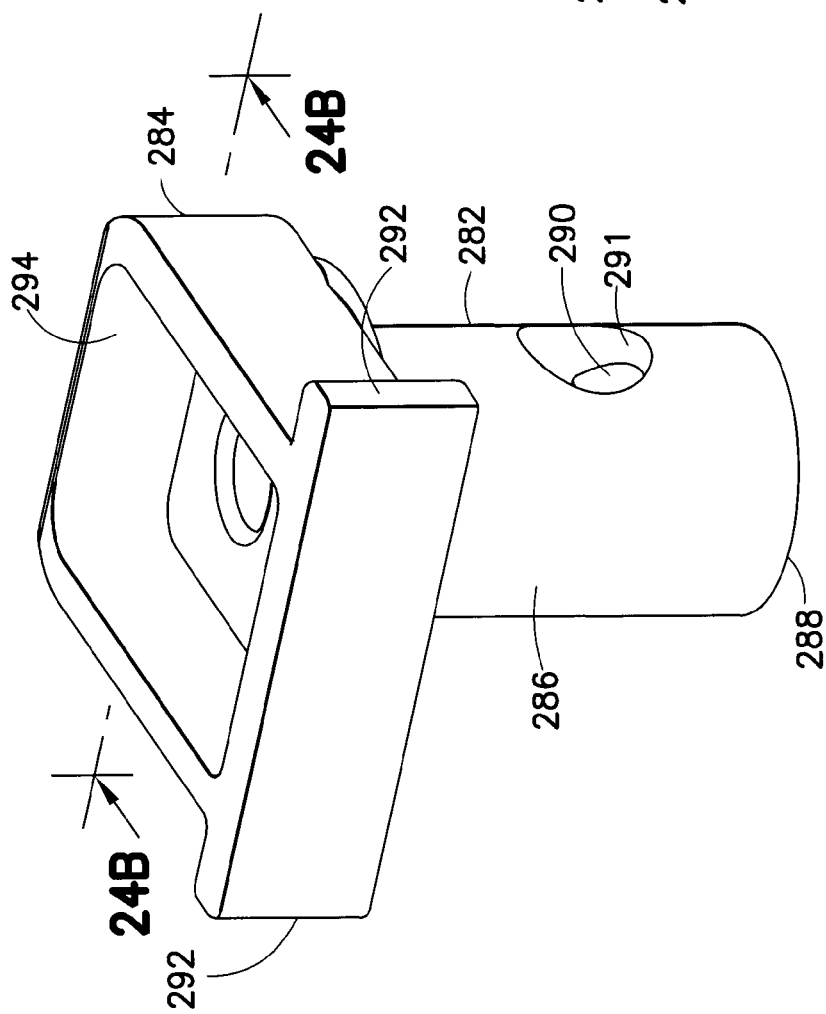
FIG. 24A is an isometric perspective view of an outlet selector valve body used in the fluid pump device shown in FIG. 2.

Referring further to FIGS. 20-21, in operation, when the pressure in the inlet manifold channels 236 is greater than the pressure within the associated pump cylinders 104, the inlet check valves 194 deform to allow fluid flow, designated by arrows $F_1$, into the pump chamber 106 of the associated pump cylinders 104. When the pressure within the pump cylinders 104 is greater than the pressure within the associated inlet manifold channels 236, the inlet check valves 194 are pressed against the dish-shaped recesses 252 formed in the rear or proximal side 234 of the manifold plate 230, and prevent fluid flow out of the pump cylinders 104 into the corresponding inlet manifold channel 236. Similarly, when pressure within the pump cylinders 104 is greater than pressure in the outlet manifold channel 244, the outlet check valves 196 associated with the pump cylinders 104 deform to allow fluid flow, as designated by arrows $F_2$, from the pump cylinder 104. When the pressure in the outlet manifold channel 244 is greater, the outlet check valves 196 associated with the pump cylinders 104 are pressed into the respective recessed areas 158 defined in the elongated recess 154 on the front side 140 of the front plate 102 to seal the respective sets of outlet openings 162 and top openings 160 in the front plate 102 leading to the pump chambers 106 of the pump cylinders 104 and prevent fluid flow from the outlet manifold channel 244 into the pump cylinders 104.

Referring additionally to FIGS. 22-26, the manifold plate 230 further comprises an outlet selector valve cylinder 264 extending upward from a top portion of the manifold plate 230 and, in particular, upward from the outer flange 258 which forms a border around the front side 232 of the manifold plate 230. The outlet selector valve cylinder 264 defines a valve bore 266 to accept the body of the outlet selector valve 280 therein. The valve bore 266 and a connecting passage 268 thereto are desirably located above the outlet manifold channel 244, permitting any air that is initially trapped in the outlet manifold channel 244 to rise up into the connecting passage 268 and valve bore 266 during the fluid priming process.

The outlet selector valve 280 controls fluid delivery or output from the pump 10. The valve bore 266 is in fluid communication with the outlet manifold channel 244 via the connecting passage 268. The outlet selector valve cylinder 264 further defines a pair of outlet ports 270, 272, including a patient outlet port 270 that accepts a swabable valve 274 and a waste outlet port 272. The swabable valve 274 may be secured within the patient outlet port 270 via medical grade adhesive, solvent bonding, laser and ultrasonic welding, and like joining techniques. As an alternative, the patient port 270 may be overmolded around the stem of the swabable valve 274, which eliminates the need for adhesive, solvents, or welding. The swabable valve 274 is generally used to connect the patient supply set 40 to the patient outlet port 270. Because the valve is swabable, multiple connections may be made without compromising the connection. A self-sealing silicone stem (not shown) in the swabable valve 274 also prevents fluid drips when the patient supply set 40 is removed.

The outlet selector valve 280 comprises a unitary outlet selector valve body 282 with an actuator interface head 284 and a depending valve stem 286 that terminates in a rounded or tapered bottom edge or end 288. Suitable material choices for the outlet selector valve body 282 include, but are not limited to: polyethylene (plain and fiber reinforced), polypropylene, nylon (including fiber reinforced), Ultem® PEI (polyetherimide), polycarbonate (plain and with silicone or siloxane), and like materials. The valve stem 286 defines a 90° flow passage 290 which tapers smoothly to the bottom edge or end 288 of the valve stem 286. The "bell" shape of the flow passage 290 which tapers to the rounded bottom end 288 of the valve stem 286 minimizes the potential for air bubbles to become trapped below the valve stem 286. The flow passage terminates 290 at one side of the valve stem 286 to define an outlet port 291 for fluid communication with the patient outlet port 270 and the waste outlet port 272. The actuator interface head 284 of the outlet selector valve body 282 is adapted to interface with a valve actuator, described herein, associated with the drive and actuating system 400 which operates the pump 10. The valve actuator controls operation of the outlet selector valve 280 to place the valve stem 286 in orientations at least to: (1) place the flow passage 290 in fluid communication with the patient outlet port 270 and, thus, in fluid communication with the connecting passage 268 leading to the outlet manifold channel 244; (2) place the flow passage 290 in fluid communication with the waste outlet port 272 and, thus, in fluid communication with the connecting passage 268 leading to the outlet manifold channel 244; and (3) place the flow passage 290 in a shut-off position or "off" position where the flow passage 290 is not aligned with either the patient outlet port 270 or the waste outlet port 272, thereby preventing fluid flow from the outlet manifold channel 244 to either outlet port 270, 272.

The actuator interface head 284 is generally T-shaped and comprises, for example, two (2) outwardly extending tabs 292 and a recessed area 294 for engagement with the valve actuator associated with the drive and actuating system 400. The T-shape of the actuator interface head 284 allows the outlet selector valve body 282 to slide into engagement with the valve actuator and also "keys" the outlet selector valve body 282 so that it may be engaged by the valve actuator in only one particular orientation. This interface between the actuator interface head 284 and the valve actuator of the drive and actuating system 400 also prevents the outlet selector valve body 282 from being ejected upward from the outlet selector valve cylinder 264 on the manifold plate 230 under high operating pressure.

Additionally, the outlet selector valve 280 comprises a rear or proximal pressure sensing port 296 defined in the outlet selector valve cylinder 264 supporting the outlet selector valve body 282 that supports a pressure sensing diaphragm 298, which interfaces with the drive and actuating system 400 so that fluid pressure in the valve bore 266 may be measured. The pressure sensing diaphragm 298 is a thin polyurethane (and like polymeric materials) diaphragm that is used to measure the fluid pressure in the outlet manifold channel 244. The pressure sensing diaphragm 298 is desirably overmolded into the pressure sensing port 296 and seals the port 296 while transferring the fluid pressure within the pressure sensing port 296 to its exterior surface. The pressure sensing diaphragm 298 allows the pressure in the outlet manifold channel 244, which is connected to the valve bore 266 via the connecting passage 268, to be measured at any time, not just when injecting fluid into a patient. As one example, during fluid priming or flushing operations, the control system 800 can monitor the pressure in the outlet manifold channel 244 and determine if the waste collection tube set 46 is blocked or kinked. A load cell or like device, provided as part of the drive and actuating system 400, interfaces with the diaphragm 298 to measure the fluid pressure through the diaphragm 298, as described herein in connection with the drive and actuating system 400.

As noted previously, the waste collection system 44 is connected to the waste outlet port 272 on the outlet selector valve cylinder 264 on the manifold plate 230 and is used to collect and store waste fluids. In particular, the waste collection tube set 46 is connected to the waste outlet port 272 to conduct waste fluids to the waste collection container 48 when the outlet selector valve 280 is actuated to place the flow passage 290 in fluid communication with the waste outlet port 272.

Figure 25A:
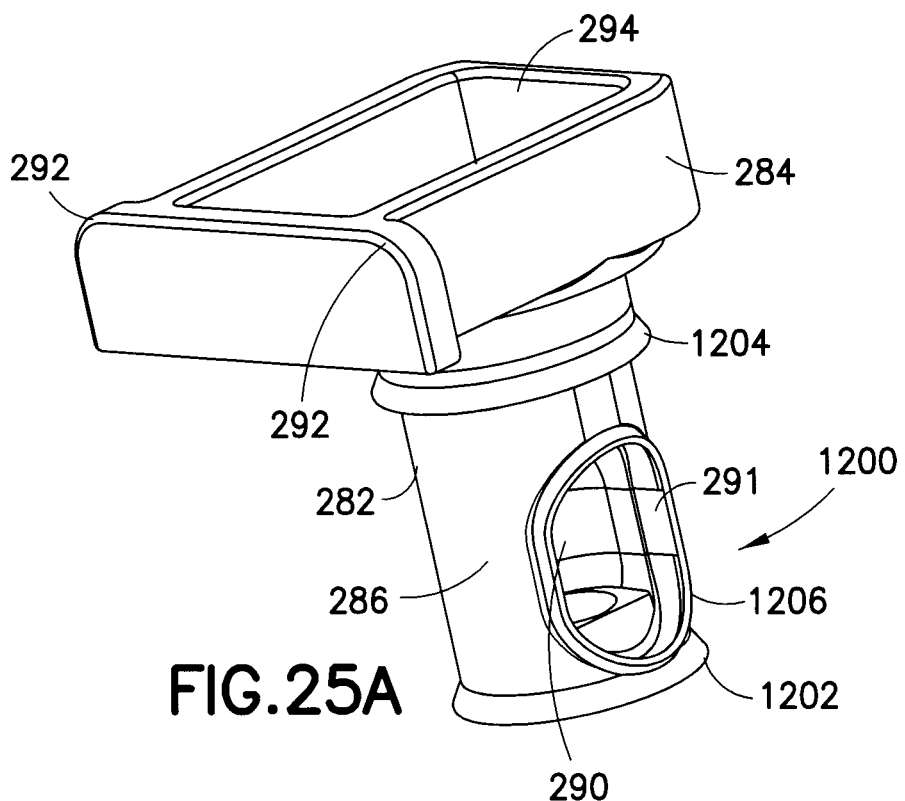
FIGS. 25A-25Q illustrate additional embodiments of the outlet selector valve wherein the outlet selector valve body is embodiment with different sealing arrangements.
Figure 25B:
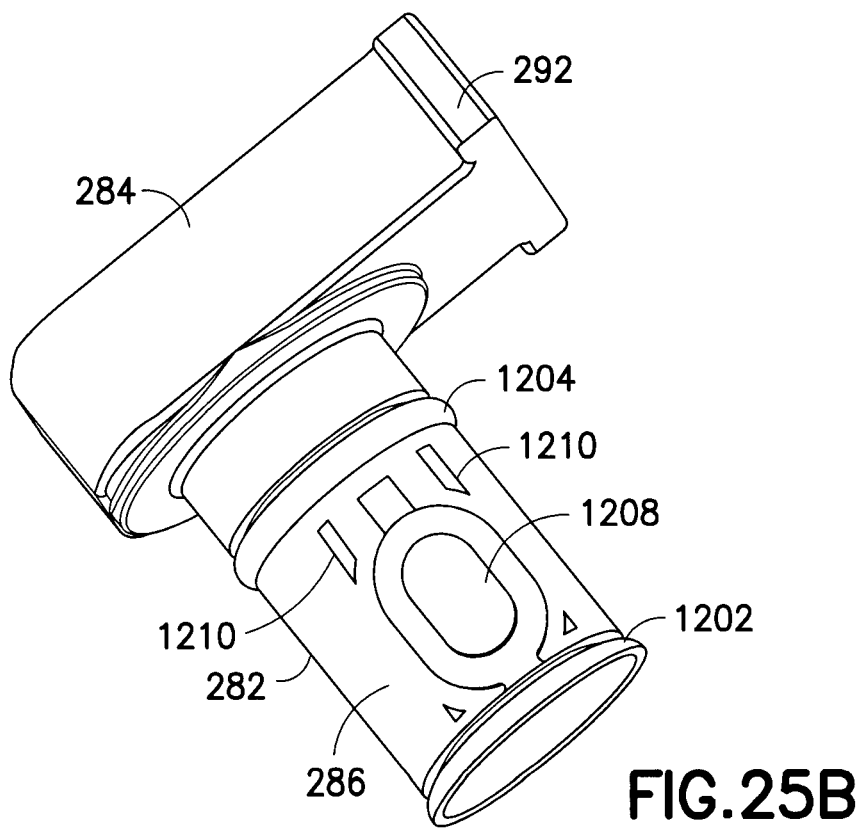
Figure 25C:
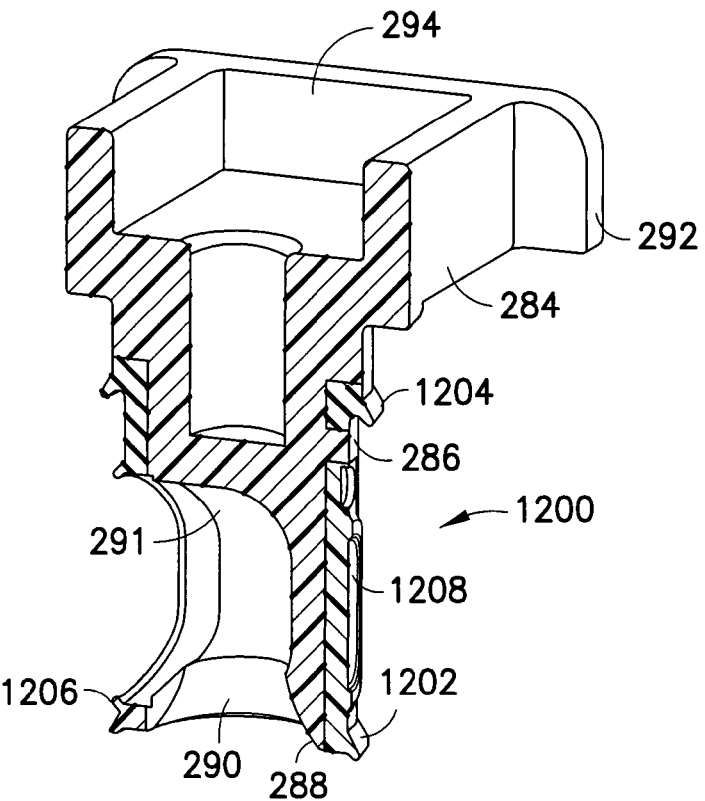
Figure 25D:
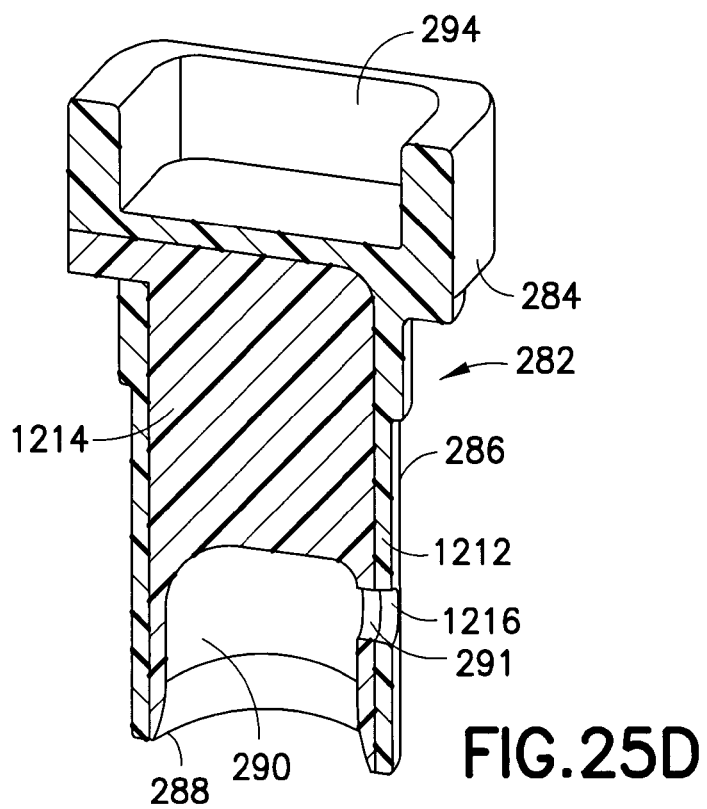
Figure 25E:
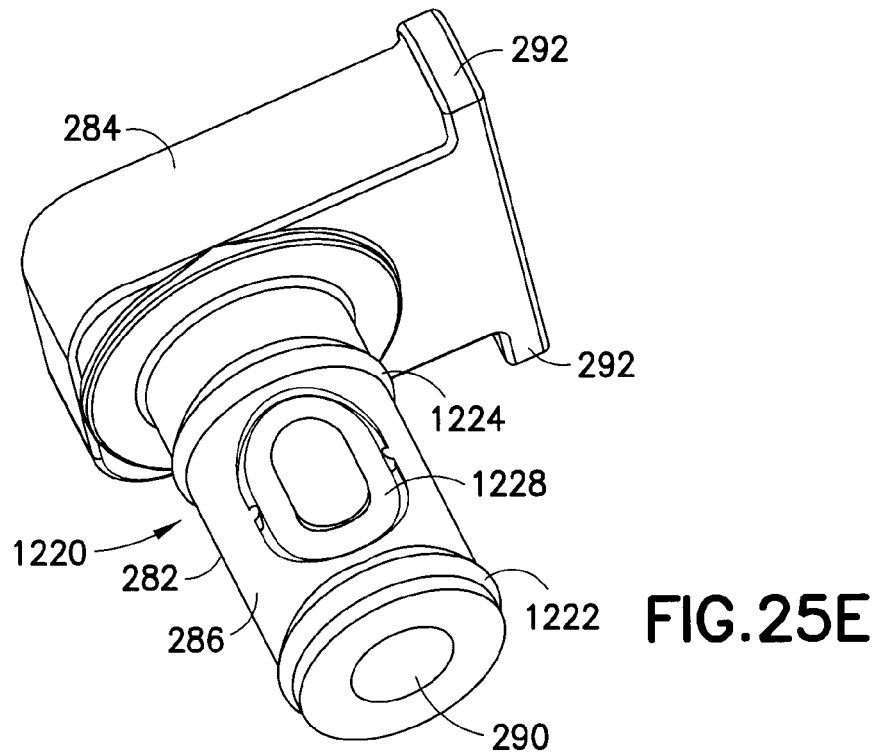
Figure 25F:
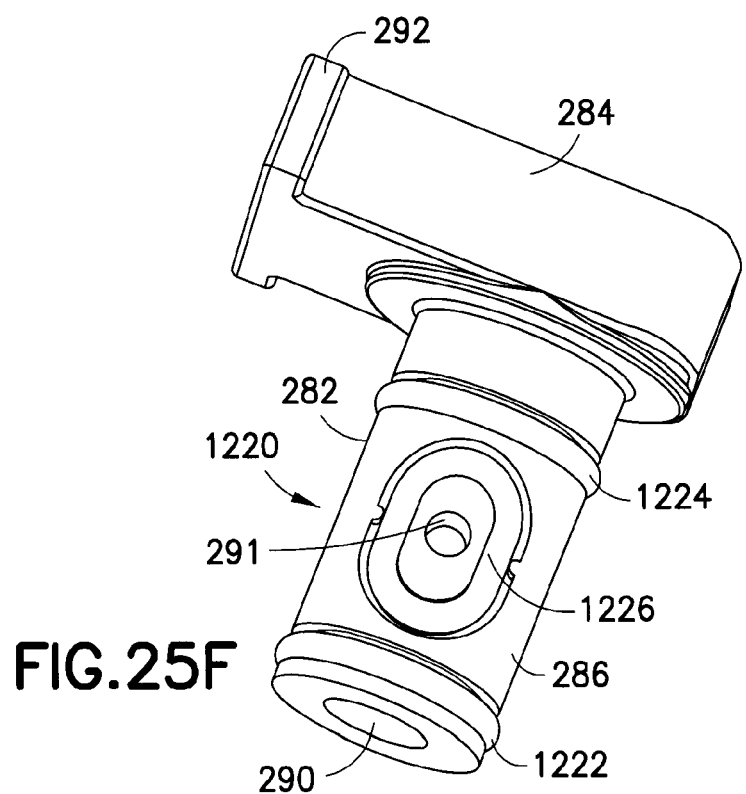
Figure 25G:
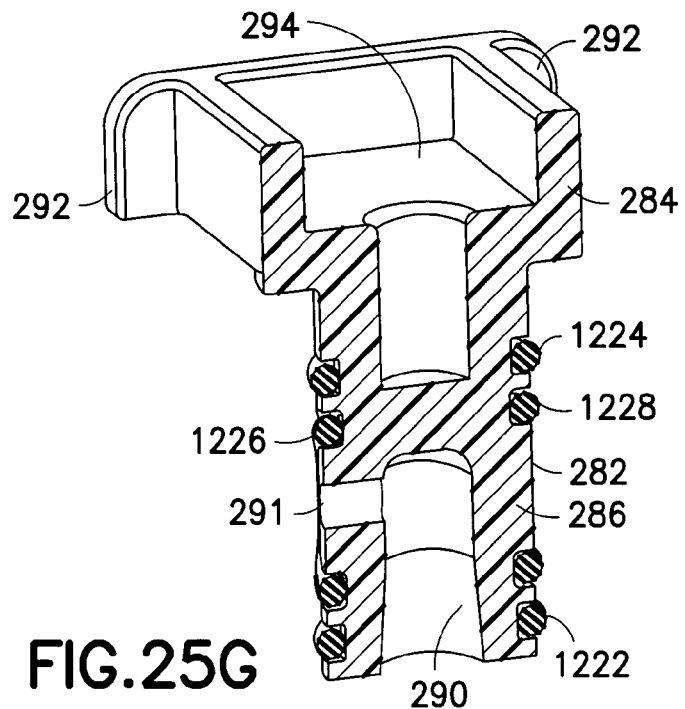
Figure 25H:
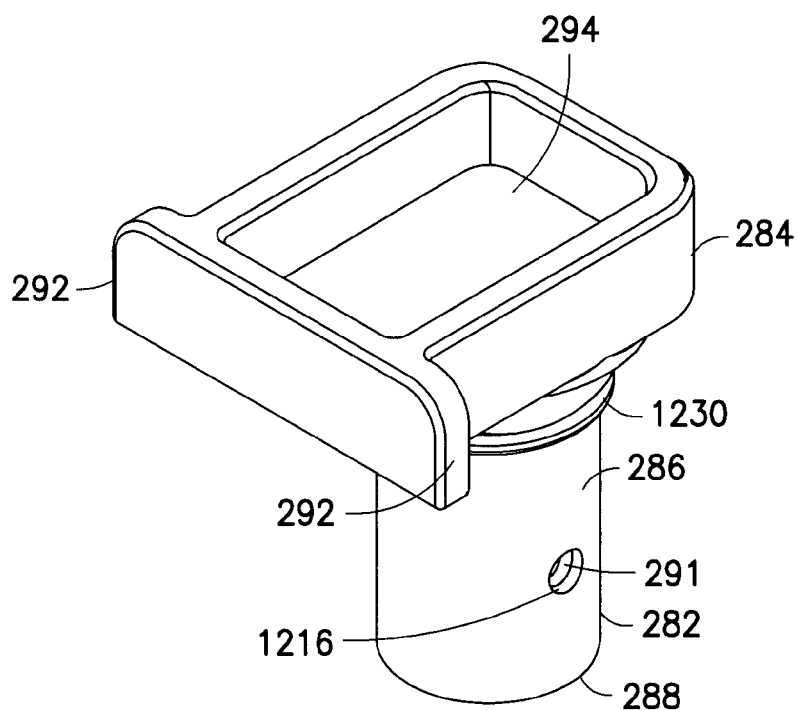
Figure 25I:
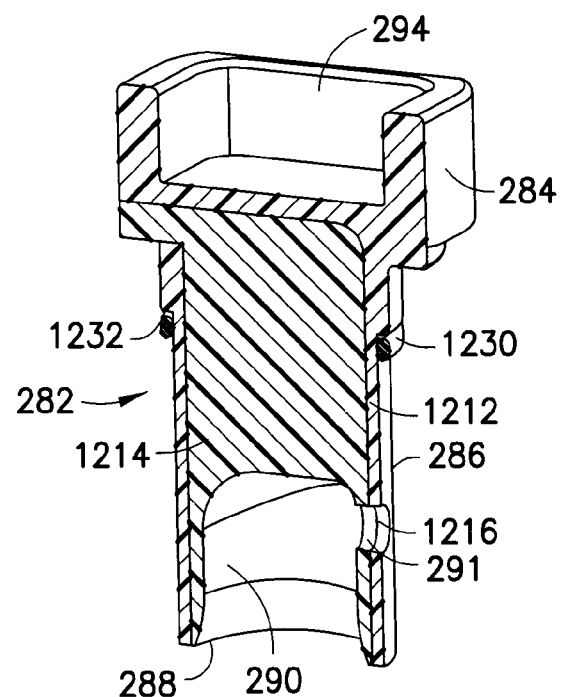
Figure 25J:
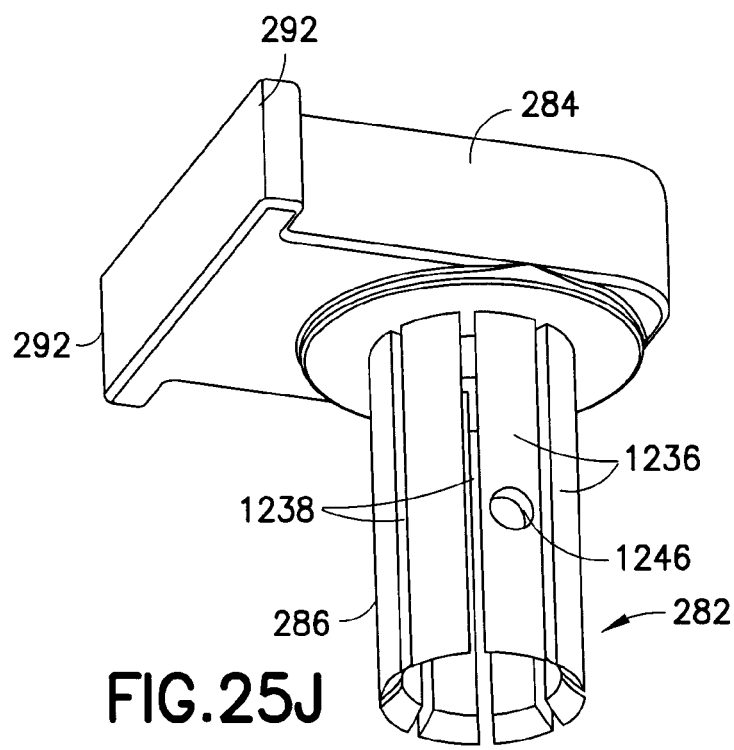
Figure 25K:
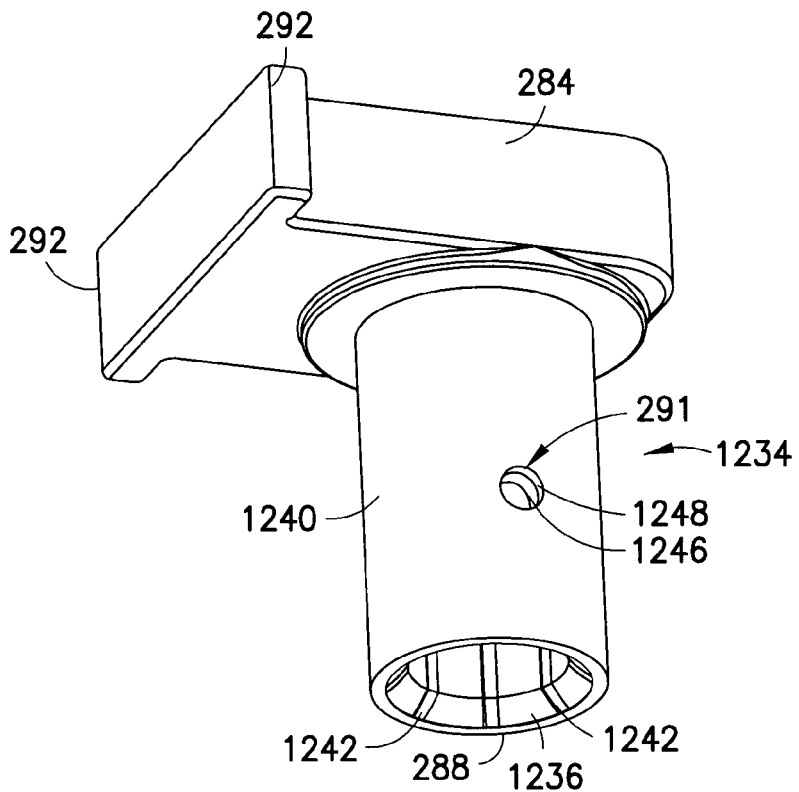
Figure 25L:
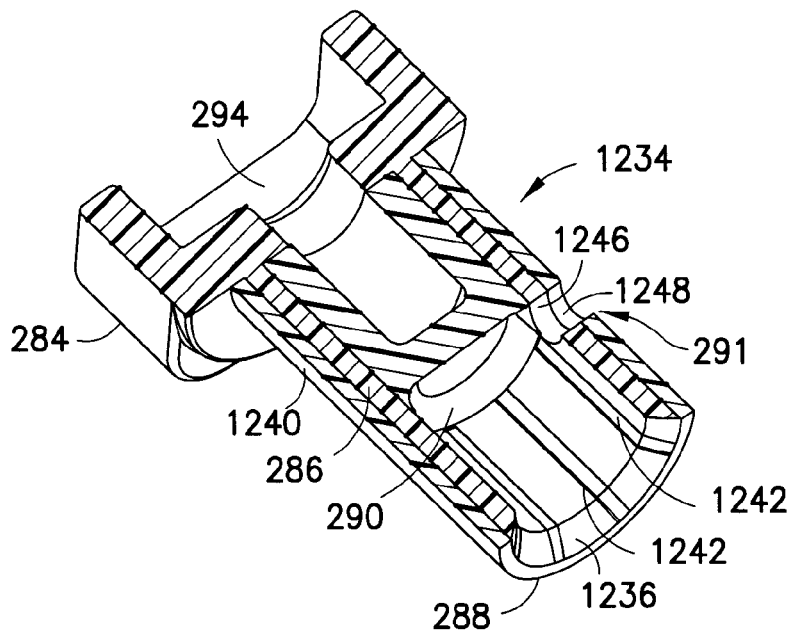
Figure 25M:
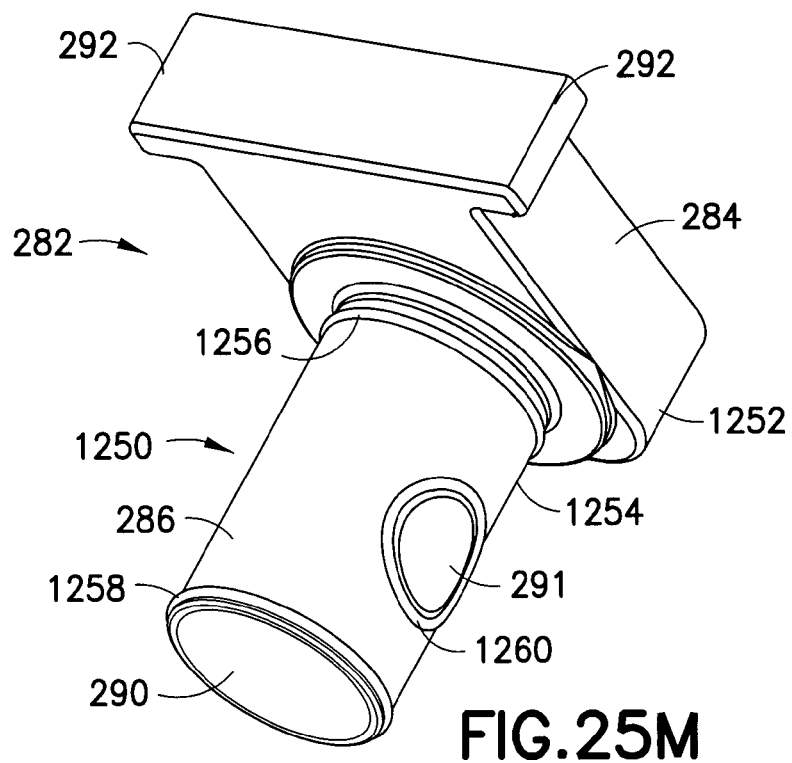
Figure 25N:
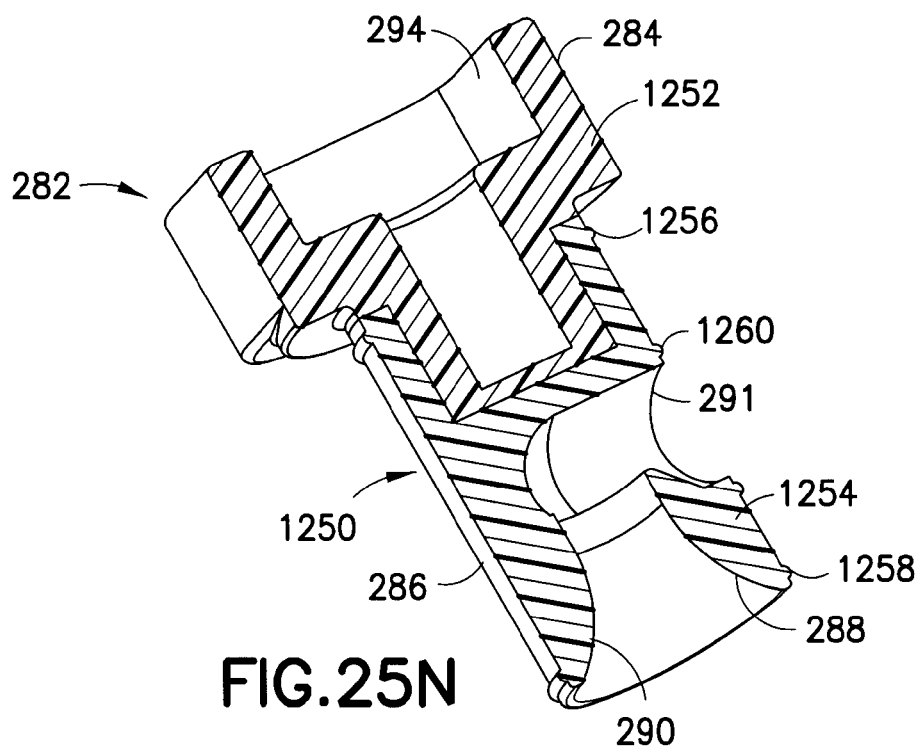
Figure 25O:
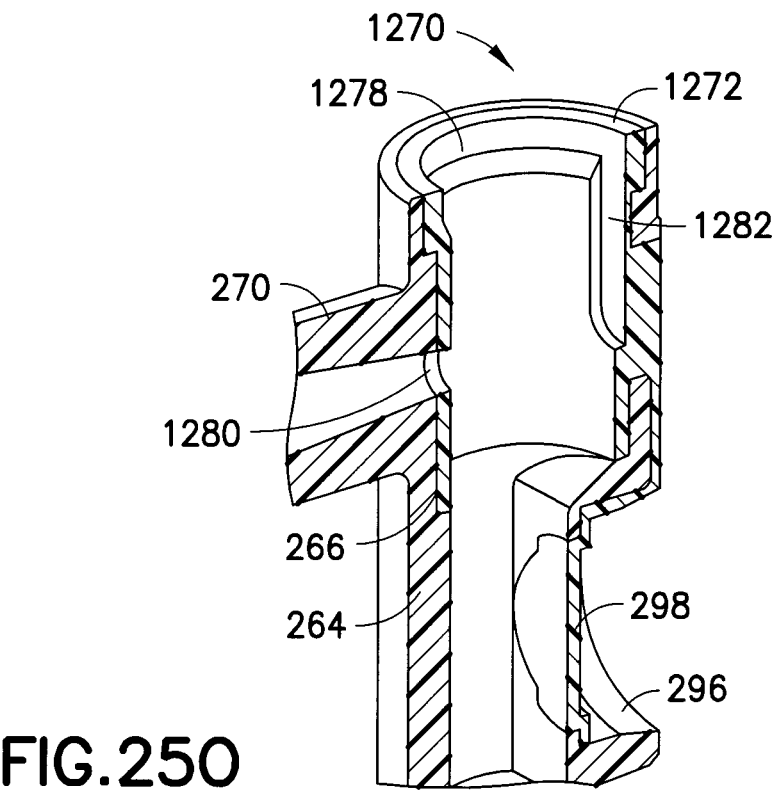
Figure 25P:
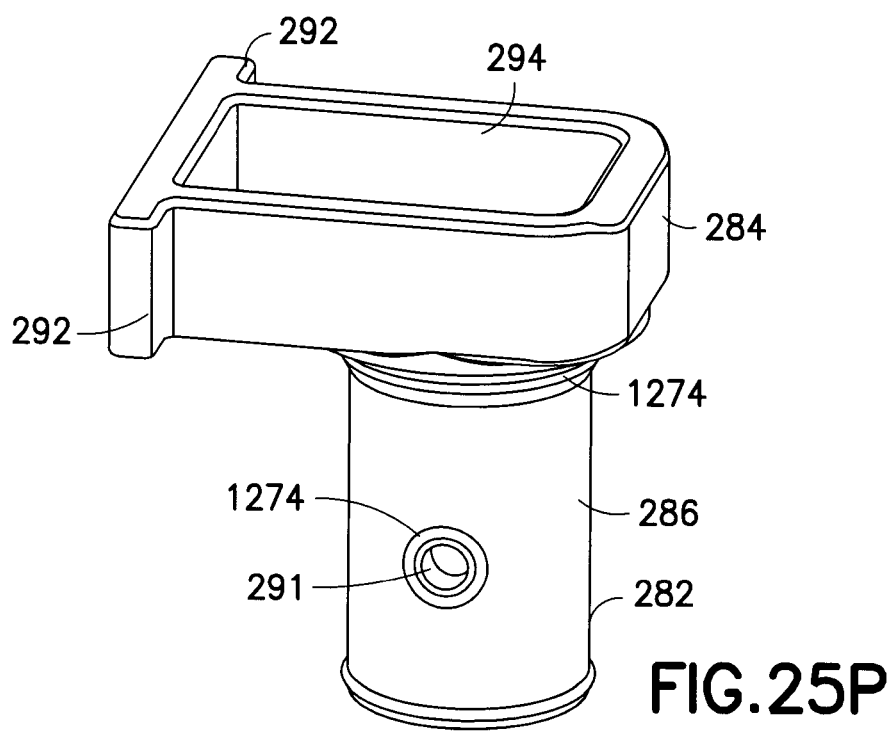
Figure 25Q:
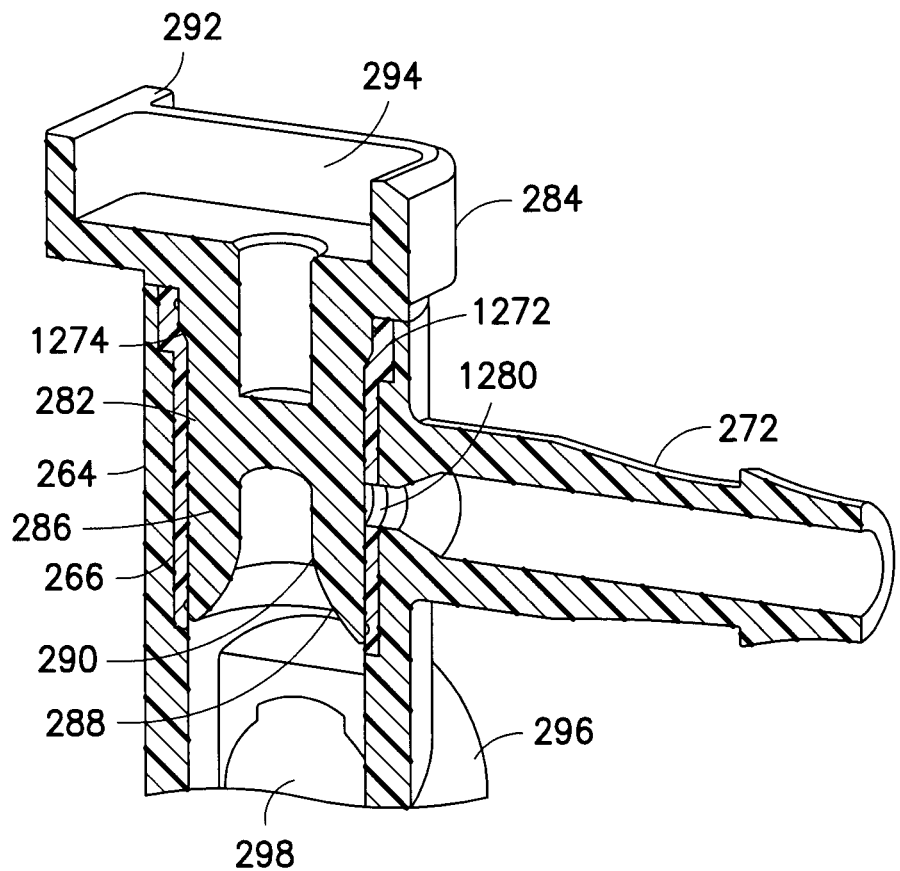
Figure 26:
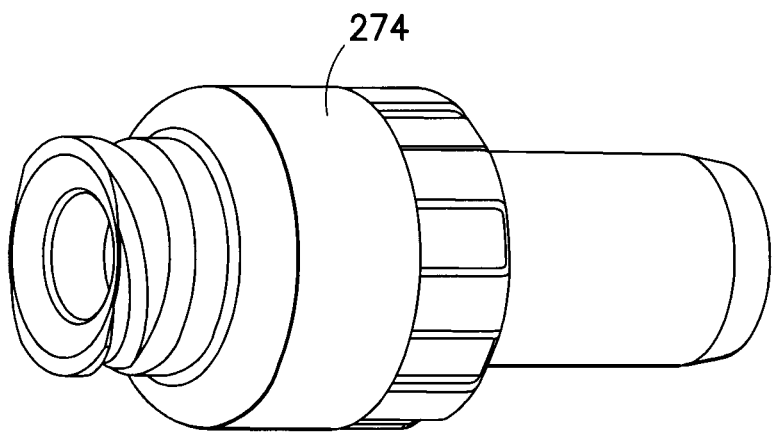
FIG. 26 is an isometric perspective view of a swabable valve for use in association with the outlet selector valve shown in FIG. 24.

FIGS. 25A-25Q illustrate additional embodiments of the outlet selector valve body 282, wherein the outlet selector valve body 282 is embodied with different sealing arrangements. In a first such example shown in FIGS. 25A-25C, a lip seal arrangement 1200 is provided which comprising compliant overmolded lips seals formed, for example, of thermoplastic material such as TPU (thermoplastic polyurethane), on the rigid valve stem 286. The compliant seals allow the valve stem 286 to be sealed in the valve bore 266 of the outlet selector valve cylinder 264 on the manifold plate 230. The valve stem 286 may be a rigid polycarbonate stem having the attached flexible thermoplastic lip seal arrangement 1200. The lip seal arrangement 1200 comprises a lower lip seal 1202 that provides a compliant seal between a lower portion of the valve stem 286 and the valve bore 266 and centers the valve stem 286 within the valve bore 266. Additionally, the lip seal arrangement 1200 comprises an upper lip seal 1204 that prevents ingress of foreign particles into the valve bore 266 and prevents fluid from exiting the valve bore 266 if any of the other lip seals leak. Further, the lip seal arrangement 1200 comprises a port lip seal 1206 that surrounds the outlet port 291 defined by the flow passage 290 on the sidewall of the valve stem 286 and provides a compliant seal between the sidewall of the valve stem 286 and the valve bore 266 of the outlet selector valve cylinder 264 on the manifold plate 230. Moreover, the lip seal arrangement 1200 comprises an isolation seal 1208 that is located on the valve stem 286 at a position approximately 180° opposite from the port lip seal 1206. The isolation seal 1208 is used to isolate the patient outlet port 270 from the waste outlet port 272 when the valve stem 286 is in the "off" position, wherein each of these ports are isolated from one another and the flow passage 290. The geometry of the lip seals 1202, 1204, 1206 provide a higher level of sealing force when high pressure fluid is in contact with the seals (e.g., the seals are hydraulically energized).

The flow passage 290 has an inlet at the bottom of the valve stem 286 and is always connected to the outlet manifold channel 244, as described previously The outlet port 291 is located on the sidewall of the valve stem 286 and may be rotated to direct flow to either the patient outlet port 270 or the waste outlet port 272. The shape of the flow passage 290 minimizes the potential for trapping air bubbles, as described previously. Additionally, as the outlet port 291 is at a higher elevation than the inlet to the flow passage 290, there is a natural tendency for air bubbles to rise to the selected outlet port, the patient outlet port 270 or the waste outlet port 272, and be ejected typically from the outlet selector valve 280 via the waste outlet port 272.

The diameter of the lip seals 1202, 1204, 1206 is slightly larger than the diameter of the valve bore 266 so that when the valve stem 286 is assembled into the valve bore 266, the lip seals 1202, 1204, 1206 are slightly compressed against the wall of the valve bore 266. At low fluid pressures, the initial compression from the assembly process is sufficient to seal against low fluid pressures and, because the seals are compliant and easily deformed, the sealing force (and frictional torque) between the valve stem 286 and the valve bore 266 of the outlet selector valve cylinder 264 is low. At high fluid pressures, the lip seals 1202, 1204, 1206 become "hydraulically energized." The hydraulic pressure of the fluid against the lip seals 1202, 1204, 1206 creates an additional sealing force. This additional force presses the lip seals 1202, 1204, 1206 more firmly against the outlet selector valve cylinder 264 as the pressure increases, and higher pressures result in greater sealing forces without requiring a large degree of initial compression.

When the valve stem 286 is positioned so that the flow passage 290 is in fluid connection with the patient outlet port 270, the lower lip seal 1202 prevents high pressure fluid from entering the annular space around the valve stem 286. The port lip seal 1206 directs fluid from the center of the flow passage 290 to the patient outlet port 270 and prevents high pressure fluid from entering the annular space around the valve stem 286. Because there is no port in the outlet selector valve cylinder 264 that is directly across from the patient outlet port 270, the isolation seal 1208 is not required when the valve stem 286 is in this position. As fluid is ejected through the outlet port 291, there is a hydraulic reaction force that tends to push the valve stem 286 away from the patient outlet port 270. Rigid support pads 1210 may be provided on the side of the valve stem 286 to resist this reaction force and prevent the lower lip seal 1202 from being deformed excessively. Under normal operating conditions, the upper lip seal 1204 is used to keep the valve stem 286 centered in the valve bore 266, and prevents fluid egress if one of the other lip seals leaks.

When the valve stem 286 is positioned so that the flow passage 290 is in fluid connection with the waste outlet port 272, the lower lip seal 1202 prevents low pressure fluid from entering the annular space around the valve stem 286. The port lip seal 1206 directs fluid from the center of the flow passage 290 to the waste outlet port 272 and prevents low pressure fluid from entering the annular space around the valve stem 286. Because there is no port in the outlet selector valve cylinder 264 that is directly across from the waste outlet port 272, the isolation seal 1208 is not required when the valve stem 286 is in this position. The patient outlet port 270 is connected to the annular space around the valve stem 286 and, because this annular space is not connected to any other port at this time, the patient outlet port 270 remains isolated from all other ports. Under normal operating conditions, the upper lip seal 1204 is used to keep the valve stem 286 centered in the valve bore 266, and prevents fluid egress if one of the other lip seals leaks.

In a second sealing example shown in FIG. 25D, the valve stem 286 is formed with a thin cylindrical wall 1212 and an elastomeric core 1214 is disposed in the thin-walled cylindrical valve stem 286. The open center of the valve stem 286 is filled with a compliant elastomeric core 1214 made from materials such TPU (thermoplastic urethane) or silicone rubber, and defines the flow passage 290 to provide a defined fluid pathway through the valve stem 286. The thin cylindrical sidewall 1212 defines an aperture 1216 connected to the outlet port 291 of the flow passage 290. The upper portion of the valve body 282 maintains the features described previously for interfacing with the drive and actuating system 400. The thin cylindrical wall 1212 of the valve stem 286 and forming the lower portion of the valve body 282 may be easily deformed to allow the outside diameter of the valve stem 286 to conform to and seal against the valve bore 266 of the outlet selector valve cylinder 264. The elastomeric core 1214 defines the flow passage 290, which serves to direct fluid from the inlet thereto to the outlet port 291 connected to the aperture 1216 in the valve stem 286, and the flow passage 290 maintains the features described previously for minimizing the potential for trapped air and stagnant regions in the flow path. The elastomeric core 1214 is generally soft and compliant enough that it does not significantly stiffen the cylindrical wall or walls 1212 of the valve stem 286. When the valve stem 286 is subjected to internal pressure, the cylindrical sidewall 1212 of the valve stem 286 expands outward to increase the sealing force between the outer diameter of the valve stem 286 and the valve bore 266.

In a third sealing example shown in FIGS. 25E-25G, a sealing arrangement 1220 similar to sealing arrangement 1200 described previously is provided but now comprises a plurality of o-ring seals on the valve stem 286, which is a rigid polycarbonate stem and has the same general structure as described previously in connection with FIGS. 24A-24B and FIGS. 25A-25C. In one embodiment of the sealing arrangement 1220, four (4) o-ring seals 1222-1228 are installed in grooves molded in the valve stem 286. A first o-ring seal 1222 provides a compliant seal between the lower portion of the valve stem 286 and the valve bore 266 and centers the valve stem 286 within the valve bore 266. A second o-ring seal 1224 prevents the ingress of foreign particles into the valve bore 266 and prevents fluid from exiting the valve bore 266 if any of the other seals leak. A third o-ring seal 1226 surrounds the outlet port 291 in the sidewall of the valve stem 286 and provides a compliant seal between the valve stem 286 and valve bore 266 of the outlet selector valve cylinder 264. A fourth isolation o-ring seal 1228 is located on the valve stem approximately 180° opposite from the third o-ring seal 1226 surrounding the outlet port 291. The isolation o-ring seal 1228 is used to isolate the patient outlet port 270 from the waste outlet port 272 when the valve stem 286 is in the "off" position. The o-ring seals 1222-1228 may be made of any type of suitable elastomeric material including polyurethane, silicone or EPDM.

In a hybrid embodiment shown in FIGS. 25H-25I, the valve stem 286, as shown in FIG. 25D having a thin cylindrical wall 1212 and an elastomeric core 1214 disposed in the thin-walled cylindrical valve stem 286, is combined with a sealing o-ring 1230 disposed in a groove in or seated against a ledge 1232 defined by the upper portion of the valve stem 286. The o-ring 1230 may be made of silicone rubber, polyurethane, EPDM or other suitable elastomer. Any fluid that may leak between the valve stem 286 and the outlet selector valve cylinder 264 is prevented from leaking outside of the outlet selector valve cylinder 264 by the upper o-ring 1230 at the top of the valve stem 286.

In another sealing arrangement 1234 as shown in FIGS. 25J-25L, the valve stem 286 is segmented to define a plurality of finger elements 1236 with spaces 1238 in-between, and the valve stem 286 is enclosed by a cooperating sleeve element 1240. Each finger element 1236 acts like a cantilevered leaf spring that is biased to expand outward against the wall of the valve bore 266. The finger elements 1236 may be molded in a cylindrical configuration, as shown, or may be molded in a conical formation such that the finger elements 1236 compress inward to initially install the valve stem 286 into the valve bore 266. In either configuration, the finger elements 1236 provide a radial outward force against the valve bore 266 to improve sealing.

The sleeve element 1240 serves as the sealing surface against the wall of the valve bore 266 and may be made of TPU and other suitable elastomeric materials. The sleeve element 1240 comprises internal, axially-extending radial ridges 1242 that are trapped in the spaces 1238 in-between the finger elements 1236, forcing the finger elements apart 1236 and radially-outward. The sleeve element 1240 further defines the upper end of the flow passage 290 and corresponding apertures 1246, 1248 are defined in the valve stem 286 and the sleeve element 1240, respectively, to define the outlet port 291 of the flow passage 290. In use with low fluid pressures, the spring action of the finger elements 1236 presses the sleeve element 1240 radially outward until it is sealed against the wall of the valve bore 266. The radial ridges 1242 that are trapped in the spaces 1238 in-between the finger elements 1236 may also help to force the finger elements 1236 circumferentially apart, increasing the sealing force. In use with high fluid pressures, fluid pressure inside of the flow passage 290 in the valve stem 286 also helps to generate a radial-outward force on the finger elements 1236 and the sleeve element 1240, increasing the sealing force against the wall of the valve bore 266.

In another sealing arrangement 1250 as shown in FIGS. 25M-25N, the valve body 282 is of composite form, namely having an upper portion 1252 formed of a stiff polycarbonate material or like material, and a compliant lower portion 1254 formed of TPU or other suitable elastomeric materials. The lower portion 1254 generally forms the valve stem 286 while the upper portion 1252 defines the features described previously for interfacing with the drive and actuating system 400. The lower portion 1254 generally forming the valve stem 286 has integral upper and lower sealing beads 1256, 1258 to seal against the wall of the valve bore 266 and another sealing bead 1260 to form a seal about the outlet port 291 of the flow passage 290 to create sufficient sealing force around this port. The material used for the lower portion 1254 generally forming the valve stem 286 may have a higher durometer (and higher stiffness) than the material used for the various fluid seals in the preceding sealing arrangements described in connection with FIGS. 25A-25L.

In yet another sealing arrangement 1270 as shown in FIGS. 25O-25Q, a sleeve or liner 1272 formed of compliant sealing material is seated within the valve bore 266 of the outlet selector valve cylinder 264 instead of on the valve stem 286. The valve body 282 has the same general configuration as described previously in connection with FIGS. 24A-24B, with the addition of an upper ridge or ledge or sealing bead 1274 formed below the actuator interface head 284 and an exterior raised bead 1276 around the outlet port 291 of the flow passage 290 in the valve stem 286 to ensure suitable sealing characteristics in the valve bore 266. The valve body 282 may be made of a rigid material such as polycarbonate. The elastomeric sleeve or liner 1272 may be made of TPU or a similar elastomer. The liner 1272 defines an upper recessed area 1278 to receive the ridge or ledge and/or sealing bead 1274 provided on the valve stem 286, and defines respective side apertures 1280 to provide fluid communication with the outlet port 291 of the flow passage 290 in the valve stem 286, and the patient outlet port 270 and the waste outlet port 272. The liner 1272 may include one or more axial recessed areas 1282 to prevent contact with the exterior raised bead 1276 around the outlet port 291 of the flow passage 290, and this axial recessed area 1282 is a suitable location to orient the raised bead 1276 during shipment or storage of the pump device 10. By placing the raised bead 1276 in the recessed area 1282 during shipping and storage, the liner 1272 is less likely to experience compression set or creep which could cause a reduction in sealing characteristics. It may also be desirable to integrate the pressure sensing diaphragm 298 as part of the liner 1272 to consolidate components.

Figure 27:
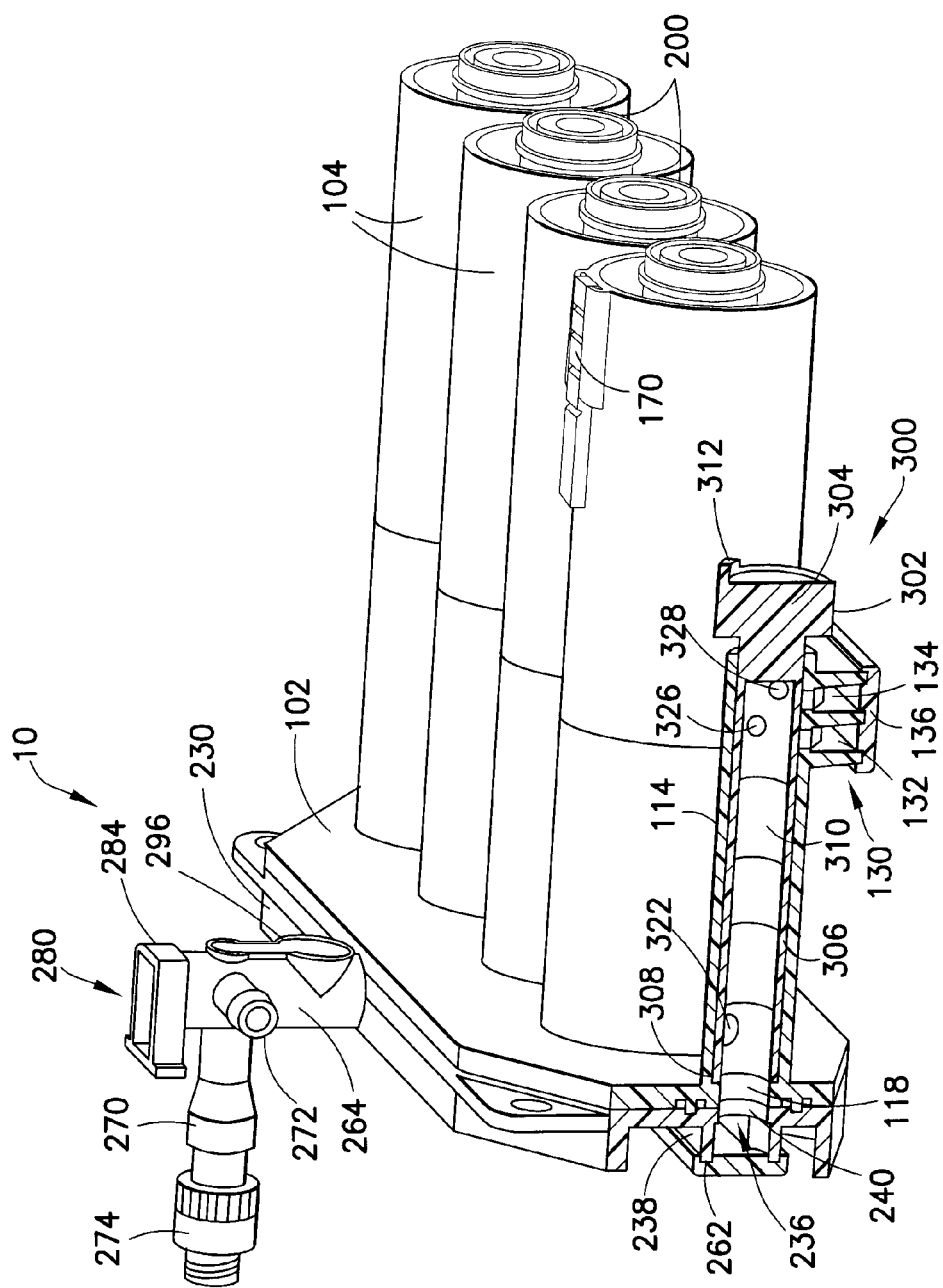
FIG. 27 is a cross-sectional perspective view taken along line 27-27 in FIG. 3.

Referring further to FIGS. 27-29, as noted in the foregoing, an inlet selector valve 300 is provided in each of the inlet selector valve cylinders 114. Each inlet selector valve cylinder 114 defines a cylindrical chamber 116 that accepts the inlet selector valve 300 which is rotationally operable within the inlet selector valve cylinder 114. The drive and actuating system 400 which operates the pump 10 also desirably includes separate valve actuators that operate the respective inlet selector valves 300. The respective inlet selector valves 300 each comprise an inlet selector valve body 302 with an actuator interface head 304 and an elongated and hollow valve stem 306 that terminates in a distal edge or end 308 which abuts (or is disposed in proximity to) the front plate 102 and extends about the front or distal end opening 118 formed in the front plate 102. The valve stem 306 defines an axial bore or passage 310. The actuator interface head 304 of the inlet selector valve body 302 is adapted to interface with an inlet selector valve actuator, described herein, associated with the drive and actuating system 400. The actuator interface head 304 may be generally round or circular in shape and comprises a proximally extending tab 312, or a plurality of such tabs 312, and an interface engagement member 314 formed internally within the actuator interface head 304. The proximally extending tab 312 and internal engagement member 314 form interfacing features for engagement with the inlet selector valve actuator associated with the drive and actuating system 400. For safety purposes, it is desirable for the valve stem 306 to be engaged to the drive and actuating system 400 in one particular angular orientation. If the valve stem 306 can be installed in more than one angular orientation, it could be possible to deliver the wrong type of fluid.

The valve stem 306 defines a series of radial inlet openings or ports 320 that connect to the central or axial passage 310. The radial inlet openings or ports 320 are located at different angular locations around the valve stem 306 and at different axial locations along the valve stem 306. The radial inlet openings or ports 320 include a first inlet port 322 for placing the first inlet port 122 on the receiving inlet selector valve cylinder 114 in fluid communication with the axial passage 310 in the valve stem 306, a second inlet port 324 for placing the second inlet port 124 on the receiving inlet selector valve cylinder 114 in fluid communication with the axial passage 310 in the valve stem 306, and third and fourth inlet ports 326, 328 positioned to allow fluid communication between either of the saline channels 132, 134 of the saline manifold 130 and the axial passage 310 in the valve stem 306. The respective inlet ports 322, 324, 326, 328 are defined at different angular locations around the valve stem 306 and are positioned at spaced axial locations along the valve stem 306 so that, at most, only one of these inlet ports 322-328 permits fluid communication with the axial passage 310 in the valve stem 306 at any given time, and thereby permit fluid flow into the valve stem 306 from the first inlet port 122, second inlet ports 124, or one of the saline channels 132, 134. In particular, the respective inlet ports 322-328 are defined at different angular locations around the valve stem 306 and spaced axial locations along the valve stem 306 so that only one of the first and second inlet ports 122, 124 and the saline channels 132, 134 of the saline manifold 130 is in fluid communication with the axial bore or passage 310 in the valve stem 306 at any given time. Accordingly, if the first inlet port 322 is in fluid communication with the first inlet port 122, the second inlet port 124 is blocked by the valve stem 306 to fluid flow, as are both of the saline channels 132, 134 of the saline manifold 130. Similarly, if the second inlet port 324 is in fluid communication with the second inlet port 124, the first inlet port 122 is blocked by the valve stem 306 to fluid flow, as are both of the saline channels 132, 134 of the saline manifold 130. If the third inlet port 326 is aligned with the first or forward saline channel 132, the first and second inlet ports 122, 124 are blocked to fluid flow by the valve stem 306, as is the second or rearmost saline channel 134. Further, if the fourth inlet port 328 is aligned with the second or rearmost saline channel 134, the first and second inlet ports 122, 124 are blocked to fluid flow by the valve stem 306, as is the first or forward saline channel 132.

In the depicted arrangement, the inlet ports 322-328 are axially spaced along the valve stem 306, with the first inlet port 322 located near the distal end 308 of the valve stem 306 and the last or fourth inlet port 328 located near the actuator interface head 304. As explained previously, the foregoing axial order of the ports 122-126 and corresponding ports 322-328 is desirable for air management issues. In particular, in the pump 10 in the accompanying figures, the "left" saline source S1 is connected to the left saline port 126 so that the rearmost saline channel 134 is filled first with saline for priming purposes. The rearmost or fourth inlet port 334 in the valve stem 306 is located in the rearmost position to establish fluid communication with the rearmost saline channel 134 to allow the entire inlet selector valve 300 to be primed with saline from the far rear or proximal end. If this "saline" port was located in any other "forward" position, it would not be possible to remove all of the air from the length of the inlet selector valve 300 as air would be trapped behind this position. It is noted that the distance from the saline inlet port 328 and the proximal or rear end of axial passage 310 adjacent the actuator interface head 304 is minimized as much as possible to limit the potential for air bubbles to be trapped behind this inlet port 328 and the end of the axial passage 310.

Figure 28A:
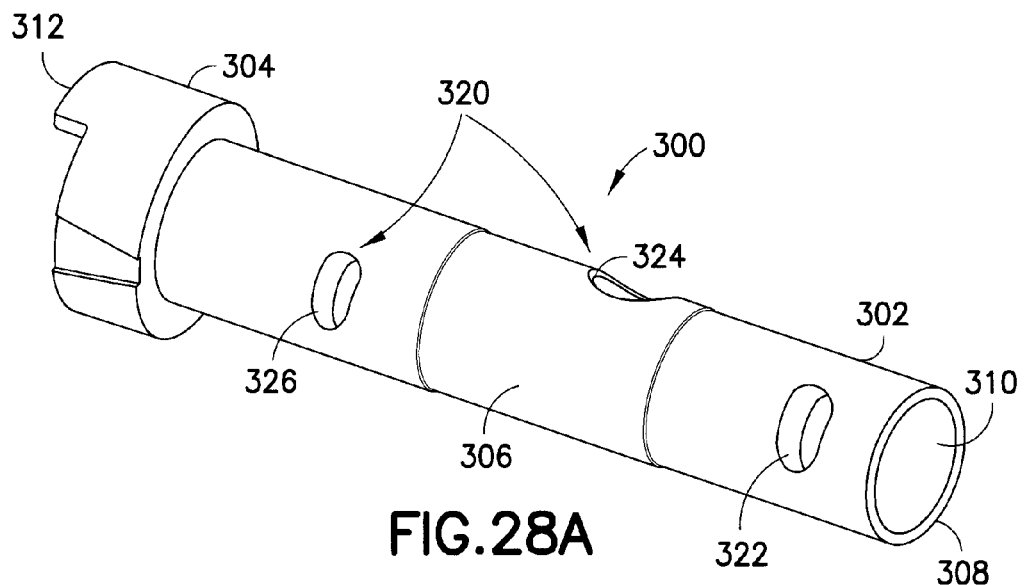
FIG. 28A is an isometric front perspective view of an inlet selector valve stem used in the fluid pump device shown in FIG. 2.
Figure 28B:
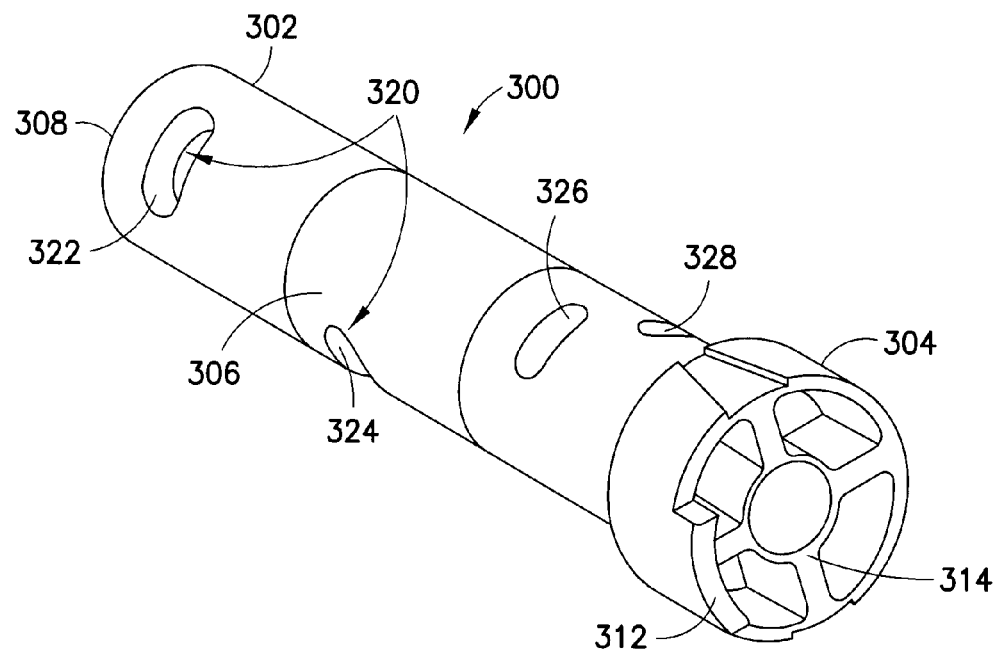
FIG. 28B is an isometric rear perspective view of the inlet selector valve stem used in the fluid pump device shown in FIG. 2.

Referring specifically to FIGS. 28C-28D, the inlet selector valve 300 may be provided with a sealing arrangement 1300 on the valve stem 306. The sealing arrangement 1300 uses a series of elastomeric seals, which are similar to o-rings, to seal the valve stem 306 in the inlet selector valve cylinder 114. Each of the four inlet ports 322-328 is sealed in two (2) ways according the illustrated embodiment. First, a circular sealing bead 1302 is provided around each of the inlet ports 322-328 in the valve stem 306, and this seal prevents any fluid that may be in the central or axial passage 310 of the valve stem 306 from moving into the space between the valve stem 306 and the inlet selector valve cylinder 114. Secondly, two (2) circumferential sealing rings 1304, 1306 are axially located on either side of each inlet port 322-328, and are used to isolate the inlet ports 322-328 in the inlet selector valve cylinder 114. These circumferential seal rings 1304, 1306 prevent fluids connected to the first inlet port 122, second inlet port 124, or one of the saline channels 132, 134 from mixing with one another in the inlet selector valve cylinder 114. Each of the foregoing seals 1302, 1304, 1306 is made of TPU (thermoplastic polyurethane) or like elastomers and is attached to the rigid valve stem 306 during an overmolding process. The valve stem 306 may be made of polycarbonate and like materials. Each seal 1302, 1304, 1306 has a "D-shaped" cross-section which seals against the inlet selector valve cylinder 114.

Figure 28E:
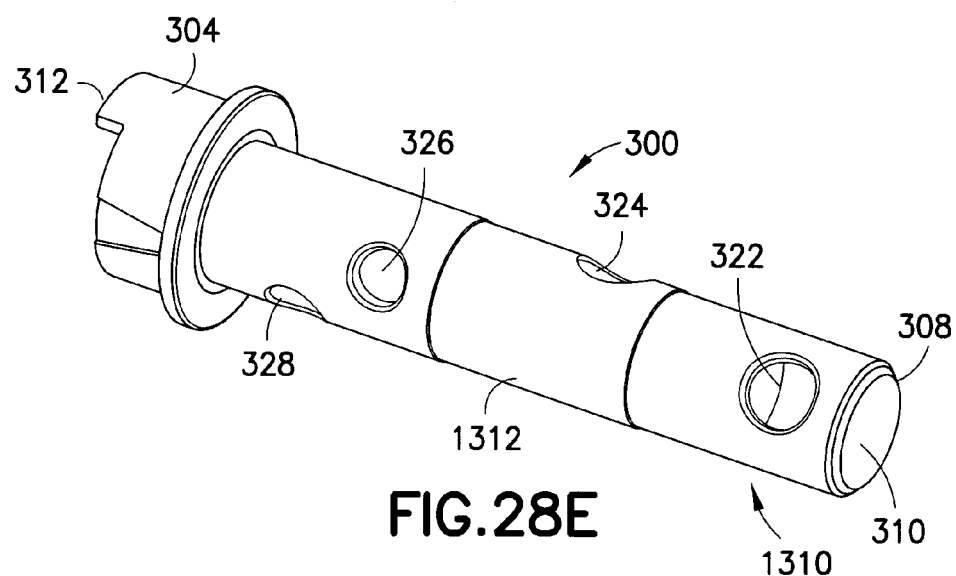
FIGS. 28E-28F are isometric perspective view of the inlet selector valve stem shown in FIGS. 28A-28B and further comprising a second exemplary sealing arrangement.
Figure 28F:
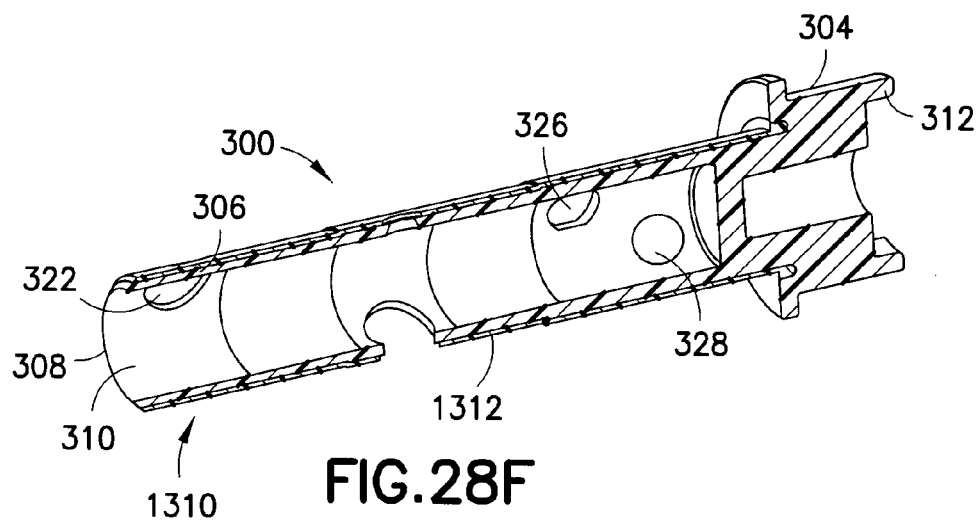

Referring to FIGS. 28E-28F, the inlet selector valve 300 may be provided with an alternative sealing arrangement 1310 on the valve stem 306. In this embodiment, a soft (TPU—thermoplastic polyurethane, or like material) sleeve 1312 is overmolded onto the rigid valve stem 306, which may be polycarbonate to provide rigidity and torsional stiffness to the valve stem 306. The overmolded sleeve 1312 provides a compliant surface to allow the valve stem 306 to seal against the against the inlet selector valve cylinder 114. The compliant surface allows the valve stem 306 to fully seal against the interior wall of the inlet selector valve cylinder 114 even if surface imperfections are present in either component.

With the foregoing radial and axial locations for the inlet ports 322-328, the inlet selector valve actuators, described herein, of the drive and actuating system 400 control operation of the right and left inlet selector valves 300 to place the valve stem 306 in an orientation to: (1) connect the first inlet port 322 with the first inlet port 122 to provide fluid communication between a first source of therapeutic or diagnostic (e.g., pharmaceutical) fluid A1, B1 contained in a connected fluid source container 30 and the corresponding inlet manifold channel 236, while the second inlet port 124 and both of the saline channels 132, 134 of the saline manifold 130 are blocked to fluid flow by the valve stem 306; (2) connect the second inlet port 324 with the second inlet port 124 to provide fluid communication between a second source of therapeutic or diagnostic (e.g., pharmaceutical) fluid A2, B2 contained in a connected fluid source container 30 and the corresponding inlet manifold channel 236, while the first inlet port 122 and both of the saline channels 132, 134 of the saline manifold 130 are blocked to fluid flow by the valve stem 306; (3) connect the third inlet port 326 with the first or forward saline channel 132 of the saline manifold 130 to connect the third inlet port 326 with the first or forward saline channel 132 of the saline manifold 130 via saline port 332 (FIG. 5B) to provide fluid communication between a second source of saline S2 contained in a connected fluid source container 30 and the corresponding inlet manifold channel 236, while the first and second inlet ports 122, 124 and the second or rear saline channel 134 of the saline manifold 130 are blocked to fluid flow by the valve stem 306; (4) connect the fourth inlet port 328 with the second or rearmost saline channel 134 of the saline manifold 130 via saline port 334 (FIG. 5B) to provide fluid communication between a first source of saline S1 contained in a connected fluid source container 30 and the corresponding inlet manifold channel 236, while the first and second inlet ports 122, 124 and the first or forward saline channel 132 of the saline manifold 130 are blocked to fluid flow by the valve stem 306; and (5) an "OFF" position wherein the valve stem 306 is in a position to block each of the first and second inlet ports 122, 124 and the first and second saline channels 132, 134, thereby preventing fluid flow from the various external fluid sources contained in the fluid source containers 30 to the corresponding inlet manifold channel 236. Thus, at least a total of five (5) different operational states are present for each of these inlet selector valves 300 in the embodiment of the pump 10 found in the accompanying figures. However, this embodiment should not be considered limiting as additional inlet ports (not shown) may be provided on the respective inlet selector valve cylinders 114, with corresponding inlet ports (not shown) being provided in the valve stem 306 of the respective inlet selector valves 300 to accommodate additional connected fluid sources as desired.

Figure 5A:
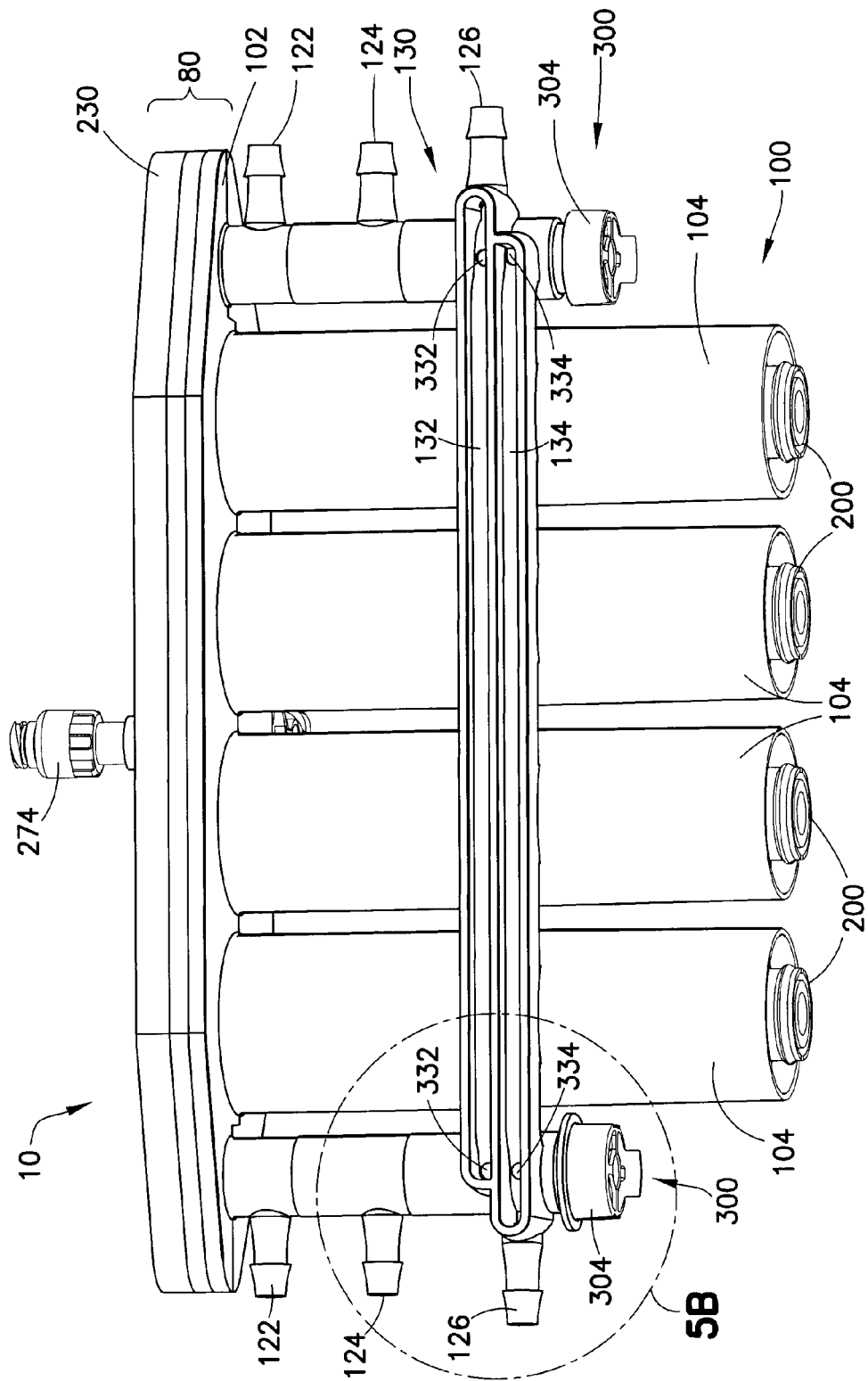
FIG. 5A is a bottom view of the fluid pump device shown in FIG. 2.
Figure 5B:
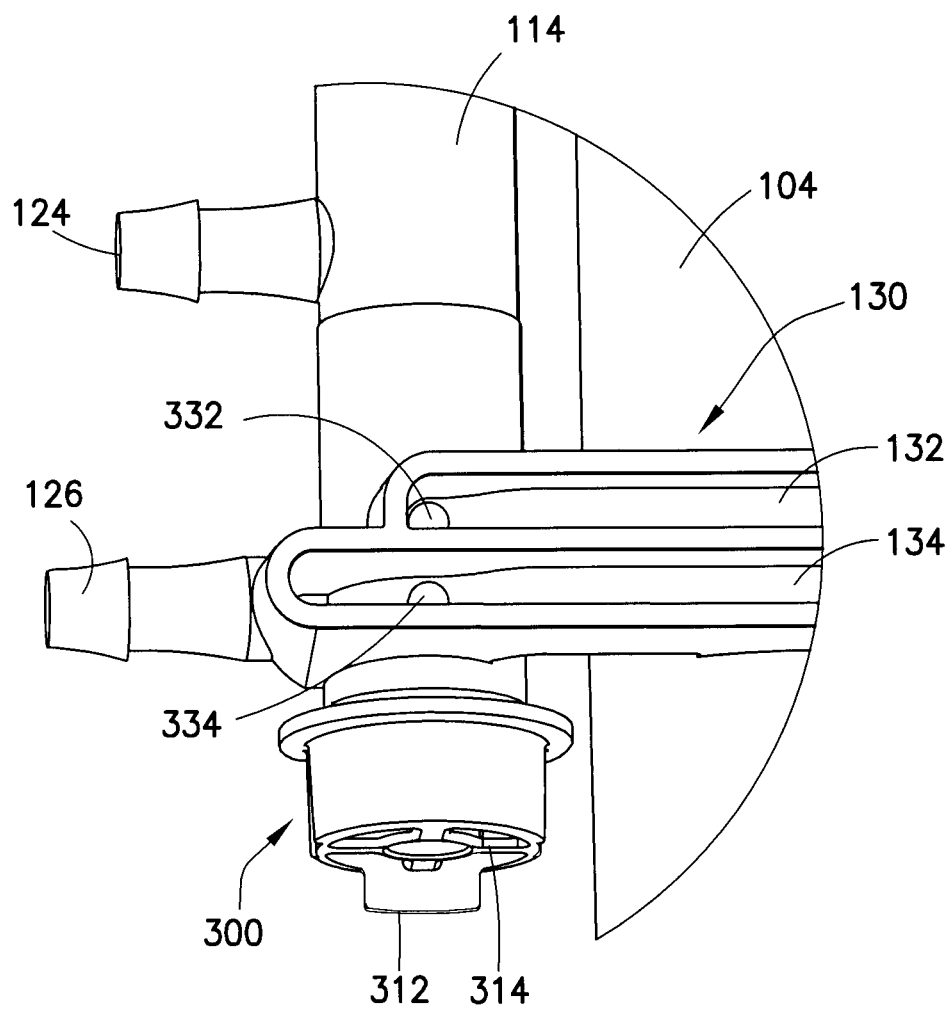
FIG. 5B is a detail view of detail 5B in FIG. 5A.
Figure 7:
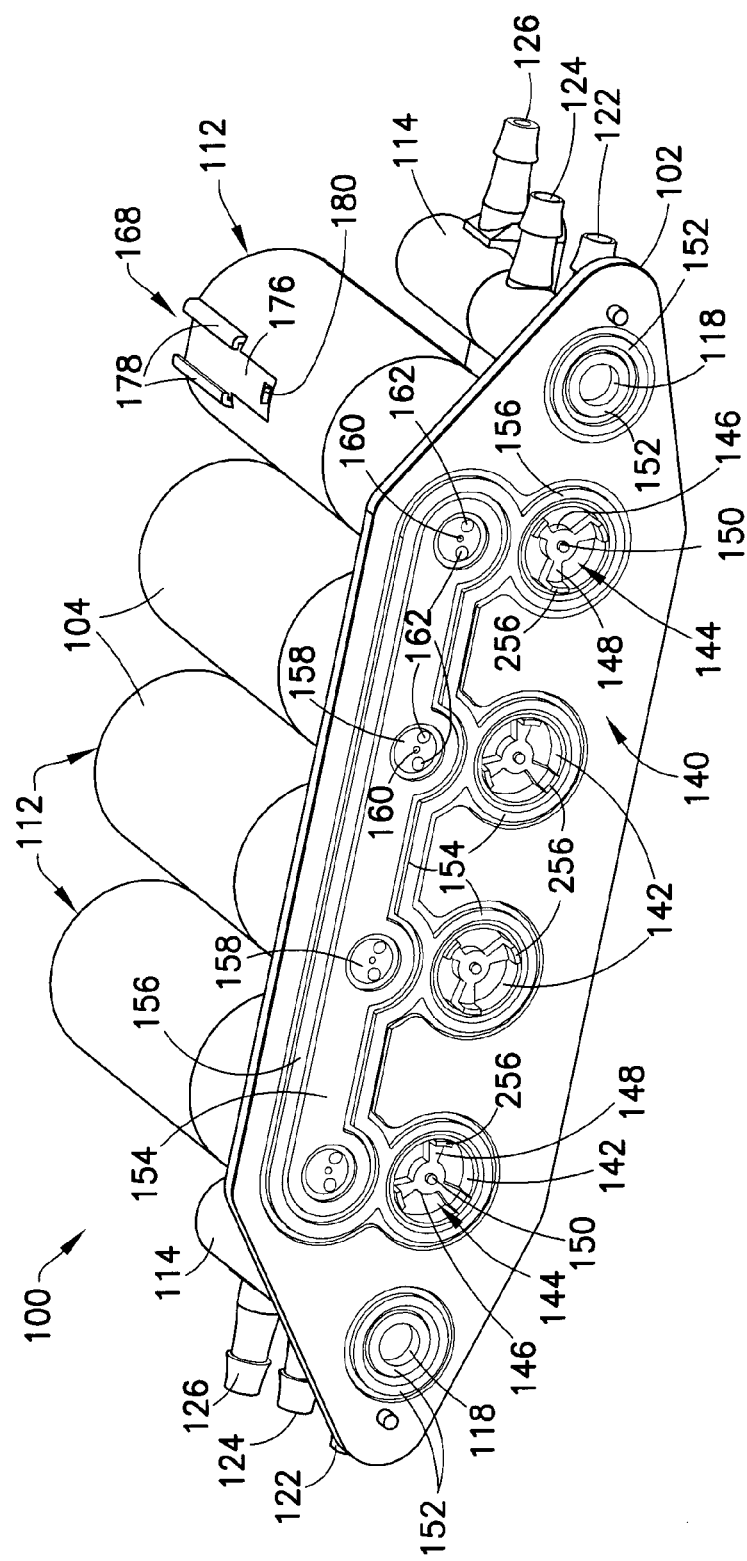
FIG. 7 is a front perspective view of a pump body of the fluid pump device shown in FIG. 2.
Figure 8:
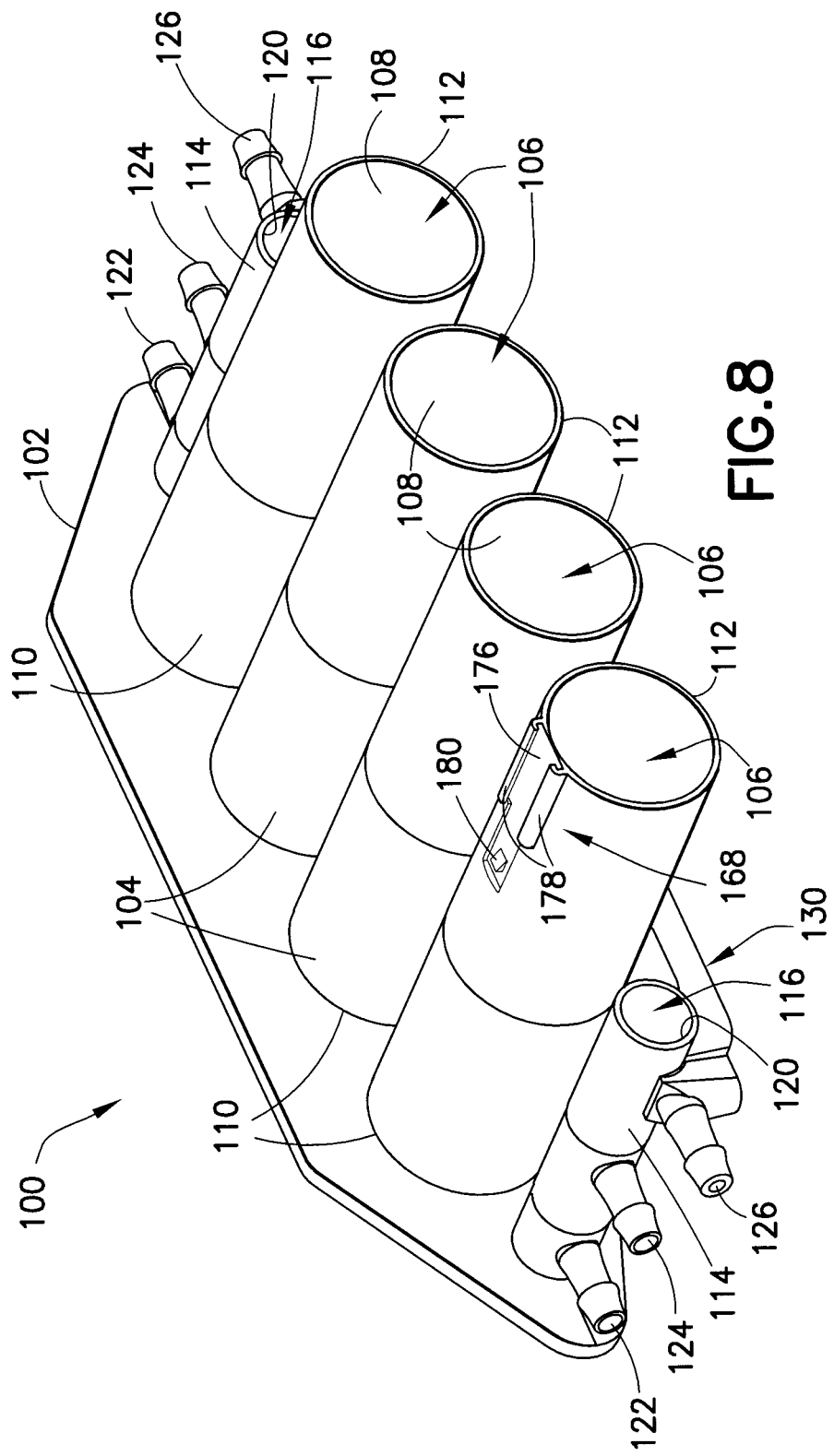
FIG. 8 is a rear perspective view of the pump body shown in FIG. 7.

Referring specifically to FIGS. 5A and 5B, it will be understood that the saline manifold 130 is formed to extend across the pump cylinders 104 and has opposing ends that connect to the respective inlet selector valve cylinders 114. With this construction, the saline channels 132, 134 extend the length between the two (2) outboard inlet selector valve cylinders 114. Saline ports 332, 334 are defined in the bottom of each of the inlet selector valve cylinders 114 to connect the inlet selector valve cylinders 114 to the saline channels 132, 134. The first or forward saline ports 332 connect the inlet selector valve cylinders 114 to the first or forward saline channel 132 and the second or rear saline ports 334 connect the inlet selector valve cylinders 114 to the second or rear saline channel 134. Accordingly, when the valve stem 306 of the actuated inlet selector valve 300 is rotated to connect the third inlet or "saline" port 326 with the first or forward saline channel 132 of the saline manifold 130, the third inlet "saline" port 326 is actually aligned with the first or forward saline port 332 in the inlet selector valve cylinder 114. Additionally, when the valve stem 306 of the actuated inlet selector valve 300 is rotated to connect the fourth inlet "saline" port 328 with the second or rear saline channel 134 of the saline manifold 130, the fourth inlet or "saline" port 328 is actually aligned with the second or rear saline port 334 in the inlet selector valve cylinder 114.

In the exemplary configuration of the pump 10 depicted in the accompanying figures, the left side inlet ports 122, 124 may be connected, respectively, to two (2) different sources of therapeutic or diagnostic (e.g., pharmaceutical) fluids, A1, A2, to be received in the two (2) left pump cylinders 104, and the left side saline port 126 may be connected to a first source of saline, designated as "S1". Fluid "A1" provided in one of the fluid source containers 30 may be connected to first inlet port 122 and fluid "A2" provided in one of the fluid source containers 30 may be connected to the second inlet port 124, or vice versa, on the left side 18 of the pump 10. Likewise, the right side inlet ports 122, 124 may be connected, respectively, to two (2) different sources of therapeutic or diagnostic (e.g., pharmaceutical) fluid, B1, B2 to be received in the two (2) right pump cylinders 104, and the right side saline port 126 may be connected to the second source of saline, designated as "S2". The two (2)-channel saline manifold 130 permits saline from either saline source S1, S2 to be pulled into either of the inlet selector valves 300 during operation of the pump 10. Fluid "B1" provided in one of the fluid source containers 30 may be connected to first inlet port 122 and fluid "B2" provided in one of the fluid source containers 30 may be connected to the second inlet port 124, or vice versa, on the right side 16 of the pump 10. Further, fluids A1, A2 may be connected to the right side inlet ports 122, 124 in any desired pairing, and the fluids B1, B2 may be connected to the left side inlet ports 122, 124 in any desired pairing as an alternative configuration for the pump 10. Accordingly, for exemplary purposes only in this disclosure, fluid flow of the fluids A1, A2 contained in the fluid source containers 30 is controlled by the left side inlet selector valve 300 and fluid flow of the fluids B1, B2 contained in the fluid source containers 30 is controlled by the right side inlet selector valve 300. As noted previously, the respective inlet selector valves 300 may draw saline from either of the saline channels 132, 134 of the saline manifold 130. Hence, the respective inlet selector valves 300 may draw from either saline source S1, S2. Accordingly, each "half" of the pump 10 has a single inlet selector valve 300 that allows selection from several fluid sources that are to be fed into the two (2) associated pump cylinders 104. Thus, control of fluids to the two (2) left side pump cylinders 104 is provided by the left side inlet selector valve 300 and control of fluids to the two (2) right side pump cylinders 104 is provided by the right side inlet selector valve 300.

The initial angular orientation of the valve stem 306 of the inlet selector valves 300 may be preset by the manufacturer and this orientation may be encoded into the pump indicator plate 170 and/or into identifying indicia 172 on the pump body 100, described previously. The control system 800 can thereby determine the initial or preset angular orientation of the valve stem 306 and operate the drive and actuating system 400 accordingly. If the angular orientation of the valve stem 306 is not needed for control by the control system 800 (such as if a read-write RFID tag is used for the identifying indicia 172) the valve stem 306 of the inlet selector valves 300 may have any suitable initial angular orientation such as the "OFF" position outlined previously. Once associated with the drive and actuating system 400, the respective plungers 200 may be driven forward into the pumping zone 164 of the pump chambers 106 until the distal end of the plunger 200 contacts the distal end wall 110 of the pump cylinder 104. Priming of the various fluid pathways in the pump 10 may be then be conducted.

The storage/isolation zone 166 has a larger diameter than the primary working/pumping zone 164 in each of the pump cylinders 104 to allow the forward or distal end lip seal 218 to reside in an uncompressed state within the large diameter storage/isolation zone 166 during storage. If this seal 218 was stored in the working/pumping zone 164, there is the possibility that the seal 218, over time, could "creep" or "relax" or take a compression set to the point that it would no longer be adequately squeezed/compressed during use, preventing it from sealing appropriately.

Figure 32:
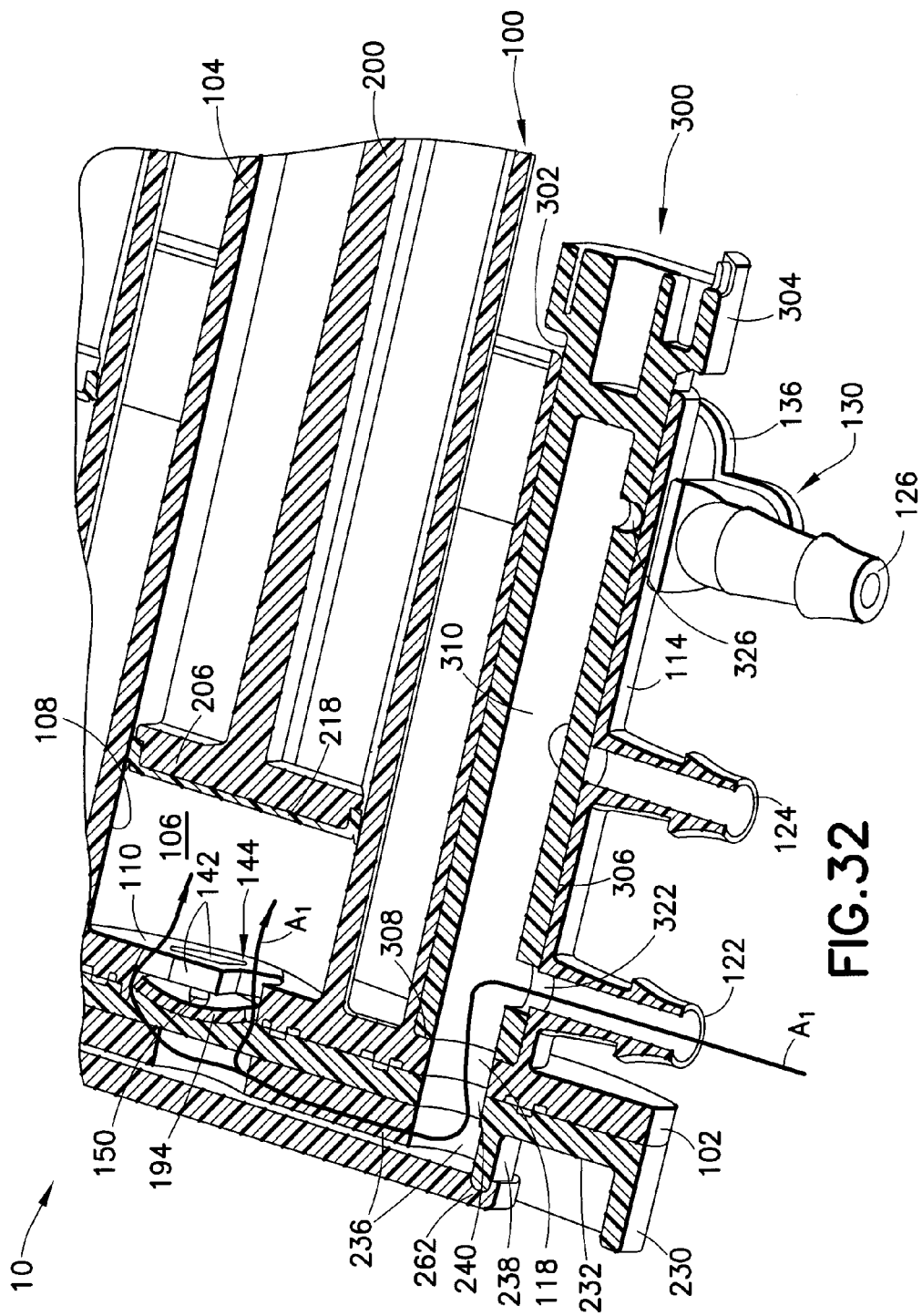
FIG. 32 is a horizontal cross-sectional and perspective view of a right side portion of the fluid pump device shown in FIG. 2 to show inflow from a first fluid source container associated with the fluid pump device.

Referring further to FIGS. 30-36, general operation of one of the "primed" pump cylinders 104 in the pump 10 will now be provided with reference primarily to the right outboard pump cylinder 104 of the pump body 100 as shown in FIGS. 32-36. Initially, as shown by the horizontal cross-sectional view of the pump 10 shown in FIG. 30, the respective plungers 200 are located in the isolation zone 166 in the pump chamber 106 of the respective pump cylinders 104, and the inlet selector valves 300 are in the "OFF" position. Assuming priming of the fluid pathways in the pump 10 has been completed, the right side selector valve 300 may be actuated to, for example, place the valve stem 306 in an angular orientation in the inlet selector valve cylinder 114 to permit fluid communication between the first inlet port 322 in the valve stem 306 and the first inlet port 122 on the right inlet selector valve cylinder 114, as shown in FIG. 32. Retraction of the plunger 200 in the pump chamber 106 of the right outboard pump cylinder 104 results in fluid B1 in the connected fluid source container 30 being drawn through the axial passage 310 in the valve stem 306 and into the right side inlet manifold channel 236 to act upon the underlying inlet check valve 194 and open the inlet check valve 194 (see also the previous discussion of FIG. 20). The fluid flow acts upon the inlet check valve 194 supported by the inlet check valve support structure 144 in the inlet opening 142 and opens the inlet check valve 194 so that fluid B1 may pass through the inlet opening 142 and enter the pump chamber 106 of the pump cylinder 104. The inlet check valve 194 regulates the fluid flow into the pump chamber 106 of the pump cylinder 104. The fluid flow of fluid B1 is identified by arrow $A_1$ in FIG. 32.

Figure 33:
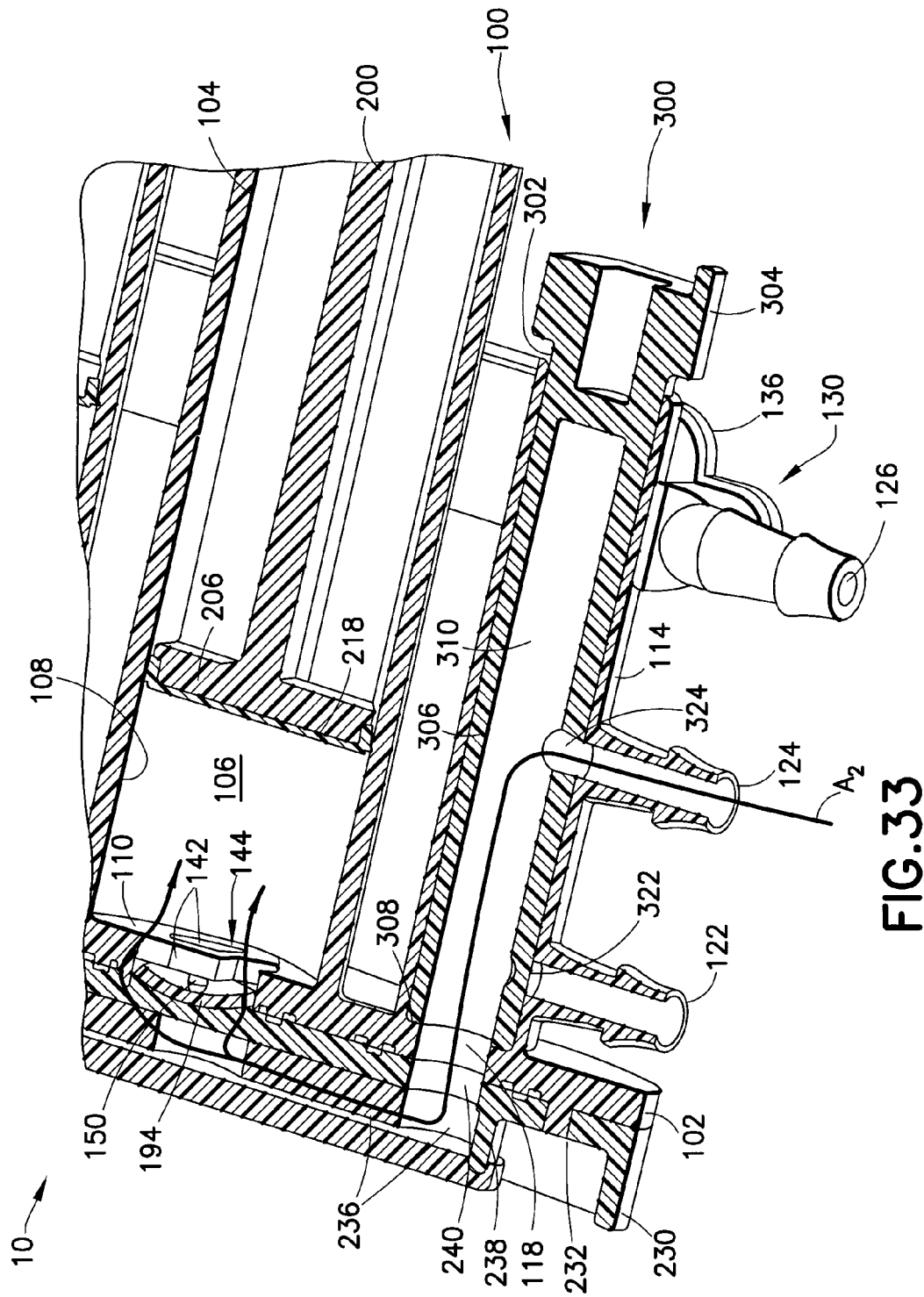
FIG. 33 is a horizontal cross-sectional and perspective view of a right side portion of the fluid pump device shown in FIG. 2 to show inflow from a second fluid source container associated with the fluid pump device.

Next, if desired, a second therapeutic or diagnostic (e.g., pharmaceutical) fluid may be drawn into the pump chamber 106 of the right outboard pump cylinder 104 to be mixed with the fluid B1 present in the pump chamber 106. If so, the right side selector valve 300 may be actuated to place the valve stem 306 in an angular orientation in the inlet selector valve cylinder 114 to permit fluid communication between the second inlet port 324 in the valve stem 306 and the second inlet port 124 on the inlet selector valve cylinder 114, as shown in FIG. 33. Additional retraction of the plunger 200 in the pump chamber 106 of the right outboard pump cylinder 104 results in fluid B2 in the connected fluid source container 30 being drawn through the axial passage 310 in the valve stem 306 and into the right side inlet manifold channel 236 to act upon the underlying inlet check valve 194 and open the inlet check valve 194 (see also the previous discussion of FIG. 20). The fluid flow acts upon the inlet check valve 194 supported by the inlet check valve support structure 144 in the inlet opening 142 and opens the inlet check valve 194 so that the fluid B2 may pass through the inlet opening 142 and enter the pump chamber 106 of the pump cylinder 104. The inlet check valve 194 regulates the fluid flow into the pump chamber 106 of the pump cylinder 104. The fluid flow of fluid B2 is identified by arrow $A_2$ in FIG. 33. In the scenario presented in the foregoing, it is assumed that fluid B1 is different from fluid B2, but these fluids may also be the same medical fluid as well. This example is provided to illustrate mixing of fluids in the respective pump chambers 106 of the pump cylinders 104, if so desired, and with appropriate safety protocols in the control system 800 relating to the mixing of fluids. As an alternative, if the fluids B1, B2 are the same fluid, the fluid delivery system 2 may deliver fluid continuously from the fluid source container 30 holding fluid B1 until this container is exhausted, and the system 2 may then switch to the "backup" fluid source container 30 holding fluid B2.

Figure 34:
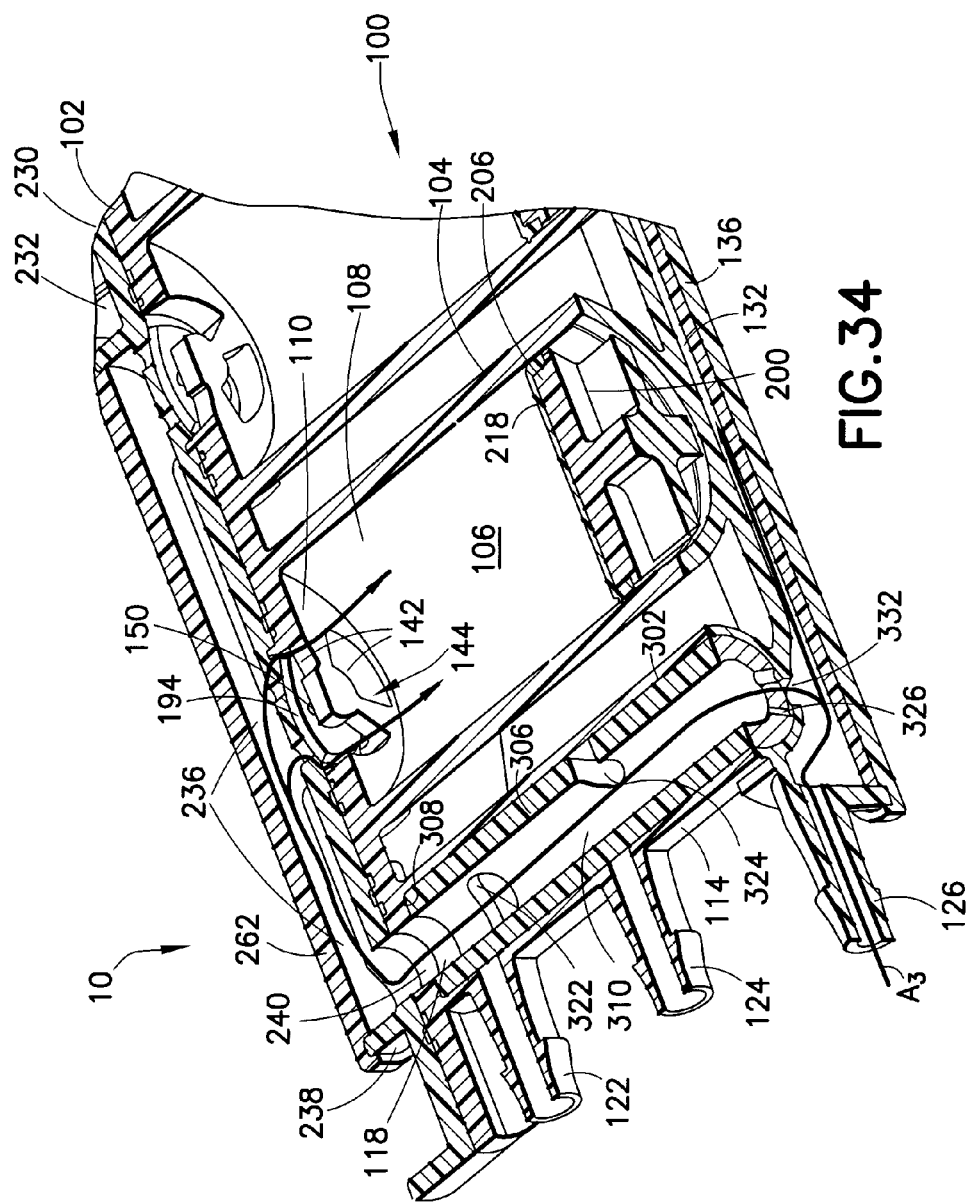
FIG. 34 is a horizontal cross-sectional and perspective view of a right side portion of the fluid pump device shown in FIG. 2 to show inflow from a right side saline source associated with the fluid pump device.

Further, if desired, saline from the saline sources S1, S2 contained in the connected saline fluid source containers 30 provided on opposite sides of the pump 10 may be drawn into the pump chamber 106 of the right outboard pump cylinder 104 to be mixed with the fluids B1, B2 present in the pump chamber 106. The rights side inlet selector valve 300 may be operated to draw from either saline source S1, S2. In a desirable operational practice, mixing saline S1, S2 with fluids B1 and/or B2 can occur by delivering saline with the two (2) pump cylinders 104 on one side of the pump 10 and delivering the diagnostic or therapeutic (e.g., pharmaceutical) fluids B1, B2 with the two (2) pump cylinders 104 on the other side of the pump 10. In the present example, if it is desired, for example, to next mix in saline S2, the right side selector valve 300 may be actuated to place the valve stem 306 in an angular orientation to permit fluid communication between the third inlet port 326 in the valve stem 306 and the saline port 332 in the inlet selector valve cylinder 114 which connects to the first or forward saline channel 132 of the saline manifold 130, as shown in FIG. 34. Further retraction of the plunger 200 in the pump chamber 106 of the right outboard pump cylinder 104 results in saline S2 in the connected fluid source container 30 being drawn from the saline channel 132 through the saline port 332 in the inlet selector valve cylinder 114 into the axial passage 310 in the valve stem 306 and into the right side inlet manifold channel 236 to act upon and open the underlying inlet check valve 194 (see also the previous discussion of FIG. 20). The fluid flow acts upon the inlet check valve 194 supported by the inlet check valve support structure 144 in the inlet opening 142 and opens the inlet check valve 194 so that the saline S2 may pass through the inlet opening 142 and enter the pump chamber 106 of the pump cylinder 104. The inlet check valve 194 regulates the fluid flow into the pump chamber 106 of the pump cylinder 104. The fluid flow of saline S2 is identified by arrow $A_3$ in FIG. 34.

Figure 35:
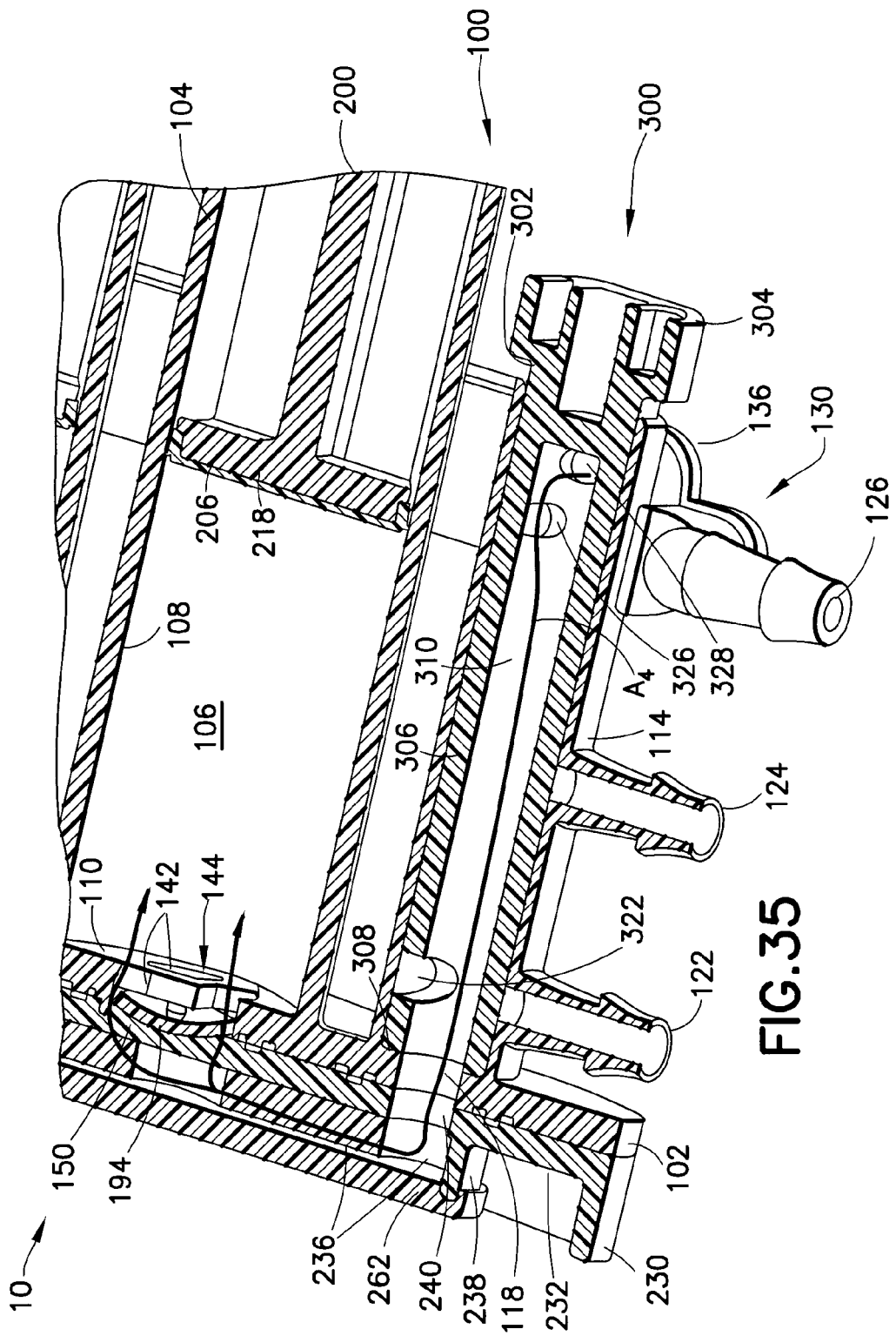
FIG. 35 is a horizontal cross-sectional and perspective view of a right side portion of the fluid pump device shown in FIG. 2 to show inflow from a left side saline source associated with the fluid pump device.
Figure 36:
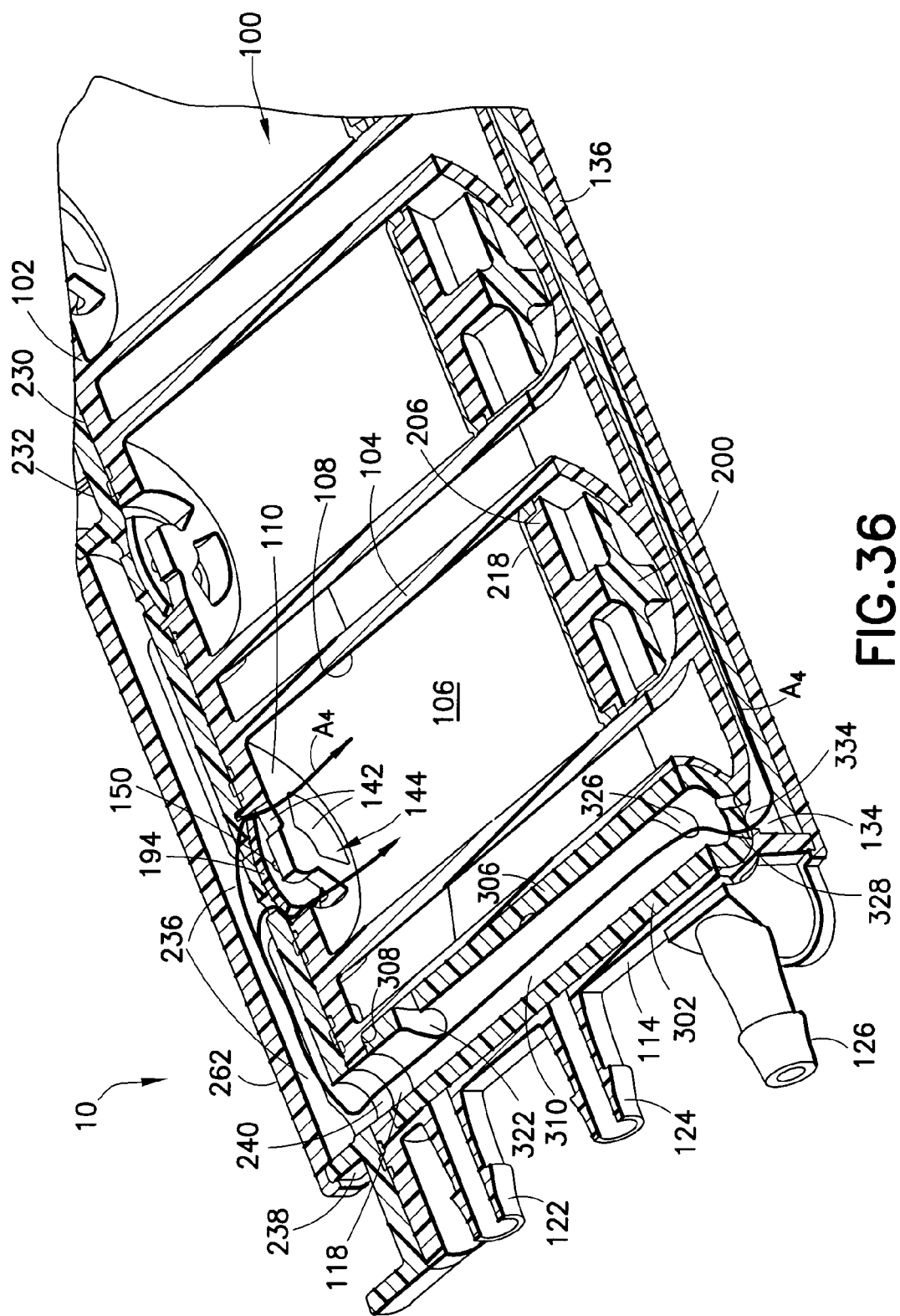
FIG. 36 is an enlarged view of the cross-sectional perspective view shown in FIG. 35.

Moreover, if saline S1 is also desired to be mixed into the fluids B1, B2 and saline S2 now present in the pump chamber 106 of the pump cylinder 104, the right side selector valve 300 may be actuated to place the valve stem 306 in an angular orientation to permit fluid communication between the fourth inlet port 328 in the valve stem 306 and the saline port 334 in the inlet selector valve cylinder 114 which connects to the second or rearmost saline channel 134 of the saline manifold 130, as shown in FIGS. 35-36. Further retraction of the plunger 200 in the pump chamber 106 of the right outboard pump cylinder 104 results in saline S1 in the connected fluid source container 30 being drawn from the saline channel 134 through the saline port 334 in the inlet selector valve cylinder 114 into the axial passage 310 in the valve stem 306 and into the right side inlet manifold channel 236 to act upon and open the underlying inlet check valve 194 (see also the previous discussion of FIG. 20). The fluid flow acts upon the inlet check valve 194 supported by the inlet check valve support structure 144 in the inlet opening 142 and opens the inlet check valve 194 so that the saline S1 may pass through the inlet opening 142 and enter the pump chamber 106 of the pump cylinder 104. The inlet check valve 194 regulates the fluid flow into the pump chamber 106 of the pump cylinder 104. The fluid flow of saline S1 is identified by arrow $A_4$ in FIGS. 35-36.

As will be clear from the foregoing, retraction of the plungers 200 in the pump chambers 106 of the respective pump cylinders 104 results in fluid being drawn into the corresponding inlet manifold channel 236 to act upon the inlet check valves 194. The fluid flow acts upon the inlet check valves 194 and the inlet check valves 194 regulate the fluid flow into the pump chambers 106 of the pump cylinders 104. When the pressure in the inlet manifold channel 236 is greater than the pressure within the pump chambers 106 of the pump cylinders 104, such as when the plungers 200 are retracted in the pump cylinders 104, the inlet check valves 194 deform to allow fluid flow into the pump chambers 106. When the pressure within the pump chambers 106 of the pump cylinders 104 is greater than the pressure within the inlet manifold channel 236, such as when the plungers 200 are moving forward or distally within the pump cylinders 104, the inlet check valves 194 are pressed against the check valve recesses 252 formed in the rear or proximal side 234 of the manifold plate 230, and prevent fluid flow out of the pump cylinders 104 into the corresponding inlet manifold channel 236.

Figure 30:
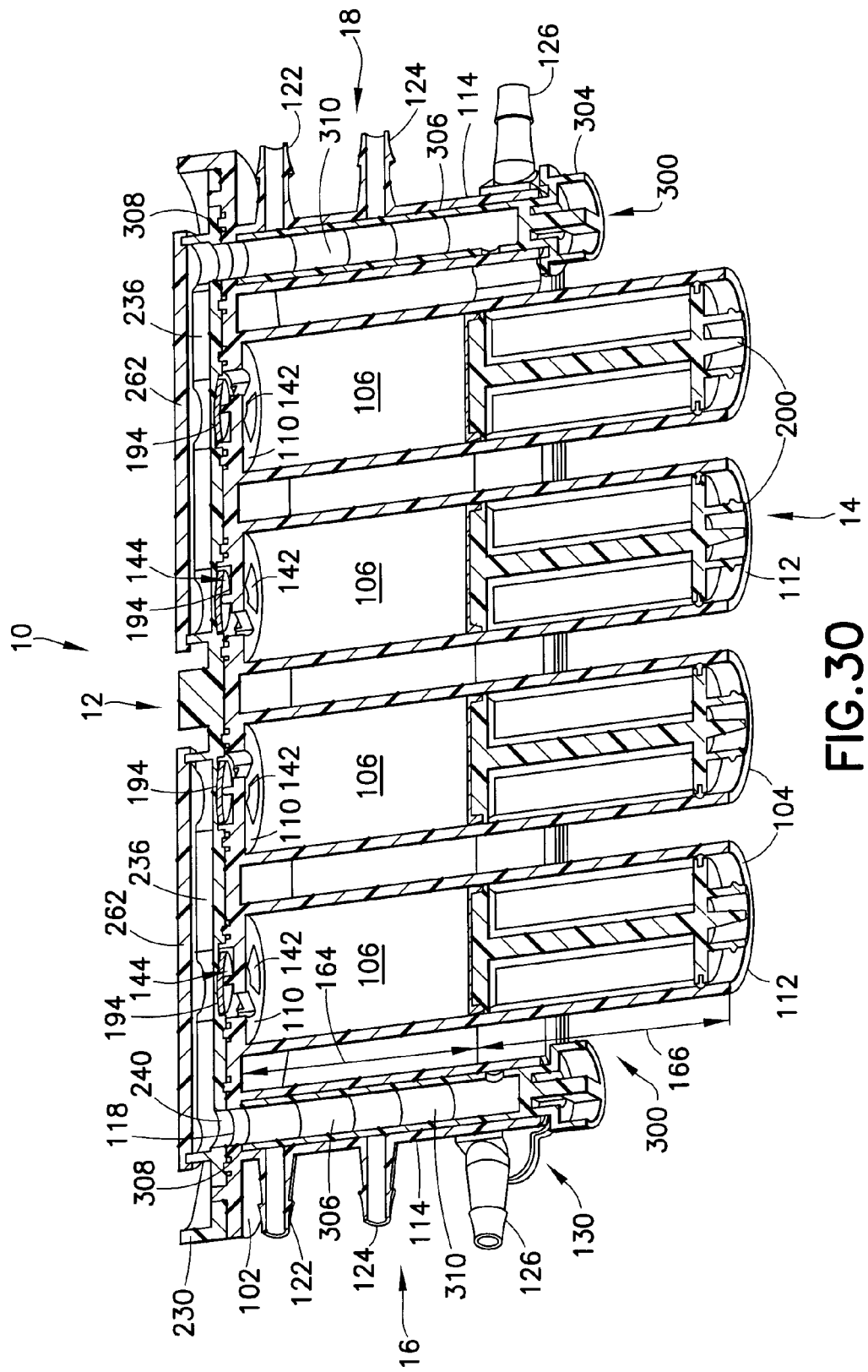
FIG. 30 is a cross-sectional perspective view taken along line 30-30 in FIG. 3.
Figure 31:
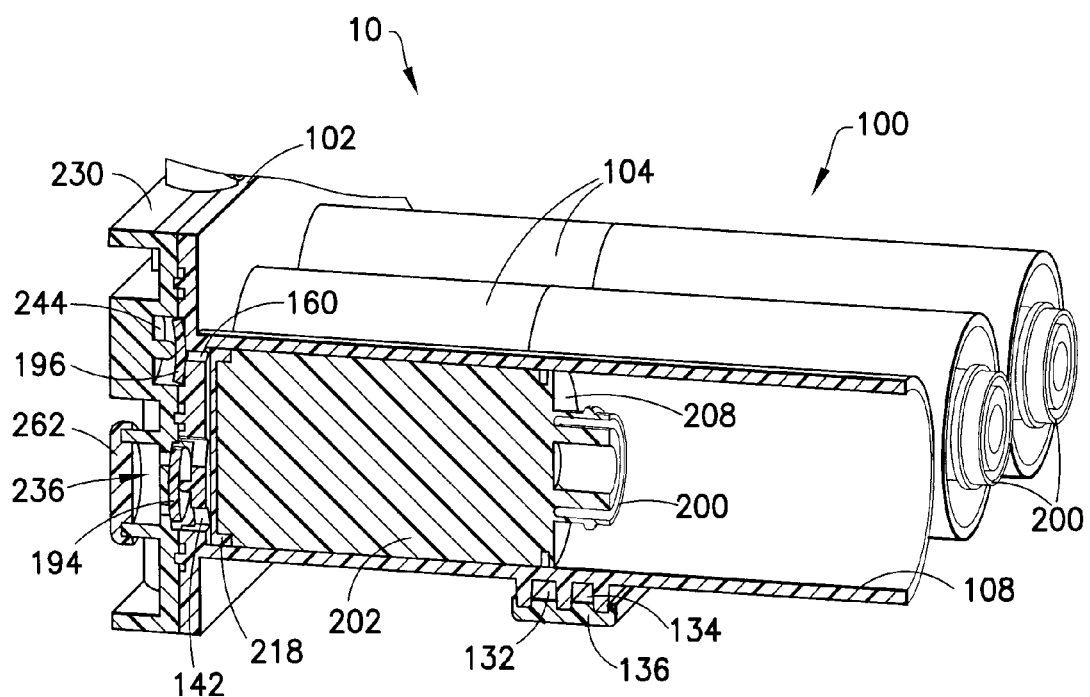
FIG. 31 is a cross-sectional perspective view of one of the pump cylinders of the fluid pump device of FIG. 2 showing a forward-most position of the plunger disposed in the right inboard pump cylinder.

As fluid enters the pump chamber 106 of the pump cylinder 104 via the inlet opening 142 as the plunger 200 is retracted within the pump cylinder 104, the fluid enters the front pumping zone 164 of the pump cylinder 104. The rear isolation zone 166 of the pump cylinder 104 is present for sterility purposes, as described previously. The inner diameter of the pump cylinder 104 in the area of pumping zone 164 is desirably slightly smaller than the inner diameter of the pump cylinder 104 in the area of the isolation zone 166. The larger inner diameter of the pump cylinder 104 in the area of the isolation zone 166 serves as a storage location for the plunger 200 prior to use and prevents the front lip seal 218 from being compressed and permanently deformed during long-term storage. This storage configuration is shown in FIG. 30, discussed previously. During use, the front lip seal 218 remains within the front pumping zone 164 of the pump cylinder 104 and the rear bead seal 220 remains in the rear isolation zone 166. Since the two (2) seals 218, 220 do not contact the same surfaces, the potential for contamination from the ambient environment is reduced.

For each of the inlet selector valves 300, the rearmost saline port 334 on the inlet selector valve cylinder 114 is located near the rear or proximal end opening 120 and, accordingly, located near the proximal end of the axial passage 310 in the valve stem 306 of the inlet selector valve body 302 to allow substantially the entire valve 300 to be primed using saline. During priming, air is pushed by the priming saline from the rear of the selector valve 300 down the length of the axial passage 310 in the valve stem 306 and into the associated inlet manifold channel 236 and into the pump chambers 106 of the associated pump cylinders 104. Desirably, the axial passage 310 in the valve stem 306 is generally horizontal rather than oriented at an angle or having a slope, which enhances air bubble removal. However, if desired, the axial passage 310 in the valve stem 306 may generally slope upward toward the corresponding inlet manifold channel 236 to aid in air removal from the valve stem 306. The inlet selector valve cylinder 114 and valve stem 306 of the inlet selector valve 300 are also generally parallel to the corresponding pump cylinders 106. As a result of the foregoing arrangement and priming sequence, stagnation regions or "dead areas" are minimized in the inlet selector valve cylinder 114 and in the axial passage 310 in the valve stem 306, minimizing the potential for trapped air bubbles. Saline S1 or saline S2 contained in the fluid source containers 30 may be used for priming of the pump 10 with fluid. As saline is much less expensive than most therapeutic or diagnostic (e.g., pharmaceutical) fluids, it is preferred for priming operations for the pump 10. After a fluid injection or infusing procedure involving a therapeutic or diagnostic (e.g., pharmaceutical) fluid has occurred, it may be desirable to flush the contents of the pump chambers 106 of the pump cylinders 104 from the pump 10, and the saline S1, S2 in the connected fluid source containers 30 may be used for this purpose. This "saline" flushing step also desirably flushes residual fluids in the flow paths upstream and downstream from the pump cylinders 104.

Referring to FIGS. 29A-29H, the inlet ports 322-328 in the valve stem 306 of the inlet selector valves 300 are desirably placed at respective angular locations to minimize "cross-over" of unprimed inlet ports 122, 124 or an unprimed port 332, 334 connected to the saline manifold 130. In practice, the rearmost saline port 334 is primed first with saline as the first installed fluid source container 30 is a saline fluid source container 30 that is installed in the left rear position on the pump 10, and minimization of "cross over" is primarily a concern with respect to inlet 122, 124 and saline port 332. Crossing over an unprimed port can undesirably introduce air into the axial passage 310 in the valve stem 306 of the selector valve 300. Accordingly, the rearmost saline channel 134 of the saline manifold 130 is supplied by the saline source S1 connected to the saline port 126 located on the left side 18 of the pump 10 and delivers saline to rearmost inlet port 328 on both the left and right inlet selector valves 300. Next, the forward saline channel 132 is supplied by the saline source S2 connected to the saline port 126 located on the right side 16 of the pump 10 and delivers fluid to the next-to-rearmost inlet port 326 on both the left and right inlet selector valves 300. The inlet ports 322-328 are located so that the valve stem 306 may be moved from a position permitting fluid communication between the rearmost inlet port 328 and the saline port 334 to the saline channel 134 connected to the left side saline fluid source containers 30 containing saline "S1" and the "OFF" position of the valve stem 306, without any of the remaining inlet ports 322-326 crossing over any of the inlet ports 122, 124 of the inlet selector valve cylinder 114 or the forward saline port 332 leading to the saline channel 132 of the saline manifold 130. Accordingly, the valve stem 306 may be rotated from any inlet port 122, 124 with an installed or connected fluid source and any saline port 332, 334 with an installed or connected saline source S1, S2 to any other such port with an installed or connected fluid source without crossing over an unprimed inlet port. FIGS. 29A-29H show several exemplary scenarios showing how the angular positioning of the inlet ports 322-328 prevents "cross-over" of unprimed fluid ports.

Figure 29A:
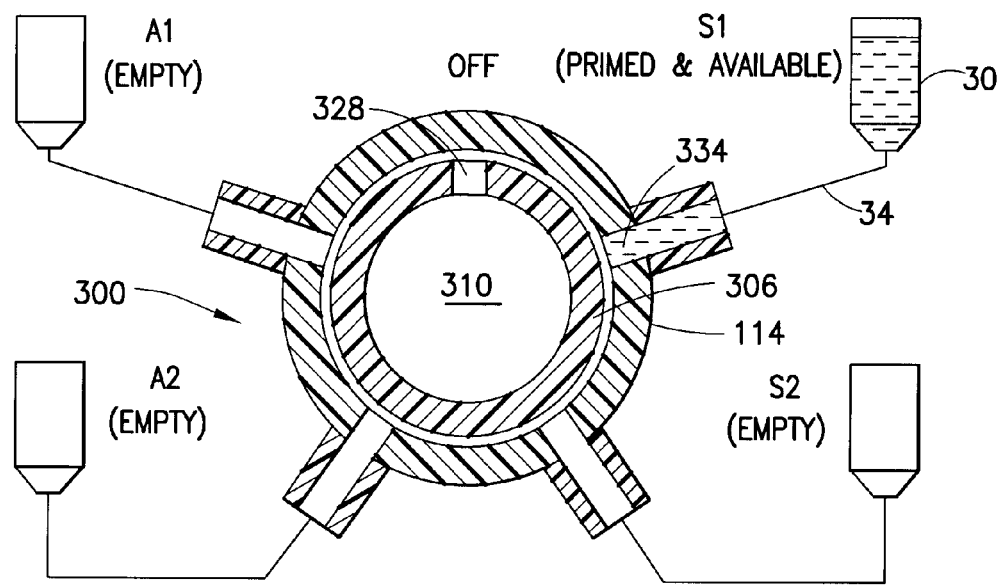
FIGS. 29A-29H are schematic cross-sectional views of the inlet selector valve showing exemplary operation thereof.
Figure 29B:
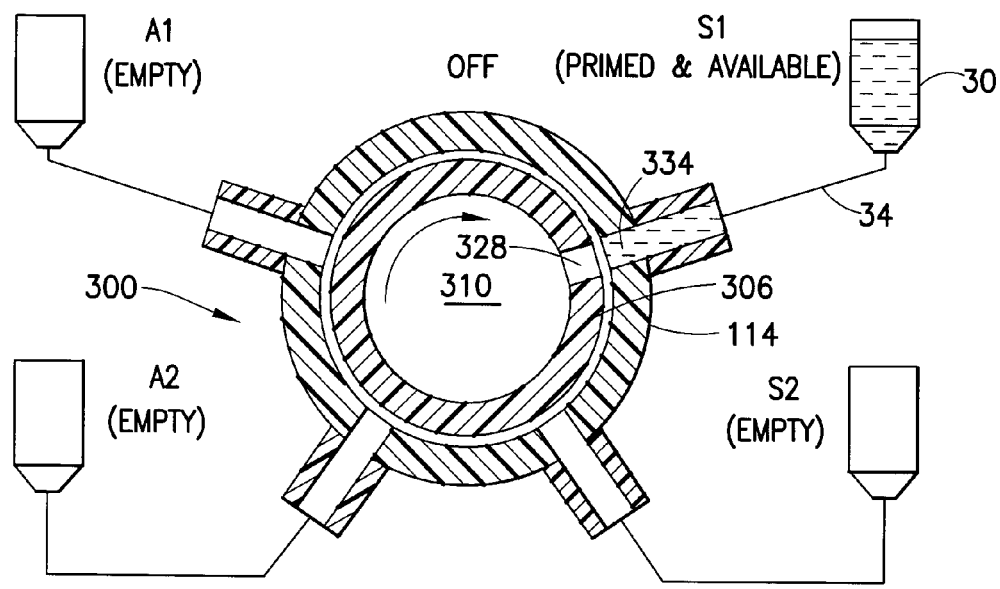

In FIG. 29A, the valve stem 306 of the inlet selector valve 300 is shown at an "OFF" position and a saline fluid source container 30 containing saline S1 has been installed, primed, and is ready for use as the first "saline" port S1. As shown in FIG. 29B, the valve stem 306 may be rotated between the OFF position and the first saline port S1 without having to pass over any unprimed ports, such as ports A1, A2, or S2, as discussed herein. If the valve stem 306 passes over an unprimed port, it is possible for air to be introduced into the axial passage 310 in the valve stem 306 of the inlet selector valve 300. This air could eventually be delivered to the patient outlet port 270 and to the patient unless the fluid injection is aborted by the control system 800. As shown by FIGS. 29A-29B, the first saline port S1 is always desired to be the first primed port because if the second saline port S2 was primed before the first saline port S1, the valve stem 306 would be forced to pass over the unprimed first saline port S1.

Figure 29C:
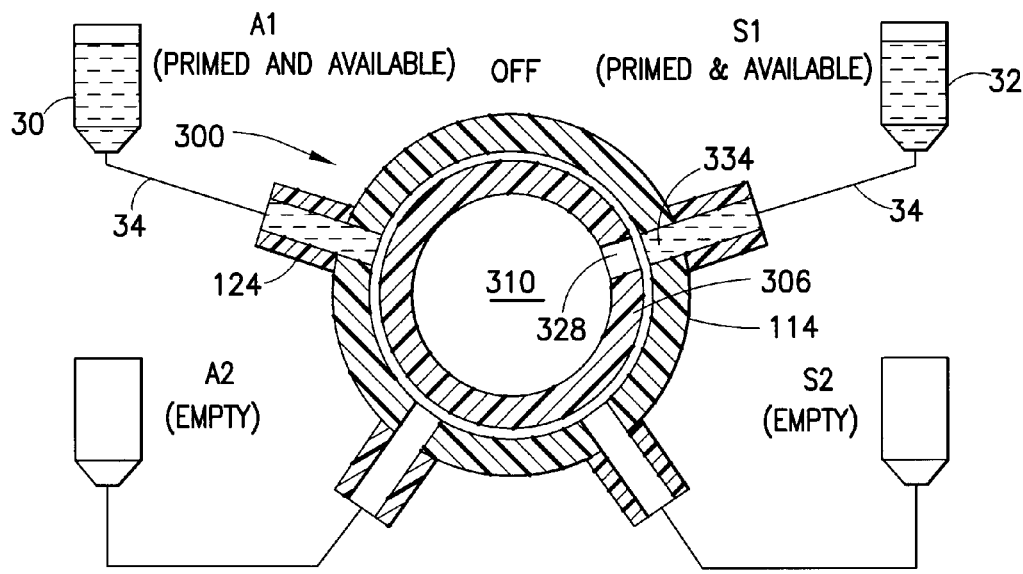
Figure 29D:
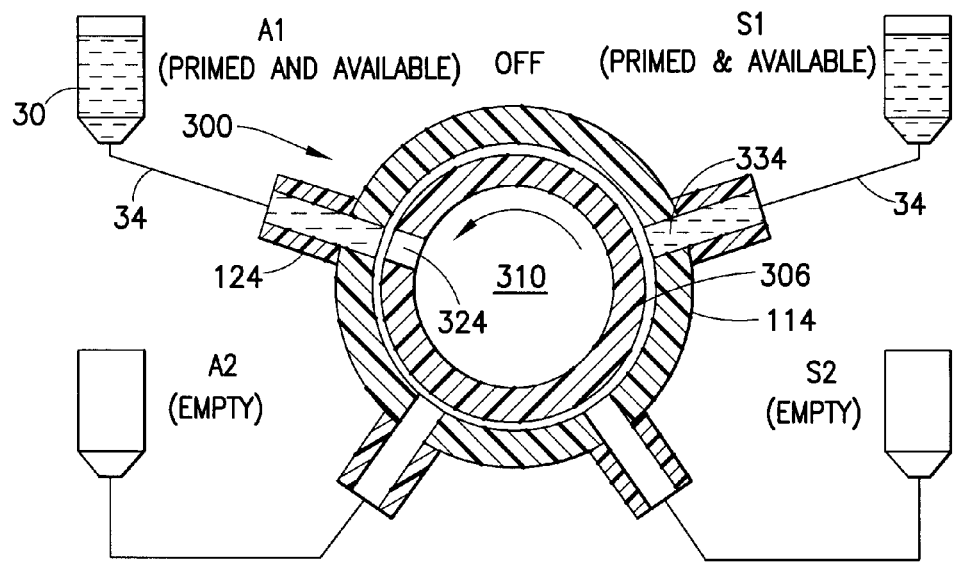

FIGS. 29C and 29D show the inlet selector valve 300 after the first saline port S1 and a first "contrast" port A1 have been installed, primed, and are ready for use. Again, in this situation, the valve stem 306 may be freely rotated from the first saline port S1, past the OFF position, and to the first contrast port A1 without having to pass over any unprimed ports, such as ports A2 or S2. Again, if the second "contrast" port A2 had been primed with fluid before the first contrast port A1, the valve stem 306 of the inlet selector valve 300 would have to pass over the unprimed first contrast port A1. For this reason, the fluid source containers 30 should be loaded in a specific order as outlined herein. In brief, the first saline source S1 should be installed before the second saline source S2, the first "medical" fluid source A1 should be installed before the second such source A2, etc.

Figure 29E:
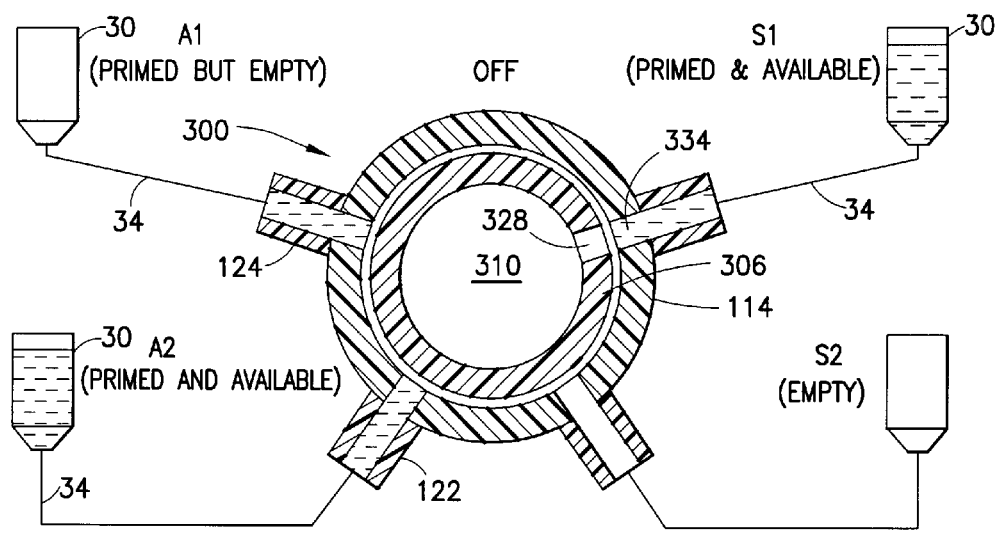
Figure 29F:
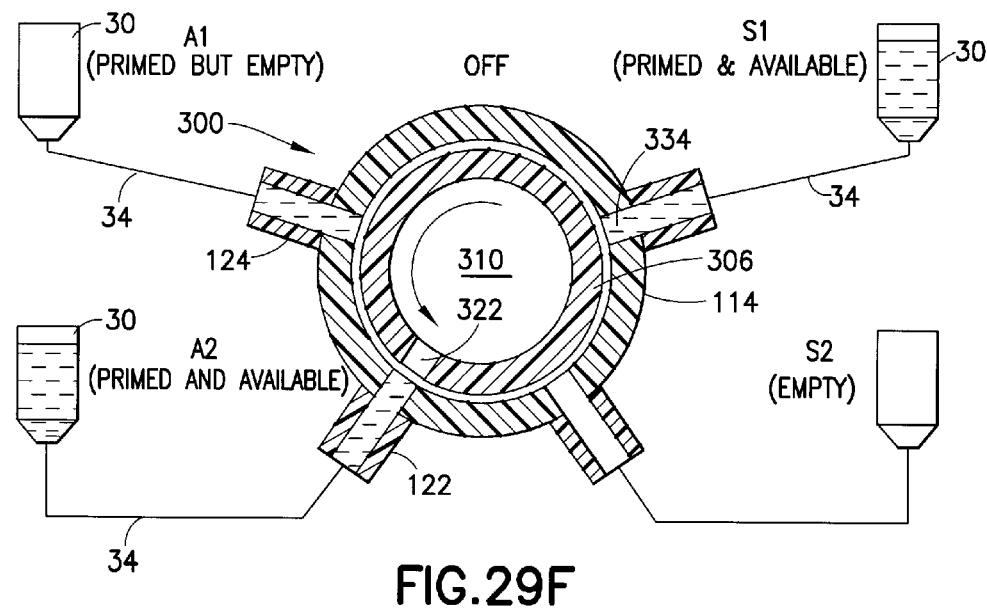

FIGS. 29E and 29F show the inlet selector valve 300 after the fluid source container 30 containing the first contrast source A1 has run empty and the fluid source container 30 containing the second contrast source A2 has been installed. When the fluid source container 30 containing the first contrast source A1 runs empty, an air detector associated with the connected fluid supply tube 34 alerts the control system 800, which actuates the drive and actuating system 400 to stop using the fluid source container 30 before any air can be drawn into the inlet selector valve 300. Thus, the fluid supply tube 34 connected to the fluid source container 30 containing the first contrast source A1 remains primed even though the fluid source container 30 is now empty. The valve stem 306 may be moved from the first saline port S1, past the OFF position, past the still-primed first contrast port A1, and to the second, primed contrast port A2 without having to pass over an unprimed port, such as the second saline port S2. Even though the fluid supply container 30 connected to the first contrast port A1 is now empty, the valve stem 306 can still pass over this port because the connected fluid supply tube 34 remains primed with fluid.

Figure 29G:
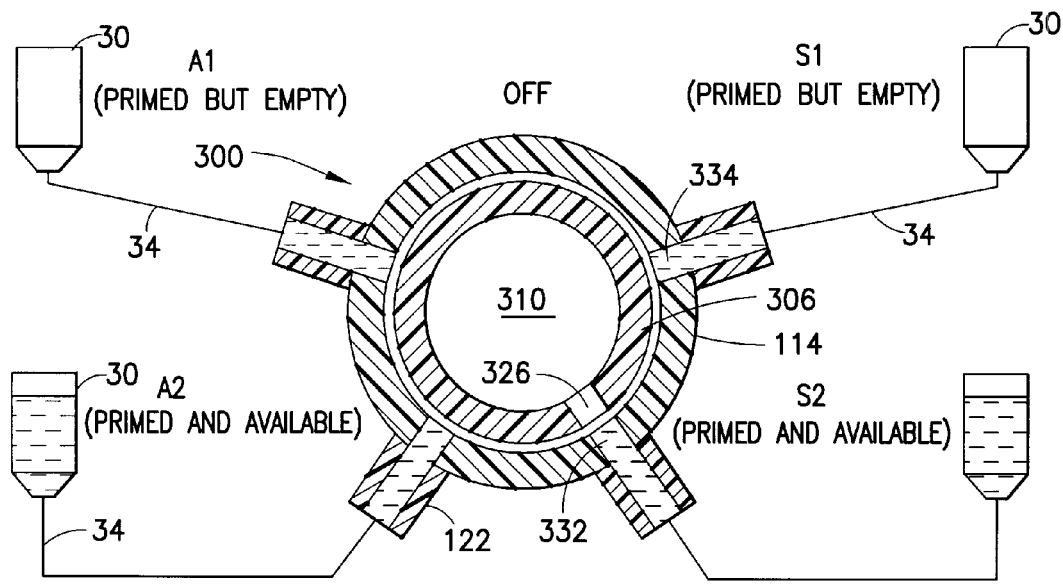
Figure 29H:
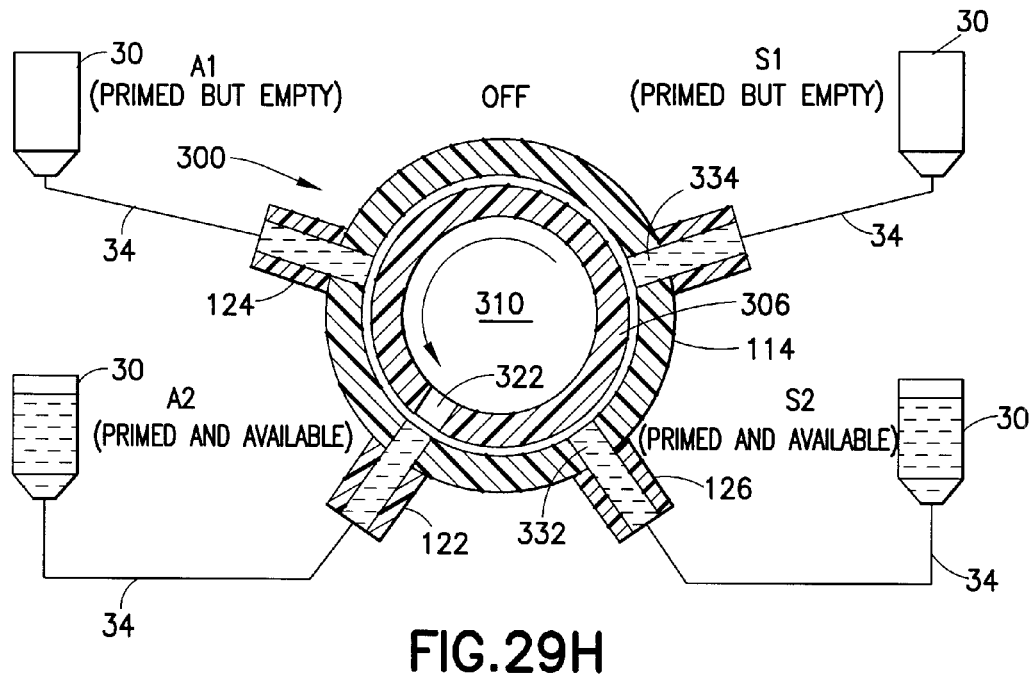

FIGS. 29G and 29H show the inlet selector valve 300 after the fluid source containers 30 containing the first saline source S1 and the first contrast port A1 have run empty and the fluid source container 30 containing the second saline source S2 has been installed. Again, in a similar manner to the foregoing, the first saline port S1 and the first contrast port A1 remain primed even though their respective fluid source containers 30 have run empty. If the valve stem 306 is initially located at the second saline port S2, it may be safely moved past the first saline port S1, the OFF position, and the first contrast port A1 ports to access the second contrast port A2.

As will be clear from all the foregoing, fluid as selected by the inlet selector valve 300 enters the associated inlet manifold channel 236 via the corresponding or registering openings 118, 240 in the front plate 102 of the pump body 100 and in the manifold plate 230. The left and right inlet manifold channels 236 are located low across the manifold plate 230 below the outlet manifold channel 244 to allow trapped air to rise upward and into the pump chambers 106 of the respective pump cylinders 104 during saline priming. The inlet manifold channels 236 are also formed with smooth interior surfaces and curvatures to avoid "dead ends" to minimize the potential for trapped air bubbles and to allow fluids to be easily flushed from the pump 10. Moreover, the width and height of the inlet manifold channels 236 are sized and shaped to minimize the pressure drop (e.g., flow restriction) while keeping the total enclosed volume to a minimum to minimize the volume of fluid required to prime the pump 10. Fluid from the inlet selector valve 300 is available to either or both of the pump cylinders 104 on the same side of the pump 10.

Figure 37:
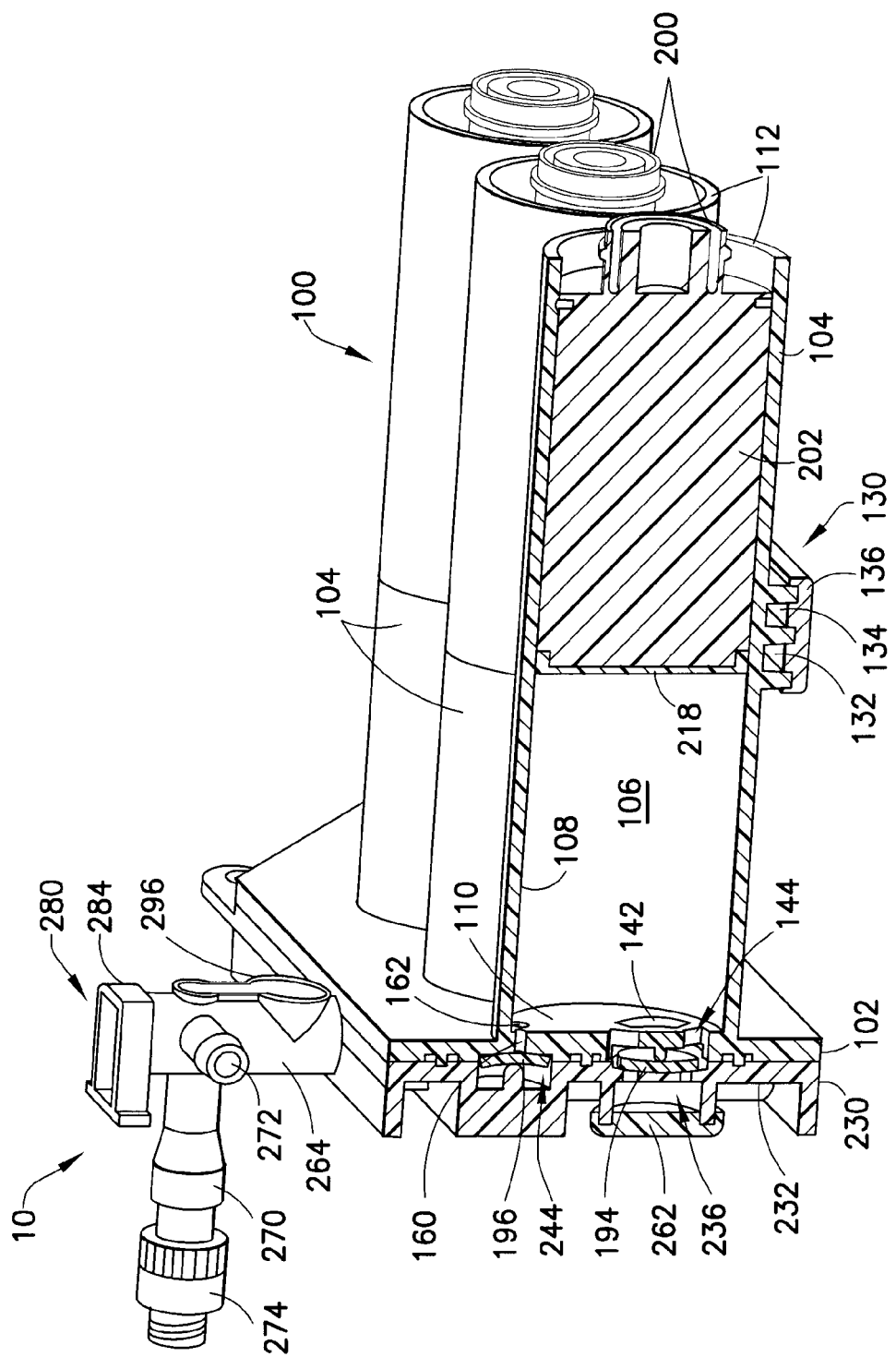
FIG. 37 is a cross-sectional perspective view taken through a pump cylinder of the fluid pump device shown in FIG. 2, and showing an inlet check valve and an outlet check valve of the fluid pump device.
Figure 38:
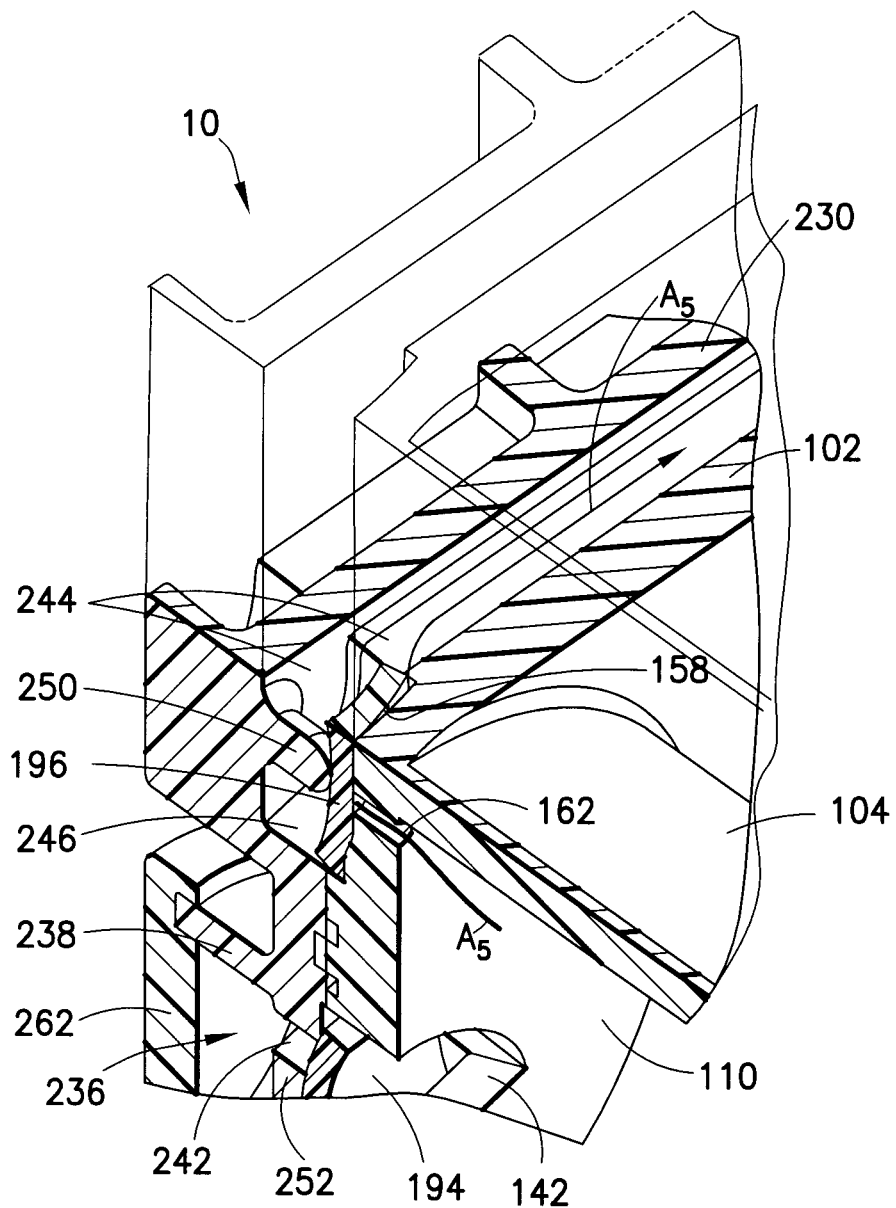
FIG. 38 is a cross-sectional and perspective view that is an enlargement of a portion of the view shown in FIG. 37.
Figure 39:
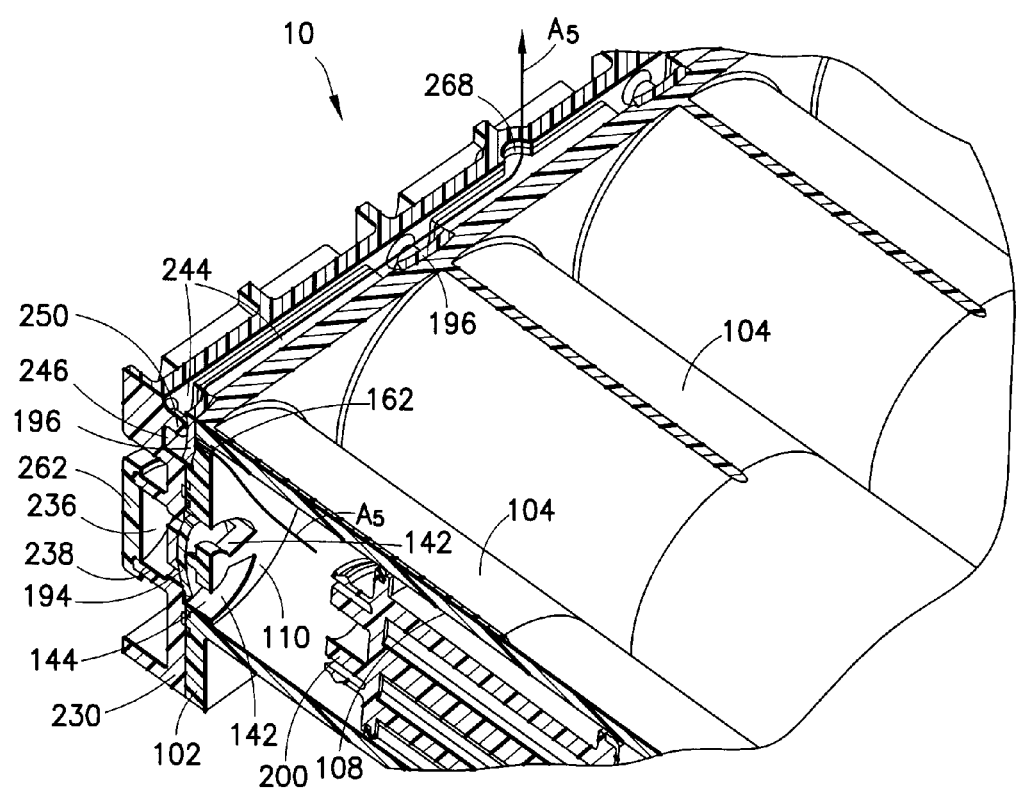
FIG. 39 is a cross-sectional perspective view taken through the same pump cylinder shown in FIG. 37, and showing fluid flow in an outlet manifold channel of the fluid pump device.

Referring further to FIGS. 37-39, during the forward or distal movement of the plunger 200 in the pump chamber 106 of the pump cylinder 104, pressure within the pump chamber 106 of the pump cylinder 104 is greater than the pressure in the outlet manifold channel 244, and the outlet check valve 196 associated with the pump cylinder 104 deforms to allow fluid flow from the pump cylinder 104. Accordingly, in the example described previously, the pump chamber 106 of the right outboard pump cylinder 104 contains a fluid mixture comprising diagnostic or therapeutic (e.g., pharmaceutical) fluids B1, B2 and saline S1, S2. As the plunger 200 in the right outboard pump cylinder 104 is moved forward or distally in the pump cylinder 104, pressure within the pump chamber 106 is greater than the pressure in the outlet manifold channel 244 and the outlet check valve 196 associated with the right outboard pump cylinder 104 deforms to allow a fluid flow of the fluid mixture comprising fluids B1, B2 and saline S1, S2 to exit the right outboard pump cylinder 104 via the air egress opening 160 and outlet openings 162 present in the distal end wall 110 of the pump cylinders 104, and enter the outlet manifold channel 244. The fluid flow of the fluid mixture comprising fluids B1, B2 and saline S1, S2 from the pump chamber 106 to the outlet manifold channel 244 is identified by arrow $A_5$ in FIGS. 38-39. The outlet manifold channel 244 collects the fluid ejected from each of the four (4) pump cylinders 104 and directs the combined fluid flow via the connecting passage 268 leading to the outlet selector valve 280 and the flow passage 290 therein. Accordingly, in the foregoing example, the fluid flow of the fluid mixture comprising fluids B1, B2 and saline S1, S2 is delivered under pressure into the outlet manifold channel 244 and enters the connecting passage 268 leading to the flow passage 290 in the outlet selector valve 280. The outlet selector valve 280 may selectively direct the fluid mixture to the patient outlet port 270 having the patient supply set 40 connected thereto, or to the waste outlet port 272 having the waste collection system 44 connected thereto.

Conversely, when the pressure in the outlet manifold channel 244 is greater, such as when the plunger 200 is retracted in the pump cylinder 104, the outlet check valve 196 associated with the pump cylinder 104 is pressed into the recessed area 158 defined in the elongated recess 154 on the front side 140 of the front plate 102 to seal the outlet openings 162 and top opening 160 in the front plate 102 leading to the pump chamber 106 of the pump cylinder 104 and prevents fluid flow from the outlet manifold channel 244 into the pump cylinder 104. This result occurs for each of the outlet check valves 196 to prevent fluid flow from the respective pump cylinders 104 when the corresponding plunger 200 is retracted in the pump chamber 106 of the pump cylinder 104.

The outlet check valves 196 regulate the fluid flow from each pump cylinder 104. Because pressure restrictions are not a significant concern on the outlet side of the pump 10, the one or more outlet openings 162 and the top opening 160 to each of the pump cylinders 104 may be small in comparison to the inlet openings 142 to the pump cylinders 104 to reduce the pressure stresses on the corresponding outlet check valves 196. Additionally, the preload pins 250 in the outlet check valve receiving recesses 246 located in outlet manifold channel 244 apply a relatively high force to the outlet check valves 196, which causes the valves 196 to have a relatively high cracking pressure and help prevent free-flow due to gravity from the fluid source containers 30 to the outlet selector valve 280. The compression of the preload pins 250 and the thickness of the polymeric discs comprising the outlet check valves 196 may be optimized to prevent free-flow due to gravity from the fluid source containers 30 to the outlet selector valve 280. The preload pins 250 apply a biasing or preload force to the polymeric discs comprising the outlet check valves 196 so that a certain minimum fluid pressure, often termed "cracking pressure", is required to cause the polymeric disc to initially open. Generally, the fluid source containers 30 as associated with the pump 10 are located at a higher elevation than the location where the patient supply set 40 connects to the pump 10, namely, the patient outlet port 270. Accordingly, there is a possibility that fluid could flow under gravity alone from the fluid source container(s) 30 to the patient when the pump 10 is not operating. To prevent this situation, the preload on the outlet check valves 196 may be made high enough that their cracking pressure is greater than this head pressure.

The outlet manifold channel 244 collects the fluid ejected from each of the four (4) pump cylinders 104 and directs the combined fluid flow to the outlet selector valve 280. The outlet selector valve 280 allows the fluid output to be directed to either patient outlet port 270 having the patient supply set 40 connected thereto, or to the waste outlet port 272 having the waste collection system 44 connected thereto. As noted previously, the valve stem 286 may be rotated to one of three (3) possible positions, including: (1) placing the flow passage 290 in fluid communication with the patient outlet port 270; (2) placing the flow passage 290 in fluid communication with the waste outlet port 272; and (3) placing the flow passage 290 in a shut-off position wherein flow to either the patient outlet port 270 or the waste outlet port 272 is prevented.

As noted previously, the manifold plate 230 is laser welded to the front plate 102 of the pump body 100 to secure these two components together and form a hermetic seal around critical fluid path areas. Because the outlet manifold channel 244 is generally under high pressure, for example, at least 400 psi and, often, at least 500 psi and greater, the welded seam in the perimetrical recess 156 around the outlet manifold channel 244 may not be fully capable of repeatedly withstanding the high stresses while maintaining a hermetic seal. To reduce the stress on this particular welded joint, the drive and actuating system 400 includes a spring-loaded clamp (described herein) to apply several hundred pounds of force to the rear side of the front plate 102 of the pump body 100 and allows the pump 10 to withstand fluid pressure of at least 400 psi and, desirably, at least 500 psi and greater. This clamping force likewise prevents separation of the laser weld joint or joints between the front plate 102 of the pump body 100 and the manifold plate 230.

As previously noted, various versions and embodiments of the fluid supply set 32 may be associated with the pump 10 to meet different patient and/or procedural needs, as described herein. The combination of the pump 10 and a specific configuration of the fluid supply set 32 forms the multi-use or multi-patient disposable set for the fluid delivery system or unit 2. Referring further to FIGS. 40-43, each of the various versions and embodiments of the fluid supply set 32 comprises one or more fluid supply tubes 34 each having one end connected to the pump 10 and the opposing end connected to a spike 36 used to access a fluid source container 30. In certain variations or configurations, the fluid supply set 32 may allow the fluid source containers 30 to be replaced without contamination of the pump 10.

Figure 40:
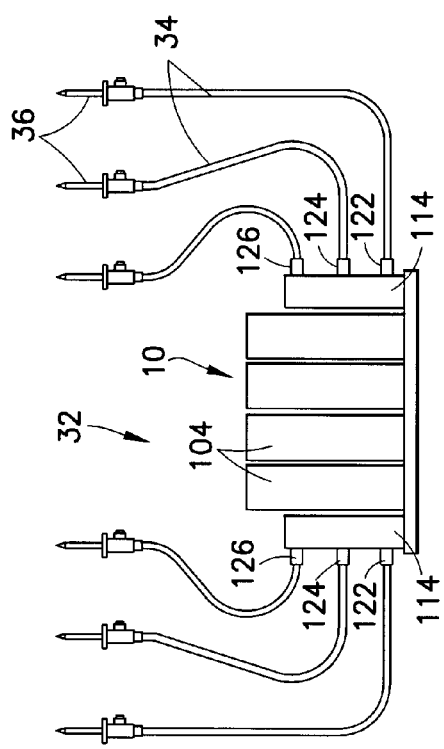
FIG. 40 is a schematic view showing the fluid pump device of FIG. 2 with a first or basic embodiment of a fluid supply set associated with the fluid pump device.

A "basic" embodiment of the fluid supply set 32 is shown in FIG. 40. The basic fluid supply set 32 comprises six (6) fluid supply tubes 34 which connect six (6) fluid source containers 30 to the six (6) inlet ports 122, 124, 126 on the inlet selector valve cylinders 114 on the pump body 100. The basic configuration is for a typical end user performing, for example, 8-12 procedures per day and be may be used, for example, on up to about 15 patients. In this configuration, two (2) contrast fluid source containers 30 containing contrast fluids A1, A2, for example, the same type or brand of contrast fluid, may be connected to the first and second inlet ports 122, 124 on the left side inlet selector valve cylinder 114, and two (2) contrast fluid source containers 30 containing contrast fluids B1, B2, for example, the same type or brand of contrast fluid but different from contrast fluids A1, A2, may be connected to the first and second inlet ports 122, 124 on the right side inlet selector valve cylinder 114. However, if desired, the same type of fluid may be present in all four (4) of the foregoing installed fluid source containers 30. Fluid source containers 30 containing saline S1, S2 are connected to the saline ports 126 on each of the inlet selector valve cylinders 114 in the manner discussed previously. The basic fluid supply set 32 typically has permanently attached spikes 36 on the free end of each of the fluid supply tubes 34, and the other end of each of the fluid supply tubes 34 is permanently connected to the respective inlet ports 122, 124, 126. However, one or more of the spikes 36 may be replaceable spikes if so desired. For example, replaceable spikes 36 may be provided for accessing the saline fluid source containers 30 containing saline S1, S2. Once the fluid source container 30 attached to each spike 36 is empty, that particular fluid supply tube 34 and the associated inlet port 122, 124, 126 should no longer be used because of the contamination risk involved in changing out a fluid source container 30.

Figure 41:
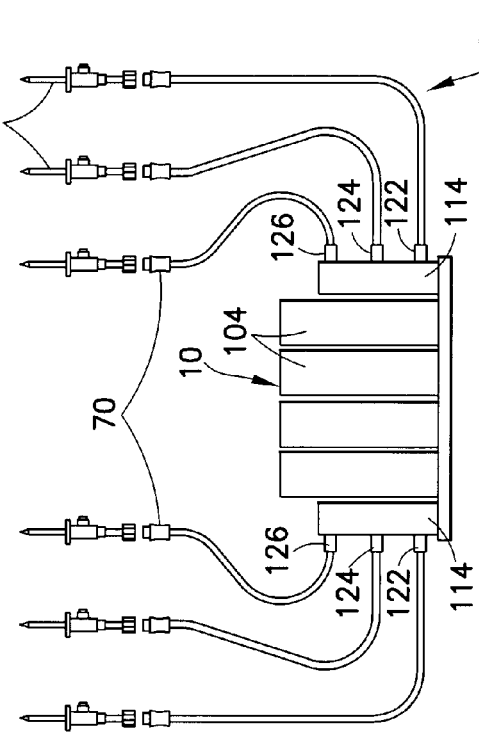
FIG. 41 is a schematic view showing the fluid pump device of FIG. 2 with a second or high-use embodiment of the fluid supply set associated with the fluid pump device.

In FIG. 41, a "high-use" fluid supply set 32 is shown and differs only from the basic configuration in that all the spikes 36 are replaceable. A swabable valve 70 may be provided on the free end of the fluid supply tubes 32 for connection to the spikes 36. In this variation, one fluid source container 30 may be attached to each spike 36 and, once empty, the empty container 30 and used spike 36 may be removed and discarded. The permanently attached swabable valve 70 may then be cleaned and a new spike 36 attached to the valve 70. Multiple fluid source containers 30 may be installed on a given fluid supply set 32 as long as the spike 36 is replaced with each new container 30 and the corresponding swabable valves 70 are cleaned appropriately.

Figure 42:
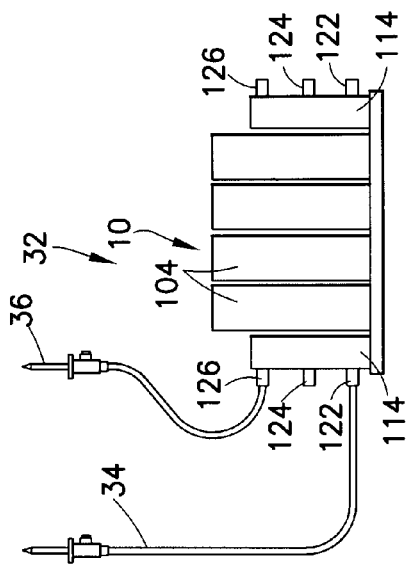
FIG. 42 is a schematic view showing the fluid pump device of FIG. 2 with a third or limited-use embodiment of the fluid supply set associated with the fluid pump device.

In FIG. 42, another variation of the fluid supply set 32 is shown and intended for limited use with only a few patients, such as may occur on a weekend. This variation of the fluid supply set 32 may be used, for example, on up to about five (5) patients and has a single fluid source container 30 containing a desired therapeutic or diagnostic (e.g., pharmaceutical) fluid connected to one of the first inlet ports 122 on the left or right side inlet selector valve cylinders 114. A saline fluid source container 30 containing saline is connected to the saline port 126 on the same inlet selector valve cylinder 114. The spikes 36 are shown permanently attached to fluid supply tubes 34 so once a fluid source container 30 is empty, that particular fluid supply tube 34 and inlet port 122, 126 should no longer be used. However, swabable valves 70 may also be used in the manner shown in FIG. 41.

Figure 43:
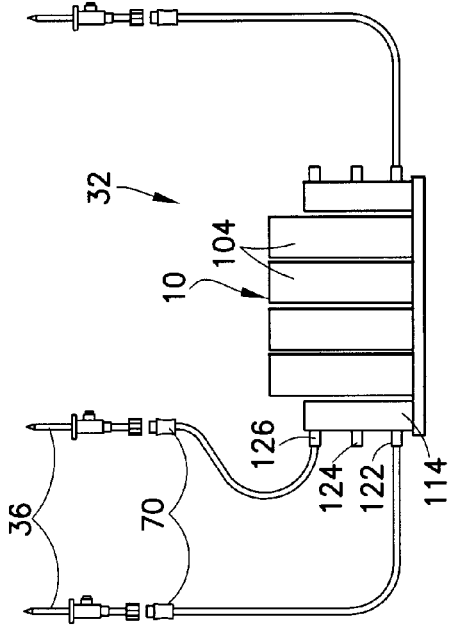
FIG. 43 is a schematic view showing the fluid pump device of FIG. 2 with a fourth and additional limited-use embodiment of the fluid supply set associated with the fluid pump device that may be used with single-patient fluid source containers.

In FIG. 43, a further variation of the fluid supply set 32 is shown and is intended for use with small, single-patient fluid source containers 30. This variation is intended to be used, for example, for up to about 15 patients. In this variation, a first type of therapeutic or diagnostic (e.g., pharmaceutical) fluid A1 in a fluid source container 30 is connected to the first inlet port 122 on one of the inlet selector valve cylinders 114, and a second type of therapeutic or diagnostic (e.g., pharmaceutical) fluid B1 is connected to the first inlet port 122 on the other inlet selector valve cylinder 114. Saline S1 in a fluid source container 30 is connected to the saline port 126 on one of the inlet selector valve cylinders 114. In this variation, swabable valves 70 are provided on the free ends of the fluid supply tubes 32 for connection to replaceable spikes 36. Accordingly, once the fluid source container 30 attached to the respective spikes 36 is empty, the empty container 30 and used spike 36 may be removed and discarded. The permanently attached swabable valve 70 may then be cleaned and a new spike 36 may be attached to the valve 70, along with a new fluid source container 30.

As shown in FIG. 44, the single-patient supply set 40 generally comprises medical tubing having opposed free ends each with a fluid connector 42. The patient-end fluid connector 42 is used to make a fluid connection to a catheter inserted into a patient to convey a desired fluid or mixture of fluids to a desired location within the patient's body. The patient-end fluid connector 42 may include a check valve (not shown) to prevent reverse flow from the patient. The other free end fluid connector 42 is connected to the patient outlet port 272 on the outlet selector valve cylinder 264 on the manifold plate 230.

Further, FIG. 45 shows the waste collection system 44 associated with a pump 10 having a "high-use" fluid supply set 32. As described previously, the waste collection system 44 generally comprises a waste collection tube set 46 connected to a waste collection container 48 used to collect and store waste fluids. The waste collection tube set 46 is adapted to make a fluid connection with the pump 10. In particular, the waste collection system 44 is connected to the waste outlet port 272 on the outlet selector valve cylinder 264 on the manifold plate 230, as noted previously, and the waste collection tube set 46 conducts waste fluids to the waste collection container 48 when the outlet selector valve 280 is actuated to place the flow passage 290 in fluid communication with the waste outlet port 272. A check valve (not shown) may be incorporated into the fluid connector on the waste collection tube set 46 which prevents accidental reverse flow from the waste collection container 48 into the pump 10. Additionally, if the waste collection container 48 is removed and replaced with a new waste collection container 48, the check valve prevents the contents of the full waste collection container 48 from being ejected during handling.

As noted in the foregoing, the fluid delivery system 2 comprises a drive and actuating system 400 that interfaces with the pump 10 to provide the motive forces for operating the various components of the pump 10. Referring next to FIGS. 46-60, details of the drive and actuating system 400 will be described. The drive and actuating system 400 is supported by a mobile support or superstructure 700 that also supports a fluid management system 720 for supporting, maintaining, and monitoring the various diagnostic or therapeutic (e.g., pharmaceutical) fluids to be associated with the pump 10. Particularly, the fluid management system 720 provides air management functions for the fluid delivery system 2, as described herein in connection with FIG. 60. The mobile support or superstructure 700 permits the fluid delivery system 2 to be a mobile system for applications in various medical environments, such as medical imaging suites that utilize a computed tomography (CT) scanner, as an example. As a result, the fluid delivery system 2 may be positioned in close proximity to the patient during a fluid injection and scanning procedure and a "short" patient supply set 40 may be used. Additionally, depending upon the type of procedure being performed, it may be desirable to place the fluid delivery system 2 either in front of the CT scanner gantry or behind the gantry. This placement is typically determined by whether the scan is being performed with the patient's hands/arms above their head for chest and abdominal scans, or at their sides for head and neck scans. Further, the system 2 may easily be moved out of the way to permit the patient to be placed on or removed from the bed of the CT scanner. Furthermore, the fluid delivery system 2 includes a control system 800, as noted previously, for coordinating and controlling operation of the various components and functions of the drive and actuating system 400 and fluid management system 720, each supported on the mobile support 700.

Figure 46A:
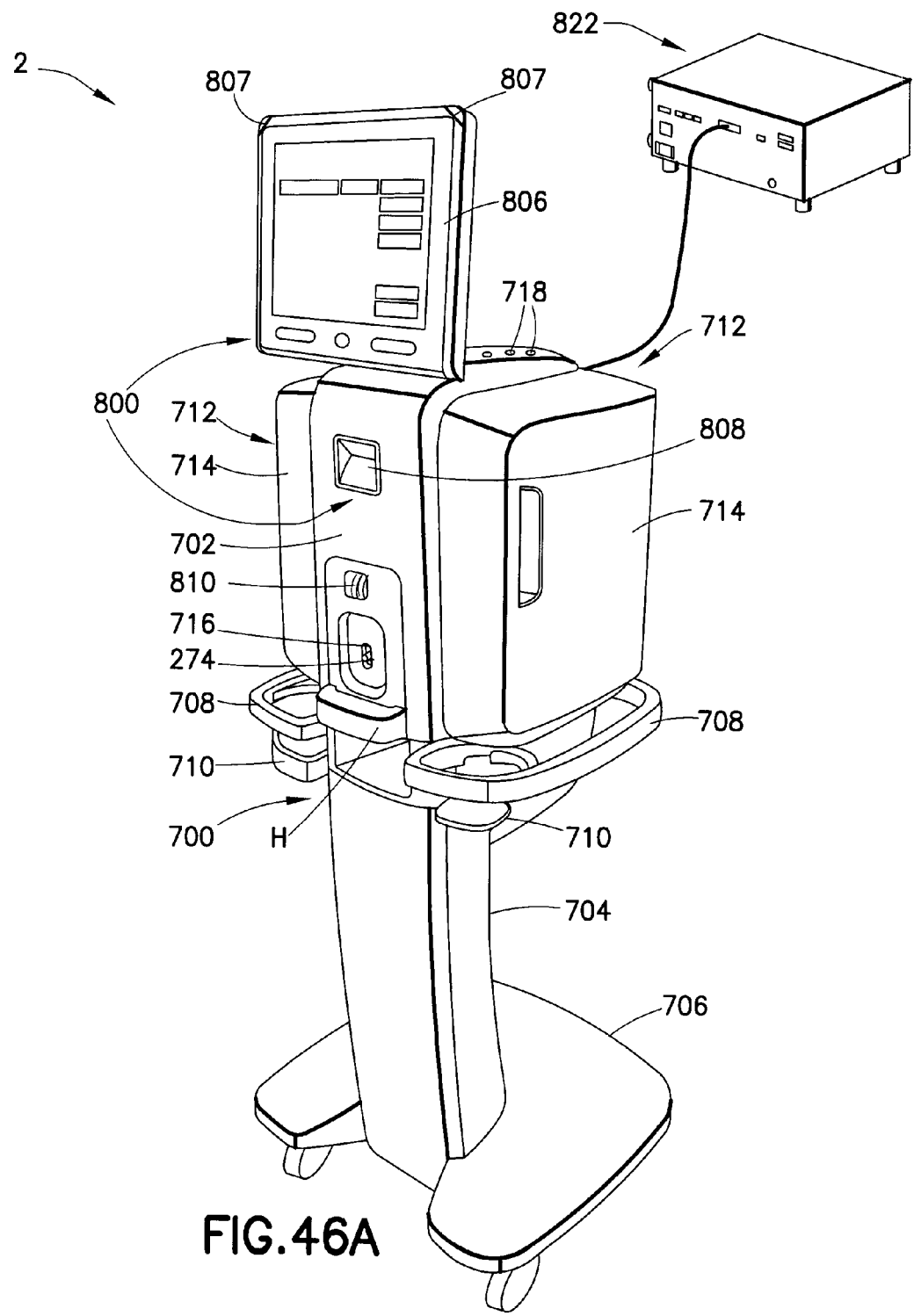
FIG. 46A is a perspective view of the fluid delivery system for continuous multi-fluid delivery applications embodied as a mobile system.
Figure 46B:
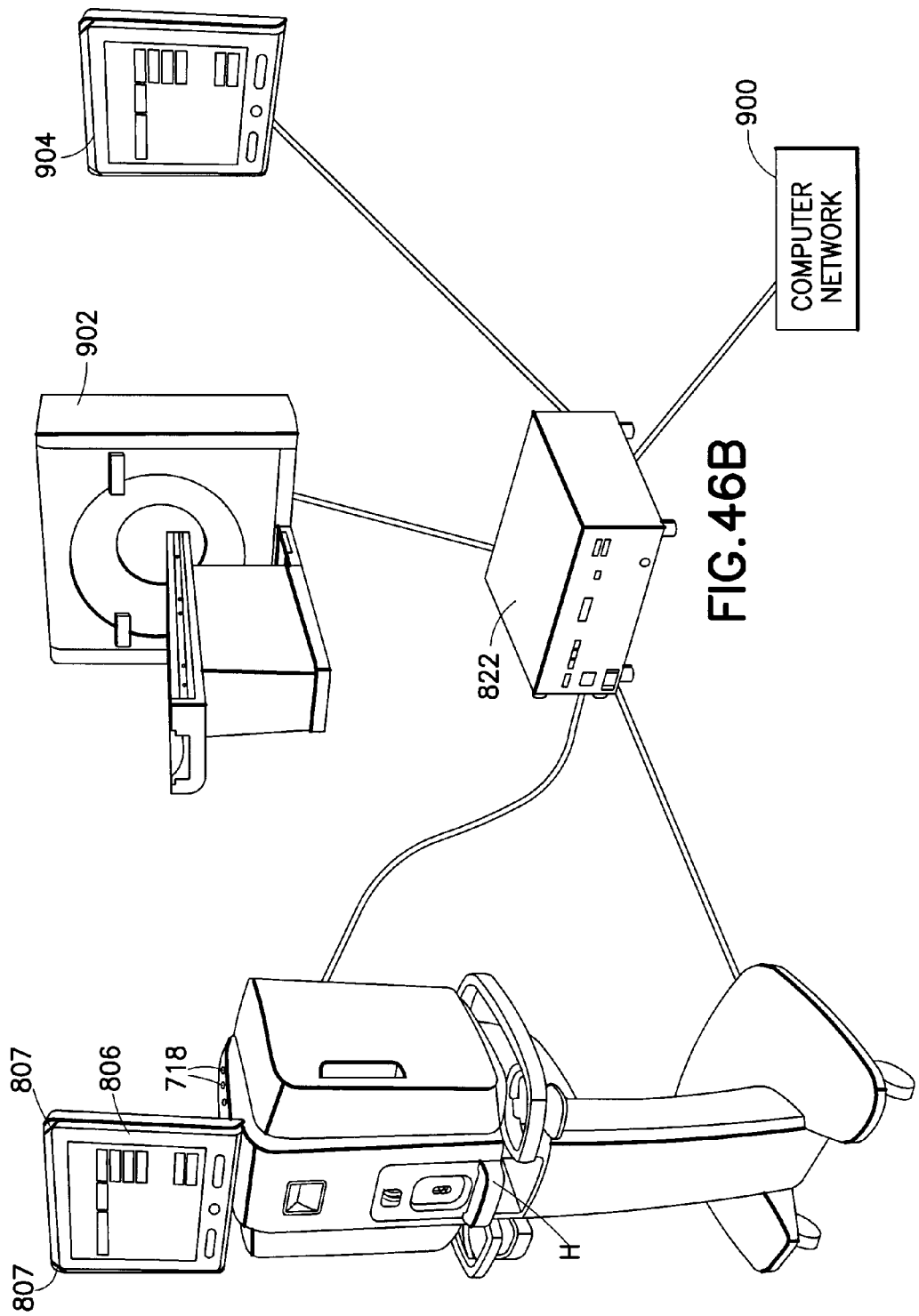
FIG. 46B is a schematic view of the fluid delivery system of FIG. 46A shown interfacing with external devices including a remotely located display, computed tomography scanner, and a computer network as examples.
Figure 47:
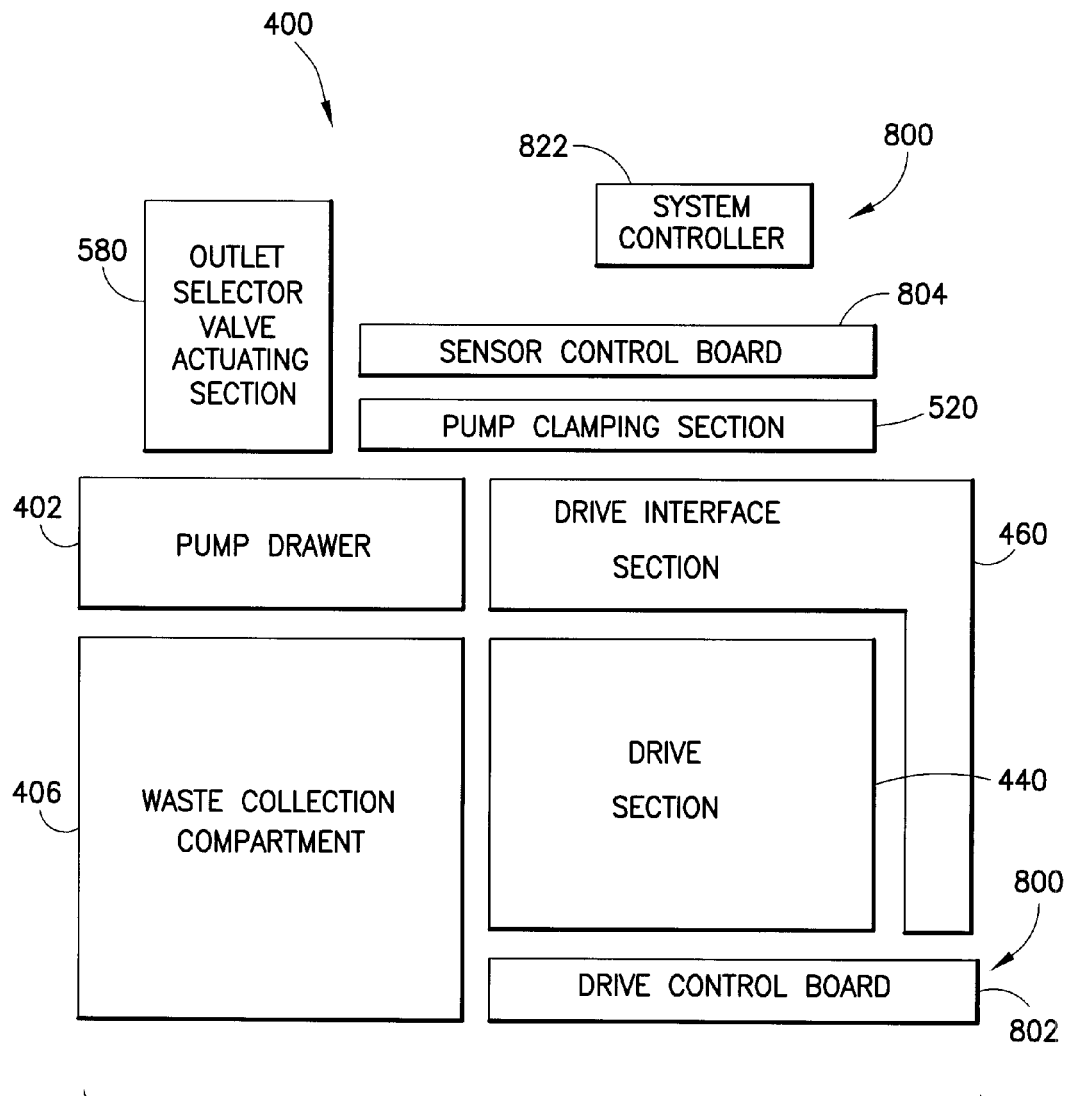
FIG. 47 is a schematic representation of a drive and actuating system for the fluid delivery system shown in FIG. 46A, and further showing features of a control system for the fluid delivery system.
Figure 48:
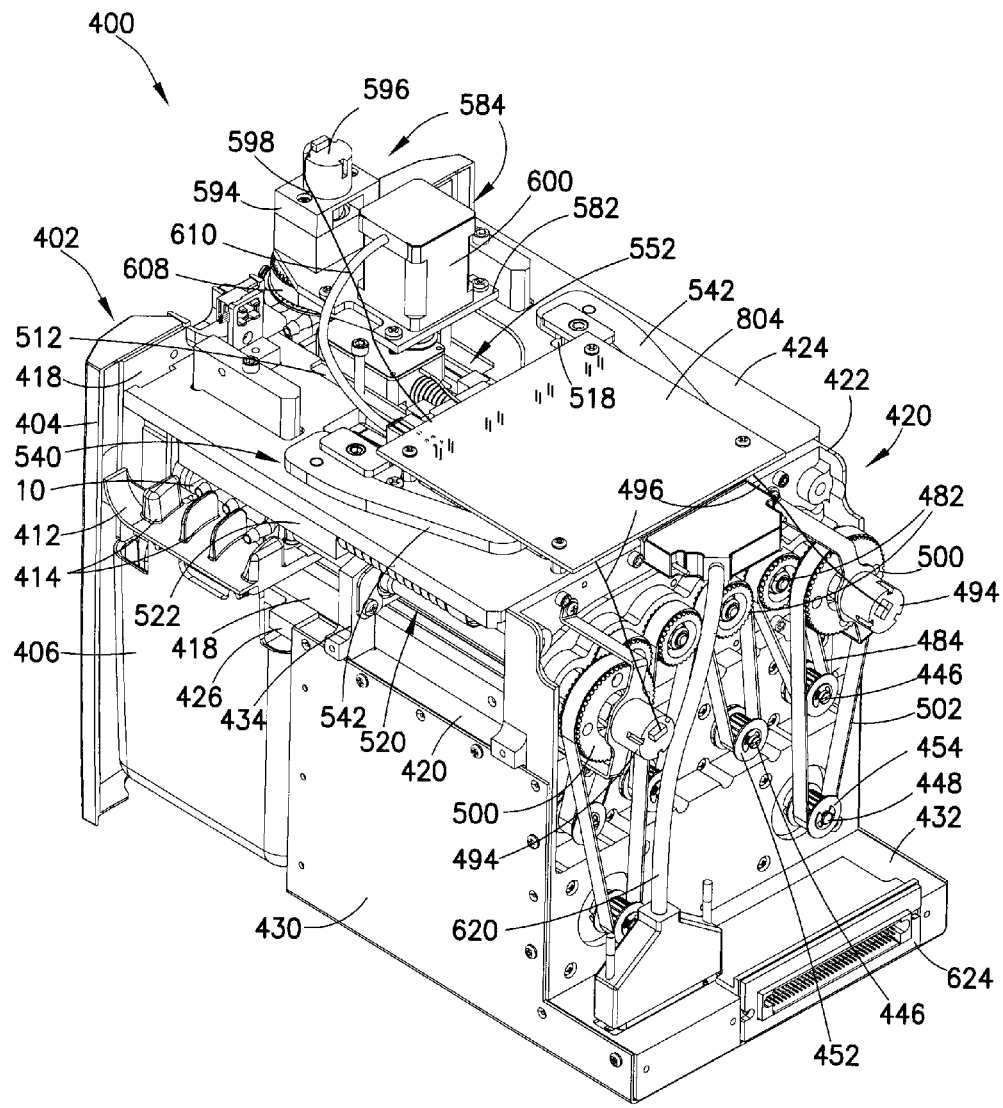
FIG. 48 is a top perspective of the drive and actuating system for the fluid delivery system shown in FIG. 46A, with a pump drawer in a closed position.
Figure 49:
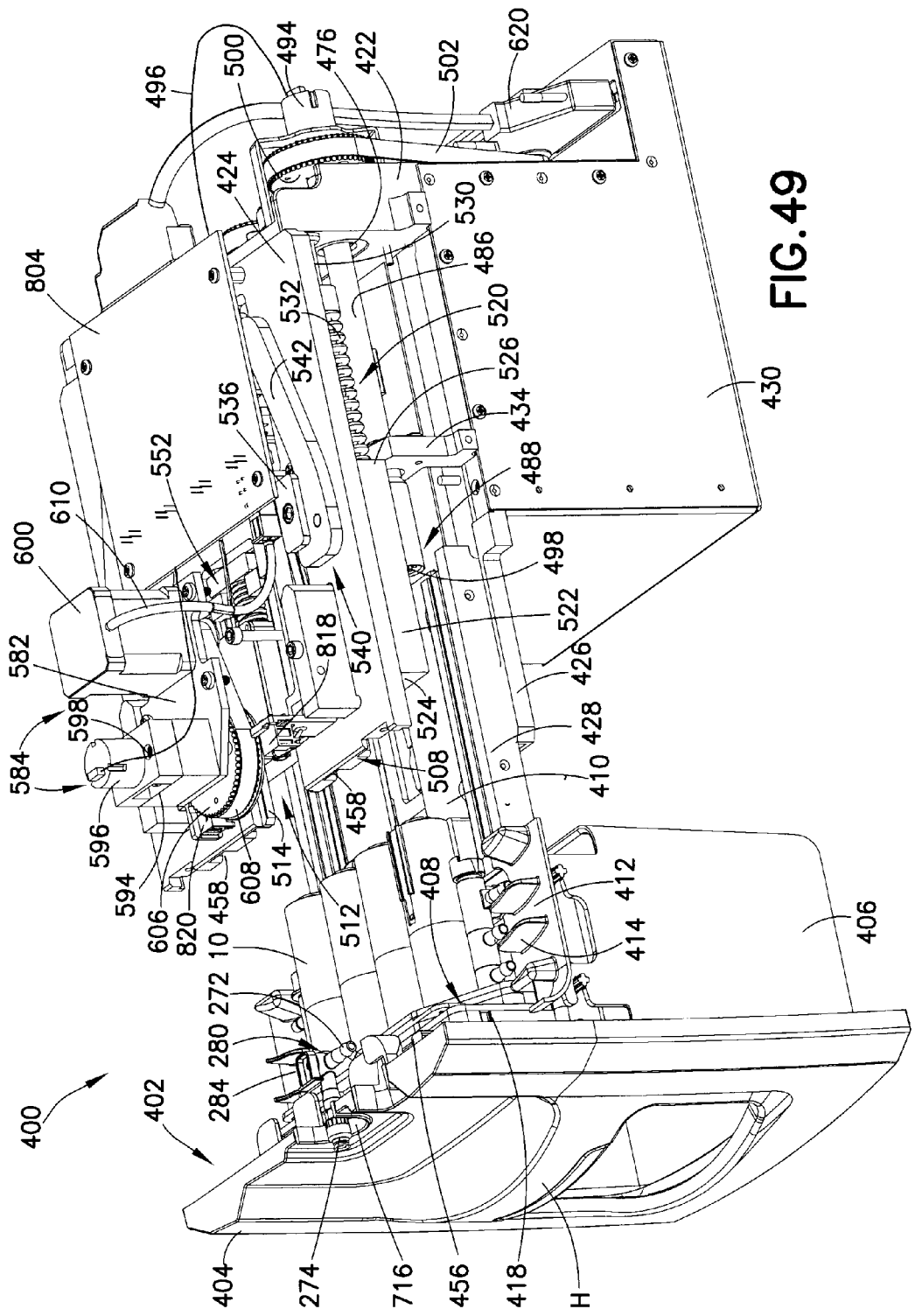
FIG. 49 is a top perspective view of the drive and actuating system for the fluid delivery system shown in FIG. 46A, with the pump drawer in an open position.
Figure 50:
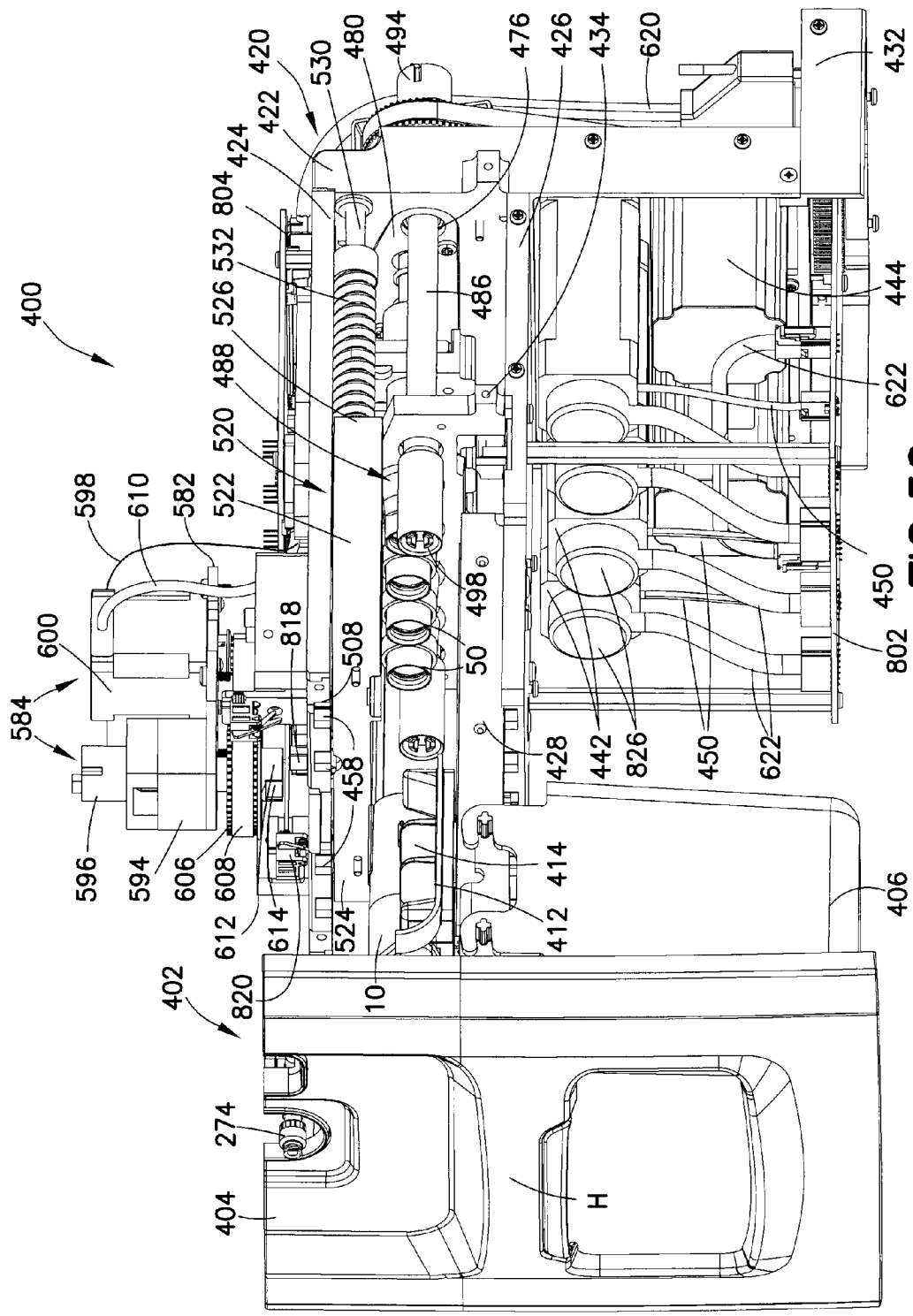
FIG. 50 is a side perspective view of the drive and actuating system for the fluid delivery system shown in FIG. 46A, with the pump drawer in the open position.
Figure 51:
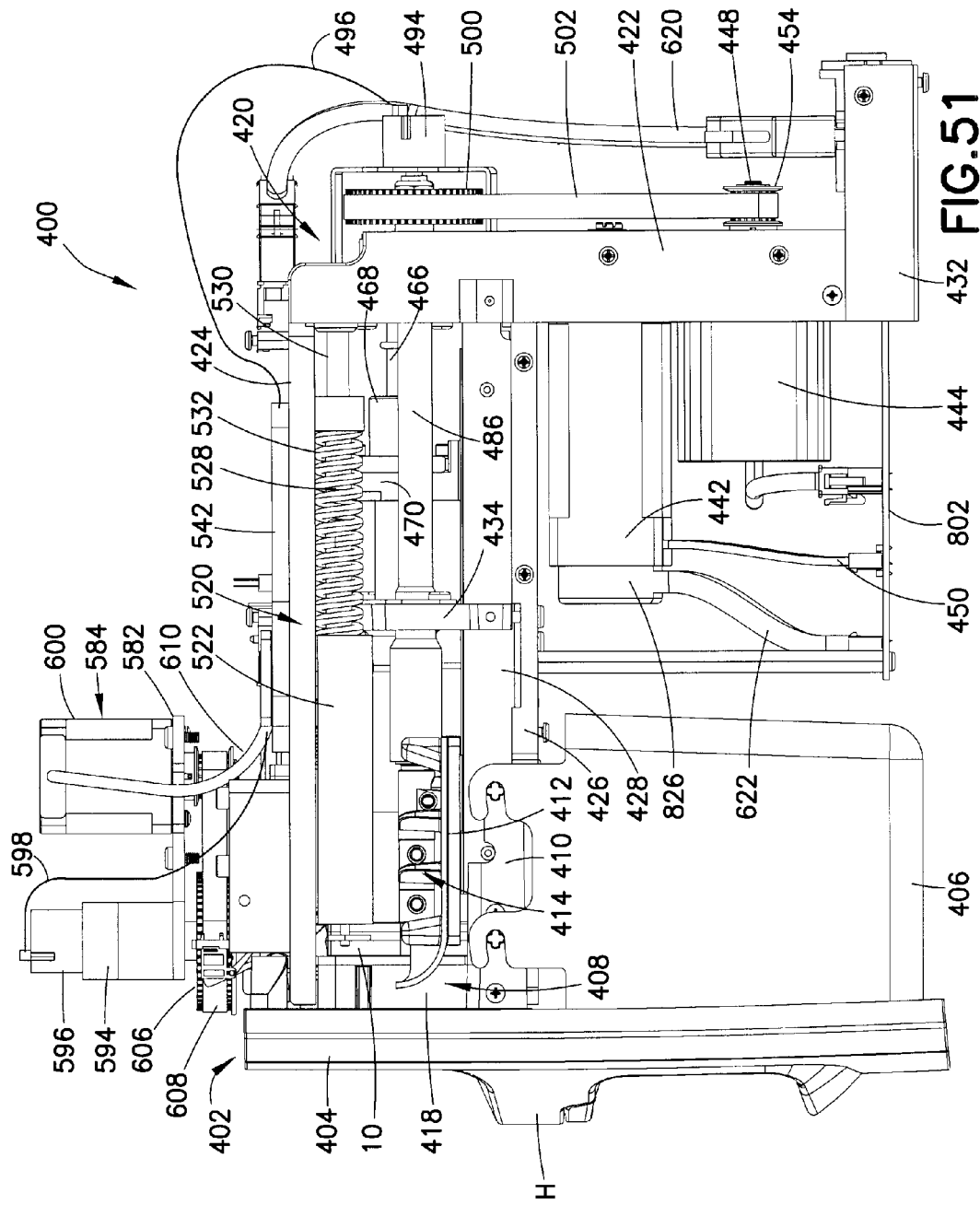
FIG. 51 is a side view of the drive and actuating system for the fluid delivery system shown in FIG. 46A, with the pump drawer in the closed position.
Figure 52:
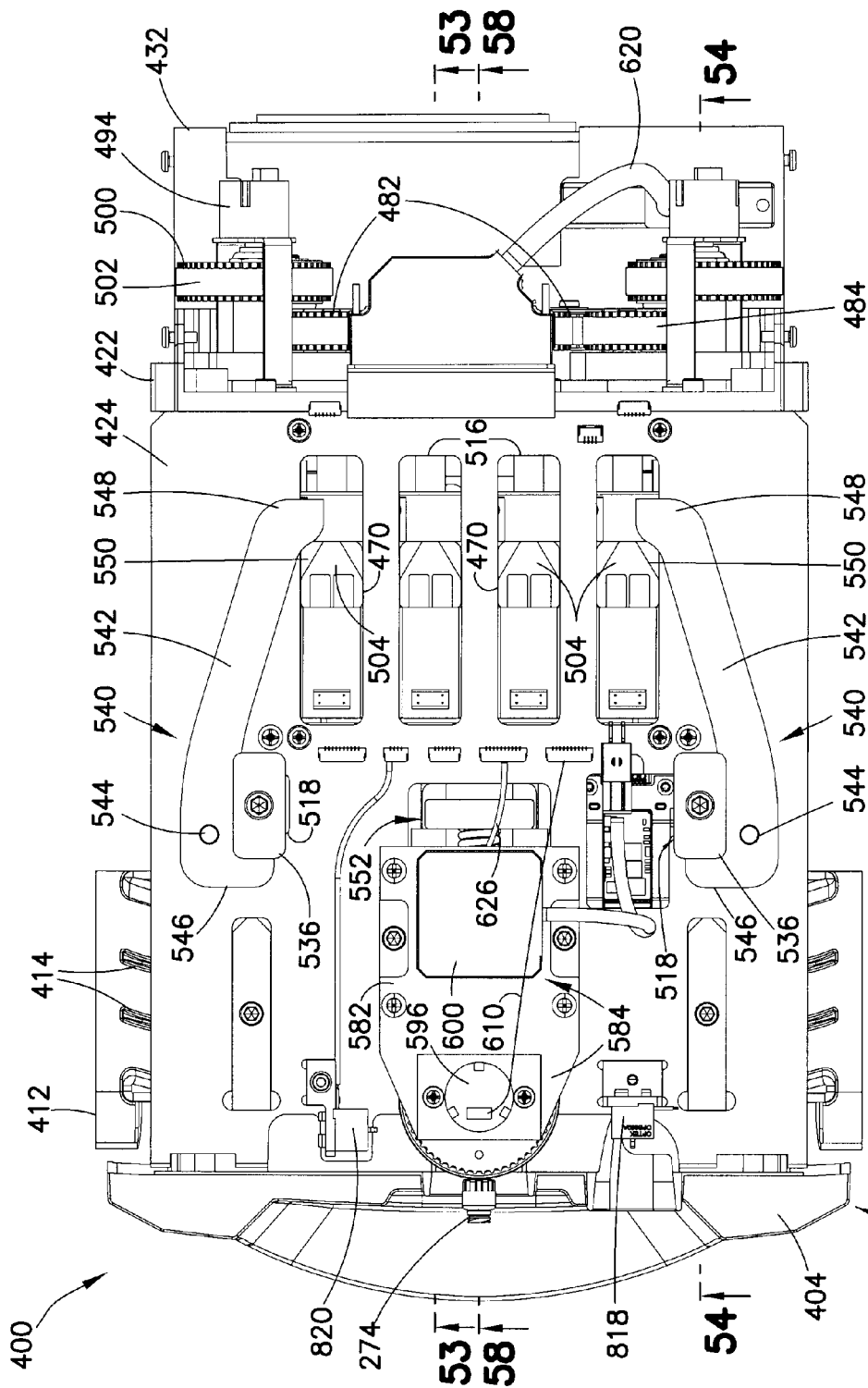
FIG. 52 is a top view of the drive and actuating system for the fluid delivery system shown in FIG. 46A, with the pump drawer in the closed position.
Figure 53:
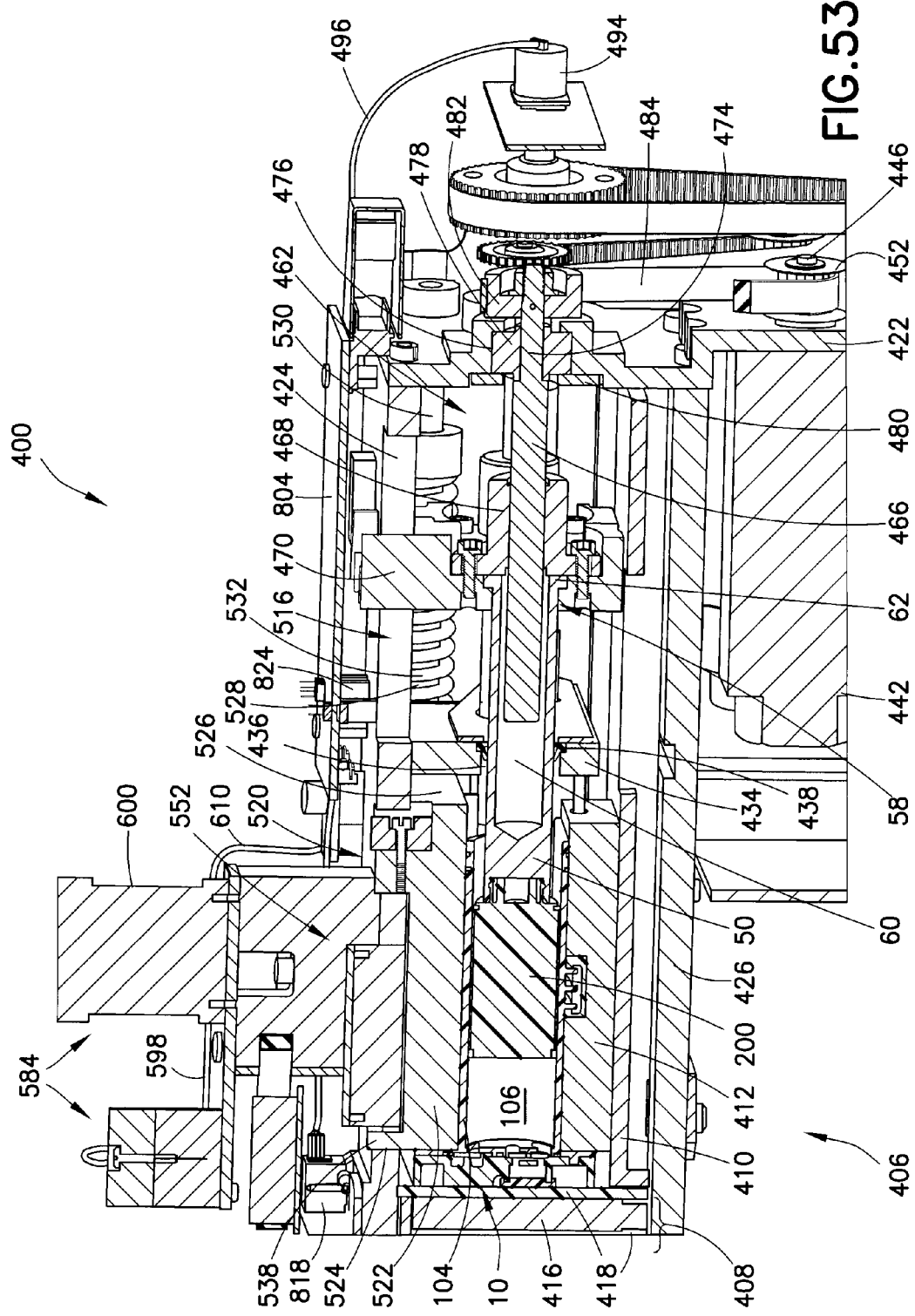
FIG. 53 is a cross-sectional view of the drive and actuating system for the fluid delivery system shown in FIG. 46A, taken along line 53-53 in FIG. 52.

FIG. 47 is a block schematic representation of the drive and actuating system 400 of the fluid delivery system 2. Generally, the drive and actuating system 400 comprises a movable pump drawer section 402 that is extendable and retractable on the mobile support 700 to allow loading/unloading of the pump 10 into/from the pump drawer 402. The drive and actuating system 400 also comprises a drive section 440 that generates the motive forces for reciprocal operation of the pistons 50 operating the respective plungers 200 and rotational operation of the inlet selector valves 300. Additionally, the drive and actuating system 400 comprises a drive interface section 460 that translates and/or transmits the motive forces from the drive section 440 to the pistons 50 and inlet selector valves 300. Further, the drive and actuating system 400 comprises a pump clamping section 520, also referred to herein as a pump clamping mechanism 520, that secures the pump 10 in association with the drive and actuating system 400. Furthermore, the drive and actuating system 400 comprises an outlet selector valve actuating section 580 that operates the outlet selector valve 280 on the pump 10. The drive and actuating system 400 desirably further supports several components of the control system 800, including a drive control board 802 that is electronically connected and interfaced with the control system 800 to enable the control system to control operation of the drive section 440, and a sensor control board 804 used to collect sensor information from various sensors in the drive and actuating system 400 and relay this electronic information to the control system 800 to enable the control system 800 to control operation of the drive section 440, drive interface section 460, pump clamping mechanism 520, and outlet selector valve actuating section 580. Each of the foregoing sections is described hereinafter in connection with FIGS. 46-60.

The pump drawer 402 is generally extendable and retractable from the mobile support 700 and comprises a drive and actuating support structure 420 that mounts and supports the various components of the drive section 440, drive interface section 460, pump clamping section 520, and outlet selector valve actuating section 580. The pump drawer 402 includes a handle housing portion 404 and a waste collection compartment 406 to accommodate the waste collection container 48 and at least portions of the associated waste collection tubing set 46, which were described previously. The handle housing portion 404 is supported by a composite drawer support structure 408 that is mechanically affixed to a drawer shelf plate 410. The handle housing portion 404 is mounted to the drawer support structure 408 so that the handle housing portion 404 forms a portion of the cosmetic outer face of the pump drawer 402.

A pump cradle 412 is fixedly mounted on the top side of the drawer shelf plate 410 to support and maintain the pump 10 on the drawer shelf plate 410. The pump cradle 412 is preformed to the shape of the pump 10 to secure the pump 10 in the pump drawer 402 and comprises preformed cradle appendages 414 to interface with the fluid supply tubes 34 of the various embodiments of the fluid supply sets 32 described previously. The cradle appendages 414 are formed for easy loading of the pump 10 in the pump drawer 402. The handle housing portion 404 may be a singular component or a composite structure, as indicated above, that includes a reinforcing and locking support plate 416 sandwiched between two face plates 418. A drawer handle H is formed integrally on the outside face of the handle housing portion 404 to enable a user to slidably operate the pump drawer 402. The waste collection compartment 406 may be detachably suspended from lateral sides of the drawer shelf plate 410. The locking support plate 416 may be made of metal such as stainless steel or another metal suitable for applications in medical environments, and the face plates 418 may be polymeric covering face plates that have suitability for improving the ornamental or cosmetic exterior appearance of the pump drawer 402.

The drive and actuating support structure 420 comprises a rear support plate 422 that supports a top, distally-extending support plate 424 and a bottom, distally-extending support plate 426. The drawer shelf plate 410 of the pump drawer 402 is journalled for slideable movement relative to the bottom support plate 426 by a pair of mounting flanges 428 mounted on opposing sides of the top side of the bottom support plate 426. A drive enclosure or housing 430 may be secured to the bottom support plate 426 to enclose a region forward or distal of the rear support plate 422 and below the bottom support plate 426. The drive enclosure 430 encloses the various drive motors of the drive section of the drive and actuating system 400 as well as the drive control board 802, as described herein. A base plate 432 may be connected to or extend from the lower end of the rear support plate 422 to support the drive control board 802, and support rods may extend from the drive control board 802 to the bottom support plate 426 for rigidity purposes. An intermediate support plate 434 is located on top of the bottom support plate 426 and forward of the rear support plate 422 to support the drive pistons 50 and actuator components used to operate the inlet selector valves 300, as described hereinafter. Several support openings 436 are provided in the intermediate support plate 434 for the drive pistons 50 and the actuator components used to operate the inlet selector valves 300. Support elements 438 are provided in each of the support openings 436 in the intermediate support plate 434 to support the drive pistons 50 and actuator components used to operate the inlet selector valves 300. These support elements 438 may be bushings in the case of the drive pistons 50 and support ball bearings in the case of the actuator components.

As noted in the foregoing, the drawer shelf plate 410 of the pump drawer 402 is journalled for slideable movement relative to the bottom support plate 426 by a pair of mounting flanges 428 mounted on opposing sides of the top side of the bottom support plate 426. This slideable movement permits the pump drawer 402 to move from a closed position in which the pump drawer 402 is received within the mobile support 700 to an extended position outward from the mobile support 700 to permit a user to load a pump 10 into the pump cradle 412. The handle H on the handle housing portion 404 is used by the user to extend and close the pump drawer 402. The sliding movement of the drawer shelf plate 410 enables the handle housing portion 404 and the waste collection compartment 406 depending from the drawer shelf plate 410 to be moved together as a singular unit from the closed or retracted position of the pump drawer 402 to the extended or loading position of the pump drawer 402. The pair of mounting flanges 428 mounted on opposing sides of the top side of the bottom support plate 426 support the drawer shelf plate 410 in both the extended or loading position of the pump drawer 402 and the closed or retracted position of the pump drawer 402 and an extension limiter may be provided so that the drawer shelf plate 410 cannot be extended to a point where the pump drawer 402 disengages entirely from the mounting flanges 428. As described further herein, a locking connection may be provided between the locking support plate 416 and the drive and actuating support structure 420 to lock the pump drawer 402 in the closed position so that the pump 10 is secured during operation of the fluid delivery system 2.

Figure 54:
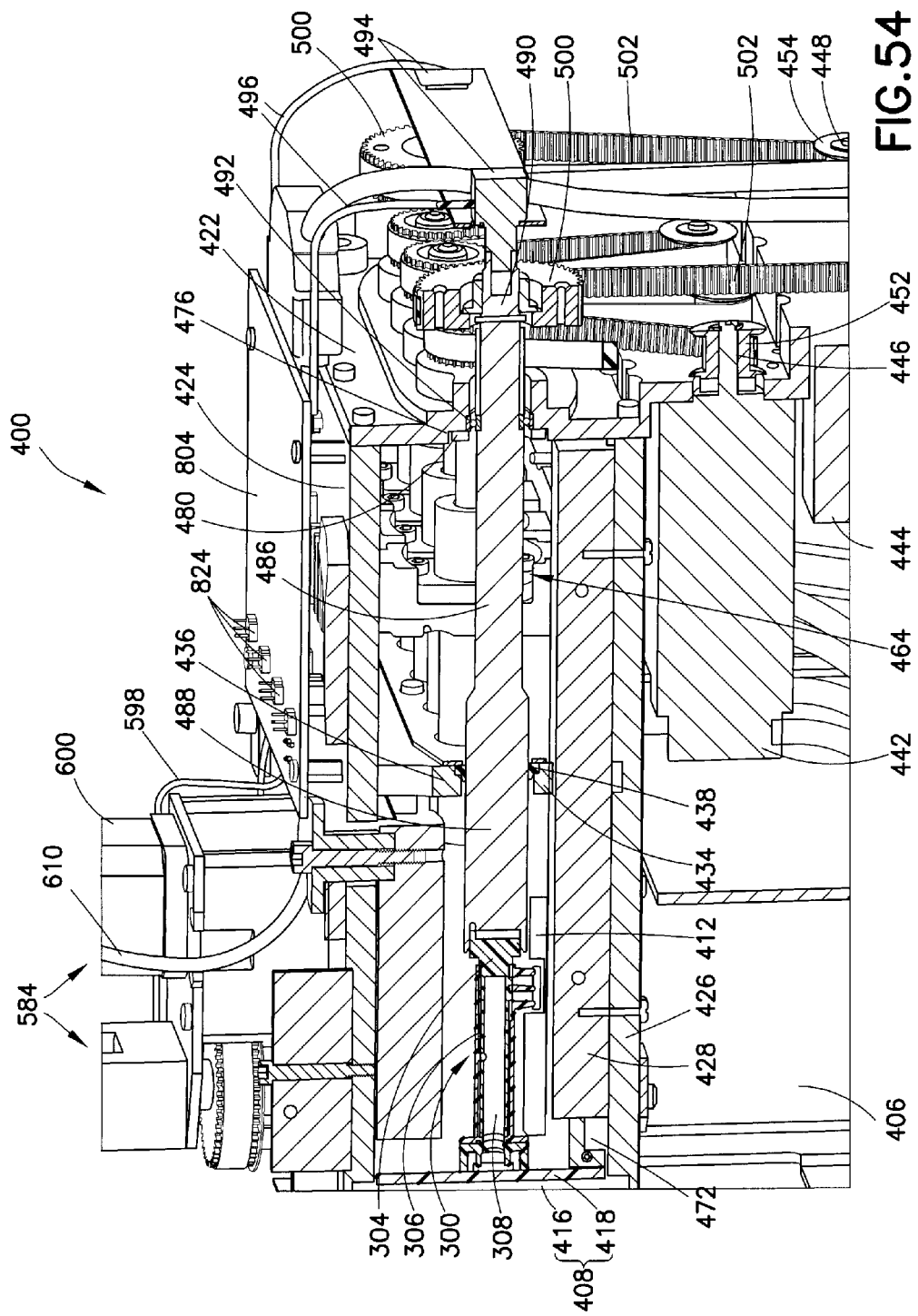
FIG. 54 is a cross-sectional view of the drive and actuating system for the fluid delivery system shown in FIG. 46A, taken along line 54-54 in FIG. 52.
Figure 55:
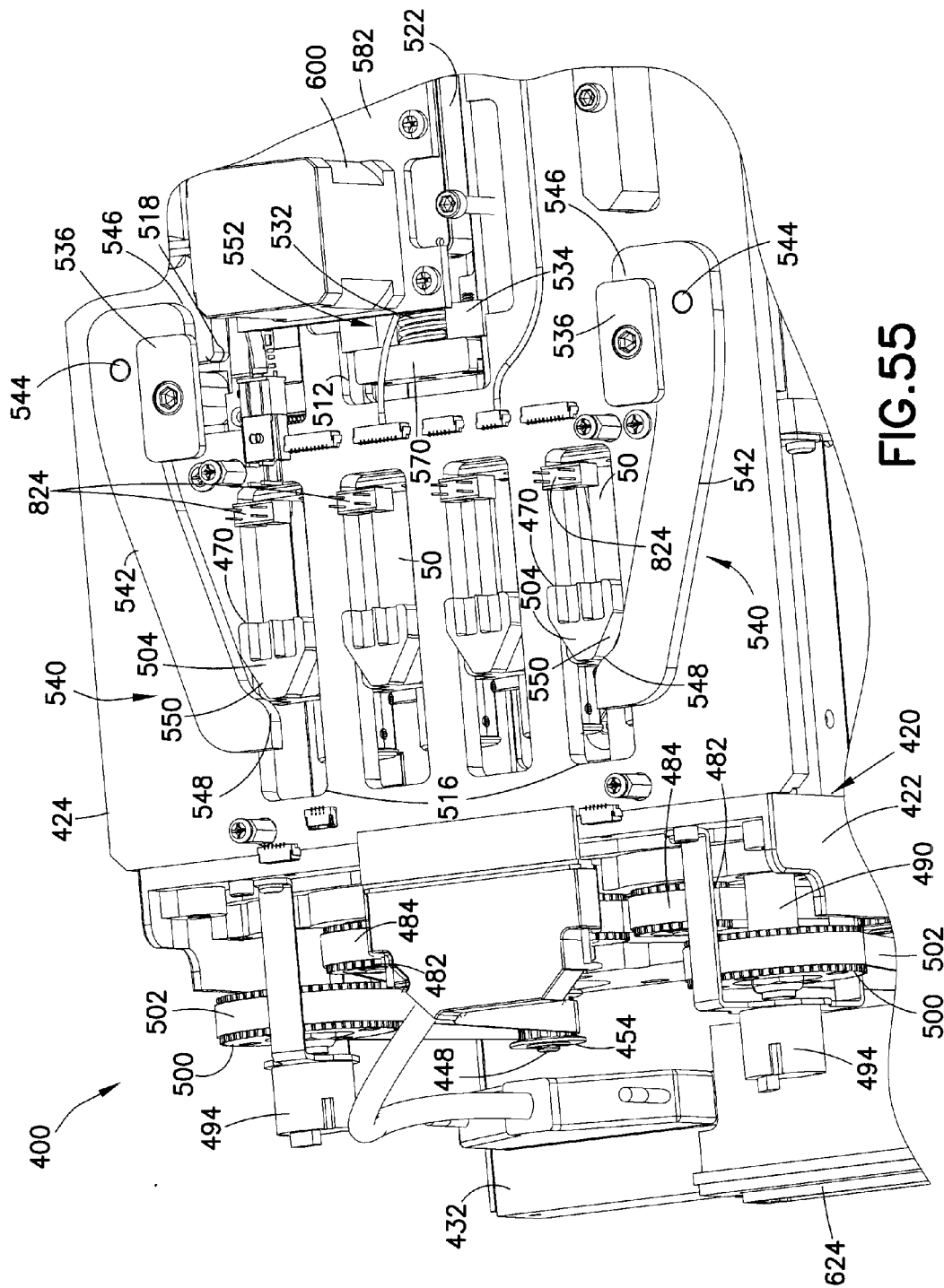
FIG. 55 is a top perspective view of a rear portion of the drive and actuating system for the fluid delivery system shown in FIG. 46A.
Figure 56:
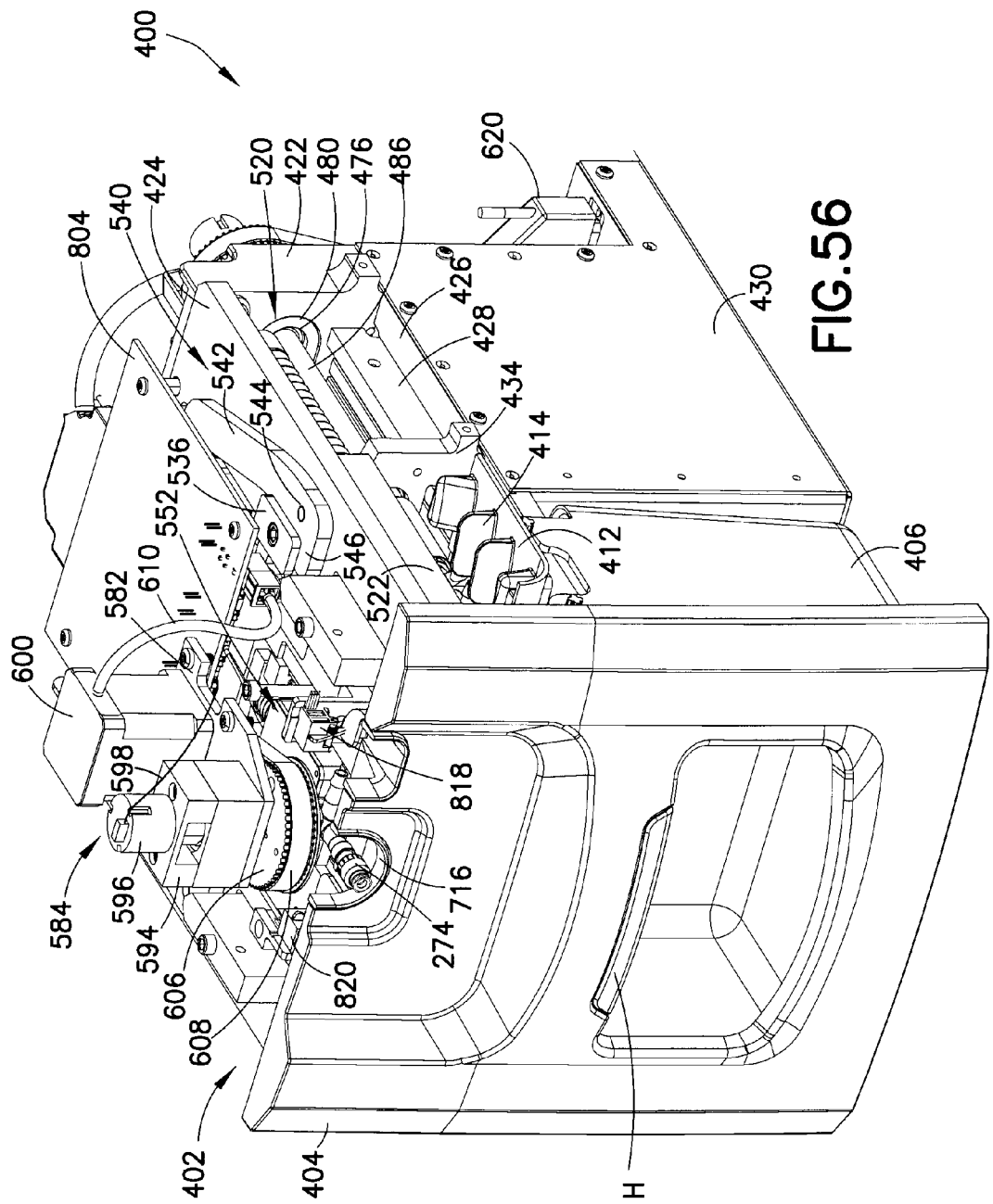
FIG. 56 is a front perspective view of the drive and actuating system for the fluid delivery system shown in FIG. 46A, with the pump drawer in the closed position.
Figure 57:
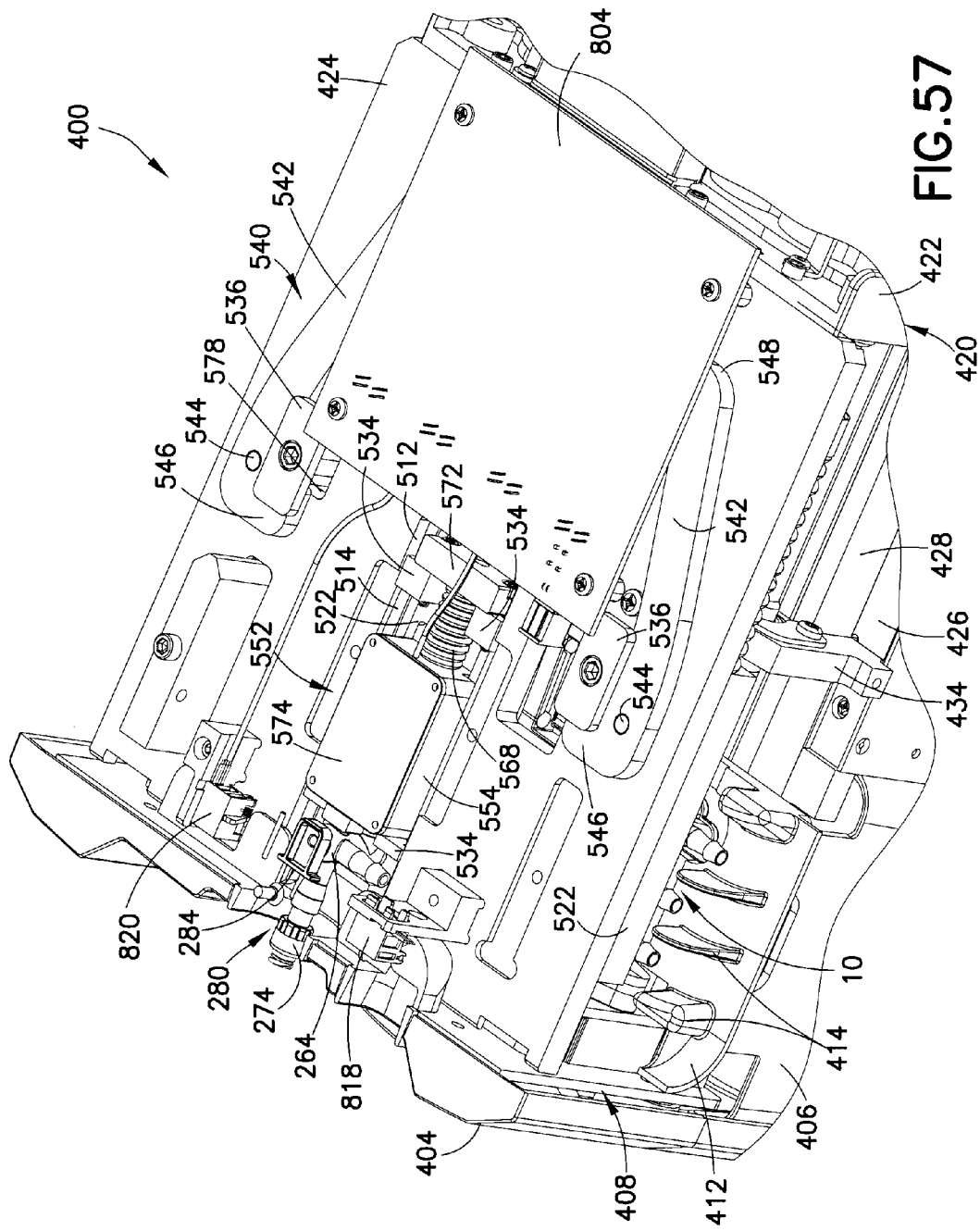
FIG. 57 is a top perspective view of a front portion of the drive and actuating system for the fluid delivery system shown in FIG. 46A.
Figure 58:
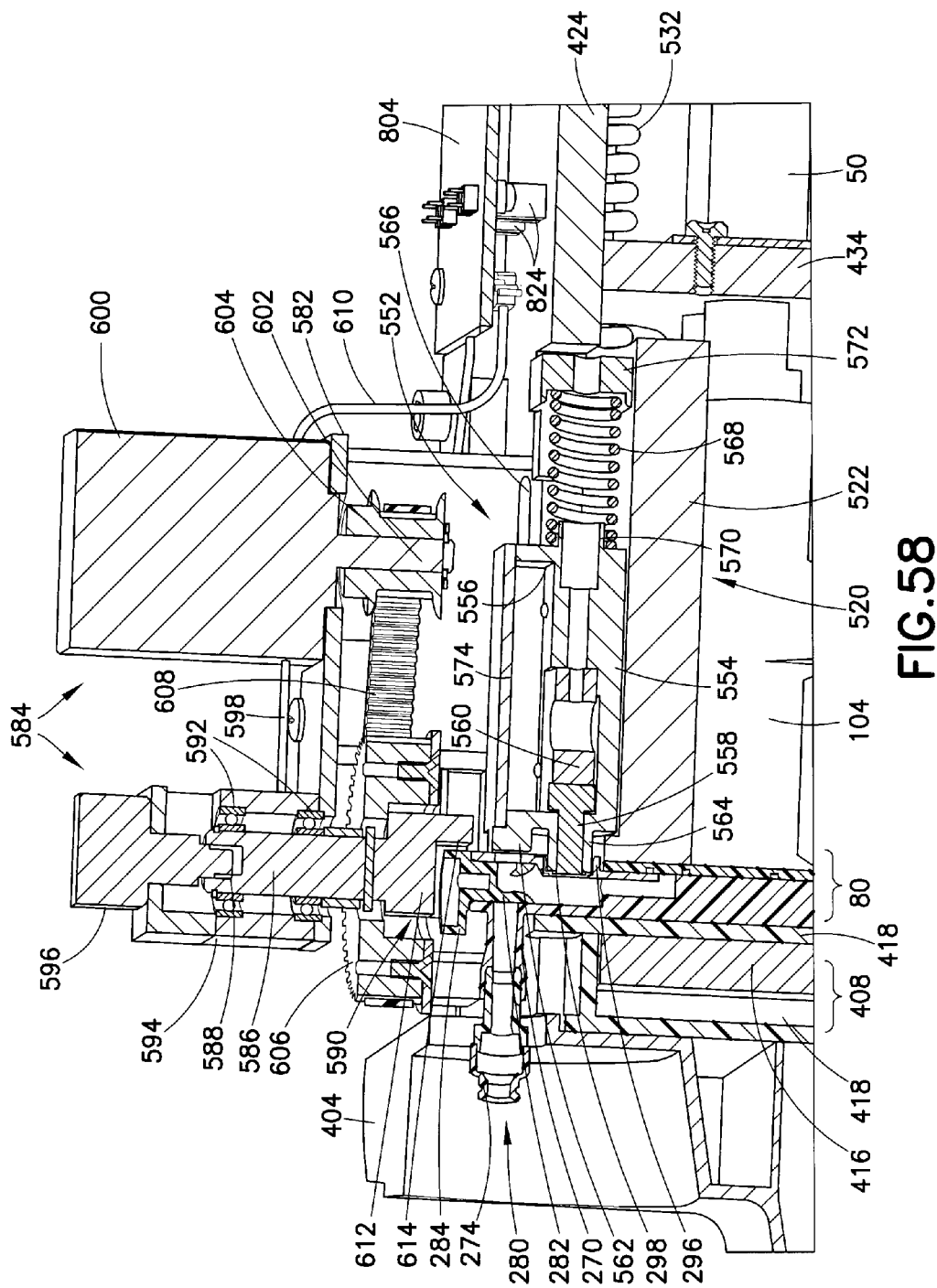
FIG. 58 is a cross-sectional view of the drive and actuating system for the fluid delivery system shown in FIG. 46A, taken along line 58-58 in FIG. 52.
Figure 59:
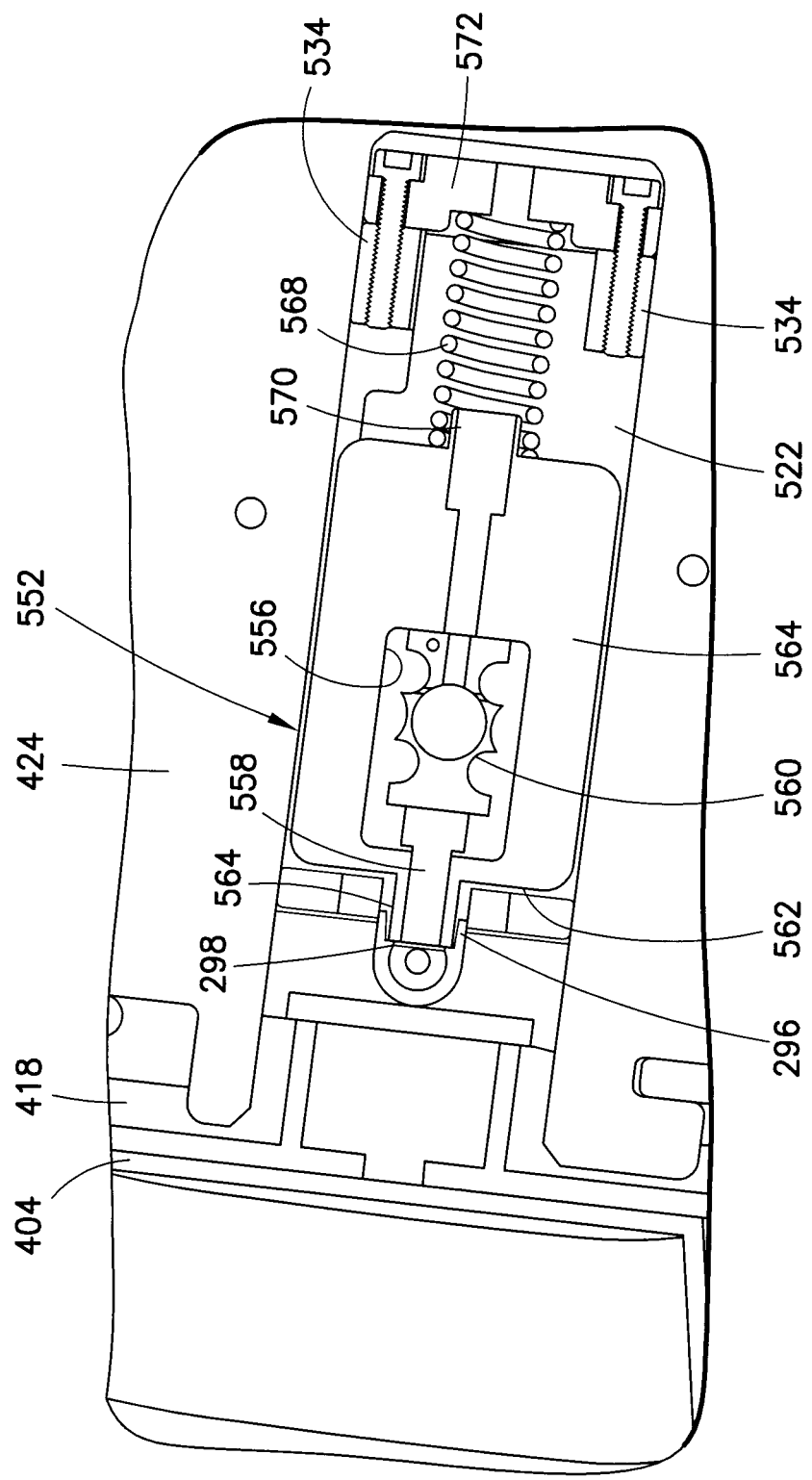
FIG. 59 is a top view of a pressure measurement mechanism for the fluid delivery system shown in FIG. 46A.

The drive section 440 comprises, in the present embodiment, four (4) piston actuator drive motors 442, such as servomotors and the like, that provide the motive forces which drive four (4) respective piston linear actuators 462 that individually operate the drive pistons 50. A home sensor 824 is provided for each of the piston linear actuators 462 so that the piston drive motors 442 may move the four (4) piston linear actuators 462 to a "home" position by moving them until the "home sensor" 824 for each actuator 462 is tripped thereby resetting their positions to zero. Each home sensor 824 is electronically connected with the sensor control board 804 as best shown in FIGS. 54 and 58. Additionally, a motor encoder count 826 is associated with each of the four (4) piston drive motors 442 and records an encoder count each time the piston drive motor 442 advances or retracts, for example, advances or retracts a distance equivalent to 0.075 μL of displacement of the plungers 200 in the respective pump cylinders 104 of the pump body 100 of the pump 10. Each drive motor encoder 826 is electronically connected with the drive control board 802.

The drive section 440 comprises a pair of inlet selector valve actuator drive motors 444, such as stepper motors and the like, that provide the motive forces which drive a pair of inlet selector valve actuators 464 that independently operate the respective inlet selector valves 300, as also described herein. The piston drive motors 442 are mounted to the front or distal facing side of the rear support plate 422 beneath the bottom support plate 426 and each have a drive shaft 446 extending through an opening in the rear support plate 422 to output motive forces to the piston linear actuators 462. Likewise, the respective inlet selector valve drive motors 444 are mounted to the front or distal facing side of the rear support plate 422 beneath the bottom support plate 426 and each have a drive shaft 448 extending through an opening in the rear support plate 422 to provide motive forces to the inlet selector valve actuators 464. The respective drive motors 442, 444 are electronically controlled by the control system 800 via respective electronic connections 450 with the drive control board 802. A drive pulley 452 is mounted to the drive shaft 446 of each of the piston drive motors 442 and, likewise, a drive pulley 454 is mounted to the drive shaft 448 of each of the inlet selector valve drive motors 444. As will be appreciated from the foregoing, a piston drive motor 442 is provided for each of the drive pistons 50 and an inlet selector valve drive motor 444 is provided for each of the inlet selector valves 300 based on the pump 10 comprising four (4) separate pump cylinders 104 and two (2) separate inlet selector valves 300. However, as noted previously, this exemplary configuration should not be deemed limiting as other configurations with a fewer or increased number of pump cylinders 104 and inlet selector valves 300 may be desirable for the fluid delivery system 2.

As mentioned in the foregoing, a locking connection is desirably provided between the locking support plate 416 and the drive and actuating support structure 420 to lock the pump drawer 402 in the closed position so that the pump 10 may be secured during operation of the fluid delivery system 2 or at other suitable times. This locking connection may be provided by a series of locking teeth 456 on the upper end or edge of the locking support plate 416 that engages a corresponding series of locking slots 458 provided in a front or distal end 508 of the opposing top support plate 424. The locking slots 458 may define a generally L-shaped configuration to receive the locking teeth 456. The locking support plate 416 is sandwiched and supported between the two opposing face plates 418 so as to be capable of limited lateral, side-to-side movement between the face plates 418. This limited lateral, side-to-side movement enables the locking teeth 456, after having engaged the L-shaped locking slots 458, to be placed into the transversely extending or "dog leg" of the locking slots 458 from a longitudinal or entry leg of the locking slots 458 by limited lateral movement of the locking support plate 416. The movement of the locking teeth 456 into the transversely extending portion or "dog leg" of the locking slots 458 places the pump drawer 402 into a locked position or state. A similar set of "lower" locking teeth (not shown) to the "upper" locking teeth 456 may be provided on the bottom of the locking support plate 416 to engage similar "lower" locking slots (not shown) to the "upper" locking slots 458 provided in the bottom support plate 426.

The locking slots 458 generally oppose the locking teeth 456 so that when the pump drawer 402 is moved by the user to the closed or retracted position, the locking teeth 456 are automatically engaged in the longitudinal or entry legs of the locking slots 458. A lock actuator (not shown), such a cam mechanism, may be provided to actuate the locking support plate 416 between the foregoing locked position (e.g., in which the locking teeth 456 engage a transversely extending portion of the locking slots 458) and the release or unlocked position in which the locking teeth 456 are aligned with the longitudinal or entry leg of the locking slots 458 that are aligned with the locking teeth 456. A drawer closed sensor 818 is provided on the top support plate 424 to determine the presence of the locking teeth 456 in the locking slots 458. The drawer closed sensor 818 is electronically coupled to the sensor control board 804 and, thereby, the control system 800 can determine when the locking teeth 456 are engaged in the locking slots 458 and whether the lock actuator should be actuated to move the locking support plate 416 laterally into a locking engagement with the transversely extending portion of the locking slots 458 so the locking support is locked with the top and bottom support plates 424, 426, or unlocked from the top and bottom support plates 424, 426 so that the pump drawer 402 may be opened for loading or removal of the pump 10.

As noted in the foregoing, a lock actuator (not shown), such as a cam mechanism, may be associated with the locking support plate 416 to move the locking support plate 416 between the locked and unlocked positions. The cam mechanism may be operated or actuated by extension and retraction of one of the two (2) inboard piston linear actuators 462, described herein, and, typically, the left inboard piston linear actuator 462 in the embodiment of the drive and actuating system 400 shown in FIGS. 47-59. The operation of the left inboard piston linear actuator 462 moves the cam mechanism to move the locking support plate 416 between the locked and unlocked positions, which locks and unlocks the pump drawer 402. For example, retraction of one of the inboard piston linear actuators 462, typically, the left inboard piston linear actuator 462, moves the cam mechanism to move the locking support plate 416 laterally to the unlocked position, which unlocks the pump drawer 402. The pump drawer 402 has right and left sides corresponding to the right and left sides 16, 18 of the pump 10. The user may then open the pump drawer 402 and insert the pump 10 into the pump drawer 402. The user may then close the pump drawer 402. Once the pump drawer 402 is closed, the control system 800 is so alerted by the drawer closed sensor 818, as noted in the foregoing, and may actuate the left inboard piston linear actuator 462 to move the locking support plate 416 to lock the pump drawer 402. In particular, the control system 800 detects that the pump drawer 402 is closed via the drawer closed sensor 818 and operates the drive motor 442 associated with the left inboard piston linear actuator 462 to move the left inboard piston linear actuator 462 slightly forward to actuate the cam mechanism to move the locking support plate 416 laterally to the locked position. The control system 800 confirms that the pump drawer 402 has been locked with a drawer locked sensor 820 provided on the top support plate 424 which may detect the shifted lateral position of the locking support plate 416. It will be appreciated that a manually-actuated locking device may be provided in place of the foregoing automated lock actuator or may be provided as an augmentation to the automated lock actuator, and have a handle or other suitable manual actuator on the exterior of the mobile support 700 for operation by the user or operator. The drawer locked sensor 820 may be used as a safety device in that, if this sensor is not tripped to indicate that the pump drawer 402 is closed, no drive motion will be permitted by the control system 800 in order to prevent possible user injury.

The drive interface section 460 is provided to convert the rotary output of the drive shafts 446 of the piston drive motors 442 into reciprocal translational motion of the drive pistons 50 and, further, transfer and translate the rotary output of the drive shafts 448 of the inlet selector valve drive motors 444 into corresponding and controlled rotational movement of the inlet selector valve actuators 464, which control the angular positioning of the respective inlet selector valves 300 and, hence, the operational state of the inlet selector valves 300. In one exemplary embodiment, the drive interface section 460 comprises four (4) piston linear actuators 462 in the form of ball screw linear actuators that convert the rotational drive output of the drive shafts 446 of the piston drive motors 442 into reciprocal translational movement of the pistons 50 so that the pistons 50 may reciprocally and independently operate the plungers 200 in the respective pump cylinders 104. In the illustrated embodiment, each ball screw-type piston linear actuator 462 comprises a ball screw shaft 466 rotationally journalled in a ball screw nut 468 by threaded engagement as is well-known in the mechanical arts. Each ball screw nut 468 is fixedly mounted to an individual slide block 470 and may be mounted for guided sliding reciprocal movement on a support platform 472 disposed between the mounting flanges 428 on the top side of the top support plate 424 of the drive and actuating support structure 420.

The ball screw shafts 466 each have a proximal portion 474 extending through a corresponding mounting opening 476 in the rear supporting plate 422. The proximal portion 474 of each ball screw shaft 466 is rotationally supported in the receiving mounting opening 476 by a suitable rotational, thrust support bearing 478. A support plate 480 is provided on the distal or front side of the rear support plate 422 to restrain the bearings 478 in the respective mounting openings 476. As will be understood from the view in FIG. 53, the respective pistons 50 each have a proximal end 58 and define a central or axial bore 60 opening externally at the proximal end 58. The proximal end 58 of each of the pistons 50 may have a lip or flange 62 for mounting the proximal end 58, in any desirable manner, to a corresponding slide block 470 so that reciprocal movement of the individual slide blocks 470 results in concurrently reciprocal movement of the connected drive piston 50. The proximal portion 474 of each of the ball screw shafts 466 has an actuator pulley 482 mounted thereto, and a timing belt 484 is reeved about the drive pulley 452 on the drive shaft 446 of the corresponding piston drive motor 442 and the actuator pulley 482 to rotationally interface the drive shaft 446 and the ball screw shaft 466. The pulleys 452, 482 and timing belt 484 permit the driving rotational movement of the associated drive shaft 446 to be imparted to the ball screw shaft 466 as will be understood to those skilled in the mechanical arts. As the ball screw shaft 466 rotates clockwise or counterclockwise, the ball screw nut 468 converts this rotational motion to linear reciprocal motion of the associated slide block 470 and, hence, linear motion of the connected drive piston 50. The drive pistons 50 are supported in the respective support openings 436 in the intermediate support plate 434 by the support elements 438, namely bushings, in the respective support openings 436 to support the linear reciprocal movement of the drive pistons 50 in the support openings 436.

The respective inlet selector valve actuators 464 are rotational motion actuators adapted to transfer and translate the rotary output of the drive shafts 448 of the inlet selector valve drive motors 444 into corresponding and controlled rotational movement of the inlet selector valve actuators 464 which control the angular positioning of the respective inlet selector valves 300 and, hence, the operational state of the inlet selector valves 300. The respective inlet selector valve actuators 464 comprise a selector rod 486 having a distal or actuator end 488 adapted to interface with the actuator interface head 304 on the inlet selector valve body 302 of the corresponding inlet selector valves 300, and a proximal end 490 extending through one of the respective mounting openings 476 in the rear supporting plate 422. The selector rods 486 are rotationally supported in the respective mounting openings 476 by a suitable rotational support bearing 492 and restrained in the respective mounting openings 476 by the same support plate 480, noted previously, used to secure the rotational, thrust support bearings 478 supporting the proximal portion 474 of the ball screw shafts 466 in the respective mounting openings 476 in the rear supporting plate 422. An electro-mechanical angular position sensor 494, such as a rotary encoder, is mechanically coupled to the proximal end 490 of each selector rod 486. The angular position sensor 494 is electronically linked to the control system 800 via an electronic link or connection 496 to the sensor control board 804. The angular position sensors 494 are operable to determine the specific angular orientation of the valve stem 306 of the inlet selector valve body 302 of the associated inlet selector valve 300, which is relayed to the control system 800 via the sensor control board 804. Accordingly, by controlled operation of the inlet selector valve drive motors 444 by the control system 800, the associated inlet selector valve 300 may be angularly positioned to one of the several operating positions discussed previously.

The distal end 488 of each of the selector rods 486 may be configured with engagement or interface elements 498 to interface with corresponding engagement components or structures on the actuator interface head 304 of the inlet selector valve body 302 of the selector valves 300. As discussed previously, these corresponding engagement components or structures include the proximal tab 312 and interface engagement member 314 formed on the actuator interface head 304. As mentioned previously, for safety purposes, it is desirable for the valve stem 306 to be engaged to the drive and actuating system 400 in only one particular angular orientation. Thus, the foregoing features on the actuator interface head 304 preferably require the valve stem 306 to be in one particular orientation for engagement with the engagement or interface elements 498 and this information may be encoded into the pump indicator plate 170 and/or into identifying indicia 172 on the pump body 100, described previously. The control system 800 can thereby determine the initial or preset angular orientation of the valve stem 306 in the inlet selector valve cylinder 114 and operate the inlet selector valve actuators 464 to engage the valve stem 306 in the right angular orientation. If the valve stem 306 can be engaged in more than one angular orientation, the wrong type of fluid could possibly be delivered to the patient. The wrong type of fluid could be delivered because, with more than one angular engagement orientation, there would no longer be a uniquely-predefined relationship between the angular position sensor 494 and the actual position of the valve stem 306 of the inlet selector valve 300, and the control system 800 could cause the inlet selector valve 300 to be oriented in an unintended position whereby an unintended fluid is delivered by the pump 10.

The respective selector rods 486 are supported in the support openings 436 in the intermediate support plate 434 to permit free rotational movement of the selector rods 486. As noted previously, a support element 438, such as a bushing, is provided in each of the support openings 436 in the intermediate support plate 434 that support the linear reciprocal movement of the drive pistons 50. In the case of the selector rods 486, the support elements 438 are support ball bearings that facilitate the rotational motion of the respective pair of selector rods 486. The proximal end 490 of each of the respective selector rods 486 has an actuator pulley 500 mounted thereto, and a timing belt 502 is reeved about the drive pulley 454 on the drive shaft 448 of the driving inlet selector valve drive motor 444 and the actuator pulley 500 to rotationally interface the drive shaft 448 and the selector rod 486. The pulleys 454, 500 and timing belt 502 permit the driving rotational movement of the associated drive shaft 448 to be transferred and imparted to the associated selector rod 486. As the drive shaft 448 rotates clockwise or counterclockwise, the pulleys 454, 500 and timing belt 502 transmit the rotary motion to the selector rod 486 so that the corresponding inlet selector valve 300 may be angularly positioned to one of the several operating positions discussed previously, or any angular position programmed into the control system 800. The pulleys 454, 500 and timing belt 502 permit controlled rotational movement of the drive shaft 448 to be transferred and imparted to the associated selector rod 486, while the angular position sensor 494 continuously monitors the angular position of the selector rod 486 and, hence, enables the control system 800 to determine and control the specific angular orientation of the valve stem 306 of the inlet selector valve body 302 of the associated inlet selector valve 300. The actuator pulley 500 on the proximal end 490 of each of the respective selector rods 486 may be secured to the selector rod 486 via a suitable mechanical fastener arrangement and the respective angular position sensors 494 may be supported for mechanical connection to the proximal end 490 of the respective selector rods 486 by a support bracket mounted to the rear or proximal side of the rear support plate 422. The respective slide blocks 470, discussed previously, also each define a tapered top end portion 504, the use of which is discussed herein.

As noted previously, the pump clamping section or mechanism 520 of the drive and actuating system 400 secures the pump 10 in association with the drive and actuating system 400. The top support plate 424 generally defines a proximally extending portion or slot 512 extending rearward or proximally from the front or distal end 508 of the top support plate 424. The proximally extending slot 512 includes opposed interior ledges 514 along the walls of the proximal slot 512 which support certain components of the pump clamping section or mechanism 520, as described herein. A series of elongated apertures 516 are also provided in the top support plate 424 forward or distal of the proximal end of top support plate 424 to allow the top end portions 504 of the slide blocks 470 to project upward through the top support plate 424 and, additionally, for guiding the sliding reciprocal movement of the slide blocks 470 relative to the upper support plate 424. Accordingly, a total of four (4) elongated apertures 516 are provided in the top support plate 424 forward or distal of the proximal end of the top support plate 424, one for each of the four (4) slide blocks 470 in the illustrated embodiment of the fluid delivery system 2. Additionally, a pair of actuator apertures 518 is provided in the top support plate 424 distal or forward of the slide block apertures 516, for purposes described herein.

The pump clamping section or mechanism 520 generally comprises a clamping block 522 having a front or distal end 524 and a rear or proximal end 526. A pair of guide rods 528 extends proximally or rearward from the clamping block 522. The guide rods 528 are opposed, respectively, by a corresponding pair of distally-extending guide rods 530 mounted to the front or distal side of the rear support plate 422. A pair of preloaded clamping springs 532 is mounted on the two opposing pairs of guide rods 528, 530 to apply a biasing force to the clamping block 522 in the direction of the pump drawer 402 and, particularly, the drawer support structure 408 of the pump drawer 402. The clamping block 522 is vertically supported by a series of spaced, C-shaped support appendages 534 that extend upward from the clamping block 522 to engage the opposed ledges 514 along the walls of the proximal slot 512 in the top support plate 424 so that the clamping block 522 is supported to depend below the top support plate 424. In the illustrated embodiment, a total of four (4) support appendages 534 are provided, including two (2) forward or distal support appendages 534 and two (2) rear or proximal support appendages 534. The body of the clamping block 522 is positioned below the top support plate 424 and the top support plate 424 restrains the clamping block 522 against upward movement, while the engagement of the clamping block support appendages 534 with the opposed ledges 514 along the walls of the proximal slot 512 in the top support plate 424 permits forward and rearward movement in the proximal slot 512 in the top support plate 424.

Generally, in use, when a pump 10 is loaded into the pump cradle 412 in the pump drawer 402, as described previously, the clamping block 522 is used to exert a compressive force on the pump manifold 80 and, in particular, the rear or proximal side of the front plate 102 of the pump body 100. This compressive force is applied to the sealing element (e.g., O-ring, gasket, or weld, typically a laser weld) located in the perimetrical recess 156 around the respective dish-shaped recessed areas 252 and around the outlet manifold channel 244. The compressive force seals the sealing element (e.g., O-ring, gasket, or laser or ultrasonic weld) in the perimetrical recess 156 and permits the pump manifold 80 to withstand higher pressures. As noted previously, a laser weld joint typically occupies the location of the perimetrical recess 156 in the accompanying figures, but an O-ring, gasket or like element may alternatively be provided in this location, if desired. The compressive force of the clamping block 522 similarly secures the sealing element, whether provided as a weld joint, O-ring, gasket, etc., to enable the pump manifold 80 to withstand higher operating pressures. Another feature of the pump clamping mechanism 520, and the clamping block 522 in particular, is to assist in preventing the pump 10 from moving when in use. When the respective plungers 200 are retracted in the pump cylinders 104, there is both a frictional force due to the friction between the plunger seals 218, 220 on the respective plungers 200 and the interior wall 108 of the pump cylinders 104, and a vacuum force due to the vacuum in the pump cylinders 104 during filling (e.g., retraction or withdrawal of the plungers 200 in the pump cylinders 104.) These frictional and vacuum forces "pull" the entire pump body 100 rearwards in the pump cradle 412. The pump clamping mechanism 520 acts against these frictional and vacuum forces to help hold the pump 10 in place.

The outer flange 258 and stiffening ribs 260 on the front face or side 232 of the manifold plate 230 transfer the clamping force applied by the clamping block 522 to the laser welded joint, O-ring, or gasket in the perimetrical recess 156 that is subjected to relatively high fluid pressure and stress, as well as to the other laser weld joint or joints between the manifold plate 230 and the front or distal plate 102 of the pump body 100. Additionally, the manifold caps 262 enclosing the respective right and left inlet manifold channels 236 and the stiffening ribs 260 on the front face or side 232 of the manifold plate 230 all lie substantially in the same plane so that the clamping force applied by the clamping block 522 to the manifold 80 does not deflect the front plate 102 of the pump body 100 and manifold plate 230 unevenly and/or in such a way as to damage the various laser weld joints between the manifold plate 230 and the front or distal plate 102 of the pump body 100 and, particularly, the laser weld joint in the perimetrical recess 156 that is subjected to relatively high fluid pressure and stress. This front "planar" configuration allows the clamping block 522 to prevent of the foregoing features from deflecting when subjected to high loads. Without the clamping force applied by the clamping block 522, the various laser welded joints and molded features of the pump body 100 and manifold plate 230 would likely have to be much stronger and stiffer.

The clamping block 522 further comprises a pair of actuator blocks 536 that extend upward through the respective lateral apertures 518 in the top support plate 424. The lateral actuator block apertures 518 are slightly larger and longer than the actuator blocks 536 to permit limited movement, in a forward or rearward direction, by the actuator blocks 536 in the actuator block apertures 518. Such movement is provided to enable a small retraction of the clamping block 522 in the proximal slot 512 in the top support plate 424 and toward the rear support plate 422 to permit loading and unloading of the pump 10 from the pump cradle 412 without having to manually retract the clamping block 522 and compress the clamping springs 532. The clamping block 522 further defines a forward lip or flange 538 provided on a top side or surface of the clamping block 522.

A clamp actuating mechanism 540 is provided to enable a small retraction of the clamping block 522 in the proximal slot 512 in the top support plate 424 and toward the rear support plate 422 to permit loading and unloading of the pump 10 from the pump cradle 412. The clamp actuating mechanism 540 is adapted to retract the clamping block 522 from engagement with the front plate 102 of the pump body 100 of the pump 10 without manual manipulation of the clamping bock 522. The clamp actuating mechanism 540 comprises, for example, a pair of pivoting cam arms 542 that are pivotally connected by pivot pins 544 to the top support plate 424. The cam arms 542 are pivotally connected to the top side of the top support plate 424 outboard of the actuator blocks 536 to interface with the actuator blocks 536. The cam arms 542 comprise a first or hook end 546 that is in operative engagement with the respective actuator blocks 536 that extend upward through the respective actuator block openings 518 in the top support plate 424. The opposing second ends of the cam arms 542 are formed as cam ends 548 which contact the top end portions 504 of the slide blocks 470 of the two (2) outer or outboard slide blocks 470 that project upward through the two (2) outer or outboard slide block apertures 516 in the top support plate 424. The top end portions 504 of at least these two (2) outer or outboard slide blocks 470 comprise a tapered cam surface 550 opposing the cam ends 548 of the cam arms 542 so that rearward movement of the two (2) outer or outboard slide blocks 470 induces an outward pivotal movement of the cam arms 542 about their respective pivot pins 544. In particular, when it is desired to load or unload a disposable pump 10 from the pump cradle 412 in the pump drawer 402, the piston linear actuators 462 associated with the two (2) outer slide blocks 470 may be driven so that the slide blocks 470 move proximally or rearward in their slide block aperture 518 toward the rear support plate 422. This proximal or rearward movement causes the tapered cam surface 550 on the top end portions 504 of the two (2) outer slide blocks 470 to contact the cam end 548 on each of the cam arms 542 and pivot the cam arms 542 about pivot pins 544. The cam ends 548 on the cam arms 542 pivot laterally outward toward the lateral outer sides of the top support plate 424 while the hook ends 546 of the cam arms 542 move the respective actuator blocks 536, extending upward from the clamping block 522, slightly rearward or proximally in their respective actuator block openings 518 in the top support plate 524 and toward the rear support plate 422 thereby slightly compressing the associated clamping springs 532. As the actuator blocks 536 move rearward or proximally, the clamping block 522 is removed from contacting compressive engagement with the pump 10 and, in particular, from compressive engagement with the rear or proximal side of the front plate 102 of the pump body 100 of the pump 10. The pump 10 may then be removed from the pump cradle 412 in the pump drawer 402 without hindrance from the clamping block 522 and replaced with a new pump 10. Once a new pump 10 is placed in the pump cradle 412 and the pump drawer 402 is closed and locked, as described in the foregoing, the piston linear actuators 462 associated with the two (2) outer slide blocks 470 may be driven so that the slide blocks 470 move distally or forward in their slide block apertures 518 and enabling the clamping block 522 to compressively engage the rear or proximal side of the front plate 102 of the pump body 100 of the replacement pump 10.

The pump clamping section or mechanism 520 further comprises a pressure measurement mechanism 552 for interfacing with the outlet selector valve 280 and, in particular, the rear or proximal pressure sensing port 296 defined in the outlet selector valve cylinder 264 on the manifold plate 230. The pressure measurement mechanism 552 comprises a hollow support block or housing 554 seated on a top face of the clamping block 522. The support block or housing 554 defines an interior chamber 556 that supports a pressure sensor interface pin 558 and a pressure measurement load cell 560 operatively engaged with the pressure sensor interface pin 558. The support block or housing 554 comprises a front or distal end 562 defining a cylindrical front or distal port 564 defining a through bore through which the pressure sensor interface pin 558 projects so as to extend outward from the front port 564 to contact the pressure sensing diaphragm 298 in the rear or proximal pressure sensing port 296 in the outlet selector valve cylinder 264 on the manifold plate 230. The distal end 562 of the support block 554 is in contact or seats against the top lip or flange 538 on the clamping block 522. The front port 564 is adapted to engage the rear or proximal pressure sensing port 296. The pressure measurement load cell 560 is in operative engagement with the pressure sensor interface pin 558 so that fluid pressure changes as exerted on the pressure sensing diaphragm 298 in the rear or proximal pressure sensing port 296, which reflects the fluid pressure changes in the outlet manifold channel 244, are transmitted to the pressure measurement load cell 560. The pressure measurement load cell 560 converts movement of the pressure sensing diaphragm 298 into an electronic signal that is transmitted to the sensor control board 804 via an electronic link or connection 566. The sensor control board 804 continuously relays this pressure information to the control system 800 so that fluid pressure within the outlet manifold channel 244 may be measured and tracked. This measurement enables the control system 800 to ascertain the fluid pressure in the patient outlet port 270 or the waste outlet port 272 depending on the rotational position of the outlet selector valve 280.

The pressure measurement load cell 560 is preloaded by a preload spring 568 which is supported at one end on a spring guide 570 extending rearward or proximally from the rear side of the support block or housing 554, and has a second end secured to a spring support 572 secured to the two (2) rearmost (e.g., proximal) support appendages 534 extending upward from the clamping block 522. A cover 574 may be provided to enclose the interior chamber 556 in the support block 554. The support block 554 may be secured against upward movement in the proximally extending slot 512 in the top support plate 424 by a suitable restricting connection with the opposed ledges 514 along the walls of the proximal slot 512 or suitable connection with the clamping block 522 itself. The preload spring 568 provides sufficient preloading to the pressure measurement load cell 560 and further ensures that the front port 564 on the front or distal end 562 of the support block 554 remains operatively seated or engaged in the rear or proximal pressure sensing port 296 in the outlet selector valve cylinder 264 on the manifold plate 230 when the pump 10 is in operation and under pressure. The operative engagement between the front port 564 and the pressure sensing port 296 maintains operative contact or interface between the pressure sensor interface pin 558, which projects outward or distally from the front port 564, and the pressure sensing diaphragm 298 in the pressure sensing port 296 in the outlet selector valve cylinder 264. Although many pressure sensing devices are available that use a diaphragm and load cell to measure pressure, in the present embodiment, since the pressure sensing diaphragm 298 is located in the disposable pump 10 and the pressure measurement load cell 560 and pressure sensor interface pin 558 are located in the reusable drive and actuating system 400, a more robust and sensitive load cell may be used for the pressure measurement load cell 560. This arrangement allows the fluid-contacting diaphragm 298 to be replaced frequently for sterility purposes, while permitting the use of a high-precision load cell for the pressure measurement load cell 560.

From the foregoing, it will be understood that the clamp actuating mechanism 540, which retracts the clamping block 522 from compressive engagement with the front plate 102 of the pump body 100, as described in the foregoing, also affects operation of the foregoing pressure measurement mechanism 552. For example, if a pump 10 is loaded in the pump cradle 412 in the pump drawer 402 and it is desired to remove the existing pump 10, the piston linear actuators 462 associated with the two (2) outer or outboard slide blocks 470 may be operated so that the slide blocks 470 move proximally or rearward in their respective slide block apertures 518 toward the rear support plate 422, which concurrently moves the clamping block 522 proximally or rearward via the clamp actuating mechanism 540 as discussed in the foregoing. This movement disengages the clamping block 522 from contact with the front plate 102 of the pump body 100 of the pump 10. As the support block 554 is supported by the clamping block 522, forward or rearward movement of the clamping block 522 likewise moves the pressure measurement mechanism 552 in its entirety. Accordingly, as the clamp actuating mechanism 540 retracts the clamping block 522 in the manner described previously, the pressure measurement mechanism 552 is likewise retracted and the front port 564 on the front or distal end 562 of the support block 554 is likewise disengaged from the rear or proximal pressure sensing port 296 in the outlet selector valve cylinder 264 on the manifold plate 230, and the pressure sensor interface pin 558 is removed from operative contact with the pressure sensing diaphragm 298 in the pressure sensing port 296. Upon loading of a new pump 10 in the pump drawer 402, the piston linear actuators 462 associated with the two (2) outer or outboard slide blocks 470 may be driven so that the slide blocks 470 move distally or forward in their respective slide block apertures 518 and enable the clamping block 522 to compressively engage the rear or proximal side of the front plate 102 of the pump body 100 of the replacement pump 10. This distal or forward movement of the clamping block 522 likewise places the front port 564 on the front or distal end 562 of the support block 554 in engagement with the rear or proximal pressure sensing port 296 in the outlet selector valve cylinder 264 on the manifold plate 230, and the pressure sensor interface pin 558 is placed in operative contact or engagement with the pressure sensing diaphragm 298 in the pressure sensing port 296 in the outlet selector valve cylinder 264. As noted previously, the preload spring 568 provides sufficient preloading to the pressure measurement load cell 560 and further ensures that the front port 564 on the front or distal end 562 of the support block 554 remains operatively seated or engaged in the rear or proximal pressure sensing port 296 in the outlet selector valve cylinder 264 on the manifold plate 230 when the pump 10 is in operation and under pressure.

In operation, fluid pressure transmitted through the pressure sensing diaphragm 298 applies a representative force to the pressure measurement load cell 560, which converts the pressure-dependent force to an electronic signal that can be used by the control system 800. The force applied to the pressure sensor interface pin 558 is substantially proportional to the fluid pressure and the cross-sectional area of the pressure sensing diaphragm 298. Since the cross-sectional area of the pressure sensing diaphragm 298 remains substantially constant, the output of the pressure measurement load cell 560 is generally proportional to the fluid pressure. Features may be provided between the front port 564 on the front or distal end 562 of the support block 554 and the rear or proximal pressure sensing port 296 in the outlet selector valve cylinder 264 to ensure proper alignment between the pressure measurement load cell 560 and the disposable pump 10. The elastomeric pressure sensing diaphragm 298 is desirably formed during a secondary molding operation that occurs after the manifold plate 230 is molded.

The outlet selector valve actuating section 580 is disposed on top of the top support plate 424 that supports the various components of the outlet selector valve actuating section 580. The outlet selector valve actuating section 580 provides the drive and mechanical interfacing components for operating the outlet selector valve 280. The outlet selector valve actuating section 580 comprises a support platform 582 disposed and supported on the top side of the top support plate 424. The support platform 582 extends across the proximal slot 512 in the top support plate 424. The outlet selector valve actuating section 580 further comprises an outlet selector valve actuator 584 driven by an outlet selector valve drive motor 600. The outlet selector valve actuator 584 comprises an actuator element 586 comprising an upper or top end 588 and a lower or bottom end 590. The top end 588 of the actuator element 586 is rotationally supported by suitable rotational support bearings 592 in an actuator enclosure housing 594 supported on the support platform 582. The rotational support bearing 592 in the actuator enclosure 594 vertically and rotationally supports the upper or top end 588 of the actuator element 586. An electro-mechanical angular position sensor 596, such as a rotary encoder, is mechanically coupled to the upper or top end 588 of the actuator element 586. The angular position sensor 596 is electronically linked to the control system 800 via an electronic link or connection 598 to the sensor control board 804. The angular position sensor 596 is operable to determine the specific angular orientation of the valve stem 286 of the outlet selector valve body 282 of the outlet selector valve 280, which is relayed to the control system 800 via the sensor control board 804. From the foregoing, it will be understood that the control system 800 receives signal information from the angular position sensor 596 associated with the actuator element 586 and may operate the drive motor 600 to set the angular orientation of the valve stem 286 of the outlet selector valve body 282 of the outlet selector valve 280 in any one of the operating states discussed previously, or any desired angular position in the outlet selector valve cylinder 264 on the manifold plate 230.

The outlet selector valve drive motor 600 is likewise supported by the support platform 582 adjacent the outlet sector valve actuator 584. The outlet selector valve drive motor 600 has an output drive shaft 602 that extends through the support platform 582. A drive pulley 604 is mounted on the drive shaft 602 below the support platform 582 and an actuator pulley 606 is mounted to the lower or bottom end 590 of the actuator element 586. A timing belt 608 is reeved about the drive pulley 604 on the drive shaft 602 and the actuator pulley 604 mounted to the lower or bottom end 590 of the actuator element 586 to rotationally interface the drive shaft 602 and the actuator element 586 so that rotation of the drive shaft 602 imparts corresponding rotary motion to the actuator element 586. The outlet selector valve drive motor 600 may be a servomotor or stepper motor that is electronically linked to the sensor control board 804 via an electronic link or connection 610 so that the control system 800 may control operation of the drive motor 600 and, hence, control operation of the outlet selector valve actuator 584. The sensor control board 804 provides power to the drive motor 600 via the electronic link or connection 610. Accordingly, by controlled operation of the outlet selector valve drive motor 600, the outlet selector valve 280 may be angularly positioned to one of the desired operating positions discussed previously, or any desired angular position, and the angular position of the valve stem 286 of the outlet selector valve 280 is monitored by the angular position sensor 596 coupled to the top end 588 of the actuator element 586 and linked to the control system 800 via the sensor control board 804.

The lower or bottom end 590 of the actuator element 586 is formed with an actuator head 612 that defines a U-shaped pocket 614 for receiving the actuator interface head 284 at the top end of the valve stem 286 of the outlet selector valve body 282 of the outlet selector valve 280. As noted previously, the actuator interface head 284 is generally T-shaped and comprises two (2) outwardly extending tabs 292. The U-shaped pocket 614 accommodates the T-shaped interface head 284 with the outward extending tabs 292 seating against the face of the actuator head 612. The T-shape of the actuator interface head 284 allows the outlet selector valve body 282 to slide into engagement with the pocket 614 in the actuator head 612 and "keys" the outlet selector valve body 282 so that it may be engaged by the actuator head 612 in only one particular orientation. The interface between the actuator interface head 284 and the actuator head 612 also prevents the outlet selector valve body 282 from being ejected upward from the outlet selector valve cylinder 264 on the manifold plate 230 under high pressure as the actuator element 586 is limited in the vertical direction by the rotation support bearings 592 in the actuator enclosure 594. The actuator element 586 is desirably vertically positioned above the clamping block 522 and the pressure measurement mechanism 552 so that when the pump 10 is loaded into the pump cradle 412 in the pump drawer 402, the actuator interface head 284 at the top end of the valve stem 286 of the outlet selector valve body 282 of the outlet selector valve 280 is diametrically opposed to the U-shaped pocket 614 in the actuator head 612. Accordingly, as the pump drawer 402 is closed, the U-shaped pocket 614 automatically receives the T-shaped actuator interface head 284.

A main power supply coupling 620 may be mounted on the base plate 432 and the rear support plate 422. The power supply coupling 620 provides power to the drive control board 802 and the sensor control board 804, and suitable power supply cabling 622 from the drive control board 802 provides power to the various piston drive motors 442 and inlet selector valve drive motors 444 in the drive section 440. The base plate 432 includes an electronic connection port 624 for electronically connecting the drive control board 802 to the control system 800. The sensor control board 804 may likewise be electronically connected to the electronic connection port 624 for electronically connecting the sensor control board 804 to the control system 800.

A power and signal coupling 620 may be connected to the drive control board 802 and the sensor control board 804. The power and signal coupling 620 provides power to the sensor control board 804, and transfers control signals between the drive control board 802 and the sensor control board 804. Suitable power supply cabling 622 from the drive control board 802 provides power to the various piston drive motors 442 and inlet selector valve drive motors 444 in the drive section 440. The drive control board 802 may include an electronic connection port 624 for electronically connecting the drive control board 802 to the control system 800. The sensor control board 804 may likewise be electronically connected to the control system 800 via the power and signal coupling 620 and electronic connection port 624. The drive control board 802 is supported by the base plate 432 extending rearward from the rear support plate 422.

Figure 60:
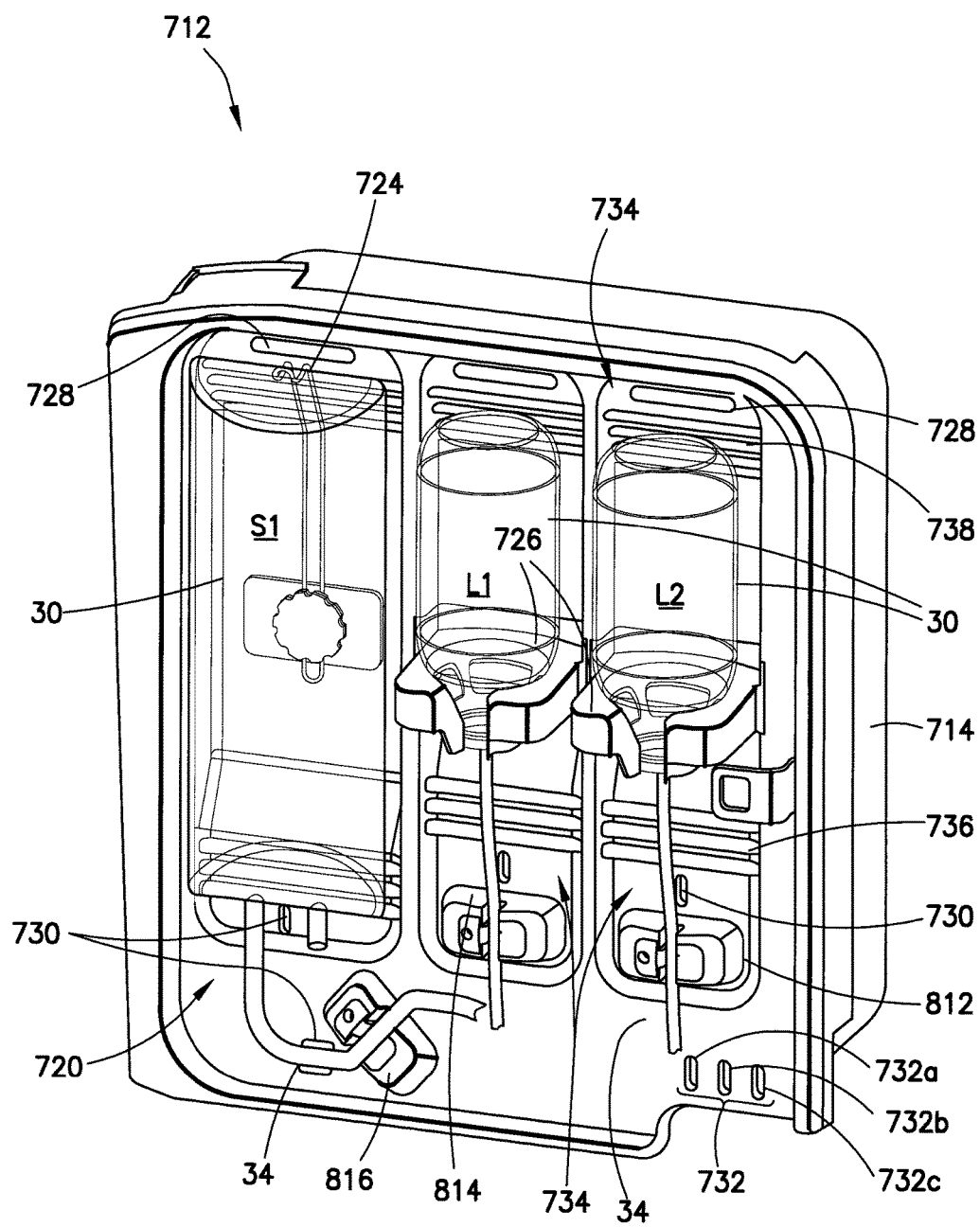
FIG. 60 is a perspective view of a fluid handling compartment provided in the mobile fluid delivery system shown in FIG. 46A.

As noted in the foregoing, the drive and actuating system 400 and, desirably, the control system 800 are supported and contained by the mobile support 700. The mobile support 700 generally comprises a support housing 702 vertically supported by a support pedestal or column 704 connected to a wheeled base 706. The wheeled base 706 permits the mobile support 700 to be movable within a hospital or like medical facility. The pedestal 704 may include a handle structure 708 for moving the mobile support 700. Bottle or container supports 710 may be provided on lateral sides of the pedestal 704 for stably supporting bottles or containers, such as the fluid source containers 30 discussed previously, during spiking operations. The bottle or container supports 710 allow bottles or containers to be spiked and to be maintained in an upright posture during spiking at a location near the pump drawer 402 since the fluid supply tubes 34 of the various embodiments of the fluid supply sets 32 are typically permanently affixed to the pump 10. Additionally, the support housing 702 may comprise two (2) lateral fluid handling compartments 712, as shown in FIG. 60, which are supported within respective lateral compartment doors 714 that close against and form part of the support housing 702 of the mobile support 700. These lateral fluid handling compartments 712 house components of the fluid management system 720 and, thus, the lateral fluid handling compartments 712 support and maintain the various diagnostic or therapeutic (e.g., pharmaceutical) fluids to be associated with the pump 10. The mobile support 700 also supports components of the control system 800, as shown in FIG. 46A. While the details of the control system 800 are provided herein, FIG. 46A shows certain components of the control system 800 supported on the support housing 702 including a local user interface display 806, typically a touch screen, a packaging reader 808 such as bar code or RFID tag reader, and a patient outlet air detector 810 which interfaces with and accepts the medical tubing of the patient supply set 40. A patient outlet port opening 716 is further provided in the support housing 702 to provide an egress opening for the swabable valve 274 seated in the patient outlet port 270 on the outlet selector valve cylinder 264 on the manifold plate 230. Further, the handle housing portion 404 and waste collection compartment 406 of the pump drawer 402 are accessible from the front of the support housing 702 and are formed to blend cosmetically as part of the support housing 702. If desired, the support housing 702 may be detachable from the pedestal 704 and may include overhead mounting points 718 on a top or upper face for mounting the support housing 702 to an overhead support system (not shown). The support housing 702 and support pedestal 704 together may have any suitable ornamental appearance.

As shown in FIG. 60, each fluid handling compartment 712 encloses a fluid management system 720. In particular, the fluid management system 720 comprises identical fluid handling arrangements, one in each fluid handling compartment 712. Each fluid handling arrangement comprises a saline container support or hanger 724 supporting a saline fluid source container 30 such as a saline bag, and a pair of fluid container supports 726 for supporting one of the fluid source containers 30 in an inverted fluid delivery orientation. Any type of support or hanger may be provided for supports or hangers 724, 726, such as those described in U.S. Pat. No. 7,240,882 to Degentesh, et al. incorporated herein by reference for this purpose.

Upper and lower indicator lights 728, 730 are provided in the interior of the fluid handling compartment 712, above and below each of the saline container support 724 and the respective fluid container supports 726. The upper and lower indicator lights 728, 730 may be controlled by the control system 800 to alert the operator via visual means (and potentially augmented by auditory or other means) as to the location in the respective fluid handling compartments 712 where the fluid source containers 30 should be placed for an injection procedure. The indicator lights 728, 730 may be color coded to correspond to a specific fluid. For example, the indicator lights 728, 730 associated with the saline support 724 may be blue, while the indicator lights 728, 730 for the fluid container supports 726 in the left fluid handling compartment 712 are green, and the indicator lights 728, 730 for the fluid container supports 726 in the right fluid handling compartment 712 are purple, as examples. Additionally, a pump connection status bar 732 is provided in the interior of each of the fluid handling compartments 712 in a lower corner and contains three (3) indicator lights, designated as 732a, 732b, 732c in FIG. 60. These indicator lights 732a, 732b, 732c correspond, respectively, to the three (3) pairs of indicator lights 728, 730 and, ideally, have the same color-coding as the corresponding indicator lights 728, 730. Accordingly, indicator light 732a may be blue to correspond to the indicator lights 728, 730 associated with the saline support 724, and indicator light 732b may be green to correspond to the indicator lights 728, 730 associated with the "center" or "middle" fluid container supports 726 in the left fluid handling compartment 712, etc.

When a new fluid source container 30 is installed in a fluid handling compartment 712, the control system 800 causes all three (3) indicator lights 728, 730, 732 for that source location to flash or blink together. The indicator lights 728, 730 respectively show the user where to place the fluid source container 30 and which associated air detector is active for that fluid source container 30. The lower indicator light 730 also shows the user which of the three (3) fluid supply tubes 34 on that side of the pump 10 should be used to connect to the fluid source container 30. Once the fluid source container 30 is installed and successfully primed, all three indicator lights 728, 730, 732 change from flashing or blinking to solid "on". This indicates that the fluid source container 30 is "active" and available for use if desired. Once the fluid source container 30 has been depleted, the control system 800 turns all three (3) indicator lights 728, 730, 732 "off" to show that the fluid source container 30 is no longer available. If the "open life" of the fluid source container 30 expires or if the user indicates that the fluid source container 30 should no longer be used, the indicator lights 728, 730, 732 are turned "off". The indicator lights 728, 730, 732 are not typically used during a fluid injection as they are typically closed behind the lateral compartment doors 714 during fluid injections.

As was described previously, each pump 10 in the illustrated embodiment comprises a pump body 100 with three (3) inlet ports 122, 124, 126 on each lateral side, including two (2) fluid inlet ports 122, 124 and a single saline inlet port 126. To accommodate this embodiment of the pump 10, each fluid handling compartment 712 is adapted to support three (3) fluid containers 30 to be associated with the inlet ports 122-126 on the lateral sides of the pump body 100. However, this configuration of the pump 10, as noted previously, is merely exemplary and should not be considered limiting. The pump 10 and the foregoing corresponding configuration of the respective fluid handling compartments 712 should not be considered as exclusive and the pump 10 and the respective fluid handling compartments 712 may be expanded to include additional fluids (e.g., four (4) or more fluids), or fewer fluids (e.g., less than three (3) fluids). However, the arrangement of two (2) fluid handling compartments 712, each supporting up to three (3) fluid source containers 30, is desirably effective for interfacing with the pump 10.

The respective fluid handling compartments 712 also each support a series of fluid inlet air detectors 812, 814, 816 for the fluid supply tubes 34 used to conduct fluids from the respective fluid source containers 30. The inlet air detectors are respectively associated with the saline container support 724 and the respective fluid container supports 726 in the fluid handling compartments 712. The air detectors 812-816 and the patient outlet air detector 810 provide air bubble detection information to the control system 800 for operational control of the fluid delivery system 2. The various air detectors 810-816 may be conventional optical or ultrasonic air detectors as are well known in the medical field.

Further, it is often desirable to maintain the fluid contained in the various fluid source containers 30 in each fluid handling compartment 712 in a warmed state for the comfort of the patient and other purposes. For example, in the case of contrast media used in radiographic imaging procedures, increasing the temperature of the contrast media also has the desirable effect of reducing the viscosity of the contrast media for easier injection into the patient, among other advantages. Accordingly, each fluid handling compartment 712 is warmed by a convective heating system 734. The convective heating system 734 may include devices or components (not shown) that may intake air through an intake vent 736 in each fluid handling compartment 712, warm the air across a heating system, such as simple electrical resistance coils, and return the heated air into the interior of the fluid handling compartment 712 via an air outlet vent 738.

During a fluid injection, one or more indicator lights 807 on the user interface display 806 may be turned on by the control system 800 to show which fluids are being injected. For example, the indicator lights 807 may be two (2) multi-color indicator lights located in the top left and right corners of the user interface display 806. The indicator lights 807 may be either flashing or solid "on" and may emit white, blue, green, purple, etc. light depending on the fluid being injected. For example, if saline is being injected into the patient, the indicator lights 807 may be blue based on the color convention discussed previously in connection with the indicator lights 728, 730, 732 in the fluid handling compartments 712. Both indicator lights 807 desirably always display the same state (flashing or solid "on" and the same color). Additional and larger indicator lights (not shown) may be placed on the user interface display 806 or on the support housing 702 and may be sized so that a user is able to see these indicator lights from anywhere in the room where the fluid delivery system 2 is located. These "larger" indicator lights (not shown) desirably indicate when the fluid delivery system 2 is armed and during a fluid injection, and may show which type of fluid is currently being injected. For example, if saline is being injected, these larger indicator lights can flash blue, and if contrast from the left fluid handing compartment 712 is being injected, the larger indicator lights can flash green.

It will be appreciated that the control system 800 comprises a system controller or computer 822 with appropriate software for controlling operation of the fluid delivery system 2 and this controlling computer may physically reside on-board the mobile support 700, or be located at some external location, such as in a control room, and interface via a hardwired connection or wireless connection, as desired, with the electronic components associated with the support housing 702, such as the drive control board 802 and sensor control board 804, sensors, such as the angular position sensors 494, 596, drawer closed sensor 818, and drawer locked sensor 820, as examples, and the user interface display 806. While the microprocessor and like components for controlling the various components of the drive and actuating system 400 may reside entirely with the system controller 822, these control components may be distributed between the system control computer 822 and the drive control board 802 and sensor control board 804 as desired by one skilled in the computer field. The system controller 822 may interface via wired or wireless connections with external devices such as a computer network 900 (via an Ethernet connection), a CT scanner 902, a remotely located display 904, such as a touch screen, and like external devices, as shown in FIG. 46B. Further, it will be appreciated by one skilled in the computer field that all of the processing, data storage, and other computer-implemented tasks may be performed by the control system 800, the system controller 822 or any other device with such capabilities that is in communication with the control system 800 and/or the system controller 822. Such a device may be in communication with the control system 800 and system controller 822 via a computer network 900 or any other means for wired or wireless data communication.

This disclosure now provides further information on the assembly of the pump 10 for use in the fluid delivery system 2. The following discussion is intended as exemplary and non-limiting as to an assembly for process for constructing the disposable pump 10. Before beginning assembly of a "batch" or "run" of pumps 10, the operator enters a manufacturing batch number and pump type number into a manufacturing process control computer in a production facility. If the pump sequential identification numbering does not begin with 00001, the starting number is also be specified. The manufacturing process control computer assigns a unique, sequential identification to each pump 10. This number typically begins with 00001 for the first pump 10 of the batch and is incremented by 1 for each subsequent pump 10. Next, the saline manifold cap 136 is installed over the saline manifold channels 132, 134 and is welded, typically laser welded, to the pump body 100. The inlet and outlet check valves 194, 196 are placed in their respective recesses, described previously. The front manifold plate 230 may then be installed onto the pump body 100, capturing the check valves 194, 196 between these two components. The front manifold plate 230 is then welded, typically laser welded, to the pump body 100. An inlet manifold cap 262 is installed onto each of the two channel members 238 forming the respective inlet manifold channels 236.

The manufacturing process control computer next selects an inlet selector valve position number for each pump 10 and this number may be assigned sequentially starting with 01 for the first pump 10 in the batch and incrementing by one (1) for each subsequent pump 10. Once a maximum permitted value has been reached, for example 36, the counter is reset back to a value of 01 for the next or $37^{th}$ pump 10. Alternatively, the manufacturing process control computer may randomly select a number between 01 and a maximum permitted value, for example 36, for the initial angular position of the valve stem 306 of the inlet selector valves 300, instead of sequentially assigning values. The designated inlet selector valve position number is combined with the uniquely-assigned serial number along with other information as desired, such as the manufacturing lot code and pump type/configuration identifier. This combined data is then encoded into a 14-character string. The 14-character data string is used, for example, to create the identifying indicia 172, such as a barcode label, that can be laser-etched directly onto the pump 10, as described previously in this disclosure. The encoded data string is used to generate a corresponding machine-readable barcode matrix, as an example, and the label desirably also contains the same information in human-readable alphanumeric characters. A mist of silicone lubricant may be sprayed onto the interior wall surface of the pump cylinders 104, onto the interior surface of the inlet selector valve cylinders 114, and onto the interior surface of the outlet selector valve cylinder 264 on the manifold plate 230. Next, at a valve insertion assembly station of the manufacturing facility, the manufacturing process equipment reads the identifying indicia 172, such as a barcode label, on the pump body 100, the encoded information is decoded using a decoding algorithm, and the inlet selector valve position number is extracted. The extracted inlet selector valve position number is used in conjunction with a look-up table to determine the assembled positions of the left and right inlet selector valves 300. For example, if the extracted inlet selector valve position number was 19/36, the valve stem 306 of the left inlet selector valve 300 may be placed in one predetermined position, such as angular position "4" which corresponds to a specific angular orientation of the valve stem 306 in the left inlet selector valve cylinder 114, and the valve stem 306 of the right inlet selector valve 300 may be placed in another predetermined position, such as angular position "1" which corresponds to a specific angular orientation of the valve stem 306 in the right inlet selector valve cylinder 114. Next, the two (2) valve stems 306 and four (4) plungers 200 are loaded into an automated insertion fixture, which uses servomotors to adjust the angular orientation of the left and right valve stems 306 to match the angular positions indicated by the extracted inlet selector valve position number. The automated insertion fixture concurrently inserts both valve stems 306 and all four (4) plungers 200 into the respective inlet selector valve cylinders 114 and pump cylinders 104 on the pump body 100. It will be appreciated that the valve stems 306 and the plungers 200 may be inserted into the respective inlet selector valve cylinders 114 and pump cylinders 104 on the pump body 100 in a two or more step process, for example, one at a time.

Additionally, for the outlet selector valve 280, the valve stem 286 of the outlet selector valve body 282 is inserted into the outlet selector valve cylinder 264 on the manifold plate 230. Prior to insertion, the angular orientation of the valve stem 286 is adjusted to ensure that the flow passage 290 is aligned or in fluid communication with the waste outlet port 272 on the outlet selector valve cylinder 264. Next, the fluid supply tubes 34 are attached to the inlet ports 122, 124, 126 on the inlet selector valve cylinders 114 via, for example, integral barbs on the inlet ports 122, 124, 126. Next, the pump indicator plate 170 is installed into the recessed groove 176 on the outside of one of the pump cylinders 104. The indicator plate 170, as described previously, contains grooves 174 which indicate at least the specific pump configuration of the pump 10 based on the associated fluid supply set 32 for the pump 10. The groove pattern 174 in the pump indicator plate 170 matches the configuration of the pump 10 and its associated fluid supply tubes 34 (see FIGS. 40-43). The waste collection tube set 46 with attached waste collection container 48 is attached to the waste outlet port 272 on the outlet selector valve cylinder 264 on the manifold plate 230.

While embodiments of a fluid delivery system including a fluid pumping device, optionally provided as a disposable pump cassette, and methods of assembling and use and operation thereof were provided in the foregoing description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A selector valve for a medical fluid delivery device, the selector valve comprising:
    a valve bore in fluid communication with an outlet channel;
    a first outlet port;
    a second outlet port; and
    a selector valve body comprising a valve stem located within the valve bore and having a flow passage, wherein the selector valve body is adapted to place the flow passage in fluid communication with one of the first outlet port, the second outlet port, and a shut-off position,
    wherein the selector valve body comprises a sealing arrangement having an elastomeric core disposed within a thin-walled valve stem, wherein the thin-walled valve stem comprises a thin cylindrical sidewall in direct contact with the valve bore, and
    wherein, when the elastomeric core and the valve stem are subjected to internal fluid pressure, the thin cylindrical sidewall of the valve stem expands outward to increase a sealing force between an outer diameter of the valve stem and the valve bore.

2. The selector valve of claim 1, wherein the first outlet port is a patient outlet port in fluid communication with a patient fluid supply set and the second outlet port is a waste outlet port in fluid connection with a waste receptacle.

3. The selector valve of claim 1, further comprising an actuator interface head adapted to interface with a valve actuator associated with a drive and actuating system.

4. The selector valve of claim 3, wherein the valve actuator controls operation of the selector valve body.

5. The selector valve of claim 1, further comprising a proximal pressure sensing port comprising a pressure sensing diaphragm.

6. The selector valve of claim 1, wherein the thin cylindrical sidewall of the valve stem defines an aperture connected to an outlet port and the elastomeric core defines the flow passage to direct fluid to the outlet port.

* * * * *

UNITED STATES PATENT AND TRADEMARK OFFICE
CERTIFICATE OF CORRECTION

PATENT NO.        : 9,700,672 B2                  Page 1 of 2
APPLICATION NO.   : 14/346064
DATED             : July 11, 2017
INVENTOR(S)       : Capone et al.

It is certified that error appears in the above-identified patent and that said Letters Patent is hereby corrected as shown below:

In the Specification

In Column 11, Line 59, delete "actuating system 800," and insert -- actuating system 400, --, therefor.

In Column 18, Line 48, delete "portions or parts 212" and insert -- portions or parts --, therefor.

In Column 18, Lines 65-66, delete "interface member 212." and insert -- interface member 210. --, therefor.

In Column 24, Line 42, delete "terminates 290" and insert -- 290 terminates --, therefor.

In Column 27, Line 21, delete "(thermoplastic urethane)" and insert -- (thermoplastic polyurethane) --, therefor.

In Column 28, Lines 36-37, delete "apart 1236" and insert -- 1236 apart --, therefor.

In Column 30, Lines 57-58, delete "fourth inlet port 334" and insert -- fourth inlet port 328 --, therefor.

In Column 34, Line 66, delete "rights side" and insert -- right side --, therefor.

In Column 36, Lines 4-5, delete "check valve recesses 252" and insert -- check valve receiving recesses 246 --, therefor.

In Column 36, Line 48, delete "pump cylinders 106." and insert -- pump cylinder 104. --, therefor.

In Column 41, Line 25, delete "fluid supply tubes 32" and insert -- fluid supply tubes 34 --, therefor.

In Column 41, Line 63, delete "fluid supply tubes 32" and insert -- fluid supply tubes 34 --, therefor.

Signed and Sealed this
Twenty-ninth Day of May, 2018

Andrei Iancu
*Director of the United States Patent and Trademark Office*

In Column 42, Lines 11-12, delete "patient outlet port 272" and insert -- patient outlet port 270 --, therefor.